United States Patent [19]

Rendina et al.

[11] Patent Number: 5,405,830
[45] Date of Patent: Apr. 11, 1995

[54] HERBICIDAL BICYCLIC ETHERS

[75] Inventors: Alan R. Rendina; Wendy S. Taylor, both of Wilmington, Del.

[73] Assignee: E. I. Du Pont de Nemours and Company, Wilmington, Del.

[21] Appl. No.: 94,130

[22] PCT Filed: Jan. 9, 1992

[86] PCT No.: PCT/US92/00031
§ 371 Date: Jul. 29, 1993
§ 102(e) Date: Jul. 29, 1993

[87] PCT Pub. No.: WO92/13861
PCT Pub. Date: Aug. 20, 1992

Related U.S. Application Data

[63] Continuation-in-part of Ser. No. 648,001, Jan. 30, 1991, abandoned.

[51] Int. Cl.⁶ .................... A01N 43/08; C07D 307/00
[52] U.S. Cl. .................... 504/298; 504/235; 504/247; 544/336; 546/141; 546/153; 546/269; 548/454; 549/52; 549/463
[58] Field of Search .......... 549/463; 504/298

[56] References Cited

U.S. PATENT DOCUMENTS

| | | | |
|---|---|---|---|
| 4,486,219 | 12/1984 | Powell | 71/88 |
| 4,536,586 | 8/1985 | Powell | 549/463 |
| 4,670,041 | 6/1987 | Payne et al. | 71/92 |
| 4,798,621 | 1/1989 | Ackerson et al. | 71/90 |
| 4,828,603 | 5/1989 | Patel et al. | 71/88 |

FOREIGN PATENT DOCUMENTS

| | | | |
|---|---|---|---|
| 343859 | 11/1989 | European Pat. Off. | |
| WO89/02219 | 3/1989 | WIPO | A01N 43/12 |
| 91/03464 | 3/1991 | WIPO | |

*Primary Examiner*—Bernard Dentz

[57] ABSTRACT

This invention relates to certain herbicidal ethers, agriculturally suitable compositions thereof, and a method for their use as broad spectrum preemergent or postemergent herbicides.

9 Claims, No Drawings

HERBICIDAL BICYCLIC ETHERS

CROSS-REFERENCE TO RELATED APPLICATION

This application is a 371 or PCT/US92/0031 filed Jan. 9, 1992 and a CIP of Ser. No. 07/648,001 filed Jan. 30, 1991 and now abandoned.

BACKGROUND OF THE INVENTION

This invention relates to certain herbicidal ethers, agriculturally suitable compositions thereof, and a method for their use as broad spectrum preemergent or postemergent herbicides.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around railroad tracks, storage tanks and industrial storage areas. There are many products commercially available for these purposes, but the search continues for products which are more effective, less costly and environmentally safe.

Payne et al., U.S. Pat. No. 4,567,283 and Payne et al., U.S. Pat. No. 4,670,041 disclose a variety of herbicidal bicyclic ethers of the Formula

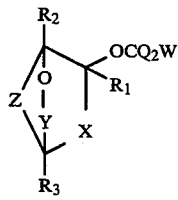

U.S. Pat. No. 4,798,621 and WO 8,902,219 both disclose bicyclic ethers and their method-of-use in rice.

U.S. Pat. No. 4,486,219 discloses bicyclic ethers of the formula:

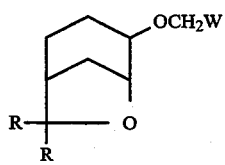

WO91/03464 discloses bicyclic ethers such as:

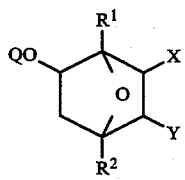

wherein inter alia
X and Y are independently $C(R^3)$ $(R^4)OR^5$;

$R^5$ is $C_1$–$C_3$alkyl, $C_2$–$C_4$alkenyl, $C_3$–$C_4$alkynyl, $CH_2$-phenyl or $C_1$–$C_4$alkyl substituted with $OR^8$ or $OCF_3$;

It is an object of the present invention to provide compounds and compositions which exhibit herbicidal activity on a variety of weed species. It is a further object of the present invention to provide compounds and compositions that are herbicidally safe to rice, cereals and broadleaf crops. It is a feature of the present invention to furnish novel oxabicyclo ethers that exhibit useful herbicidal activity. These and other objects, features and advantages will become apparent with respect to the following description of the invention.

SUMMARY OF THE INVENTION

This invention pertains to compounds of Formulae I, II, III and IV including stereoisomers thereof, suitable agricultural compositions containing them and the use of said compounds or compositions as broad spectrum preemergent and postemergent herbicides:

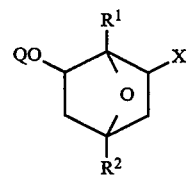
I

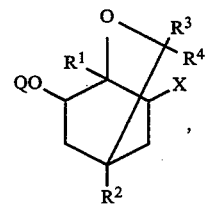
II

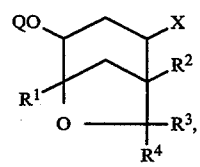
III

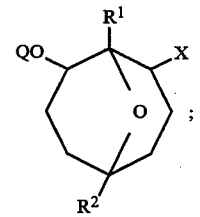
IV wherein
$R^1$ is straight chain $C_1$–$C_3$alkyl
$R^2$ is H, $C_1$–$C_4$alkyl, $C_2$–$C_4$alkenyl or $C_2$–$C_4$alkynyl;
$R^3$ and $R^4$ are independently H, $C_1$–$C_4$alkyl, $C_2$–$C_4$alkenyl, $C_2$–$C_4$alkynyl or $C_1$–$C_3$alkyl substituted with $OCH_3$ or $OCH_2CH_3$;

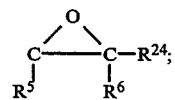

X is $CR^5R^6Y^1$, $CR^5{=}CR^6Y^3$ or $R^5 R^6$
$R^5$ and $R^6$ are independently H or $C_1$–$C_3$alkyl $Y^1$ is H; $C_1$–$C_4$alkyl optionally substituted with $Y^2$; $C_3$–$C_6$cycloalkyl; CN; $C(O)NR^7R^8$; $C(O)NHOR^9$; $CO_2R^{10}$; $C(O)R^{11}C(OR^{22})$ $(OR^{23})R^{11}$; CHO; $CH(OR^{22})$ $(OR^{23})$; $CH$-$NOR^{16}CR^{11}$=$NOR^{17}$; $SR^{15}$; halogen; $C_2$–$C_4$alkenyl optionally substituted with 1–3 halogens, $CO_2(C_1$–$C_3$alkyl), CN or CHO; $C_2$–$C_4$alkynyl optionally substituted with halogen; $S(O)_nR^{12}$; $SO_2NR^{13}R^{14}$; $NO_2N_3SCN$; phenyl optionally substituted with 1–3 substituents selected from $CH_3$, $OCH_3$, $SCH_3$, $CF_3$ and halogen; imidazole; triazole; tetrazole; or

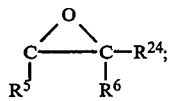

$Y^2$ is CN; $C(O)NR^7R^8$; $C(O)NHOR^9$; $CO_2R^{10}$; $C(O)R^{11}$; CHO; CH=$NOR^{16}$; $CR^{11}$=$NOR^{17}$; $SR^{15}$; 1–3 halogens $C_2$–$C_4$alkenyl optionally substituted with 1–3 halogens; $C_2$–$C_4$alkynyl optionally substituted with halogen; $S(O)_nR^{12}$; $SO_2NR^{13}R^{14}$; $NO_2$; $N_3$; SCN; phenyl optionally substituted with 1–3 substituents selected from $CH_3$, $OCH_3$, $SCH_3$, $CF_3$ and halogen; imidazole triazole tetrazole or

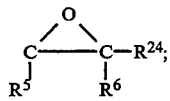

$Y^3$ is H, $C_1$–$C_3$alkyl, CN, $CO_2R^{10}$, $C(O)R^{11}$, CHO or halogen;
$R^7$ $R^8$ $R^{13}$ and $R^{14}$ are independently H or $C_1$–$C_3$ alkyl; $R^7$ and $R^8$ may be taken together to form a 5- or 6-membered ring and $R^{13}$ and $R^{14}$ may be taken together to form a 5- or 6-membered ring;
$R^9$, $R^{12}$, $R^{16}$ and $R^{17}$ are independently $C_1$–$C_3$alkyl;
$R^{10}$ is H; $C_1$–$C_6$alkyl optionally substituted with 1–3 halogens, $OR^{18}$, CN or phenyl optionally substituted with 1–3 substituents selected from halogen, $CH_3$ and $OCH_3$; $C_3$–$C_4$alkenyl; or $C_3$–$C_4$ alkynyl;
$R^{11}$ is $C_1$–$C_6$alkyl optionally substituted with 1–3 halogens, $OR^{18}$, CN or phenyl optionally substituted with 1–3 substituents selected from halogen, $CH_3$ and $OCH_3$; $C_2$–$C_4$alkenyl; $C_2$–$C_4$ alkynyl; or phenyl optionally substituted with 1–3 substituents selected from halogen, $CH_3$ and $OCH_3$;
$R^{15}$ is H, $C_1$–$C_3$alkyl or benzyl;
n is 1 or 2;
Q is $CH_2W$ or

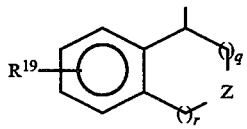

q and r are independently 0–2;
$R^{18}$ is H or $C_1$–$C_3$alkyl;
$R^{19}$ is H, halogen, $C_1$–$C_3$alkyl, $OR^{20}$, $SR^{20}$ or CN;
$R^{20}$ is $C_1$–$C_3$alkyl or $C_1$–$C_3$haloalkyl;
Z is $CH_2$, $NR^{21}$, O, S or may be CH and taken to form a double bond with an adjacent carbon;
$R^{21}$ is H or $C_1$–$C_3$alkyl;
$R^{22}$ and $R^{23}$ are independently $C_1$–$C_3$alkyl or may be taken to from a 5- or 6-membered ring;

$R^{24}$, $R^{25}$ and $R^{26}$ are independently H or $C_1$–$C_2$alkyl;
W is phenyl optionally substituted with 1–3 substituents selected from halogen, $C_1$–$C_3$alkyl, $C_1$–$C_3$alkoxy, OH, CN, $C_1$–$C_3$ haloalkyl, $C_1$–$C_3$haloalkoxy, $C_1$–$C_3$alkylthio, $C_2$–$C_4$alkenyl and $C_2$–$C_4$alkynyl or W is a 5-, 6- or 7-membered heterocyclic ring containing 1 to 3 heteroatoms selected from the group 0–2 nitrogens, 0–2 oxygens and 0–2 sulfurs, each ring optionally substituted with 1–2 substituents selected from halogen, $CH_3$ and $OCH_3$;
provided that
1) in compounds of Formulas I and II, $Y^1$ is other than H, $C_1$–$C_4$alkyl or halogen, and $Y^2$ is other than halogen(s);
2) in compounds of Formula IV, when Q is other than $CH_2W$, then $Y^1$ is other than H or $C_1$–$C_4$alkyl;
3) the sum of q and r is 0–2; and
4) if the sum of q and r is O then Z is $CH_2$.

A representative exemplification of the aforementioned heterocycles includes but is not limited to pyrrole, furan, thiophene, tetrahydropyran, tetrahydrofuran, isoxazole, oxazole, pyrazole, imidazole, thiazole, pyridine and pyrazine In the above definitions, the term "alkyl", used either alone or in compound words such as "haloalkyl" or "alkylthio", includes straight chain or branched alkyl, e.g. methyl, ethyl, n-propyl, isopropyl or the different butyl isomers.

"Alkoxy", "alkenyl" and "alkynyl" includes straight chain or branched isomers, e.g. ethoxy, n-propyloxy, isopropyloxy, 1-propenyl, 2-propenyl and 3-propenyl.

"Halogen" either alone or in compound words such as "haloalkyl", means fluorine, chlorine, bromine or iodine The compounds of the invention which are preferred for either their biological activity and/or ease of synthesis are:
1. Compounds of Formulae I, II, III or IV wherein:
    W is phenyl optionally substituted by 1–2 substituents selected from F, Cl, Br, $CH_3$ and $OCH_3$ or W is tetrahydropyran, tetrahydrofuran, thiophene, isoxazole, pyridine or pyrazine, each ring optionally substituted with 1–2 substituents selected from F, Cl, Br, $CH_3$ and $OCH_3$;
    Q is $CH_2W$ or

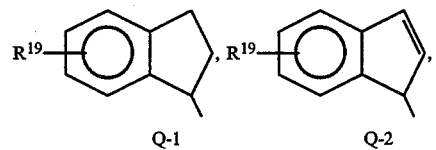

Q-1    Q-2

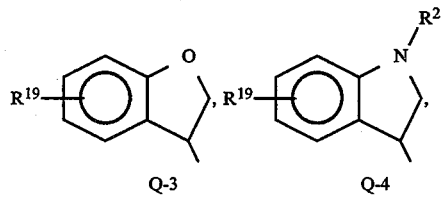

Q-3    Q-4

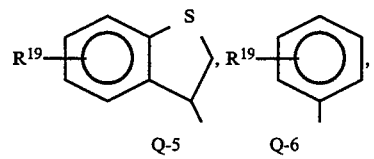

Q-5    Q-6

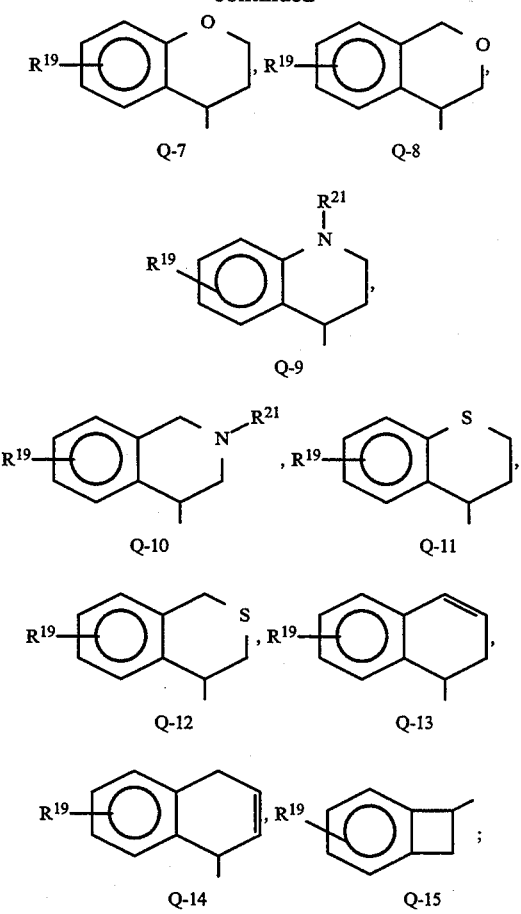

2. Compounds of Preferred I wherein:
   $R^2$ is H, $C_1$–$C_3$alkyl, $C_2$–$C_3$alkenyl or $C_2$–$C_3$ alkynyl.
3. Compounds of Preferred 2 wherein:
   $R^3$ is H, $C_1$–$C_3$alkyl, $C_3$–$C_4$alkenyl or $C_3$–$C_4$ alkynyl; and
   $R^4$ is H, $C_1$–$C_3$alkyl, $C_3$–$C_4$alkenyl or $C_3$–$C_4$ alkynyl.
4. Compounds of Preferred 3 wherein:
   $Y^1$ is H; $C_1$–$C_2$alkyl; $C_3$–$C_6$ cycloalkyl; $C(O)NR^7R^8$; $C(O)NHOR^9$; $CO_2R^{10}$; $C(O)R^{11}$; $C(O)R^{11}$; $C(OR^{22})(OR^{23})R^{11}$; CHO; $CH(OR^{22})(OR^{23})$; $CH{=}NOR^{16}$; $CR^{11}{=}NOR^{17}$; halogen; $C_2$–$C_4$alkenyl optionally substituted with 1–2 halogens, $CO_2(C_1$–$C_3$ alkyl), CN, or CHO; $C_2$–$C_4$alkynyl optionally substituted with halogen; $SO_2NR^{13}R^{14}$; $NO_2$; $N_3$; phenyl optionally substituted with 1–3 substituents selected from $CH_3$, $OCH_3$, $SCH_3$, $CF_3$ and halogen; imidazole; triazole; tetrazole;

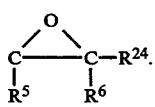

5. Compounds of Preferred 4 wherein:
   Q is $CH_2W$ or Q-1, Q-3, Q-4, Q-6, Q-7, Q-8 or Q-15,
   $R^5$ and $R^6$ are independently
   W is phenyl optionally substituted with 1–2 substituents selected from F, Cl, Br and $CH_3$; tetrahydrofuran thiophene optionally substituted with Cl or Br; or pyridine.
6. Compound of Preferred 5 wherein:
   $R^1$ is $CH_3$ or $CH_2CH_3$;
   $R^2$ is H, $CH_3$, $CH_2CH_3$ or allyl;
   $R^3$ and $R^4$ are H;
   $Y^1$ is CN, $C(O)N(CH_3)_2$, $CO_2(C_1$–$C_2$alkyl), halogen, $C_2$–$C_4$alkenyl or $C_2$–$C_4$alkynyl;
   $Y^3$ is H, $C_1$–$C_3$alkyl, CN, $CO_2(C_1$–$C_2$alkyl) or halogen.
7. Compounds of Preferred 6 wherein the compound is of Formula I.
8. Compounds of Preferred 6 wherein the compound is of Formula II.
9. Compounds of Preferred 6 wherein the compound is of Formula III.
10. Compounds of Preferred 6 wherein the compound is of Formula IV.

Compounds of the invention which are specifically preferred for their biological activity and/or ease of synthesis are the compounds of Preferred 6 and 9 which are:

(2-endo, 4-endo )-(±)-4-[(2,6-difluorophenyl)-methoxy]-5-methyl -6-oxa-bicyclo[3.2.1 ]octane-2-acetonitrile; (2-endo, 4-endo)-(±)-5-ethyl-4-[(2-fluorophenyl) -methoxy ]-6-oxabicyclo[3.2.1]octane-2-acetonitrile (2-endo, 4-endo )-(±)-5-ethyl-4-(phenylmethoxy)-6-oxabicyclo [3.2.1 ]octane-2-acetonitrile (2-endo, 4-endo)-(±)-4-[(2,6-difluorophenyl)-methoxy]-5-ethyl-6-oxabicyclo [3.2.1 ]octane-2-acetonitrile (2-endo, 4-endo)-(±)-5-ethyl-4-[(2-fluorophenyl)-methoxy]-5-methyl-6-oxabicyclo[3.2.1]octane-2 -acetonitrile;

(2-endo, 4-endo)-(±)-4-[(2-fluorophenyl)methoxy]-5-methyl-6-oxabicyclo[3.2.1]octane-2-acetonitrile;

(2-endo, 4-endo )-(±)-2-(bromomethyl)-5-methyl-4-(phenylmethoxy)-6-oxabicyclo[3.2.1]octane;

(2-endo, 4-endo)-(±)-5-ethyl-4-[(2-fluorophenyl) -methoxy]-2-(iodomethyl)-6-oxabicyclo[3.2.1]-octane;

(2-endo, 4-endo)-(±)-4-[(2-chlorophenyl)methoxy]-5-methyl-6-oxabicyclo[3.2.1]octane-2-acetonitrile;

(2-endo, 4-endo)-(±)-2-(iodomethyl)-5-methyl-4-(phenylmethoxy)-6-oxabicyclo[3.2.1]octane; and (2-endo, 4-endo)-(±)-5-ethyl-2-[(methylthio)methyl]-4-(phenylmethoxy)-6-oxabicyclo[3.2.1]octane.

Compounds of Formulae I–IV that have the QO group syn with respect to the oxygen-containing bridge are usually more herbicidally active than the anti form. The present invention contemplates all of the herbicidally active forms resulting from synthesis and from deliberately created mixtures.

Compositions comprising the above compounds suitable for controlling the growth of undesired vegetation are also contemplated as within the scope of this invention. Such compositions comprise an effective amount of any of the compounds disclosed herein and at least one of the following: surfactant, solid, or liquid diluent.

A method for controlling the growth of undesired vegetation by applying the compounds or composition of the invention to the locus to be protected is similarly considered to be within the scope of the invention. These methods comprise applying to the locus to be protected an effective amount of any of the compounds disclosed herein. Of particular importance is the method wherein the locus to be protected is corn and/or soybeans.

DETAILED DESCRIPTION OF THE INVENTION

The compounds of the invention are prepared by treating the appropriately substituted oxabicycloalkanols Ia–IVa (which are compounds of Formula I-IV as defined above wherein Q is H) with a compound of the formula Qx in which X is a halogen atom or a mesyloxy or a tosyloxy group or the like. This reaction is carried out, as shown in Scheme 1, in the presence of a strong base, such as an alkali metal hydride, in an inert solvent, such as ethers, aromatic hydrocarbons, dimethylformamide and the like. Suitable temperatures for the reaction are preferably from 20° C. to 100° C. The product ethers are recovered and isolated by conventional techniques.

Scheme 1

Ia-IVa $\xrightarrow[\text{base}]{QX}$ I-IV

The alkylating agents QX are prepared in the conventional manners known to those skilled in the art from the alcohols QOH.

The alcohols, QOH, are generally known in the art and are most conveniently prepared through metal hydride (e.g. sodium borohydride) reduction of the corresponding carbonyl compounds or the corresponding ketones which can be derived by Friedel-Crafts type cyclization of derivatives of phenylalkylcarboxylic acid, phenoxyalkylcarboxylic acids, benzyloxyalkylcarboxylic acids, phenylthioalkylcarboxylic acids, and benzylthioalkylcarboxylic acids. Details may be found in a) T. Laird in *Comprehensive Organic Chemistry*, D. Barton and W. D. Ollis, ed., Vol. 1, pp. 1165–1168, Pergamon Press, New York (1979);
b) M. H. Palmer and N. M. Scollick, *J. Chem. Soc., C.*, (1968), 2833;
c) C. E. Dolgliesck and Mann, *J. Chem. Soc.*, (1945), 893;
d) C. D. Hurd and S. Hayao, *J. Am. Chem. Soc.*, (1954), 76, 4299 and 5056; and
e) R. Lesser, *Chem. Ber.* (1923), 56, 1642.

Alternatively, the compounds of Formulas I–IV may be prepared by the coupling procedure described in Scheme 2, which is used in cases where the standard Williamson ether synthesis proves problematic. This procedure uses a Lewis acidic metal oxide wherein the metal can remove the halide ion by forming an insoluble precipitate. For example, silver (I) oxide can be used and the silver halide is the co-product. Alternative metal oxides that may be used are HgO, CaO, MgO. N,N-Dimethylformamide and ethereal solvents, such as diethyl ether, tetrahydrofuran, dioxane, or 1,2-dimethoxyethane are the preferred solvents. Other solvents likely to provide good yields include dipolar aprotic solvents like dimethyl sulfoxide, acetone, and N,N'-dimethylpro-pyleneurea.

Scheme 2

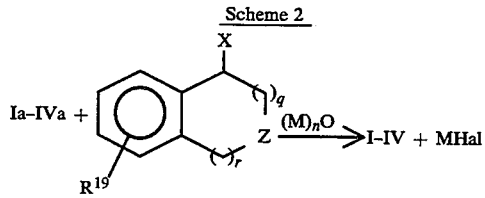

Scheme 2 (continued)

n is 1 or 2

The oxabicycloalkanols Ia–IVa can be obtained generally by one or more of the following routes:
 directly by a) epoxidation-cyclization of unsaturated cyclic alcohols, with or without isolation of the epoxy alcohol intermediates;
 indirectly by b) Dieis-Alder reactions of furans with dienophiles; or by
 c) Diels-Alder reactions of other dienes with dienophiles.

Non-limiting illustrations of the preparation of representative compounds follow.

The compounds of Formula Ia are synthesized through the sequence shown in Scheme 3. Dieis-Alder adducts are formed from readily available furans and from dienophiles including acrylate esters, acrolein, acryloylchloride, and the like (see Murai et al., *J. Chem. Soc., Chem. Comm.*, 221 (1981); and Kotsuki et al., *Bull. Chem. Soc. Jpn.* 57, 3339 (1984), and Laszlo et al., *Tet. Let.*, 25, 4387 (1984) for Dieis-Alder methodology). For example, the Dieis-Alder adduct 2 is prepared from furan 3 and acryloyl chloride. Treatment of (2) with alcohol and base at 0° to ambient temperature produces the corresponding ester. This intermediate is treated with the appropriate Grignard reagent (e.g., $R^3M$) or reducing agent (e.g., lithium aluminum hydride) as shown in Equation 3b.

Treatment with a babe (e.g., sodium hydride) and toluenesulfonyl chloride in an inert solvent, such as tetrahydrofuran, at ambient temperature to 100° C. produces 4. Tosylate 4 is treated with a metal halide (such as potassium iodide or potassium bromide), cyanide, mercaptide, a Grignard reagent, a metallo-enolate or other suitably substituted nucleophiles (generally designated Y) to produce 5. Treatment of 5 with a peroxide, such as hydrogen peroxide or m-chloroperbenzoic acid, in a suitable solvent, such as methylene chloride, yields an epoxide. This intermediate is treated with a reducing agent, such as lithium triethylborohydride or lithium aluminum hydride, to reductively open the epoxide to produce alcohol Ia, using the method of Krishnamurthy et al., *J. Amer. Chem. Soc.*, 95, 8486 (1973), as shown in Equation 3c. Alternatively, 5 can be treated to hydroboration conditions followed by oxidation with alkaline peroxide to produce Ia (for representative conditions see Takano et al., *J. Chem. Soc. Chem. Comm.*, 1371 (1989)). The synthesis indicated for Ia is where $R^3$ and $R^4$ are the same and thus there are two $R^3$ groups.

Scheme 3

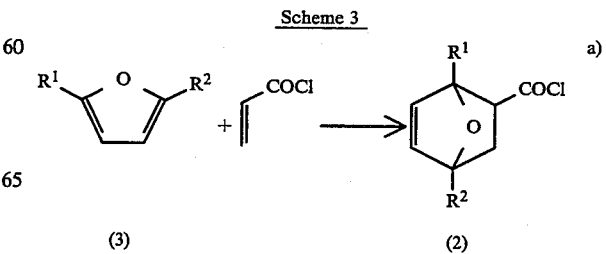

Scheme 3 -continued

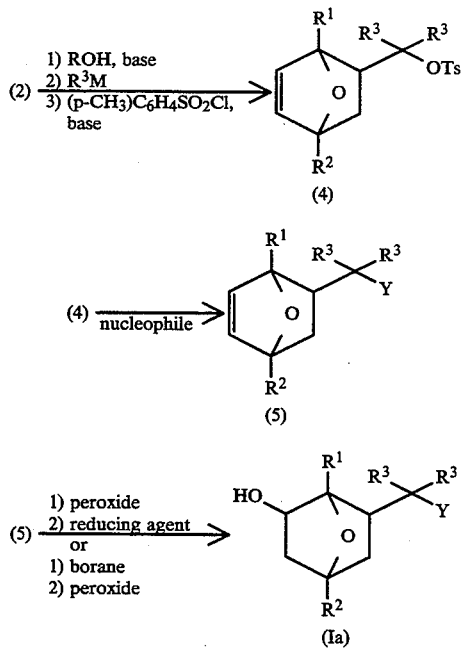

Alternatively, compounds of Formula Ia may be synthesized through the sequence shown in Scheme 4, in which groups $R^3$ and $R^4$ may be varied independently. The Dieis-Alder adducts 6 prepared from furan 3 and a vinyl carbonyl 7 are treated with the appropriate Grignard reagent (e.g., $R^4M$) or reducing reagent to produce alcohol 8. Alcohol Ia can then be prepared via the routes previously described in Equations 3b and 3c and 3d or modifications thereof.

Scheme 4

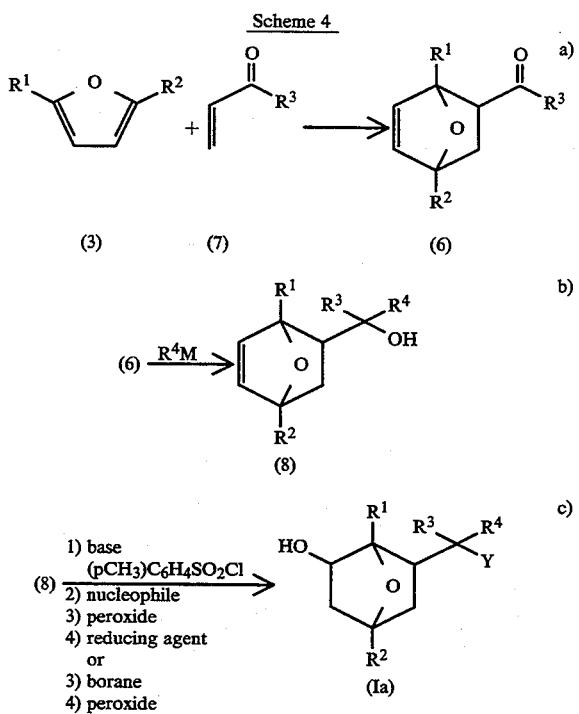

Compounds of Formula IIa can be prepared by the method described in Scheme 5 or modifications known in the art. Cyclohexene a can be prepared via a Dieis-Alder reaction using the methods of Alder et al., *Chem Ber.*, 86, 1312 (1953). Treatment of the diester a with a Grignard reagent (e.g., $R^3M$) or a reducing agent yields 15 the diol derivative 10. Treatment with toluenesulfonyl chloride and base (e.g., pyridine), followed by treatment with a nucleophile as described earlier in Equation 3c yields 11. Treatment of 11 with peroxide and acid, as taught in U.S. Pat. No. 4,542,244 yields alcohol IIa. In situations where the endo form is desired, it can be obtained by oxidation of the 2-exo-IIa to the corresponding ketone, followed by reduction of the ketone with a reducing agent, such as sodium borohydride. The synthesis of compounds IIa indicated involves $R^3$ and $R^4$ being the same, thus there appears two $R^3$ groups.

Scheme 5

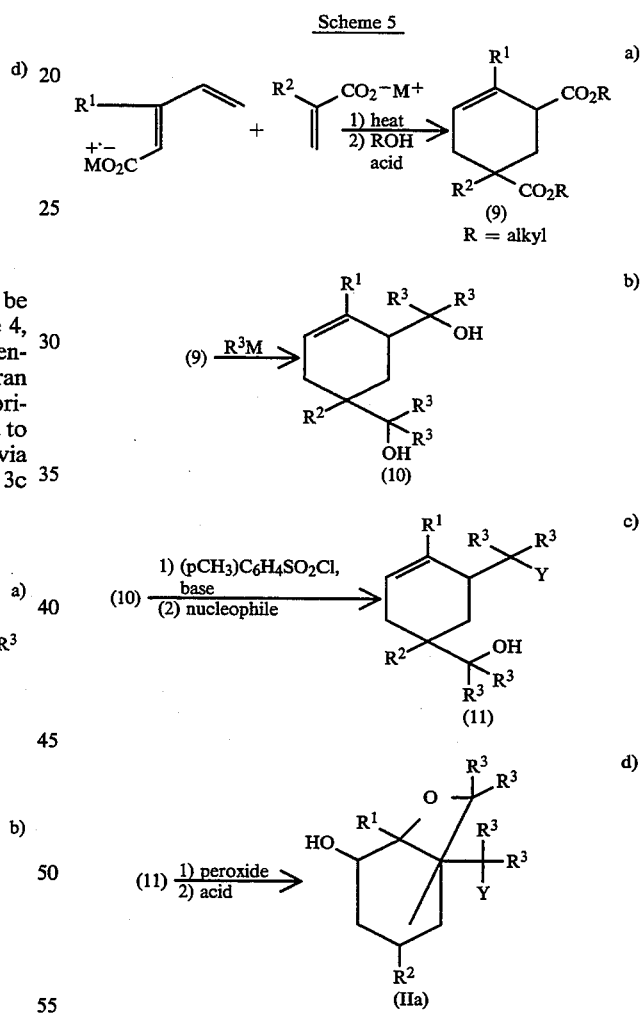

Compounds of Formula IIIa can be prepared by the method described in Scheme 6 or by modifications thereof. Cyclohexene 12 can be prepared via a Dials-Alder from readily available dienophiles, such as maleic anhydride, and a diene component, such as isoprene or butadiene, using the methods of Fieset et al. *J. Amer. Chem. Soc.*, 64, 802 (1942) or Woodward et al. *J. Amer. Chum. Soc.*, 70, 1161 (1948).

Treatment of 12 with a Grignard reagent or reducing agent yields the diol derivative. Treatment of 13 with peroxide and acid as taught in U.S. Pat. No. 4,542,244 yields 14. Diol 14 is converted to rosylate 15 using toluenesulfonyl chloride and base. Treatment with a suitable nucleophile as described in Equation 3c yields IIIa. In situations where the endo form is desired, it can be obtained by oxidation of the 2-exo-16 to the corresponding ketone, followed by reduction of the ketone with a reducing agent, such as sodium borohydride. Alternatively, rosylate 15 can also be converted to the ether by treatment with QX and a strong base, followed by treatment with a suitable nucleophile to yield IIIa. In the synthesis described $R^3$ and $R^4$ are the same, thus the presence of two $R^3$ groups is shown.

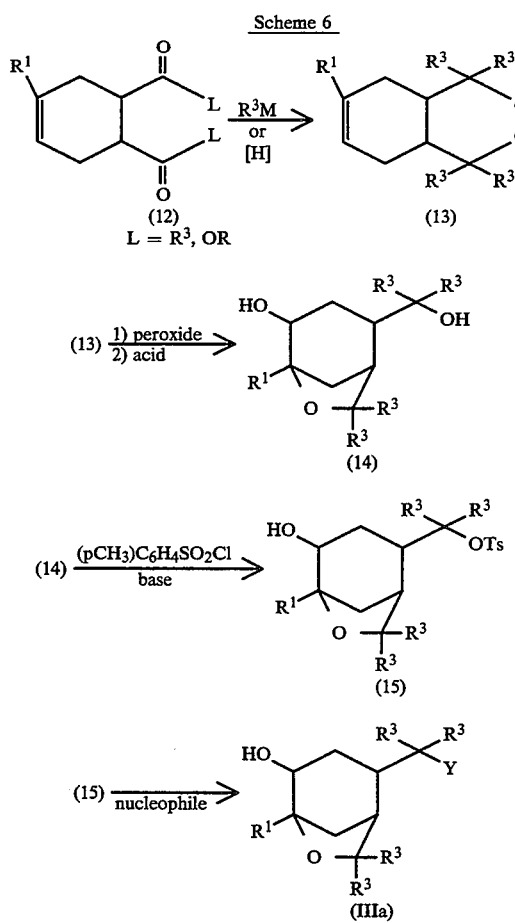

Compounds of Formula IV can be prepared by the method described in Scheme 7. Hydroxylation of 1,5-cyclooctadiene with a catalytic amount of osmium tetroxide and trimethylamine oxide as stoichiometric oxidant, adapted from a literature procedure (Ray et al., Tat. Lett., 21, 449 (1980)), followed by Williamson ether coupling reaction with appropriate alkylation agent QX, as described previously, yields ether 16. Oxidation of this alcohol using Jones reagent, as described by Heap et al., J. Chem. Soc. B., 164 (1966), yields ketone 17, which is alkylated with an appropriately substituted alkyl halide or sulfonate using an amide base $MN(R)_2$ under conditions known in the art to generate 18. Alternatively, 18 can be prepared from the alcohol resulting from the alkylation of 17 with an appropriately substituted carbonyl compound, by conversion to the corresponding tosylate and displacement with a nucleophile Y. Addition of an appropriate Grignard reagent $R^1M$ or reducing agent (such as sodium borohydride) to the carbonyl group produces alcohol 19, which is cyclized to yield the desired ether IV by means of the alkoxymercuration/demercuration sequence (Bordwell et al., J. Amer. Chem. Soc., 88, 993 (1966)).

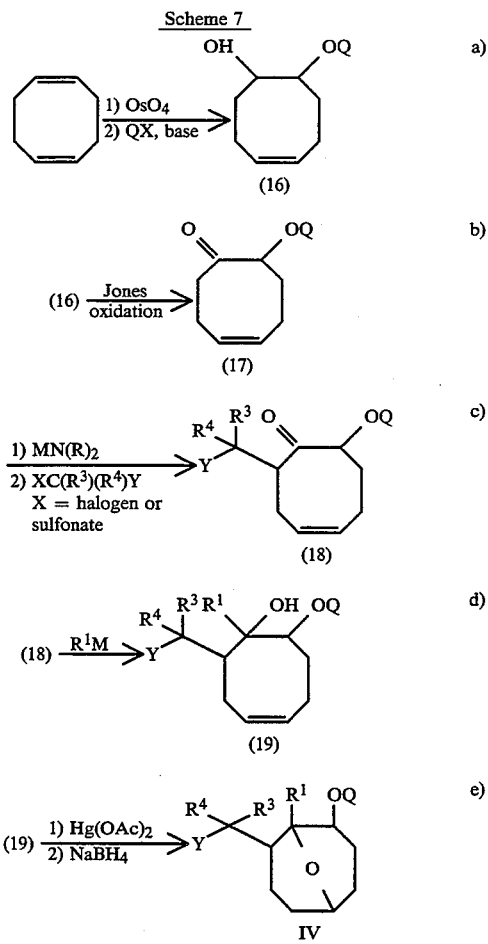

The following examples represent the preparation of typical species of the invention. The examples are for illustration and should not be regarded as limiting the invention in any way.

EXAMPLE 1

2-endo, 4-endo-(±)-5-methyl-4-phenylmethoxyl-2-(2-propenyl)-6-oxabicyclo[3.2.1]octane Step A: (±)-4-Methyl-4-cyclohexene-1,2-dicarboxylic anhydride To 50 ml (0.50 mol) of isoprene was added 25 g (0.26 mol) of maleic anhydride portionwise with cooling. The reaction mixture was stirred at ambient temperature for four hours. The excess isoprene was removed under vacuum to give 40.5 g of a white solid, m.p. 63°–65° C. NMR (CDCl$_3$): 5.70 (br s,1H), 3.45 (m, 2H), 2.50 (m, 4H), 1.81 (s,3H). IR (KBr): 2900, 1840, 1770, 1445, 1235, 965, 920, 800.

Step B: (±)-Cis-4-methyl-4-cyclohexene-1,2-dimethanol

To 300 ml of tetrahydrofuran at 0° C. was added 16.0 g (0.42 mol) lithium aluminum hydride portionwise keeping the reaction temperature between 0° C. and 5° C. A solution of 33.0 g (0.20 mol) of 4-methyl-4-cyclohexene-1,2dicarboxylic anhydride in 100 ml of tetrahydrofuran was added dropwise over 2 hours keeping the temperature between 0° C. and 10° C. The reaction mixture was warmed to ambient temperature and stirred for 2 hours. The reaction was cooled to 0° C. and 35 ml of ethyl acetate was added. dropwise, followed by dropwise addition of 35 ml isopropanol and 35 ml water. The reaction mixture was filtered through celite using acetone, dried with MgSO4, filtered, and concentrated to 33.0 g of oil. Flash chromatography in 3:1 hexanes-ethylacetate, followed by 1:1 hexanes-ethylacetate and finally ethylacetate alone yielded 18.2 g of oil. NMR (CDCl3): 5.35 (br s,1H), 3.68 (m,2H), 3.60 (m,2H), 3.10 (br s,2H), 2.05 (br s,6H), 1.64 (s,3H). IR (neat): 3500-3100, 1730w, 1440, 1010. MS (CI): 157 (M+I), 139,121.

Step C: 2-endo, 4-exo-(±)-4-hydroxy-5-methyl-6-oxabicyclo[3.2.1]octane-2-methanol To a suspension of 39.0 g (0.124 mol) of 55% m-chloroperbenzoic acid in 400 ml of methylene-chloride at 0° C. was added 19.4 g (0.124 mol) of (±)-cis-4-methyl-4-cyclohexene-1,2-dimethanol in 100 ml of methylene chloride over 15 minutes keeping the temperature less than 8° C. The reaction mixture was warmed to ambient temperature and stirred for 24 hours. The reaction was cooled to 0° C. and 30 ml of a saturated aqueous solution of Na2S2O3 was added dropwise keeping the temperature less than 8° C. The reaction mixture was dried with MgSO4, filtered, and concentrated under reduced pressure. Flash chromatography in 3:1 hexanes-ethylacetate, 1:1 hexanes-ethylacetate, then ethylacetate alone yielded 6.1 g oily solid. NMR (CDCl3): 3.80 (br d, 2H), 3.60 (br d, 1H), 3.45 (d,2H), 2.70 (br s,2H), 2.42 (br s,1H), 2.0 (m), 1.5 (m), 1.33 (s,3H). IR (neat): 3400-3200, 2900, 1450, 1380, 1060, 1000, 820. MS (CI): 173 (M+1), 213,155.

Step D: 2-endo, 4-exo-(±)-[4-hydroxy-5-methyl-6-oxabicyclo[3.2.1]-octan-2-yl) methyl 4-methylbenzenesulfonate To 14.9 g (0. 086 mol) of 2-endo-4-exo- (+)-4-hydroxy-5-methyl-6-oxabicyclo[3.2.1]octane-2-methanol in 25 ml of pyridine at 0° C. was added 18.06 g (0.095 mol) of p-toluene-sulfonylchloride portionwise keeping the temperature less than 5° C. The reaction was stirred at 0° C. for 10 minutes, then 0.97 g (0.008 mol) 4-dimethylaminopyridine was added. The reaction was warmed to ambient temperature and stirred for 6 hours. An additional 9.00 g of p-toluenesulfonyl chloride and 1.00 g of 4-dimethylamino pyridine were added and the reaction mixture was stirred for 72 hours. To the reaction was added 20 ml water. The mixture was extracted twice with ether and then twice with methylene chloride. The combined organic layers were dried, filtered, and concentrated under reduced pressure. Flash chromatography using 3:1 hexanes-ethylacetate, then 1:1 hexanes-ethylacetate yielded 21.03 g of white solid, m.p. 87°-89° C. NMR (CDCl3): 7.76 d(2H), 7.38 d(2H), 3.83 d(2H), 3.6 m(3H), 2.46 s(3H), 2.38 m(1H), 2.21 m(1H), 1.5 m, 1.30 s(3H). IR (neat): 3440 br, 2950, 2900, 1609, 1459, 1360, 1190, 1180, 1070, 1050, 960, 830, 820, 680. MS (CI): 327 (M+I), 344, 309.

Step E: 2-endo-(±)-5-methyl-2-[[[(4-methylphenyl)-sulfonyl]oxy]-methyl]-6-oxabicyclo[3.2.1]octan-4-one To 64.5 ml (0.13 mol) of 2M oxalyl chloride in methylene chloride at −78° C. was added dropwise 13.7 ml (0.19 mol) dimethyl sulfoxide in 20 ml methylene chloride. The reaction was stirred for 10 minutes, then 21.03 g (0.06 mol) of 2-endo, 4-exo(±)-[4-hydroxy-5-methyl-6-oxabicyclo[3.2.1]-octan-2-yl ]methyl 4-methyl benzenesulfonate in 50 ml methylene chloride was added dropwise to the reaction mixture. The reaction was stirred at −78° C. for 45 minutes, then 40.5 ml (0.29 mol) of triethylamine in 40 ml of methylene chloride was added dropwise. The reaction mixture was warmed to ambient temperature and stirred for 20 hours. To the reaction was added 50 ml water. The reaction was extracted with methylene chloride. The organic layer was washed with water, dried over MgSO4, filtered, and concentrated under reduced pressure. Flash chromatography in 3:1 hexanesethylacetate, followed by 1:1 hexanes-ethylacetate yielded 19.99 g of white solid, m.p. 104°-106° C. NMR (CDCl3): 7.80 d (2H), 7.37 d (2H), 3.95 m (4H), 2.62 m(1H), 2.47 s (3H), 2.4-2.0 m, 1.80 d(1H), 1.32 s (3H). IR (neat): 2950 br, 1730, 1605, 1365, 1190, 1102, 970, 950, 840, 810, 670, 560, 525. MS (CI): 342 (M+NH4+).

Step F: 2-endo, 4-endo- (±)-[4-hydroxy-5-methyl-6-oxabicyclo[3.2.1]octan-2-yl]methyl4-methylbenzene sulfonate To 19.99 g (0.06 mol) of 2-endo-(±)-5-methyl-2-[[[(4-methylphenyl)sulfonyl]oxy]-methyl]-6-oxabicyclo-[3.2.1]octan-4-one in 200 ml tetrahydrofuran at −78° C. was added 92.5 ml of 1M lithium triethylborohydride in tetrahydrofuran. An additional 5.0 ml of 1M lithium triethylborohydride was added. The reaction was warmed to ambient temperature and stirred for 20 hours. The reaction was cooled to 0° C. and 20 ml water was added dropwise. The reaction was extracted with ether twice, then with methylene chloride twice. The combined organic layers were dried over MgSO4, filtered, and concentrated under reduced pressure. Flash chromatography in 3:1 hexanes-ethylacetate, followed by 1:1 hexanesethylacetate yielded 19.2 g white solid, m.p. 132°-134° C. NMR (CDCl3): 7.8 d(2H), 7.38 d(2H), 3.82 d(2H), 3.72 dd(1H), 3.62 d(1H), 3.4 ddd(1H), 2.46 s(3H), 2.4 m(1H), 2.0-0.9 m, 1.31 s(3H). MS (CI): 344 (M+NH4+).

Step G: 2-endo, 4-endo- (±)-[5-methyl-4-(phenylmethoxy) -6-oxabicyclo[3.2.1]octan-2-yl]methyl-4-methylbenzene sulfonate To 0.65 g (0.016 mol) of hexane-washed 60% sodium hydride in tetrahydrofuran was added 5.0 g (0.015 mol) of 2-endo, 4-endo-(±)-[4-hydroxy-5-methyl-6-oxabicyclo [3.2.1]-octan-2-yl]methyl4-methylbenzene sulfonate. Benzylbromide (2.0 ml, 0.017 mol) was added and the reaction stirred at 70° C. for 24 hours. The reaction was cooled to ambient temperature, water was added, and the reaction was extracted with ether. The organic layer was dried over MgSO4, filtered, and concentrated under reduced pressure. Flash chromatography in 2:1 hexanes-ethylacetate yielded an oil. NMR (CDCl3): 7.78 d(2H), 7.3 m(7H), 4.6 d(1H), 4.41 d(1H), 3.8 d(2H), 3.7 m(2H), 3.2 dd(1H), 2.46 s(3H), 2.36 m(1H), 2.0-1.0 m MS (CI): 417 (MH+) 434.

Step H: 2-endo, 4-endo-(±)-[5-methyl-4-(phenylmethoxy) -2-(2-propenyl)-6-oxabicyclo[3.2.1]octane To 0.08 g (0.40 mmol) of copper iodide in 5 ml of tetrahydrofuran at −20° C. was added 1.16 ml (1.16 mmol) of 1M vinylmagnesiumbromide in tetrahydrofuran. After stirring for 30 minutes, 0.33 g (0.79 mmol) 2-endo, 4-endo-(+)-[5-methyl-4-(phenylmethoxy)-6-oxabicyclo[3.2.1]-octan-2-yl]methyl-4-methylbenzene sulfonate was added in 5 ml tetrahydrofuran. The reaction was warmed to ambient temperature and stirred overnight The reaction was warmed to 70° and an additional 1.7 ml of vinylmagnesium bromide was added and the reaction was stirred for 3 days. The reaction was cooled to ambient temperature and water was added. The reaction was extracted twice with ether and twice with methylene chloride. The combined organic layers were dried, filtered, and concentrated under reduced pressure. Flash chromatography in 6:1 hexanes-ethylacetate yielded an oil. NMR (CDCl$_3$): 7.34 m(5H), 5.75 m(1H), 5.00 d(2H), 4.64 m(1H), 4.45 d(1H), 3.95 m(2H), 3.2 dd(1H), 2.2 m(1H), 2.0 m(4H), 1.8 m(1H), 1.6 m(1H), 1.5 m(1H), 1.36 s(3H), 1.25 m(1H), 0.91 d(1H). MS (CI): 273 (MH+) 290, 245, 181, 165.

EXAMPLE 2

2-endo, 4-endo-(±)-4-[2-fluorophenyl }methoxy]-2-(iodomethyl)-5-methyl-6-oxabicyclo[3.2.1]octane Step A: 2-endo, 4-endo-(±)-[5-methyl-4-[(2-fluorophenyl)-methoxy)-6-oxabicyclo[3.2.1]octan-2-yl]methyl 4-methylbenzenesulfonate To 0.1 g (2.6 mmol) hexane-washed 60% sodium hydride in 10 ml tetrahydrofuran at 0° C. was added 0.5 g (1.5 mmol) 2-endo, 4-endo-(±)-[4-hydroxy-5-methyl-6-oxabicyclo) [3.2.1]octan-2-yl]methyl 4-methyl benzenesulfonate portionwise keeping the temperature at 0° C. The reaction was stirred for 10 minutes, then 0.31 ml (2.6 mmol) of 2-fluoro-benzylbromide was added. The reaction was warmed to 70° and stirred for 24 hours. The reaction was cooled to 0° and 5 ml water was added. The reaction was extracted twice with ether. The combined organic layers were dried over MgSO$_4$, filtered, and concentrated under reduced pressure. Flash chromatography in 3:1 hexanes-ethylacetate yielded 0.54 g of white solid, m.p. 63°–65°. NMR (CDCl$_3$):7.78 d(2H), 7.4–6.98 m, 4.62 d (1H), 4.49 d (1H), 3.85 d (2H), 3.69 m(2H), 3.22 dd(1H), 2.45 s(3H), 2.38 br(1H), 2.1–1.1 m, 1.32 s(3H). IR (neat): 2950, 2890, 1610, 1595, 1500, 1460, 1365, 1235, 1190, 1090, 960, 840, 820, 760, 670.

Step B: 2-endo, 4-endo-(±)-4-[(2-fluorophenyl)methoxy]-2-(iodomethyl)-5-methyl-6-oxabicyclo[3.2.1]octane To 0.32 g (0.74 mmol) of 2-endo, 4-endo-(±)-[5-methyl-4-[(2-fluorophenyl) methoxy)-6-oxabicyclo[3.2.1]-octan-2-yl]methyl 4-methylbenzene sulfonate in 5 ml acetone was added 0.22 g (1.47 mmol) sodium iodide.

The reaction was heated at 70° C. for 96 hours during which time an additional 0.2 g of sodium iodide was added. Water was added and the reaction was extracted twice with ether and once with methylene chloride. The combined organic layers were dried over MgSO$_4$, filtered, and concentrated under reduced pressure. Flash chromatography in 6:1 hexanes-ethylacetate yielded 0.24 g of white solid, m.p. 59°–61° C. NMR (CDCl$_3$): 7.4 t(1H), 7.26 m(1H), 7.1 t(1H), 7.0 t(1H), 4.7 d(1H), 4.5 d(1H), 3.79 m(2H), 3.25 dd(1H), 3.08 m(2H), 2.5 br(1H), 2.3 dt(1H), 2–1.2 m, 1.35 s(3H). IR (KBr): 3000–2880, 1592, 1500, 1465, 1365, 1350, 1280, 1235, 1130, 1112, 1090, 968, 842, 760. MS (CI): 408 (MNH$_4$+), 282.

EXAMPLE 3

2-endo, 4-endo-(±)-5-methyl-4-phenylmethoxy)-6-oxabicyclo[3.2.1]octan-2-methanethiol To 0.45 g (1.08 mmol) of 2-endo, 4-endo-(±)-[5-methyl-4-(phenylmethoxy)-6-oxabicyclo)[3.2.1]octan-2-yl]methyl 4-methyl benzenesulfonate in 10 ml N,N-dimethylformamide was added 0.09 g (1.62 mmol) sodium hydrogen sulfide. The reaction was heated to 70° C. for 24 hours. Water was added and the reaction was extracted twice with ether and twice with methylene chloride. The combined organic layers were dried over MgSO$_4$, filtered, and concentrated under reduced pressure. Flash chromatography in 6:1 hexanes-ethylacetate yielded an oil. NMR (CDCl$_3$): 7.32 m(5H), 4.62 d(1H), 4.42 d(1H), 3.8 m(2H), 3.2 m(1H), 2.8 m(1H), 2.6 m(1H), 2.4 m(2H), 2.2–1.1 m, 1.37 s(3H). MS (CI). 279 (MH+), 296, 187, 171.

EXAMPLE 4

2-endo, 4-endo-(±)-4-[(2,6-difluoronhenylmethoxyl-5-ethyl-2-(methylthiomethyl)-6-oxabicyclo[3.2.1]octane Step A: ±)-4-Ethyl-4-cyclohexene-1,2-dicarboxylic anhydride Maleic anhydride (19.6 g, 0.2 mol) and 20 g (0.24 mol) 2-ethyl-1,3-butadiene were stirred at ambient temperature for 24 hours. The excess 2-ethyl-1,3-butadiene was removed in vacuo to yield 36 g of white solid, m.p. 65°–67° C. IR (KBr): 2980–2860, 1835, 1770, 1235, 980, 930.

Step B: 2-endo, 4-exo-(±)-4-hydroxy-5-ethyl-6-oxabicyclo[3.2.1]octane-2-methanol To 16 g (0.42 mol) lithium aluminum hydride in 200 ml tetrahydrofuran at 0° C., was added 33.0 g (0.2 mol) (±)-4-ethyl-4-cyclohexene-1,2-dicarboxylic anhydride dropwise over 45 minutes keeping the temperature less than 5° C. The reaction was warmed to ambient temperature and stirred for 24 hours. The reaction was quenched at 0° C. by sequential addition of ethyl acetate, isopropanol, and water. The mixture was filtered through celite with acetone, dried over MgSO$_4$, filtered, and concentrated under reduced pressure. The resulting oil was dissolved in methylene chloride and cooled to 0° C. A solution of 33.6 g (0.1]mol) m-chloroperbenzoic acid was added keeping the temperature less than 5° C. The reaction was warmed to ambient temperature and stirred for 72 hours. A solution of saturated sodium thiosulfate was added, the mixture was dried over MgSO$_4$, filtered, and concentrated under reduced pressure. Flash chromatography in 3:1 hexanes-ethylacetate, followed by 1:1 hexanes-ethylacetate, followed by ethylacetate yielded 11.06 g of product. NMR (CDCl$_3$): 3.8 m (4H), 3.48 d (2H), 2.42 br t(1H), 2.2–1.5 m, 0.94 t(3H).

Step G: 2-endo, 4-exo-(±)-[4-hydroxy-5-ethyl-6-oxabicyclo[3.2.1]octan-2-yl]methyl 4-methylbenzene sulfonate To 11.06 g (0.06 mol) of 2-endo, 4-exo-(±)-4-hydroxy-5-ethyl-6-oxabicyclo[3.2.1]octane-2-methanol in pyridine at 0° C. was added 13.6 g (0.07 mol) p-toluenesulfonyl chloride portionwise. The reaction was stirred for 10 minutes, then a catalytic amount of dimethylaminopyridine was added. The reaction was stirred for 24 hours. Ether was added, and the reaction was washed sequentially with water, 10% HCl, and water, then dried over MgSO$_4$, filtered, and concentrated under reduced pressure. Flash chromatography in 3:1 hexanes-ethylacetate, then 1:1 hexane-ethylacetate yielded 10.5 g of product. NMR (CDCl$_3$): 7.76 d(2H), 7.33 d(2H), 3.83 d(2H), 3.63 m(3H), 2.3 m(2H), 2.45 s(3H), 1.98 d(1H), 1.7–1.4 m, 0.91 t (3H).

Step D: 2-endo, 4-exo-(±)-5-ethyl-2-[(methylthio)-methyl]-6-oxabicyclo[3.2.1]-octan-4-ol To 3.5 g (0.05 mol) sodium methylsulfide in 5 ml dimethylformamide was added 16.0 g (0.047 mol) 2,endo, 4-exo-(±)-[4-hydroxy-5-ethyl-6-oxabicyclo[3.2.1]octan-2-yl]methyl 4-methylbenzene sulfonate. The reaction was stirred at ambient temperature for 24 hours. Water was added and the reaction extracted with methylene chloride twice. The organic layer was dried over $MgSO_4$, filtered, and concentrated under reduced pressure. Flash chromatography in 4:1 hexanes-ethylacetate yielded 3.6 g oil. NMR ($CDCl_3$): 3.70 m (3H), 2.96 s (1H), 2.89 s (1H), 2.45 br(1H), 2.38 d(1H), 2.09 s(3H), 2.0 m(1H), 1.6 m(6H), 0.94 t(3H). MS (CI): 217 (MH+), 234, 199.

Step E: 2-endo-(±)-5-ethyl-2-[(methylthio)methyl]-6-oxabicyclo[3.2.1]octan-4-one Swern oxidation (using the conditions described in Example 1, Step E) with 3.6 g (0.0167 mol) 2-endo, 4-exo(±)-5-ethyl-2-[(methythio) methyl]-6-oxabicyclo-[3.2.1]octan-4-ol, 1]ml (0.022 mol) of 2M oxalylchloride in methylene chloride, 2.5 ml (0.035 mol) dimethylsulfoxide, and 9 ml (0.065 mol) triethylamine yielded 2.0 g of yellow oil after flash chromatography in 6:1 hexanes-ethylacetate. NMR ($CDCl_3$): 4.07 m (2H), 2.7 br t(1H), 2.55 dd(2H), 2.45 d(2H), 2.19 dd(1H), 2.19 m(1H), 2.1]s(3H), 1.7 m(3H), 0.94 t(3H). MS (CI): 215 (MH+), 232.

Step F: 2-endo, 4-endo-(±)-4-[(2,6-difluorophenyl)-methoxy]-5-ethyl-2-[(methylthio)methyl]-6-oxabicyclo[3.2.1]octane To 2.0 g (9.3 mmol) of 2-endo-(±)-5-ethyl-2-[(methylthio)methyl]-6-oxabicyclo[3.2.1]octan-4-one in tetrahydrofuran at −78° C. was added dropwise 15 ml (15 mmol) 1M lithium triethylborohydride in tetrahydrofuran. The reaction was warmed to ambient temperature. Water was added and the reaction was extracted twice with ether. The ether extracts were dried over $MgSO_4$, filtered, and concentrated under reduced pressure to yield an oil.

To 0.1 g (2.5 mmol) of hexane-washed 60% sodium hydride in tetrahydrofuran was added 0.22 g (1.0 mmol) of the above oil, followed by 0.25 g (1.2 mmol) 2,6-difluorobenzylbromide. The reaction was warmed to 70° C. and stirred 24 hours. Water was added and the reaction was extracted with ether. The ether extracts were dried over $MgSO_4$, filtered, and concentrated under reduced pressure. Flash chromatography in 20:1 hexanes-ethylacetate, followed by 3:1 hexanes ethylacetate yielded a solid, m.p. 62°–64° C. NMR ($CDCl_3$): 7.25 m(1H), 6.85 m (2H), 4.71 d (1H), 4.49 d (1H), 3.83 d (1H), 3.80 dd(1H), 3.35 dd(1H), 2.45 d(2H), 2.4 m(1H), 2.31 dt(1H), 2.11 s(3H), 2.0–1.2 m, 0.76 t(3H) MS (CI): 343 (MH+), 360.

EXAMPLE 5

2-endo, 4-endo-(±)-4-[(2-chloro-6-fluorophenyl)-methoxy]-5-ethyl-2-(methylthiomethyl-6-oxabicyclo-[3.2.1]octane To 0.1 g (2.5 mmol) of hexane-washed 60% sodium hydride in tetrahydrofuran was added 0.22 g (1.0 mmol) of 2-endo, 4-endo-(±)-5-ethyl-2-[(methylthio)methyl]-6-oxabicyclo[3.2.1]octan-4-ol, followed by 0.16 ml (1.25 mmol) of 2-chloro-6-fluorobenzyl chloride. The reaction was warmed to 70C and stirred for 24 hours. Water was added and the reaction was extracted with ether. The ether extracts were dried over $MgSO_4$, filtered, and concentrated under reduced pressure. Flash chromatography in 20:1 hexanes ethylacetate, followed by 3:1 hexanes-ethylacetate yielded a solid, m.p. 52°–54 C. NMR ($CDCl_3$): 7.2 m(2H), 6.98 m(1H), 4.79 dd(1H), 4.59 dd (1H), 3.82 d (1H), 3.79 dd (1H), 3.38 dd (1H), 2.47 d (1H), 2.47 m(2H), 2.40 dt(1H), 2.1]s(3H), 2.0–1.2 m, 0.74 t (3H). MS (CI): 359/361 (MH+), 376/378.

EXAMPLE 6

2-endo, 4-endo-(±)-5-ethyl-2-(iodomethyl)-4-phenyl-methoxy)-6-oxabicyclo-[3.2.1]octane To 0.17 g (4.2 mmol) hexane-washed 60% sodium hydride in tetrahydrofuran at 0° C. was added 1.2 g (3.5 mmol) (2-endo, 4-endo)-(±)-[4-hydroxy-5-methyl-6-oxabicyclo [3.2.1]octan-2-yl]methyl 4-methylbenzene sulfonate. After 30 minutes 0.5 ml (4.2 mmol) benzylbromide was added and the reaction warmed to 70° C. and stirred for 96 hours. Water (5 ml) was added and the reaction was extracted twice with ether. The ether extracts were dried over $MgSO_4$, filtered, and concentrated under reduced pressure. Flash chromatography in 6:1 hexanes-ethylacetate yielded 1.18 g oil. To 0.39 g (0.91 mmol) Of this oil was added 5 ml acetone and 0.27 g (1.81 mmol) sodium iodide. The reaction was heated at 70° C. for 48 hours, during which time an additional 0.2 g sodium iodide was added. Water was added and the reaction extracted twice with ether and once with methylene chloride. The combined organic layers were dried over $MgSO_4$, filtered and concentrated under reduced pressure. Flash chromatography in 6:1 hexanes-ethylacetate yielded 0.28 g of a solid, m.p. 75°–77C. NMR ($CDCl_3$): 7.3 m(5H), 4.63 d(1H), 4.44 d(1H), 3.78 m(2H), 3.4 dd(1H), 3.10 m(2H), 2.5 m(1H), 2.38 dt (1H), 1.9 m, 1.7 m, 1.4 d (1H), 1.25 m (1H), 0.82 t (3H). MS (CI): 387 (MH+) 404, 259.

EXAMPLE 3

2-endo; 4-endo-(±)-4-](2,4-difluorophenyl)methoxy]-5-methyl-6-oxabicyclo-3.2.1]octane-2-acetonitrile Step A: 2-endo, 4-endo-(±)-[5-methyl-4-[(2,4-difluorophenyl)methoxy]-6-oxabicyclo[3.2.1]octane-2-yl]methyl 4-methylbenzene sulfonate To 0.2 g (5.2 mmol) of hexane-washed 60% sodium hydride in 10 ml tetrahydrofuran at 0° C. was added 1.0 g (3.0 mmol) of 2-endo, 4-endo-(±)-[4-hydroxy-5-methyl-6-oxabicyclo[3.2.1]octan-2-yl]methyl 4-methylbenzene sulfonate portionwise keeping the temperature at 0° C. The reaction was stirred for 10 minutes, then 0.66 ml (5.2 mmol) 2,4-difluorobenzyl bromide was added. The reaction was warmed to 70C and stirred for 24 hours. The reaction was cooled to 0C and 5 ml water was added. The reaction was extracted twice with ether, dried over $MgSO_4$, filtered, and concentrated under reduced pressure. Flash chromatography in 3:1 hexanes: ethylacetate yielded 1.04 g solid, m.p. 63°–65° C. NMR ($CDCl_3$): 7.76 d(2H), 7.34 d(2H), 7.34 m(1H), 6.9 m(2H), 4.6 d(1H), 4.4 d(1H), 3.8 m(2H), 3.65 m(2H), 3.21 dd(1H), 2.46 s(3H), 2.39 m(1H), 2.1–1.1 m, 1.31 s (3H). IR (neat): 2950, 2890, 1630, 1610, 1510, 1370, 1280, 1250, 1180, 1100, 960, 850, 820, 670. MS (CI): 470, 298, 281.

Step B: 2-endo, 4-endo-(±)-4-[(2,4-difluorophenyl)-methoxy]-5-methyl-6-oxabicyclo[3.2.1]octane-2-acetonitrile To 0.50 g (1.2 mmol) 2-endo, 4-endo-(±)-[5-methyl-4-[(2,4-difluorophenyl)methoxy]-6-oxabicyclo[3.2.1]-octane-2-yl]methyl 4-methylbenzene sulfonate in 5 ml dimethylsulfoxide was added 0.16 g (2.4 mmol) potassium cyanide. The reaction was heated to 70C and stirred 24 hours. The reaction was cooled, water was added, and the reaction extracted twice with ether. The ether extracts were dried over MgSO4, filtered, and concentrated under reduced pressure. Flash chromatography in 20:1 hexanes-ethylacetate, then 10:1 hexanes-ethylacetate, then 6:1 hexanes-ethyl acetate yielded 0.273 g solid, m.p. 60°-62° C. NMR (CDCl3): 7.40 dd(1H), 6.91 m(2H), 4.62 d(1H), 4.45 d(1H), 3.89 dd(1H), 3.81 d(1H), 3.25 dd(1H), 2.40 br t(1H), 2.29 d(2H), 2.21 m(1H), 2.08 m(1H), 1.90 dd(1H), 1.58 d(1H), 1.35 s(3H), 1.35 m(1H). IR (KBr): 2950, 2910, 2260, 1630, 1615, 1512, 1440, 1280, 1118, 970, 865. MS (CI): 307, 290, 180.

By the general procedures described in Schemes 1–7 and Examples 1–7 or by obvious modifications thereof, the compounds of Tables 1–4 can be prepared.

TABLE 1

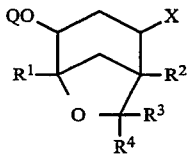

III

| Q | X | Q | X |
|---|---|---|---|
| $R^1$ is $CH_3$; $R^2 = R^3 = R^4$ is H ||||
| $CH_2(C_6H_5)$ | $CH_2CN$ | $CH_2(2\text{-pyridyl})$ | $CH_2CN$ |
| $CH_2(2\text{-}FC_6H_4)$ | $CH_2CN$ | $CH_2(2\text{-thienyl})$ | $CH_2CN$ |
| $CH_2(3\text{-}FC_6H_4)$ | $CH_2CN$ | $CH_2(2\text{-furanyl})$ | $CH_2CN$ |
| $CH_2(4\text{-}FC_6H_4)$ | $CH_2CN$ | $CH_2(2\text{-tetrahydrofuranyl})$ | $CH_2CN$ |
| $CH_2(2,4\text{-}F_2C_6H_3)$ | $CH_2CN$ | $CH_2(2\text{-tetrahydropyranyl})$ | $CH_2CN$ |
| $CH_2(2,6\text{-}F_2C_6H_4)$ | $CH_2CN$ | Q-1 | $CH_2CN$ |
| $CH_2(2,4,6\text{-}F_3C_6H_2)$ | $CH_2CN$ | Q-3 | $CH_2CN$ |
| $CH_2(2\text{-}ClC_6H_4)$ | $CH_2CN$ | Q-4 | $CH_2CN$ |
| $CH_2(3\text{-}ClC_6H_4)$ | $CH_2CN$ | Q-6 | $CH_2CN$ |
| $CH_2(4\text{-}ClC_6H_4)$ | $CH_2CN$ | Q-7 | $CH_2CN$ |
| $CH_2(2,4\text{-}Cl_2C_6H_3)$ | $CH_2CN$ | Q-8 | $CH_2CN$ |
| $CH_2(2,6\text{-}Cl_2C_6H_3)$ | $CH_2CN$ | Q-15 | $CH_2CN$ |
| $CH_2(2\text{-}(CH_3)C_6H_4)$ | $CH_2CN$ | $CH_2(2\text{-}BrC_6H_4)$ | $CH_2CN$ |
| $CH_2(3\text{-}(CH_3)C_6H_4)$ | $CH_2CN$ | $CH_2(2,6\text{-}Br_2C_6H_3)$ | $CH_2CN$ |
| $CH_2(4\text{-}(CH_3)C_6H_4)$ | $CH_2CN$ | $CH_2(2\text{-}Cl,6\text{-}FC_6H_3)$ | $CH_2CN$ |
| $CH_2(2,4,6\text{-}(CH_3)_3C_6H_2)$ | $CH_2CN$ | $CH_2(2,4,6\text{-}(CH_3)_3C_6H_2)$ | $CH_2Cl$ |
| $CH_2(2\text{-}(OCH_3)C_6H_4)$ | $CH_2CN$ | $CH_2(2\text{-}(OCH_3)C_6H_4)$ | $CH_2Cl$ |
| $CH_2(2\text{-}(CN)C_6H_4)$ | $CH_2CN$ | $CH_2(2\text{-}(CN)C_6H_4)$ | $CH_2Cl$ |
| $CH_2(2\text{-}(CF_3)C_6H_4)$ | $CH_2CN$ | $CH_2(2\text{-}(CF_3)C_6H_4)$ | $CH_2Cl$ |
| $CH_2(2\text{-}(OCF_3)C_6H_4)$ | $CH_2CN$ | $CH_2(2\text{-}(OCF_3)C_6H_4)$ | $CH_2Cl$ |
| $CH_2(2\text{-}(SCH_3)C_6H_4)$ | $CH_2CN$ | $CH_2(2\text{-}(SCH_3)C_6H_4)$ | $CH_2Cl$ |
| $CH_2(2\text{-}(CH=CH_2)C_6H_4)$ | $CH_2CN$ | $CH_2(2\text{-}(CH=CH_2)C_6H_4$ | $CH_2Cl$ |
| $CH_2(2\text{-}(C\equiv CH)C_6H_4)$ | $CH_2CN$ | $CH_2(2\text{-}(C\equiv CH)C_6H_4)$ | $CH_2Cl$ |
| $CH_2(C_6H_5)$ | $CH_2Cl$ | $CH_2(2\text{-pyridyl})$ | $CH_2Cl$ |
| $CH_2(2\text{-}FC_6H_4)$ | $CH_2Cl$ | $CH_2(2\text{-thienyl})$ | $CH_2Cl$ |
| $CH_2(3\text{-}FC_6H_4)$ | $CH_2Cl$ | $CH_2(2\text{-furanyl})$ | $CH_2Cl$ |
| $CH_2(4\text{-}FC_6H_4)$ | $CH_2Cl$ | $CH_2(2\text{-tetrahydrofuranyl})$ | $CH_2Cl$ |
| $CH_2(2,4\text{-}F_2C_6H_3)$ | $CH_2Cl$ | $CH_2(2\text{-tetrahydropyranyl})$ | $CH_2Cl$ |
| $CH_2(2,6\text{-}F_2C_6H_3)$ | $CH_2Cl$ | Q-1 | $CH_2Cl$ |
| $CH_2(2,4,6\text{-}F_3C_6H_2)$ | $CH_2Cl$ | Q-3 | $CH_2Cl$ |
| $CH_2(2\text{-}ClC_6H_4)$ | $CH_2Cl$ | Q-4 | $CH_2Cl$ |
| $CH_2(3\text{-}ClC_6H_4)$ | $CH_2Cl$ | Q-6 | $CH_2Cl$ |
| $CH_2(4\text{-}ClC_6H_4)$ | $CH_2Cl$ | Q-7 | $CH_2Cl$ |
| $CH_2(2,4\text{-}Cl_2C_6H_3)$ | $CH_2Cl$ | Q-8 | $CH_2Cl$ |
| $CH_2(2,6\text{-}Cl_2C_6H_3)$ | $CH_2Cl$ | Q-15 | $CH_2Cl$ |
| $CH_2(2\text{-}(CH_3)C_6H_4)$ | $CH_2Cl$ | $CH_2(2\text{-}BrC_6H_4)$ | $CH_2Cl$ |
| $CH_2(3\text{-}(CH_3)C_6H_4)$ | $CH_2Cl$ | $CH_2(2,6\text{-}Br_2C_6H_3)$ | $CH_2Cl$ |
| $CH_2(4\text{-}(CH_3)C_6H_4)$ | $CH_2Cl$ | $CH_2(2\text{-}Cl,6\text{-}FC_6H_3)$ | $CH_2Cl$ |
| $CH_2(C_6H_5)$ | $CH_2Br$ | $CH_2(2\text{-pyridyl})$ | $CH_2Br$ |
| $CH_2(2\text{-}FC_6H_4)$ | $CH_2Br$ | $CH_2(2\text{-thienyl})$ | $CH_2Br$ |
| $CH_2(3\text{-}FC_6H_4)$ | $CH_2Br$ | $CH_2(2\text{-furanyl})$ | $CH_2Br$ |
| $CH_2(4\text{-}FC_6H_4)$ | $CH_2Br$ | $CH_2(2\text{-tetrahydrofuranyl})$ | $CH_2Br$ |
| $CH_2(2,4\text{-}F_2C_6H_3)$ | $CH_2Br$ | $CH_2(2\text{-tetrahydropyranyl})$ | $CH_2Br$ |
| $CH_2(2,6\text{-}F_2C_6H_3)$ | $CH_2Br$ | Q-1 | $CH_2Br$ |
| $CH_2(2,4,6\text{-}F_3C_6H_2)$ | $CH_2Br$ | Q-3 | $CH_2Br$ |
| $CH_2(2\text{-}ClC_6H_4)$ | $CH_3Br$ | Q-4 | $CH_2Br$ |
| $CH_2(3\text{-}ClC_6H_4)$ | $CH_2Br$ | Q-6 | $CH_2Br$ |
| $CH_2(4\text{-}ClC_6H_4)$ | $CH_2Br$ | Q-7 | $CH_2Br$ |
| $CH_2(2,4\text{-}Cl_2C_6H_3)$ | $CH_2Br$ | Q-8 | $CH_2Br$ |
| $CH_2(2,6\text{-}Cl_2C_6H_3)$ | $CH_2Br$ | Q-15 | $CH_2Br$ |
| $CH_2(2\text{-}(CH_3)C_6H_4)$ | $CH_2Br$ | $CH_2(2\text{-}BrC_6H_4)$ | $CH_2Br$ |
| $CH_2(3\text{-}(CH_3)C_6H_4)$ | $CH_2Br$ | $CH_2(2,6\text{-}Br_2C_6H_3)$ | $CH_2Br$ |
| $CH_2(4\text{-}(CH_3)C_6H_4)$ | $CH_2Br$ | $CH_2(2\text{-}Cl,6\text{-}FC_6H_3)$ | $CH_2Br$ |
| $CH_2(2,4,6\text{-}(CH_3)_3C_6H_2)$ | $CH_2Br$ | | |
| $CH_2(2\text{-}(OCH_3)C_6H_4)$ | $CH_2Br$ | | |
| $CH_2(2\text{-}(CN)C_6H_4)$ | $CH_2Br$ | | |
| $CH_2(2\text{-}(CF_3)C_6H_4)$ | $CH_2Br$ | | |
| $CH_2(2\text{-}(OCF_3)C_6H_4)$ | $CH_2Br$ | | |
| $CH_2(2\text{-}(SCH_3)C_6H_4)$ | $CH_2Br$ | | |
| $CH_2(2\text{-}(CH=CH_2)C_6H_4)$ | $CH_2Br$ | | |

TABLE 1-continued

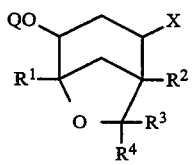

III

| Q | X | Q | X |
|---|---|---|---|
| CH$_2$(2-(C≡CH)C$_6$H$_4$) | CH$_2$Br | | |
| CH$_2$(C$_6$H$_5$) | CH$_2$I | CH$_2$(2-pyridyl) | CH$_2$I |
| CH$_2$(2-FC$_6$H$_4$) | CH$_2$I | CH$_2$(2-thienyl) | CH$_2$I |
| CH$_2$(3-FC$_6$H$_4$) | CH$_2$I | CH$_2$(2-furanyl) | CH$_2$I |
| CH$_2$(4-FC$_6$H$_4$) | CH$_2$I | CH$_2$(2-tetrahydrofuranyl) | CH$_2$I |
| CH$_2$(2,4-F$_2$C$_6$H$_3$) | CH$_2$I | CH$_2$(2-tetrahydropyranyl) | CH$_2$I |
| CH$_2$(2,6-F$_2$C$_6$H$_3$) | CH$_2$I | Q-1 | CH$_2$I |
| CH$_2$(2,4,6-F$_3$C$_6$H$_2$) | CH$_2$I | Q-3 | CH$_2$I |
| CH$_2$(2-ClC$_6$H$_4$) | CH$_2$I | Q-4 | CH$_2$I |
| CH$_2$(3-ClC$_6$H$_4$) | CH$_2$I | Q-6 | CH$_2$I |
| CH$_2$(4-ClC$_6$H$_4$) | CH$_2$I | Q-7 | CH$_2$I |
| CH$_2$(2,4-Cl$_2$C$_6$H$_3$) | CH$_2$I | Q-8 | CH$_2$I |
| CH$_2$(2,6-Cl$_2$C$_6$H$_3$) | CH$_2$I | Q-15 | CH$_2$I |
| CH$_2$(2-(CH$_3$)C$_6$H$_4$) | CH$_2$I | CH$_2$(2-BrC$_6$H$_4$) | CH$_2$I |
| CH$_2$(3-(CH$_3$)C$_6$H$_4$) | CH$_2$I | CH$_2$(2,6-Br$_2$C$_6$H$_3$) | CH$_2$I |
| CH$_2$(4-(CH$_3$)C$_6$H$_4$) | CH$_2$I | CH$_2$(2-Cl,6-FC$_6$H$_3$) | CH$_2$I |
| CH$_2$(2,4,6-(CH$_3$)$_3$C$_6$H$_2$) | CH$_2$I | | |
| CH$_2$(2-(OCH$_3$)C$_6$H$_4$) | CH$_2$I | | |
| CH$_2$(2-(CN)C$_6$H$_4$) | CH$_2$I | | |
| CH$_2$(2-(CF$_3$)C$_6$H$_4$) | CH$_2$I | | |
| CH$_2$(2-(OCF$_3$)C$_6$H$_4$) | CH$_2$I | | |
| CH$_2$(2-(SCH$_3$)C$_6$H$_4$) | CH$_2$I | | |
| CH$_2$(2-(CH=CH$_2$)C$_6$H$_4$) | CH$_2$I | | |
| CH$_2$(2-(C≡CH)C$_6$H$_4$) | CH$_2$I | | |
| CH$_2$(C$_6$H$_5$) | CH$_2$CH=CH$_2$ | CH$_2$(2-pyridyl) | CH$_2$CH=CH$_2$ |
| CH$_2$(2-FC$_6$H$_4$) | CH$_2$CH=CH$_2$ | CH$_2$(2-thienyl) | CH$_2$CH=CH$_2$ |
| CH$_2$(3-FC$_6$H$_4$) | CH$_2$CH=CH$_2$ | CH$_2$(2-furanyl) | CH$_2$CH=CH$_2$ |
| CH$_2$(4-FC$_6$H$_4$) | CH$_2$CH=CH$_2$ | CH$_2$(2-tetrahydrofuranyl) | CH$_2$CH=CH$_2$ |
| CH$_2$(2,4-F$_2$C$_6$H$_3$) | CH$_2$CH=CH$_2$ | CH$_2$(2-tetrahydropyranyl) | CH$_2$CH=CH$_2$ |
| CH$_2$(2,6-F$_2$C$_6$H$_3$) | CH$_2$CH=CH$_2$ | Q-1 | CH$_2$CH=CH$_2$ |
| CH$_2$(2,4,6-F$_3$C$_6$H$_2$) | CH$_2$CH=CH$_2$ | Q-3 | CH$_2$CH=CH$_2$ |
| CH$_2$(2-ClC$_6$H$_4$) | CH$_2$CH=CH$_2$ | Q-4 | CH$_2$CH=CH$_2$ |
| CH$_2$(3-ClC$_6$H$_4$) | CH$_2$CH=CH$_2$ | Q-6 | CH$_2$CH=CH$_2$ |
| CH$_2$(4-ClC$_6$H$_4$) | CH$_2$CH=CH$_2$ | Q-7 | CH$_2$CH=CH$_2$ |
| CH$_2$(2,4-Cl$_2$C$_6$H$_3$) | CH$_2$CH=CH$_2$ | Q-8 | CH$_2$CH=CH$_2$ |
| CH$_2$(2,6-Cl$_2$C$_6$H$_3$) | CH$_2$CH=CH$_2$ | Q-15 | CH$_2$CH=CH$_2$ |
| CH$_2$(2-(CH$_3$)C$_6$H$_4$) | CH$_2$CH=CH$_2$ | CH$_2$(2-BrC$_6$H$_4$) | CH$_2$CH=CH$_2$ |
| CH$_2$(3-(CH$_3$)C$_6$H$_4$) | CH$_2$CH=CH$_2$ | CH$_2$(2,6-Br$_2$C$_6$H$_3$) | CH$_2$CH=CH$_2$ |
| CH$_2$(4-(CH$_3$)C$_6$H$_4$) | CH$_2$CH=CH$_2$ | CH$_2$(2-Cl,6-FC$_6$H$_3$) | CH$_2$CH=CH$_2$ |
| CH$_2$(2,4,6-(CH$_3$)$_3$C$_6$H$_2$) | CH$_2$CH=CH$_2$ | | |
| CH$_2$(2-(OCH$_3$)C$_6$H$_4$) | CH$_2$CH=CH$_2$ | | |
| CH$_2$(2-(CN)C$_6$H$_4$) | CH$_2$CH=CH$_2$ | | |
| CH$_2$(2-(CF$_3$)C$_6$H$_4$) | CH$_2$CH=CH$_2$ | | |
| CH$_2$(2-(OCF$_3$)C$_6$H$_4$) | CH$_2$CH=CH$_2$ | | |
| CH$_2$(2-(SCH$_3$)C$_6$H$_4$) | CH$_2$CH=CH$_2$ | | |
| CH$_2$(2-(CH=CH$_2$)C$_6$H$_4$) | CH$_2$CH=CH$_2$ | | |
| CH$_2$(2-(C≡CH)C$_6$H$_4$) | CH$_2$CH=CH$_2$ | | |
| CH$_2$(C$_6$H$_5$) | CH$_2$SCH$_3$ | CH$_2$(2-pyridyl) | CH$_2$SCH$_3$ |
| CH$_2$(2-FC$_6$H$_4$) | CH$_2$SCH$_3$ | CH$_2$(2-thienyl) | CH$_2$SCH$_3$ |
| CH$_2$(3-FC$_6$H$_4$) | CH$_2$SCH$_3$ | CH$_2$(2-furanyl) | CH$_2$SCH$_3$ |
| CH$_2$(4-FC$_6$H$_4$) | CH$_2$SCH$_3$ | CH$_2$(2-tetrahydrofuranyl) | CH$_2$SCH$_3$ |
| CH$_2$(2,4-F$_2$C$_6$H$_3$) | CH$_2$SCH$_3$ | CH$_2$(2-tetrahydropyranyl) | CH$_2$SCH$_3$ |
| CH$_2$(2,6-F$_2$C$_6$H$_3$) | CH$_2$SCH$_3$ | Q-1 | CH$_2$SCH$_3$ |
| CH$_2$(2,4,6-F$_3$C$_6$H$_2$) | CH$_2$SCH$_3$ | Q-3 | CH$_2$SCH$_3$ |
| CH$_2$(2-ClC$_6$H$_4$) | CH$_2$SCH$_3$ | Q-4 | CH$_2$SCH$_3$ |
| CH$_2$(3-ClC$_6$H$_4$) | CH$_2$SCH$_3$ | Q-6 | CH$_2$SCH$_3$ |
| CH$_2$(4-ClC$_6$H$_4$) | CH$_2$SCH$_3$ | Q-7 | CH$_2$SCH$_3$ |
| CH$_2$(2,4-Cl$_2$C$_6$H$_3$) | CH$_2$SCH$_3$ | Q-8 | CH$_2$SCH$_3$ |
| CH$_2$(2,6-Cl$_2$C$_6$H$_3$) | CH$_2$SCH$_3$ | Q-15 | CH$_2$SCH$_3$ |
| CH$_2$(2-(CH$_3$)C$_6$H$_4$) | CH$_2$SCH$_3$ | CH$_2$(2-BrC$_6$H$_4$) | CH$_2$SCH$_3$ |
| CH$_2$(3-(CH$_3$)C$_6$H$_4$) | CH$_2$SCH$_3$ | CH$_2$(2,6-Br$_2$C$_6$H$_3$) | CH$_2$SCH$_3$ |
| CH$_2$(4-(CH$_3$)C$_6$H$_4$) | CH$_2$SCH$_3$ | CH$_2$(2-Cl,6-FC$_6$H$_3$) | CH$_2$SCH$_3$ |
| CH$_2$(2,4,6-(CH$_3$)$_3$C$_6$H$_2$) | CH$_2$SCH$_3$ | | |
| CH$_2$(2-(OCH$_3$)C$_6$H$_4$) | CH$_2$SCH$_3$ | | |
| CH$_2$(2-(CN)C$_6$H$_4$) | CH$_2$SCH$_3$ | | |
| CH$_2$(2-(CF$_3$)C$_6$H$_4$) | CH$_2$SCH$_3$ | | |
| CH$_2$(2-(OCF$_3$)C$_6$H$_4$) | CH$_2$SCH$_3$ | | |
| CH$_2$(2-(SCH$_3$)C$_6$H$_4$) | CH$_2$SCH$_3$ | | |
| CH$_2$(2-(CH=CH$_2$)C$_6$H$_4$) | CH$_2$SCH$_3$ | | |
| CH$_2$(2-(C≡CH)C$_6$H$_4$) | CH$_2$SCH$_3$ | | |
| CH$_2$(C$_6$H$_5$) | CH$_2$S(O)CH$_3$ | CH$_2$(2-pyridyl) | CH$_2$S(O)CH$_3$ |
| CH$_2$(2-FC$_6$H$_4$) | CH$_2$S(O)CH$_3$ | CH$_2$(2-thienyl) | CH$_2$S(O)CH$_3$ |

TABLE 1-continued

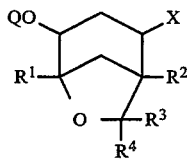

| Q | X | Q | X |
|---|---|---|---|
| CH$_2$(3-FC$_6$H$_4$) | CH$_2$S(O)CH$_3$ | CH$_2$(2-furanyl) | CH$_2$S(O)CH$_3$ |
| CH$_2$(4-FC$_6$H$_4$) | CH$_2$S(O)CH$_3$ | CH$_2$(2-tetrahydrofuranyl) | CH$_2$S(O)CH$_3$ |
| CH$_2$(2,4-F$_2$C$_6$H$_3$) | CH$_2$S(O)CH$_3$ | CH$_2$(2-tetrahydropyranyl) | CH$_2$S(O)CH$_3$ |
| CH$_2$(2,6-F$_2$C$_6$H$_3$) | CH$_2$S(O)CH$_3$ | Q-1 | CH$_2$S(O)CH$_3$ |
| CH$_2$(2,4,6-F$_3$C$_6$H$_2$) | CH$_2$S(O)CH$_3$ | Q-3 | CH$_2$S(O)CH$_3$ |
| CH$_2$(2-ClC$_6$H$_4$) | CH$_2$S(O)CH$_3$ | Q-4 | CH$_2$S(O)CH$_3$ |
| CH$_2$(3-ClC$_6$H$_4$) | CH$_2$S(O)CH$_3$ | Q-6 | CH$_2$S(O)CH$_3$ |
| CH$_2$(4-ClC$_6$H$_4$) | CH$_2$S(O)CH$_3$ | Q-7 | CH$_2$S(O)CH$_3$ |
| CH$_2$(2,4-Cl$_2$C$_6$H$_3$) | CH$_2$S(O)CH$_3$ | Q-8 | CH$_2$S(O)CH$_3$ |
| CH$_2$(2,6-Cl$_2$C$_6$H$_3$) | CH$_2$S(O)CH$_3$ | Q-15 | CH$_2$S(O)CH$_3$ |
| CH$_2$(2-(CH$_3$)C$_6$H$_4$) | CH$_2$S(O)CH$_3$ | CH$_2$(2-BrC$_6$H$_4$) | CH$_2$S(O)CH$_3$ |
| CH$_2$(3-(CH$_3$)C$_6$H$_4$) | CH$_2$S(O)CH$_3$ | CH$_2$(2,6-Br$_2$C$_6$H$_3$) | CH$_2$S(O)CH$_3$ |
| CH$_2$(4-(CH$_3$)C$_6$H$_4$) | CH$_2$S(O)CH$_3$ | CH$_2$(2-Cl,6-FC$_6$H$_3$) | CH$_2$S(O)CH$_3$ |
| CH$_2$(2,4,6-(CH$_3$)$_3$C$_6$H$_2$) | CH$_2$S(O)CH$_3$ | | |
| CH$_2$(2-(OCH$_3$)C$_6$H$_4$) | CH$_2$S(O)CH$_3$ | | |
| CH$_2$(2-(CN)C$_6$H$_4$) | CH$_2$S(O)CH$_3$ | | |
| CH$_2$(2-(CF$_3$)C$_6$H$_4$) | CH$_2$S(O)CH$_3$ | | |
| CH$_2$(2-(OCF$_3$)C$_6$H$_4$) | CH$_2$S(O)CH$_3$ | | |
| CH$_2$(2-(SCH$_3$)C$_6$H$_4$) | CH$_2$S(O)CH$_3$ | | |
| CH$_2$(2-(CH=CH$_2$)C$_6$H$_4$) | CH$_2$S(O)CH$_3$ | | |
| CH$_2$(2-(C≡CH)C$_6$H$_4$) | CH$_2$S(O)CH$_3$ | | |

R$^1$ is CH$_2$CH$_3$; R$^2$ = R$^3$ = R$^4$ is H

| Q | X | Q | X |
|---|---|---|---|
| CH$_2$(C$_6$H$_5$) | CH$_2$CN | CH$_2$(2-pyridyl) | CH$_2$CN |
| CH$_2$(2-FC$_6$H$_4$) | CH$_2$CN | CH$_2$(2-thienyl) | CH$_2$CN |
| CH$_2$(3-FC$_6$H$_4$) | CH$_2$CN | CH$_2$(2-furanyl) | CH$_2$CN |
| CH$_2$(4-FC$_6$H$_4$) | CH$_2$CN | CH$_2$(2-tetrahydrofuranyl) | CH$_2$CN |
| CH$_2$(2,4-F$_2$C$_6$H$_3$) | CH$_2$CN | CH$_2$(2-tetrahydropyranyl) | CH$_2$CN |
| CH$_2$(2,6-F$_2$C$_6$H$_3$) | CH$_2$CN | Q-1 | CH$_2$CN |
| CH$_2$(2,4,6-F$_3$C$_6$H$_2$) | CH$_2$CN | Q-3 | CH$_2$CN |
| CH$_2$(2-ClC$_6$H$_4$) | CH$_2$CN | Q-4 | CH$_2$CH |
| CH$_2$(3-ClC$_6$H$_4$) | CH$_2$CN | Q-6 | CH$_2$CN |
| CH$_2$(4-ClC$_6$H$_4$) | CH$_2$CN | Q-7 | CH$_2$CN |
| CH$_2$(2,4-Cl$_2$C$_6$H$_3$) | CH$_2$CN | Q-8 | CH$_2$CN |
| CH$_2$(2,6-Cl$_2$C$_6$H$_3$) | CH$_2$CN | Q-15 | CH$_2$CN |
| CH$_2$(2-(CH$_3$)C$_6$H$_4$) | CH$_2$CN | CH$_2$(2-BrC$_6$H$_4$) | CH$_2$CN |
| CH$_2$(3-(CH$_3$)C$_6$H$_4$) | CH$_2$CN | CH$_2$(2,6-Br$_2$C$_6$H$_3$) | CH$_2$CN |
| CH$_2$(4-(CH$_3$)C$_6$H$_4$) | CH$_2$CN | CH$_2$(2-Cl,6-FC$_6$H$_3$) | CH$_2$CN |
| CH$_2$(2,4,6-(CH$_3$)$_3$C$_6$H$_2$) | CH$_2$CN | | |
| CH$_2$(2-(OCH$_3$)C$_6$H$_4$) | CH$_2$CN | | |
| CH$_2$(2-(CN)C$_6$H$_4$) | CH$_2$CN | | |
| CH$_2$(2-(CF$_3$)C$_6$H$_4$) | CH$_2$CN | | |
| CH$_2$(2-(OCF$_3$)C$_6$H$_4$) | CH$_2$CN | | |
| CH$_2$(2-(SCH$_3$)C$_6$H$_4$) | CH$_2$CN | | |
| CH$_2$(2-(CH=CH$_2$)C$_6$H$_4$) | CH$_2$CN | | |
| CH$_2$(2-(C≡CH)C$_6$H$_4$) | CH$_2$CN | | |
| CH$_2$(C$_6$H$_5$) | CH$_2$Cl | CH$_2$(2-pyridyl) | CH$_2$Cl |
| CH$_2$(2-FC$_6$H$_4$) | CH$_2$Cl | CH$_2$(2-thienyl) | CH$_2$Cl |
| CH$_2$(3-FC$_6$H$_4$) | CH$_2$Cl | CH$_2$(2-furanyl) | CH$_2$Cl |
| CH$_2$(4-FC$_6$H$_4$) | CH$_2$Cl | CH$_2$(2-tetrahydrofuranyl) | CH$_2$Cl |
| CH$_2$(2,4-F$_2$C$_6$H$_3$) | CH$_2$Cl | CH$_2$(2-tetrahydropyranyl) | CH$_2$Cl |
| CH$_2$(2,6-F$_2$C$_6$H$_3$) | CH$_2$Cl | Q-1 | CH$_2$Cl |
| CH$_2$(2,4,6-F$_3$C$_6$H$_2$) | CH$_2$Cl | Q-3 | CH$_2$Cl |
| CH$_2$(2-ClC$_6$H$_4$) | CH$_2$Cl | Q-4 | CH$_2$Cl |
| CH$_2$(3-ClC$_6$H$_4$) | CH$_2$Cl | Q-6 | CH$_2$Cl |
| CH$_2$(4-ClC$_6$H$_4$) | CH$_2$Cl | Q-7 | CH$_2$Cl |
| CH$_2$(2,4-Cl$_2$C$_6$H$_3$) | CH$_2$Cl | Q-8 | CH$_2$Cl |
| CH$_2$(2,6-Cl$_2$C$_6$H$_3$) | CH$_2$Cl | Q-15 | CH$_2$Cl |
| CH$_2$(2-(CH$_3$)C$_6$H$_4$) | CH$_2$Cl | CH$_2$(2-BrC$_6$H$_4$) | CH$_2$Cl |
| CH$_2$(3-(CH$_3$)C$_6$H$_4$) | CH$_2$Cl | CH$_2$(2,6-Br$_2$C$_6$H$_3$) | CH$_2$Cl |
| CH$_2$(4-(CH$_3$)C$_6$H$_4$) | CH$_2$Cl | CH$_2$(2-Cl,G-FC$_6$H$_3$) | CH$_2$Cl |
| CH$_2$(2,4,6-(CH$_3$)$_3$C$_6$H$_2$) | CH$_2$Cl | | |
| CH$_2$(2-(OCH$_3$)C$_6$H$_4$) | CH$_2$Cl | | |
| CH$_2$(2-(CN)C$_6$H$_4$) | CH$_2$Cl | | |
| CH$_2$(2-(CF$_3$)C$_6$H$_4$) | CH$_2$Cl | | |
| CH$_2$(2-(OCF$_3$)C$_6$H$_4$) | CH$_2$Cl | | |
| CH$_2$(2-(SCH$_3$)C$_6$H$_4$) | CH$_2$Cl | | |
| CH$_2$(2-(CH=CH$_2$)C$_6$H$_4$) | CH$_2$Cl | | |
| CH$_2$(2-(C≡CH)C$_6$H$_4$) | CH$_2$Cl | | |
| CH$_2$(C$_6$H$_5$) | CH$_2$Br | CH$_2$(2-pyridyl) | CH$_2$Br |
| CH$_2$(2-FC$_6$H$_4$) | CH$_2$Br | CH$_2$(2-thienyl) | CH$_2$Br |
| CH$_2$(3-FC$_6$H$_4$) | CH$_2$Br | CH$_2$(2-furanyl) | CH$_2$Br |
| CH$_2$(4-FC$_6$H$_4$) | CH$_2$Br | CH$_2$(2-tetrahydrofuranyl) | CH$_2$Br |

TABLE 1-continued

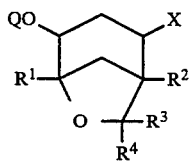

III

| Q | X | Q | X |
|---|---|---|---|
| CH$_2$(2,4-F$_2$C$_6$H$_3$) | CH$_2$Br | CH$_2$(2-tetrahydropyranyl) | CH$_2$Br |
| CH$_2$(2,6-F$_2$C$_6$H$_3$) | CH$_2$Br | Q-1 | CH$_2$Br |
| CH$_2$(2,4,6-F$_3$C$_6$H$_2$) | CH$_2$Br | Q-3 | CH$_2$Br |
| CH$_2$(2-ClC$_6$H$_4$) | CH$_2$Br | Q-4 | CH$_2$Br |
| CH$_2$(3-ClC$_6$H$_4$) | CH$_2$Br | Q-6 | CH$_2$Br |
| CH$_2$(4-ClC$_6$H$_4$) | CH$_2$Br | Q-7 | CH$_2$Br |
| CH$_2$(2,4-Cl$_2$C$_6$H$_3$) | CH$_2$Br | Q-8 | CH$_2$Br |
| CH$_2$(2,6-Cl$_2$C$_6$H$_3$) | CH$_2$Br | Q-15 | CH$_2$Br |
| CH$_2$(2-(CH$_3$)C$_6$H$_4$) | CH$_2$Br | CH$_2$(2-BrC$_6$H$_4$) | CH$_2$Br |
| CH$_2$(3-(CH$_3$)C$_6$H$_4$) | CH$_2$Br | CH$_2$(2,6-Br$_2$C$_6$H$_3$) | CH$_2$Br |
| CH$_2$(4-(CH$_3$)C$_6$H$_4$) | CH$_2$Br | CH$_2$(2-Cl,6-FC$_6$H$_3$) | CH$_2$Br |
| CH$_2$(2,4,6-(CH$_3$)$_3$C$_6$H$_2$) | CH$_2$Br | | |
| CH$_2$(2-(OCH$_3$)C$_6$H$_4$) | CH$_2$Br | | |
| CH$_2$(2-(CN)C$_6$H$_4$) | CH$_2$Br | | |
| CH$_2$(2-(CF$_3$)C$_6$H$_4$) | CH$_2$Br | | |
| CH$_2$(2-(OCF$_3$)C$_6$H$_4$) | CH$_2$Br | | |
| CH$_2$(2-(SCH$_3$)C$_6$H$_4$) | CH$_2$Br | | |
| CH$_2$(2-(CH=CH$_2$)C$_6$H$_4$) | CH$_2$Br | | |
| CH$_2$(2-(C≡CH)C$_6$H$_4$) | CH$_2$Br | | |
| CH$_2$(C$_6$H$_5$) | CH$_2$I | CH$_2$(2-pyridyl) | CH$_2$I |
| CH$_2$(2-FC$_6$H$_4$) | CH$_2$I | CH$_2$(2-thienyl) | CH$_2$I |
| CH$_2$(3-FC$_6$H$_4$) | CH$_2$I | CH$_2$(2-furanyl) | CH$_2$I |
| CH$_2$(4-FC$_6$H$_4$) | CH$_2$I | CH$_2$(2-tetrahydrofuranyl) | CH$_2$I |
| CH$_2$(2,4-F$_2$C$_6$H$_3$) | CH$_2$I | CH$_2$(2-tetrahydropyranyl) | CH$_2$I |
| CH$_2$(2,6-F$_2$C$_6$H$_3$) | CH$_2$I | Q-1 | CH$_2$I |
| CH$_2$(2,4,6-F$_3$C$_6$H$_2$) | CH$_2$I | Q-3 | CH$_2$I |
| CH$_2$(2-ClC$_6$H$_4$) | CH$_2$I | Q-4 | CH$_2$I |
| CH$_2$(3-ClC$_6$H$_4$) | CH$_2$I | Q-6 | CH$_2$I |
| CH$_2$(4-ClC$_6$H$_4$) | CH$_2$I | Q-7 | CH$_2$I |
| CH$_2$(2,4-Cl$_2$C$_6$H$_3$) | CH$_2$I | Q-8 | CH$_2$I |
| CH$_2$(2,6-Cl$_2$C$_6$H$_3$) | CH$_2$I | Q-15 | CH$_2$I |
| CH$_2$(2-(CH$_3$)C$_6$H$_4$) | CH$_2$I | CH$_2$(2-BrC$_6$H$_4$) | CH$_2$I |
| CH$_2$(3-(CH$_3$)C$_6$H$_4$) | CH$_2$I | CH$_2$(2,6-Br$_2$C$_6$H$_3$) | CH$_2$I |
| CH$_2$(4-(CH$_3$)C$_6$H$_4$) | CH$_2$I | CH$_2$(2-Cl,6-FC$_6$H$_3$) | CH$_2$I |
| CH$_2$(2,4,6-(CH$_3$)$_3$C$_6$H$_2$) | CH$_2$I | | |
| CH$_2$(2-(OCH$_3$)C$_6$H$_4$) | CH$_2$I | | |
| CH$_2$(2-(CN)C$_6$H$_4$) | CH$_2$I | | |
| CH$_2$(2-(CF$_3$)C$_6$H$_4$) | CH$_2$I | | |
| CH$_2$(2-(OCF$_3$)C$_6$H$_4$) | CH$_2$I | | |
| CH$_2$(2-(SCH$_3$)C$_6$H$_4$) | CH$_2$I | | |
| CH$_2$(2-(CH=CH$_2$)C$_6$H$_4$) | CH$_2$I | | |
| CH$_2$(2-(C≡CH)C$_6$H$_4$) | CH$_2$I | | |
| CH$_2$(C$_6$H$_5$) | CH$_2$CH=CH$_2$ | CH$_2$(2-pyridyl) | CH$_2$CH=CH$_2$ |
| CH$_2$(2-FC$_6$H$_4$) | CH$_2$CH=CH$_2$ | CH$_2$(2-thienyl) | CH$_2$CH=CH$_2$ |
| CH$_2$(3-FC$_6$H$_4$) | CH$_2$CH=CH$_2$ | CH$_2$(2-furanyl) | CH$_2$CH=CH$_2$ |
| CH$_2$(4-FC$_6$H$_4$) | CH$_2$CH=CH$_2$ | CH$_2$(2-tetrahydrofuranyl) | CH$_2$CH=CH$_2$ |
| CH$_2$(2,4-F$_2$C$_6$H$_3$) | CH$_2$CH=CH$_2$ | CH$_2$(2-tetrahydropyranyl) | CH$_2$CH=CH$_2$ |
| CH$_2$(2,6-F$_2$C$_6$H$_3$) | CH$_2$CH=CH$_2$ | Q-1 | CH$_2$CH=CH$_2$ |
| CH$_2$(2,4,6-F$_3$C$_6$H$_2$) | CH$_2$CH=CH$_2$ | Q-3 | CH$_2$CH=CH$_2$ |
| CH$_2$(2-ClC$_6$H$_4$) | CH$_2$CH=CH$_2$ | Q-4 | CH$_2$CH=CH$_2$ |
| CH$_2$(3-ClC$_6$H$_4$) | CH$_2$CH=CH$_2$ | Q-6 | CH$_2$CH=CH$_2$ |
| CH$_2$(4-ClC$_6$H$_4$) | CH$_2$CH=CH$_2$ | Q-7 | CH$_2$CH=CH$_2$ |
| CH$_2$(2,4-Cl$_2$C$_6$H$_3$) | CH$_2$CH=CH$_2$ | Q-8 | CH$_2$CH=CH$_2$ |
| CH$_2$(2,6-Cl$_2$C$_6$H$_3$) | CH$_2$CH=CH$_2$ | Q-15 | CH$_2$CH=CH$_2$ |
| CH$_2$(2-(CH$_3$)C$_6$H$_4$) | CH$_2$CH=CH$_2$ | CH$_2$(2-BrC$_6$H$_4$) | CH$_2$CH=CH$_2$ |
| CH$_2$(3-(CH$_3$)C$_6$H$_4$) | CH$_2$CH=CH$_2$ | CH$_2$(2,6-Br$_2$C$_6$H$_3$) | CH$_2$CH=CH$_2$ |
| CH$_2$(4-(CH$_3$)C$_6$H$_4$) | CH$_2$CH=CH$_2$ | CH$_2$(2-Cl,6-FC$_6$H$_3$) | CH$_2$CH=CH$_2$ |
| CH$_2$(2,4,6-(CH$_3$)$_3$C$_6$H$_2$) | CH$_2$CH=CH$_2$ | | |
| CH$_2$(2-(OCH$_3$)C$_6$H$_4$) | CH$_2$CH=CH$_2$ | | |
| CH$_2$(2-(CN)C$_6$H$_4$) | CH$_2$CH=CH$_2$ | | |
| CH$_2$(2-(CF$_3$)C$_6$H$_4$) | CH$_2$CH=CH$_2$ | | |
| CH$_2$(2-(OCF$_3$)C$_6$H$_4$) | CH$_2$CH=CH$_2$ | | |
| CH$_2$(2-(SCH$_3$)C$_6$H$_4$) | CH$_2$CH=CH$_2$ | | |
| CH$_2$(2-(CH=CH$_2$)C$_6$H$_4$) | CH$_2$CH=CH$_2$ | | |
| CH$_2$(2-(C≡CH)C$_6$H$_4$) | CH$_2$CH=CH$_2$ | | |
| CH$_2$(C$_6$H$_5$) | CH$_2$SCH$_3$ | CH$_2$(2-pyridyl) | CH$_2$SCH$_3$ |
| CH$_2$(2-FC$_6$H$_4$) | CH$_2$SCH$_3$ | CH$_2$(2-thianyl) | CH$_2$SCH$_3$ |
| CH$_2$(3-FC$_6$H$_4$) | CH$_2$SCH$_3$ | CH$_2$(2-furanyl) | CH$_2$SCH$_3$ |
| CH$_2$(4-FC$_6$H$_4$) | CH$_2$SCH$_3$ | CH$_2$(2-tetrahydrofuranyl) | CH$_2$SCH$_3$ |
| CH$_2$(2,4-F$_2$C$_6$H$_3$) | CH$_2$SCH$_3$ | CH$_2$(2-tetrahydropyranyl) | CH$_2$SCH$_3$ |
| CH$_2$(2,6-F$_2$C$_6$H$_3$) | CH$_2$SCH$_3$ | Q-1 | CH$_2$SCH$_3$ |
| CH$_2$(2,4,6-F$_3$C$_6$H$_2$) | CH$_2$SCH$_3$ | Q-3 | CH$_2$SCH$_3$ |

TABLE 1-continued

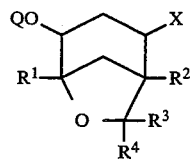

III

| Q | X | Q | X |
|---|---|---|---|
| CH₂(2-ClC₆H₄) | CH₂SCH₃ | Q-4 | CH₂SCH₃ |
| CH₂(3-ClC₆H₄) | CH₂SCH₃ | Q-6 | CH₂SCH₃ |
| CH₂(4-ClC₆H₄) | CH₂SCH₃ | Q-7 | CH₂SCH₃ |
| CH₂(2,4-Cl₂C₆H₃) | CH₂SCH₃ | Q-8 | CH₂SCH₃ |
| CH₂(2,6-Cl₂C₆H₃) | CH₂SCH₃ | Q-15 | CH₂SCH₃ |
| CH₂(2-(CH₃)C₆H₄) | CH₂SCH₃ | CH₂(2-BrC₆H₄) | CH₂SCH₃ |
| CH₂(3-(CH₃)C₆H₄) | CH₂SCH₃ | CH₂(2,6-Br₂C₆H₃) | CH₂SCH₃ |
| CH₂(4-(CH₃)C₆H₄) | CH₂SCH₃ | CH₂(2-Cl,6-FC₆H₃) | CH₂SCH₃ |
| CH₂(2,4,6-(CH₃)₃C₆H₂) | CH₂SCH₃ | | |
| CH₂(2-(OCH₃)C₆H₄) | CH₂SCH₃ | | |
| CH₂(2-(CN)C₆H₄) | CH₂SCH₃ | | |
| CH₂(2-(CF₃)C₆H₄) | CH₂SCH₃ | | |
| CH₂(2-(OCF₃)C₆H₄) | CH₂SCH₃ | | |
| CH₂(2-(SCH₃)C₆H₄) | CH₂SCH₃ | | |
| CH₂(2-(CH=CH₂)C₆H₄) | CH₂SCH₃ | | |
| CH₂(2-(C≡CH)C₆H₄) | CH₂SCH₃ | | |
| CH₂(C₆H₅) | CH₂S(O)CH₃ | CH₂(2-pyridyl) | CH₂S(O)CH₃ |
| CH₂(2-FC₆H₄) | CH₂S(O)CH₃ | CH₂(2-thienyl) | CH₂S(O)CH₃ |
| CH₂(3-FC₆H₄) | CH₂S(O)CH₃ | CH₂(2-furanyl) | CH₂S(O)CH₃ |
| CH₂(4-FC₆H₄) | CH₂S(O)CH₃ | CH₂(2-tetrahydrofuranyl) | CH₂S(O)CH₃ |
| CH₂(2,4-F₂C₆H₃) | CH₂S(O)CH₃ | CH₂(2-tetrahydropyranyl) | CH₂S(O)CH₃ |
| CH₂(2,6-F₂C₆H₃) | CH₂S(O)CH₃ | Q-1 | CH₂S(O)CH₃ |
| CH₂(2,4,6-F₃C₆H₂) | CH₂S(O)CH₃ | Q-3 | CH₂S(O)CH₃ |
| CH₂(2-ClC₆H₄) | CH₂S(O)CH₃ | Q-4 | CH₂S(O)CH₃ |
| CH₂(3-ClC₆H₄) | CH₂S(O)CH₃ | Q-6 | CH₂S(O)CH₃ |
| CH₂(4-ClC₆H₄) | CH₂S(O)CH₃ | Q-7 | CH₂S(O)CH₃ |
| CH₂(2,4-Cl₂C₆H₃) | CH₂S(O)CH₃ | Q-8 | CH₂S(O)CH₃ |
| CH₂(2,6-Cl₂C₆H₃) | CH₂S(O)CH₃ | Q-15 | CH₂S(O)CH₃ |
| CH₂(2-(CH₃)C₆H₄) | CH₂S(O)CH₃ | CH₂(2-BrC₆H₄) | CH₂S(O)CH₃ |
| CH₂(3-(CH₃)C₆H₄) | CH₂S(O)CH₃ | CH₂(2,6-Br₂C₆H₃) | CH₂S(O)CH₃ |
| CH₂(4-(CH₃)C₆H₄) | CH₂S(O)CH₃ | CH₂(2-Cl,6-FC₆H₃) | CH₂S(O)CH₃ |
| CH₂(2,4,6-(CH₃)₃C₆H₂) | CH₂S(O)CH₃ | | |
| CH₂(2-(OCH₃)C₆H₄) | CH₂S(O)CH₃ | | |
| CH₂(2-(CN)C₆H₄) | CH₂S(O)CH₃ | | |
| CH₂(2-(CF₃)C₆H₄) | CH₂S(O)CH₃ | | |
| CH₂(2-(OCF₃)C₆H₄) | CH₂S(O)CH₃ | | |
| CH₂(2-(SCH₃)C₆H₄) | CH₂S(O)CH₃ | | |
| CH₂(2-(CH=CH₂)C₆H₄) | CH₂S(O)CH₃ | | |
| CH₂(2-(C≡CH)C₆H₄) | CH₂S(O)CH₃ | | |

$R^1$ is $CH_3$; $R^2 = R^3 = R^4$ is H

| Q | X | Q | X |
|---|---|---|---|
| CH₂(C₆H₅) | CH₂C(O)N(CH₃)₂ | CH₂(C₆H₅) | CH₂CO₂CH₃ |
| CH₂(2-FC₆H₄) | CH₂C(O)N(CH₃)₂ | CH₂(2-FC₆H₄) | CH₂CO₂CH₃ |
| CH₂(2,6-F₂C₆H₃) | CH₂C(O)N(CH₃)₂ | CH₂(2,6-F₂C₆H₃) | CH₂CO₂CH₃ |
| CH₂(2-ClC₆H₄) | CH₂C(O)N(CH₃)₂ | CH₂(2-ClC₆H₄) | CH₂CO₂CH₃ |
| CH₂(2,6-Cl₂C₆H₃) | CH₂C(O)N(CH₃)₂ | CH₂(2,6-Cl₂C₆H₃) | CH₂CO₂CH₃ |
| CH₂(2-(CH₃)C₆H₄) | CH₂C(O)N(CH₃)₂ | CH₂(2-(CH₃)C₆H₄) | CH₂CO₂CH₃ |
| CH₂(2-(CN)C₆H₄) | CH₂C(O)N(CH₃)₂ | CH₂(2-(CN)C₆H₄) | CH₂CO₂CH₃ |
| CH₂(2-BrC₆H₄) | CH₂C(O)N(CH₃)₂ | CH₂(2-BrC₆H₄) | CH₂CO₂CH₃ |
| CH₂(2,6-Br₂C₆H₃) | CH₂C(O)N(CH₃)₂ | CH₂(2,6-Br₂C₆H₃) | CH₂CO₂CH₃ |
| Q-1 | CH₂C(O)N(CH₃)₂ | Q-1 | CH₂CO₂CH₃ |
| CH₂(2-Cl,6-FC₆H₃) | CH₂C(O)N(CH₃)₂ | CH₂(2-Cl,6-FC₆H₃) | CH₂CO₂CH₃ |
| CH₂(2-pyridyl) | CH₂C(O)N(CH₃)₂ | CH₂(2-pyridyl) | CH₂CO₂CH₃ |
| CH₂(C₆H₅) | CH₂C(O)N(CH₃)₂ | CH₂(C₆H₅) | CH₂CO₂CF₂CF₃ |
| CH₂(2-FC₆H₄) | CH₂C(O)N(CH₃)₂ | CH₂(2-FC₆H₄) | CH₂CO₂CF₂CF₃ |
| CH₂(2,6-F₂C₆H₃) | CH₂C(O)N(CH₃)₂ | CH₂(2,6-F₂C₆H₃) | CH₂CO₂CF₂CF₃ |
| CH₂(2-ClC₆H₄) | CH₂C(O)N(CH₃)₂ | CH₂(2-ClC₆H₄) | CH₂CO₂CF₂CF₃ |
| CH₂(2,6-Cl₂C₆H₃) | CH₂C(O)N(CH₃)₂ | CH₂(2,6-Cl₂C₆H₃) | CH₂CO₂CF₂CF₃ |
| CH₂(2-(CH₃)C₆H₄) | CH₂C(O)N(CH₃)₂ | CH₂(2-(CH₃)C₆H₄) | CH₂CO₂CF₂CF₃ |
| CH₂(2-(CN)C₆H₄) | CH₂C(O)N(CH₃)₂ | CH₂(2-(CN)C₆H₄) | CH₂CO₂CF₂CF₃ |
| CH₂(2-BrC₆H₄) | CH₂C(O)N(CH₃)₂ | CH₂(2-BrC₆H₄) | CH₂CO₂CF₂CF₃ |
| CH₂(2,6-Br₂C₆H₃) | CH₂C(O)N(CH₃)₂ | CH₂(2,6-Br₂C₆H₃) | CH₂CO₂CF₂CF₃ |
| Q-1 | CH₂C(O)N(CH₃)₂ | Q-1 | CH₂CO₂CF₂CF₃ |
| CH₂(2-Cl,6-FC₆H₃) | CH₂C(O)N(CH₃)₂ | CH₂(2-Cl,6-FC₆H₃) | CH₂CO₂CF₂CF₃ |
| CH₂(2-pyridyl) | CH₂C(O)N(CH₃)₂ | CH₂(2-pyridyl) | CH₂CO₂CF₂CF₃ |
| CH₂(C₆H₅) | CH₂CO₂CH₂CH₃ | CH₂(C₆H₅) | CH₂CHO |
| CH₂(2-FC₆H₄) | CH₂CO₂CH₂CH₃ | CH₂(2-FC₆H₄) | CH₂CHO |
| CH₂(2,6-F₂C₆H₃) | CH₂CO₂CH₂CH₃ | CH₂(2,6-F₂C₆H₃) | CH₂CHO |
| CH₂(2-ClC₆H₄) | CH₂CO₂CH₂CH₃ | CH₂(2-ClC₆H₄) | CH₂CHO |
| CH₂(2,6-Cl₂C₆H₃) | CH₂CO₂CH₂CH₃ | CH₂(2,6-Cl₂C₆H₃) | CH₂CHO |
| CH₂(2-(CH₃)C₆H₄) | CH₂CO₂CH₂CH₃ | CH₂(2-(CH₃)C₆H₄) | CH₂CHO |
| CH₂(2-(CN)C₆H₄) | CH₂CO₂CH₂CH₃ | CH₂(2-(CN)C₆H₄) | CH₂CHO |
| CH₂(2-BrC₆H₄) | CH₂CO₂CH₂CH₃ | CH₂(2-BrC₆H₄) | CH₂CHO |

TABLE 1-continued

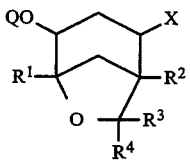

III

| Q | X | Q | X |
|---|---|---|---|
| CH$_2$(2,6-Br$_2$C$_6$H$_3$) | CH$_2$CO$_2$CH$_2$CH$_3$ | CH$_2$(2,6-Br$_2$C$_6$H$_3$) | CH$_2$CHO |
| Q-1 | CH$_2$CO$_2$CH$_2$CH$_3$ | Q-1 | CH$_2$CHO |
| CH$_2$(2-Cl,6-FC$_6$H$_3$) | CH$_2$CO$_2$CH$_2$CH$_3$ | CH$_2$(2-Cl,6-FC$_6$H$_3$) | CH$_2$CHO |
| CH$_2$(2-pyridyl) | CH$_2$CO$_2$CH$_2$CH$_3$ | CH$_2$(2-pyridyl) | CH$_2$CHO |
| CH$_2$(C$_6$H$_5$) | CH$_2$C(O)CH$_3$ | CH$_2$(C$_6$H$_5$) | CH$_2$CH=NOCH$_3$ |
| CH$_2$(2-FC$_6$H$_4$) | CH$_2$C(O)CH$_3$ | CH$_2$(2-FC$_6$H$_4$) | CH$_2$CH=NOCH$_3$ |
| CH$_2$(2,6-F$_2$C$_6$H$_3$) | CH$_2$C(O)CH$_3$ | CH$_2$(2,6-F$_2$C$_6$H$_3$) | CH$_2$CH=NOCH$_3$ |
| CH$_2$(2-ClC$_6$H$_4$) | CH$_2$C(O)CH$_3$ | CH$_2$(2-ClC$_6$H$_4$) | CH$_2$CH=NOCH$_3$ |
| CH$_2$(2,6-Cl$_2$C$_6$H$_3$) | CH$_2$C(O)CH$_3$ | CH$_2$(2,6-Cl$_2$C$_6$H$_3$) | CH$_2$CH=NOCH$_3$ |
| CH$_2$(2-(CH$_3$)C$_6$H$_4$) | CH$_2$C(O)CH$_3$ | CH$_2$(2-(CH$_3$)C$_6$H$_4$) | CH$_2$CH=NOCH$_3$ |
| CH$_2$(2-(CN)C$_6$H$_4$) | CH$_2$C(O)CH$_3$ | CH$_2$(2-(CN)C$_6$H$_4$) | CH$_2$CH=NOCH$_3$ |
| CH$_2$(2-BrC$_6$H$_4$) | CH$_2$C(O)CH$_3$ | CH$_2$(2-BrC$_6$H$_4$) | CH$_2$CH=NOCH$_3$ |
| CH$_2$(2,6-Br$_2$C$_6$H$_3$) | CH$_2$C(O)CH$_3$ | CH$_2$(2,6-Br$_2$C$_6$H$_3$) | CH$_2$CH=NOCH$_3$ |
| Q-1 | CH$_2$C(O)CH$_3$ | Q-1 | CH$_2$CH=NOCH$_3$ |
| CH$_2$(2-Cl,6-FC$_6$H$_3$) | CH$_2$C(O)CH$_3$ | CH$_2$(2-Cl,6-FC$_6$H$_3$) | CH$_2$CH=NOCH$_3$ |
| CH$_2$(2-pyridyl) | CH$_2$C(O)CH$_3$ | CH$_2$(2-pyridyl) | CH$_2$CH=NOCH$_3$ |
| CH$_2$(C$_6$H$_5$) | CH$_2$C(CH$_3$)=NOCH$_3$ | CH$_2$(C$_6$H$_5$) | CH$_2$C(Cl)=CH$_2$ |
| CH$_2$(2-FC$_6$H$_4$) | CH$_2$C(CH$_3$)=NOCH$_3$ | CH$_2$(2-FC$_6$H$_4$) | CH$_2$C(Cl)=CH$_2$ |
| CH$_2$(2,6-F$_2$C$_6$H$_3$) | CH$_2$C(CH$_3$)=NOCH$_3$ | CH$_2$(2,6-F$_2$C$_6$H$_3$) | CH$_2$C(Cl)=CH$_2$ |
| CH$_2$(2-ClC$_6$H$_4$) | CH$_2$C(CH$_3$)=NOCH$_3$ | CH$_2$(2-ClC$_6$H$_4$) | CH$_2$C(Cl)=CH$_2$ |
| CH$_2$(2,6-Cl$_2$C$_6$H$_3$) | CH$_2$C(CH$_3$)=NOCH$_3$ | CH$_2$(2,6-Cl$_2$C$_6$H$_3$) | CH$_2$C(Cl)=CH$_2$ |
| CH$_2$(2-(CH$_3$)C$_6$H$_4$) | CH$_2$C(CH$_3$)=NOCH$_3$ | CH$_2$(2-(CH$_3$)C$_6$H$_4$) | CH$_2$C(Cl)=CH$_2$ |
| CH$_2$(2-(CN)C$_6$H$_4$) | CH$_2$C(CH$_3$)=NOCH$_3$ | CH$_2$(2-(CN)C$_6$H$_4$) | CH$_2$C(Cl)=CH$_2$ |
| CH$_2$(2-BrC$_6$H$_4$) | CH$_2$C(CH$_3$)=NOCH$_3$ | CH$_2$(2-BrC$_6$H$_4$) | CH$_2$C(Cl)=CH$_2$ |
| CH$_2$(2,6-Br$_2$C$_6$H$_3$) | CH$_2$C(CH$_3$)=NOCH$_3$ | CH$_2$(2,6-Br$_2$C$_6$H$_3$) | CH$_2$C(Cl)=CH$_2$ |
| Q-1 | CH$_2$C(CH$_3$)=NOCH$_3$ | Q-1 | CH$_2$C(Cl)=CH$_2$ |
| CH$_2$(2-Cl,6-FC$_6$H$_3$) | CH$_2$C(CH$_3$)=NOCH$_3$ | CH$_2$(2-Cl,6-FC$_6$H$_3$) | CH$_2$C(Cl)=CH$_2$ |
| CH$_2$(2-pyridyl) | CH$_2$C(CH$_3$)=NOCH$_3$ | CH$_2$(2-pyridyl) | CH$_2$C(Cl)=CH$_2$ |
| CH$_2$(C$_6$H$_5$) | CH$_2$C(CH$_3$)=CH$_2$ | CH$_2$(C$_6$H$_5$) | CH$_2$C≡CH |
| CH$_2$(2-FC$_6$H$_4$) | CH$_2$C(CH$_3$)=CH$_2$ | CH$_2$(2-FC$_6$H$_4$) | CH$_2$C≡CH |
| CH$_2$(2,6-F$_2$C$_6$H$_3$) | CH$_2$C(CH$_3$)=CH$_2$ | CH$_2$(2,6-F$_2$C$_6$H$_3$) | CH$_2$C≡CH |
| CH$_2$(2-ClC$_6$H$_4$) | CH$_2$C(CH$_3$)=CH$_2$ | CH$_2$(2-ClC$_6$H$_4$) | CH$_2$C≡CH |
| CH$_2$(2,6-Cl$_2$C$_6$H$_3$) | CH$_2$C(CH$_3$)=CH$_2$ | CH$_2$(2,6-Cl$_2$C$_6$H$_3$) | CH$_2$C≡CH |
| CH$_2$(2-(CH$_3$)C$_6$H$_4$) | CH$_2$C(CH$_3$)=CH$_2$ | CH$_2$(2-(CH$_3$)C$_6$H$_4$) | CH$_2$C≡CH |
| CH$_2$(2-(CN)C$_6$H$_4$) | CH$_2$C(CH$_3$)=CH$_2$ | CH$_2$(2-(CN)C$_6$H$_4$) | CH$_2$C≡CH |
| CH$_2$(2-BrC$_6$H$_4$) | CH$_2$C(CH$_3$)=CH$_2$ | CH$_2$(2-BrC$_6$H$_4$) | CH$_2$C≡CH |
| CH$_2$(2,6-Br$_2$C$_6$H$_3$) | CH$_2$C(CH$_3$)=CH$_2$ | CH$_2$(2,6-Br$_2$C$_6$H$_3$) | CH$_2$C≡CH |
| Q-1 | CH$_2$C(CH$_3$)=CH$_2$ | Q-1 | CH$_2$C≡CH |
| CH$_2$(2-Cl,6-FC$_6$H$_3$) | CH$_2$C(CH$_3$)=CH$_2$ | CH$_2$(2-Cl,6-FC$_6$H$_3$) | CH$_2$C≡CH |
| CH$_2$(2-pyridyl) | CH$_2$C(CH$_3$)=CH$_2$ | CH$_2$(2-pyridyl) | CH$_2$C≡CH |
| CH$_2$(C$_6$H$_5$) | CH$_2$SO$_2$N(CH$_3$)$_2$ | CH$_2$(C$_6$H$_5$) | CH$_2$N$_3$ |
| CH$_2$(2-FC$_6$H$_4$) | CH$_2$SO$_2$N(CH$_3$)$_2$ | CH$_2$(2-FC$_6$H$_4$) | CH$_2$N$_3$ |
| CH$_2$(2,6-F$_2$C$_6$H$_3$) | CH$_2$SO$_2$N(CH$_3$)$_2$ | CH$_2$(2,6-F$_2$C$_6$H$_3$) | CH$_2$N$_3$ |
| CH$_2$(2-ClC$_6$H$_4$) | CH$_2$SO$_2$N(CH$_3$)$_2$ | CH$_2$(2-ClC$_6$H$_4$) | CH$_2$N$_3$ |
| CH$_2$(2,6-Cl$_2$C$_6$H$_3$) | CH$_2$SO$_2$N(CH$_3$)$_2$ | CH$_2$(2,6-Cl$_2$C$_6$H$_3$) | CH$_2$N$_3$ |
| CH$_2$(2-(CH$_3$)C$_6$H$_4$) | CH$_2$SO$_2$N(CH$_3$)$_2$ | CH$_2$(2-(CH$_3$)C$_6$H$_4$) | CH$_2$N$_3$ |
| CH$_2$(2-(CN)C$_6$H$_4$) | CH$_2$SO$_2$N(CH$_3$)$_2$ | CH$_2$(2-(CN)C$_6$H$_4$) | CH$_2$N$_3$ |
| CH$_2$(2-BrC$_6$H$_4$) | CH$_2$SO$_2$N(CH$_3$)$_2$ | CH$_2$(2-BrC$_6$H$_4$) | CH$_2$N$_3$ |
| CH$_2$(2,6-Br$_2$C$_6$H$_3$) | CH$_2$SO$_2$N(CH$_3$)$_2$ | CH$_2$(2,6-Br$_2$C$_6$H$_3$) | CH$_2$N$_3$ |
| Q-1 | CH$_2$SO$_2$N(CH$_3$)$_2$ | Q-1 | CH$_2$N$_3$ |
| CH$_2$(2-Cl,6-FC$_6$H$_3$) | CH$_2$SO$_2$N(CH$_3$)$_2$ | CH$_2$(2-Cl,6-FC$_6$H$_3$) | CH$_2$N$_3$ |
| CH$_2$(2-pyridyl) | CH$_2$SO$_2$N(CH$_3$)$_2$ | CH$_2$(2-pyridyl) | CH$_2$N$_3$ |
| CH$_2$(C$_6$H$_5$) | CH$_2$NO$_2$ | CH$_2$(C$_6$H$_5$) | CH$_2$SCN |
| CH$_2$(2-FC$_6$H$_4$) | CH$_2$NO$_2$ | CH$_2$(2-FC$_6$H$_4$) | CH$_2$SCN |
| CH$_2$(2,6-F$_2$C$_6$H$_3$) | CH$_2$NO$_2$ | CH$_2$(2,6-F$_2$C$_6$H$_3$) | CH$_2$SCN |
| CH$_2$(2-ClC$_6$H$_4$) | CH$_2$NO$_2$ | CH$_2$(2-ClC$_6$H$_4$) | CH$_2$SCN |
| CH$_2$(2,6-Cl$_2$C$_6$H$_3$) | CH$_2$NO$_2$ | CH$_2$(2,6-Cl$_2$C$_6$H$_3$) | CH$_2$SCN |
| CH$_2$(2-(CH$_3$)C$_6$H$_4$) | CH$_2$NO$_2$ | CH$_2$(2-(CH$_3$)C$_6$H$_4$) | CH$_2$SCN |
| CH$_2$(2-(CN)C$_6$H$_4$) | CH$_2$NO$_2$ | CH$_2$(2-(CN)C$_6$H$_4$) | CH$_2$SCN |
| CH$_2$(2-BrC$_6$H$_4$) | CH$_2$NO$_2$ | CH$_2$(2-BrC$_6$H$_4$) | CH$_2$SCN |
| CH$_2$(2,6-Br$_2$C$_6$H$_3$) | CH$_2$NO$_2$ | CH$_2$(2,6-Br$_2$C$_6$H$_3$) | CH$_2$SCN |
| Q-1 | CH$_2$NO$_2$ | Q-1 | CH$_2$SCN |
| CH$_2$(2-Cl,6-FC$_6$H$_3$) | CH$_2$NO$_2$ | CH$_2$(2-Cl,6-FC$_6$H$_3$) | CH$_2$SCN |
| CH$_2$(2-pyridyl) | CH$_2$NO$_2$ | CH$_2$(2-pyridyl) | CH$_2$SCN |
| CH$_2$(C$_6$H$_5$) | CH$_2$C$_6$H$_5$ | CH$_2$(C$_6$H$_5$) | CH$_2$(2-triazoyl) |
| CH$_2$(2-FC$_6$H$_4$) | CH$_2$C$_6$H$_5$ | CH$_2$(2-FC$_6$H$_4$) | CH$_2$(2-triatoyl) |
| CH$_2$(2,6-F$_2$C$_6$H$_3$) | CH$_2$C$_6$H$_5$ | CH$_2$(2,6-F$_2$C$_6$H$_3$) | CH$_2$(2-triazoyl) |
| CH$_2$(2-ClC$_6$H$_4$) | CH$_2$C$_6$H$_5$ | CH$_2$(2-ClC$_6$H$_4$) | CH$_2$(2-triazoyl) |
| CH$_2$(2,6-Cl$_2$C$_6$H$_3$) | CH$_2$C$_6$H$_5$ | CH$_2$(2,6-Cl$_2$C$_6$H$_3$) | CH$_2$(2-triazoyl) |
| CH$_2$(2-(CH$_3$)C$_6$H$_4$) | CH$_2$C$_6$H$_5$ | CH$_2$(2-(CH$_3$)C$_6$H$_4$) | CH$_2$(2-triazoyl) |
| CH$_2$(2-(CN)C$_6$H$_4$) | CH$_2$C$_6$H$_5$ | CH$_2$(2-(CN)C$_6$H$_4$) | CH$_2$(2-triazoyl) |
| CH$_2$(2-BrC$_6$H$_4$) | CH$_2$C$_6$H$_5$ | CH$_2$(2-BrC$_6$H$_4$) | CH$_2$(2-triazoyl) |

TABLE 1-continued

III

Structure: Cyclohexane with QO-, X, R¹, R², O-R³, R⁴ substituents.

| Q | X | Q | X |
|---|---|---|---|
| CH₂(2,6-Br₂C₆H₃) | CH₂C₆H₅ | CH₂(2,6-Br₂C₆H₃) | CH₂(2-triazoyl) |
| Q1 | CH₂C₆H₅ | Q-1 | CH₂(2-triazoyl) |
| CH₂(2-Cl,6-FC₆H₃) | CH₂C₆H₅ | CH₂(2-Cl,6-FC₆H₃) | CH₂(2-triazoyl) |
| CH₂(2-pyridyl) | CH₂C₆H₅ | CH₂(2-pyridyl) | CH₂(2-triazoyl) |
| CH₂(C₆H₅) | CH₂(2-imidazoyl) | CH₂(C₆H₅) | CH₂CH₂CN |
| CH₂(2-FC₆H₄) | CH₂(2-imidazoyl) | CH₂(2-FC₆H₄) | CH₂CH₂CN |
| CH₂(2,6-F₂C₆H₃) | CH₂(2-imidazoyl) | CH₂(2,6-F₂C₆H₃) | CH₂CH₂CH |
| CH₂(2-ClC₆H₄) | CH₂(2-imidazoyl) | CH₂(2-ClC₆H₄) | CH₂CH₂CN |
| CH₂(2,6-Cl₂C₆H₃) | CH₂(2-imidazoyl) | CH₂(2,6-Cl₂C₆H₃) | CH₂CH₂CN |
| CH₂(2-(CH₃)C₆H₄) | CH₂(2-imidazoyl) | CH₂(2-(CH₃)C₆H₄) | CH₂CH₂CN |
| CH₂(2-(CN)C₆H₄) | CH₂(2-imidazoyl) | CH₂(2-(CN)C₆H₄) | CH₂CH₂CN |
| CH₂(2-BrC₆H₄) | CH₂(2-imidazoyl) | CH₂(2-BrC₆H₄) | CH₂CH₂CN |
| CH₂(2,6-Br₂C₆H₃) | CH₂(2-imidazoyl) | CH₂(2,6-Br₂C₆H₃) | CH₂CH₂CN |
| Q-1 | CH₂(2-imidazoyl) | Q-1 | CH₂CH₂CN |
| CH₂(2-Cl,6-FC₆H₃) | CH₂(2-imidazoyl) | CH₂(2-Cl,6-FC₆H₃) | CH₂CH₂CN |
| CH₂(2-pyridyl) | CH₂(2-imidazoyl) | CH₂(2-pyridyl) | CH₂CH₂CN |
| CH₂(C₆H₅) | CH₂CH₂Cl | CH₂(C₆H₅) | CH₂CH₂I |
| CH₂(2-FC₆H₄) | CH₂CH₂Cl | CH₂(2-FC₆H₄) | CH₂CH₂I |
| CH₂(2,6-F₂C₆H₃) | CH₂CH₂Cl | CH₂(2,6-F₂C₆H₃) | CH₂CH₂I |
| CH₂(2-ClC₆H₄) | CH₂CH₂Cl | CH₂(2-ClC₆H₄) | CH₂CH₂I |
| CH₂(2,6-Cl₂C₆H₃) | CH₂CH₂Cl | CH₂(2,6-Cl₂C₆H₃) | CH₂CH₂I |
| CH₂(2-(CH₃)C₆H₄) | CH₂CH₂Cl | CH₂(2-(CF₃)C₆H₄) | CH₂CH₂I |
| CH₂(2-(CN)C₆H₄) | CH₂CH₂Cl | CH₂(2-(CN)C₆H₄) | CH₂CH₂I |
| CH₂(2-BrC₆H₄) | CH₂CH₂Cl | CH₂(2-BrC₆H₄) | CH₂CH₂I |
| CH₂(2,6-Br₂C₆H₃) | CH₂CH₂Cl | CH₂(2,6-Br₂C₆H₃) | CH₂CH₂I |
| Q-1 | CH₂CH₂Cl | Q-1 | CH₂CH₂I |
| CH₂(2-Cl,6-FC₆H₃) | CH₂CH₂Cl | CH₂(2-Cl,6-FC₆H₃) | CH₂CH₂I |
| CH₂(2-pyridyl) | CH₂CH₂Cl | CH₂(2-pyridyl) | CH₂CH₂I |
| CH₂(C₆H₅) | CH₂CH₂Br | CH₂(C₆H₅) | C(CH₃)₂CN |
| CH₂(2-FC₆H₄) | CH₂CH₂Br | CH₂(2-FC₆H₄) | C(CH₃)₂CH |
| CH₂(2,6-F₂C₆H₃) | CH₂CH₂Br | CH₂(2,6-F₂C₆H₃) | C(CH₃)₂CN |
| CH₂(2-ClC₆H₄) | CH₂CH₂Br | CH₂(2-ClC₆H₄) | C(CH₃)₂CN |
| CH₂(2,6-Cl₂C₆H₃) | CH₂CH₂Br | CH₂(2,6-Cl₂C₆H₃) | C(CH₃)₂CN |
| CH₂(2-(CH₃)C₆H₄) | CH₂CH₂Br | CH₂(2-(CH₃)C₆H₄) | C(CH₃)₂CN |
| CH₂(2-(CN)C₆H₄) | CH₂CH₂Br | CH₂(2-(CN)C₆H₄) | C(CH₃)₂CN |
| CH₂(2-BrC₆H₄) | CH₂CH₂Br | CH₂(2-BrC₆H₄) | C(CH₃)₂CN |
| CH₂(2,6-Br₂C₆H₃) | CH₂CH₂Br | CH₂(2,6-Br₂C₆H₃) | C(CH₃)₂CN |
| Q-1 | CH₂CH₂Br | Q-1 | C(CH₃)₂CN |
| CH₂(2-Cl,6-FC₆H₃) | CH₂CH₂Br | CH₂(2-Cl,6-FC₆H₃) | C(CH₃)₂CN |
| CH₂(2-pyridyl) | CH₂CH₂Br | CH₂(2-pyridyl) | C(CH₃)₂CN |
| CH₂(C₆H₅) | CH₂CH₃ | CH₂(C₆H₅) | CH₂CH₂CH=CH₂ |
| CH₂(2-FC₆H₄) | CH₂CH₃ | CH₂(2-FC₆H₄) | CH₂CH₂CH=CH₂ |
| CH₂(2,6-F₂C₆H₃) | CH₂CH₃ | CH₂(2,6-F₂C₆H₃) | CH₂CH₂CH=CH₂ |
| CH₂(2-ClC₆H₄) | CH₂CH₃ | CH₂(2-ClC₆H₄) | CH₂CH₂CH=CH₂ |
| CH₂(2,6-Cl₂C₆H₃) | CH₂CH₃ | CH₂(2,6-Cl₂C₆H₃) | CH₂CH₂CH=CH₂ |
| CH₂(2-(CH₃)C₆H₄) | CH₂CH₃ | CH₂(2-(CH₃)C₆H₄) | CH₂CH₂CH=CH₂ |
| CH₂(2-(CN)C₆H₄) | CH₂CH₃ | CH₂(2-(CN)C₆H₄) | CH₂CH₂CH=CH₂ |
| CH₂(2-BrC₆H₄) | CH₂CH₃ | CH₂(2-BrC₆H₄) | CH₂CH₂CH=CH₂ |
| CH₂(2,6-Br₂C₆H₃) | CH₂CH₃ | CH₂(2,6-Br₂C₆H₃) | CH₂CH₂CH=CH₂ |
| Q-1 | CH₂CH₃ | Q-1 | CH₂CH₂CH=CH₂ |
| CH₂(2-Cl,6-FC₆H₃) | CH₂CH₃ | CH₂(2-Cl,6-FC₆H₃) | CH₂CH₂CH=CH₂ |
| CH₂(2-pyridyl) | CH₂CH₃ | CH₂(2-pyridyl) | CH₂CH₂CH=CH₂ |
| CH₂(C₆H₅) | CH₃ | CH₂(C₆H₅) | CH₂CH₂CH₂CN |
| CH₂(2-FC₆H₄) | CH₃ | CH₂(2-FC₆H₄) | CH₂CH₂CH₂CN |
| CH₂(2,6-F₂C₆H₃) | CH₃ | CH₂(2,6-F₂C₆H₃) | CH₂CH₂CH₂CN |
| CH₂(2-ClC₆H₄) | CH₃ | CH₂(2-ClC₆H₄) | CH₂CH₂CH₂CN |
| CH₂(2,6-Cl₂C₆H₃) | CH₃ | CH₂(2,6-Cl₂C₆H₃) | CH₂CH₂CH₂CN |
| CH₂(2-(CH₃)C₆H₄) | CH₃ | CH₂(2-(CH₃)C₆H₄) | CH₂CH₂CH₂CN |
| CH₂(2-(CN)C₆H₄) | CH₃ | CH₂(2-(CN)C₆H₄) | CH₂CH₂CH₂CN |
| CH₂(2-BrC₆H₄) | CH₃ | CH₂(2-BrC₆H₄) | CH₂CH₂CH₂CN |
| CH₂(2,6-Br₂C₆H₃) | CH₃ | CH₂(2,6-Br₂C₆H₃) | CH₂CH₂CH₂CN |
| Q-1 | CH₃ | Q-1 | CH₂CH₂CH₂CN |
| CH₂(2-Cl,6-FC₆H₃) | CH₃ | CH₂(2-Cl,6-FC₆H₃) | CH₂CH₂CH₂CN |
| CH₂(2-pyridyl) | CH₃ | CH₂(2-pyridyl) | CH₂CH₂CH₂CN |
| CH₂(C₆H₅) | CH₂CN | CH₂(C₆H₅) | CH₂Br |
| CH₂(2-FC₆H₄) | CH₂CN | CH₂(2-FC₆H₄) | CH₂Br |
| CH₂(2,6-F₂C₆H₃) | CH₂CN | CH₂(2,6-F₂C₆H₃) | CH₂Br |
| CH₂(2-ClC₆H₄) | CH₂CN | CH₂(2-ClC₆H₄) | CH₂Br |
| CH₂(2,6-Cl₂C₆H₃) | CH₂CN | CH₂(2,6-Cl₂C₆H₃) | CH₂Br |
| CH₂(2-(CH₃)C₆H₄) | CH₂CN | CH₂(2-(CH₃)C₆H₄) | CH₂Br |
| CH₂(2-(CN)C₆H₄) | CH₂CN | CH₂(2-(CN)C₆H₄) | CH₂Br |
| CH₂(2-BrC₆H₄) | CH₂CN | CH₂(2-BrC₆H₄) | CH₂Br |

TABLE 1-continued

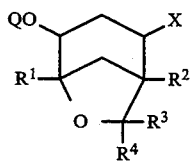

III

| Q | X | Q | X |
|---|---|---|---|
| CH$_2$(2,6-Br$_2$C$_6$H$_3$) | CH$_2$CN | CH$_2$(2,6-Br$_2$C$_6$H$_3$) | CH$_2$Br |
| Q-1 | CH$_2$CN | Q-1 | CH$_2$Br |
| CH$_2$(2-Cl,6-FC$_6$H$_3$) | CH$_2$CN | CH$_2$(2-Cl,6-FC$_6$H$_3$) | CH$_2$Br |
| CH$_2$(2-pyridyl) | CH$_2$CN | CH$_2$(2-pyridyl) | CH$_2$Br |
| CH$_2$(C$_6$H$_5$) | CH$_2$Cl | CH$_2$(C$_6$H$_5$) | CH$_2$I |
| CH$_2$(2-FC$_6$H$_4$) | CH$_2$Cl | CH$_2$(2-FC$_6$H$_4$) | CH$_2$I |
| CH$_2$(2,6-F$_2$C$_6$H$_3$) | CH$_2$Cl | CH$_2$(2,6-F$_2$C$_6$H$_3$) | CH$_2$I |
| CH$_2$(2-ClC$_6$H$_4$) | CH$_2$Cl | CH$_2$(2-ClC$_6$H$_4$) | CH$_2$I |
| CH$_2$(2,6-Cl$_2$C$_6$H$_3$) | CH$_2$Cl | CH$_2$(2,6-Cl$_2$C$_6$H$_3$) | CH$_2$I |
| CH$_2$(2-(CH$_3$)C$_6$H$_4$) | CH$_2$Cl | CH$_2$(2-(CH$_3$)C$_6$H$_4$) | CH$_2$I |
| CH$_2$(2-(CN)C$_6$H$_4$) | CH$_2$Cl | CH$_2$(2-(CN)C$_6$H$_4$) | CH$_2$I |
| CH$_2$(2-BrC$_6$H$_4$) | CH$_2$Cl | CH$_2$(2-BrC$_6$H$_4$) | CH$_2$I |
| CH$_2$(2,6-Br$_2$C$_6$H$_3$) | CH$_2$Cl | CH$_2$(2,6-Br$_2$C$_6$H$_3$) | CH$_2$I |
| Q-1 | CH$_2$Cl | Q-1 | CH$_2$I |
| CH$_2$(2-Cl,6-FC$_6$H$_3$) | CH$_2$Cl | CH$_2$(2-Cl,6-FC$_6$H$_3$) | CH$_2$I |
| CH$_2$(2-pyridyl) | CH$_2$Cl | CH$_2$(2-pyridyl) | CH$_2$I |
| | | R$^1$ is CH$_3$; R$^2$ is H; R$^3$ = R$^4$ is CH$_3$ | |
| CH$_2$(C$_6$H$_5$) | CH$_2$CN | CH$_2$(C$_6$H$_5$) | CH$_2$Cl |
| CH$_2$(2-FC$_6$H$_4$) | CH$_2$CN | CH$_2$(2-FC$_6$H$_4$) | CH$_2$Cl |
| CH$_2$(2,6-F$_2$C$_6$H$_3$) | CH$_2$CN | CH$_2$(2,6-F$_2$C$_6$H$_3$) | CH$_2$Cl |
| CH$_2$(2-ClC$_6$H$_4$) | CH$_2$CN | CH$_2$(2-ClC$_6$H$_4$) | CH$_2$Cl |
| CH$_2$(2,6-Cl$_2$C$_6$H$_3$) | CH$_2$CN | CH$_2$(2,6-Cl$_2$C$_6$H$_3$) | CH$_2$Cl |
| CH$_2$(2-(CH$_3$)C$_6$H$_4$) | CH$_2$CN | CH$_2$(2-(CH$_3$)C$_6$H$_4$) | CH$_2$Cl |
| CH$_2$(2-(CN)C$_6$H$_4$) | CH$_2$CN | CH$_2$(2-(CN)C$_6$H$_4$), | CH$_2$Cl |
| CH$_2$(2-Br$_2$C$_6$H$_4$) | CH$_2$CN | CH$_2$(2-BrC$_6$H$_4$) | CH$_2$Cl |
| CH$_2$(2,6-Br$_2$C$_6$H$_3$) | CH$_2$CN | CH$_2$(2,6-Br$_2$C$_6$H$_3$) | CH$_2$Cl |
| Q-1 | CH$_2$CN | Q-1 | CH$_2$Cl |
| CH$_2$(2-Cl,6-FC$_6$H$_3$) | CH$_2$CN | CH$_2$(2-Cl,6-FC$_6$H$_3$) | CH$_2$Cl |
| CH$_2$(2-pyridyl) | CH$_2$CN | CH$_2$(2-pyridyl) | CH$_2$Cl |
| CH$_2$(C$_6$H$_5$) | CH$_2$Br | CH$_2$(C$_6$H$_5$) | CH$_2$I |
| CH$_2$(2-FC$_6$H$_4$) | CH$_2$Br | CH$_2$(2-FC$_6$H$_4$) | CH$_2$I |
| CH$_2$(2,6-F$_2$C$_6$H$_3$) | CH$_2$Br | CH$_2$(2,6-F$_2$C$_6$H$_3$) | CH$_2$I |
| CH$_2$(2-ClC$_6$H$_4$) | CH$_2$Br | CH$_2$(2-ClC$_6$H$_4$) | CH$_2$I |
| CH$_2$(2,6-Cl$_2$C$_6$H$_3$) | CH$_2$Br | CH$_2$(2,6-Cl$_2$C$_6$R$_3$) | CH$_2$I |
| CH$_2$(2-(CH$_3$)C$_6$H$_4$) | CH$_2$Br | CH$_2$(2-(CH$_3$)C$_6$H$_4$) | CH$_2$I |
| CH$_2$(2-(CN)C$_6$H$_4$) | CH$_2$Br | CH$_2$(2-(CN)C$_6$H$_4$) | CH$_2$I |
| CH$_2$(2-BrC$_6$H$_4$) | CH$_2$Br | CH$_2$(2-BrC$_6$H$_4$) | CH$_2$I |
| CH$_2$(2,6-BrF$_2$C$_6$H$_3$) | CH$_2$Br | CH$_2$(2,6-Br$_2$C$_6$H$_3$) | CH$_2$I |
| Q-1 | CH$_2$Br | Q-1 | CH$_2$I |
| CH$_2$(2-Cl,6-FC$_6$H$_3$) | CH$_2$Br | CH$_2$(2-Cl,6-FC$_6$H$_3$) | CH$_2$I |
| CH$_2$(2-pyridyl) | CH$_2$Br | CH$_2$(2-pyridyl) | CH$_2$I |
| CH$_2$(C$_6$H$_5$) | CH$_2$-△-O | CH$_2$(C$_6$H$_5$) | CH$_2$CH=CHCO$_2$CH$_3$ |
| CH$_2$(2-FC$_6$H$_4$) | CH$_2$-△-O | CH$_2$(2-FC$_6$H$_4$) | CH$_2$CH=CHCO$_2$CH$_3$ |
| CH$_2$(2,6-F$_2$C$_6$H$_3$) | CH$_2$-△-O | CH$_2$(2,6-F$_2$C$_6$H$_3$) | CH$_2$CH=CHCO$_2$CH$_3$ |
| CH$_2$(2-ClC$_6$H$_4$) | CH$_2$-△-O | CH$_2$(2-ClC$_6$H$_4$) | CH$_2$CH=CHCO$_2$CH$_3$ |
| CH$_2$(2,6-Cl$_2$C$_6$H$_3$) | CH$_2$-△-O | CH$_2$(2,6-Cl$_2$C$_6$H$_3$) | CH$_2$CH=CHCO$_2$CH$_3$ |
| CH$_2$(2-(CH$_3$)C$_6$H$_4$) | CH$_2$-△-O | CH$_2$(2-(CH$_3$)C$_6$H$_4$) | CH$_2$CH=CHCO$_2$CH$_3$ |
| CH$_2$(2-(CN)C$_6$H$_4$) | CH$_2$-△-O | CH$_2$(2-(CN)C$_6$H$_4$) | CH$_2$CH=CHCO$_2$CH$_3$ |

TABLE 1-continued

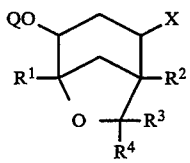

III

| Q | X | Q | X |
|---|---|---|---|
| CH₂(2-BrC₆H₄) | CH₂—△—O (CH₂-oxirane) | CH₂(2-BrC₆H₄) | CH₂CH=CHCO₂CH₃ |
| CH₂(2,6-Br₂C₆H₃) | CH₂—△—O | CH₂(2,6-Br₂C₆H₃) | CH₂CH=CHCO₂CH₃ |
| Q-1 | CH₂—△—O | Q-1 | CH₂CH=CHCO₂CH₃ |
| CH₂(2-Cl,6-FC₆H₃) | CH₂—△—O | CH₂(2-Cl,6-FC₆H₃) | CH₂CH=CHCO₂CH₃ |
| CH₂(2-pyridyl) | CH₂—△—O | CH₂(2-pyridyl) | CH₂CH=CHCO₂CH₃ |
| CH₂(C₆H₅) | CH₂CH(OCH₃)₂ | CH₂(C₆H₅) | CH₂CH=CHCN |
| CH₂(2-FC₆H₄) | CH₂CH(OCH₃)₂ | CH₂(2-FC₆H₄) | CH₂CH=CHCN |
| CH₂(2,6-F₂C₆H₃) | CH₂CH(OCH₃)₂ | CH₂(2,6-F₂C₆H₃) | CH₂CH=CHCN |
| CH₂(2-ClC₆H₄) | CH₂CH(OCH₃)₂ | CH₂(2-ClC₆H₄) | CH₂CH=CHCN |
| CH₂(2,6-Cl₂C₆H₃) | CH₂CH(OCH₃)₂ | CH₂(2,6-Cl₂C₆H₃) | CH₂CH=CHCN |
| CH₂(2-(CH₃)C₆H₄) | CH₂CH(OCH₃)₂ | CH₂(2-(CH₃)C₆H₄) | CH₂CH=CHCN |
| CH₂(2-(CN)C₆H₄) | CH₂CH(OCH₃)₂ | CH₂(2-(CN)C₆H₄) | CH₂CH=CHCN |
| CH₂(2-BrC₆H₄) | CH₂CH(OCH₃)₂ | CH₂(2-BrC₆H₄) | CH₂CH=CHCN |
| CH₂(2,6-Br₂C₆H₃) | CH₂CH(OCH₃)₂ | CH₂(2,6-Br₂C₆H₃) | CH₂CH=CHCN |
| Q-1 | CH₂CH(OCH₃)₂ | Q-1 | CH₂CH=CHCN |
| CH₂(2-Cl,6-FC₆H₃) | CH₂CH(OCH₃)₂ | CH₂(2-Cl,6-FC₆H₃) | CH₂CH=CHCN |
| CH₂(2-pyridyl) | CH₂CH(OCH₃)₂ | CH₂(2-pyridyl) | CH₂CH=CHCN |
| CH₂(C₆H₅) | CH₂CF₃ | CH₂(C₆H₅) | CH=CH(CH₃) |
| CH₂(2-FC₆H₄) | CH₂CF₃ | CH₂(2-FC₆H₄) | CH=CH(CH₃) |
| CH₂(2,6-F₂C₆H₃) | CH₂CF₃ | CH₂(2,6-F₂C₆H₃) | CH=CH(CH₃) |
| CH₂(2-ClC₆H₄) | CH₂CF₃ | CH₂(2-ClC₆H₄) | CH=CH(CH₃) |
| CH₂(2,6-Cl₂C₆H₃) | CH₂CF₃ | CH₂(2,6-Cl₂C₆H₃) | CH=CH(CH₃) |
| CH₂(2-(CH₃)C₆H₄) | CH₂CF₃ | CH₂(2-(CH₃)C₆H₄) | CH=CH(CH₃) |
| CH₂(2-(CN)C₆H₄) | CH₂CF₃ | CH₂(2-(CN)C₆H₄) | CH=CH(CH₃) |
| CH₂(2-BrC₆H₄) | CH₂CF₃ | CH₂(2-BrC₆H₄) | CH=CH(CH₃) |
| CH₂(2,6-Br₂C₆H₃) | CH₂CF₃ | CH₂(2,6-Br₂C₆H₃) | CH=CH(CH₃) |
| Q-1 | CH₂CF₃ | Q-1 | CH=CH(CH₃) |
| CH₂(2-Cl,6-FC₆H₃) | CH₂CF₃ | CH₂(2-Cl,6-FC₆H₃) | CH=CH(CH₃) |
| CH₂(2-pyridyl) | CH₂CF₃ | CH₂(2-pyridyl) | CH=CH(CH₃) |
| CH₂(C₆H₅) | CH=CH₂ | CH₂(C₆H₅) | CH=CH(CO₂CH₃) |
| CH₂(2-FC₆H₄) | CH=CH₂ | CH₂(2-FC₆H₄) | CH=CH(CO₂CH₃) |
| CH₂(2,6-F₂C₆H₃) | CH=CH₂ | CH₂(2,6-F₂C₆H₃) | CH=CH(CO₂CH₃) |
| CH₂(2-ClC₆H₄) | CH=CH₂ | CH₂(2-ClC₆H₄) | CH=CH(CO₂CH₃) |
| CH₂(2,6-Cl₂C₆H₃) | CH=CH₂ | CH₂(2,6-Cl₂C₆H₃) | CH=CH(CO₂CH₃) |
| CH₂(2-(CH₃)C₆H₄) | CH=CH₂ | CH₂(2-(CH₃)C₆H₄) | CH=CH(CO₂CH₃) |
| CH₂(2-(CN)C₆H₄) | CH=CH₂ | CH₂(2-(CN)C₆H₄) | CH=CH(CO₂CH₃) |
| CH₂(2-BrC₆H₄) | CH=CH₂ | CH₂(2-BrC₆H₄) | CH=CH(CO₂CH₃) |
| CH₂(2,6-Br₂C₆H₃) | CH=CH₂ | CH₂(2,6-Br₂C₆H₃) | CH=CH(CO₂CH₃) |
| Q-1 | CH=CH₂ | Q-1 | CH=CH(CO₂CH₃) |
| CH₂(2-Cl,6-FC₆H₃) | CH=CH₂ | CH₂(2-Cl,6-FC₆H₃) | CH=CH(CO₂CH₃) |
| CH₂(2-pyridyl) | CH=CH₂ | CH₂(2-pyridyl) | CH=CH(CO₂CH₃) |
| | R¹ is CH₃; R² is H; R³ = R⁴ is H | | R¹ is Et; R² is H; R³ = R⁴ is H |
| CH₂(C₆H₅) | CH=CHC(O)CH₃ | CH₂(C₆H₅) | CH₂N₃ |
| CH₂(2-FC₆H₄) | CH=CHC(O)CH₃ | CH₂(2-FC₆H₄) | CH₂N₃ |
| CH₂(2,6-F₂C₆H₃) | CH=CHC(O)CH₃ | CH₂(2,6-F₂C₆H₃) | CH₂N₃ |
| CH₂(2-ClC₆H₄) | CH=CHC(O)CH₃ | CH₂(2-ClC₆H₄) | CH₂N₃ |
| CH₂(2,6-Cl₂C₆H₃) | CH=CHC(O)CH₃ | CH₂(2,6-Cl₂C₆H₃) | CH₂N₃ |
| CH₂(2-(CH₃)C₆H₄) | CH=CHC(O)CH₃ | CH₂(2-(CH₃)C₆H₄) | CH₂N₃ |
| CH₂(2-(CN)C₆H₄) | CH=CHC(O)CH₃ | CH₂(2-(CN)C₆H₄) | CH₂N₃ |
| CH₂(2-BrC₆H₄) | CH=CHC(O)CH₃ | CH₂(2,6-Br₂C₆H₃) | CH₂N₃ |
| CH₂(2,6-Br₂C₆H₃) | CH=CHC(O)CH₃ | Q-1 | CH₂N₃ |
| Q-1 | CH=CHC(O)CH₃ | CH₂(2-Cl,6-FC₆H₃) | CH₂N₃ |
| CH₂(2-Cl,6-FC₆H₃) | CH=CHC(O)CH₃ | CH₂(2-pyridyl) | CH₂N₃ |

TABLE 1-continued

III

Structure: cyclohexane ring with QO at one position, X at adjacent position, R¹ and R² on ring, and an O-C(R³)(R⁴) bridge forming a fused ring.

| Q | X | Q | X |
|---|---|---|---|
| CH₂(2-pyridyl) | CH=CHC(O)CH₃ | CH₂(C₆H₅) | CH=CH₂ |
| | R¹ is Et; R² is H; R³ = R⁴ is H | CH₂(2-FC₆H₄) | CH=CH₂ |
| | | CH₂(2,6-F₂C₆H₃) | CH=CH₂ |
| CH₂(C₆H₅) | CH₃ | CH₂(2-ClC₆H₄) | CH=CH₂ |
| CH₂(2-FC₆H₄) | CH₃ | CH₂(2,6-Cl₂C₆H₃) | CH=CH₂ |
| CH₂(2,6-F₂C₆H₃) | CH₃ | CH₂(2-(CH₃)C₆H₄) | CH=CH₂ |
| CH₂(2-ClC₆H₄) | CH₃ | CH₂(2-(CN)C₆H₄) | CH=CH₂ |
| CH₂(2,6-Cl₂C₆H₃) | CH₃ | CH₂(2-BrC₆H₄) | CH=CH₂ |
| CH₂(2-(CH₃)C₆H₄) | CH₃ | CH₂(2,6-Br₂C₆H₃) | CH=CH₂ |
| CH₂(2-(CN)C₆H₄) | CH₃ | Q-1 | CH=CH₂ |
| CH₂(2-BrC₆H₄) | CH₃ | CH₂(2-Cl,6-FC₆H₃) | CH=CH₂ |
| CH₂(2,6-Br₂C₆H₃) | CH₃ | CH₂(2-pyridyl) | CH=CH₂ |
| Q-1 | CH₃ | | |
| CH₂(2-Cl,6-FC₆H₃) | CH₃ | | |
| CH₂(2-pyridyl) | CH₃ | | |
| CH₂(C₆H₅) | CH=CH(CO₂Me) | | |
| CH₂(2-FC₆H₄) | CH=CH(CO₂Me) | | |
| CH₂(2,6-F₂C₆H₃) | CH=CH(CO₂Me) | | |
| CH₂(2-ClC₆H₄) | CH=CH(CO₂Me) | | |
| CH₂(2,6-Cl₂C₆H₃) | CH=CH(CO₂Me) | | |
| CH₂(2-(CH₃)C₆H₄) | CH=CH(CO₂Me) | | |
| CH₂(2-(CN)C₆H₄) | CH=CH(CO₂Me) | | |
| CH₂(2-BrC₆H₄) | CH=CH(CO₂Me) | | |
| CH₂(2,6-Br₂C₆H₃) | CH=CH(CO₂Me) | | |
| Q-1 | CH=CH(CO₂Me) | | |
| CH₂(2-Cl,6-FC₆H₃) | CH=CH(CO₂Me) | | |
| CH₂(2-pyridyl) | CH=CH(CO₂Et) | | |

TABLE 2

I

Structure: cyclohexane ring with QO, X, R¹, R² substituents and an O bridge.

R¹ is CH₃; R² is CH₃

| Q | X | Q | X |
|---|---|---|---|
| CH₂(C₆H₅) | CH₂CN | CH₂(2-pyridyl) | CH₂CN |
| CH₂(2-FC₆H₄) | CH₂CN | CH₂(2-thienyl) | CH₂CN |
| CH₂(3-FC₆H₄) | CH₂CN | CH₂(2-furanyl) | CH₂CN |
| CH₂(4-FC₆H₄) | CH₂CN | CH₂(2-tetrahydrofuranyl) | CH₂CN |
| CH₂(2,4-F₂C₆H₃) | CH₂CN | CH₂(2-tetrahydropyranyl) | CH₂CN |
| CH₂(2,6-F₂C₆H₃) | CH₂CN | Q-1 | CH₂CN |
| CH₂(2,4,6-F₃C₆H₂) | CH₂CN | Q-3 | CH₂CN |
| CH₂(2-ClC₆H₄) | CH₂CN | Q-4 | CH₂CN |
| CH₂(3-ClC₆H₄) | CH₂CN | Q-6 | CH₂CN |
| CH₂(4-ClC₆H₄) | CH₂CN | Q-7 | CH₂CN |
| CH₂(2,4-Cl₂C₆H₃) | CH₂CN | Q-8 | CH₂CN |
| CH₂(2,6-Cl₂C₆H₃) | CH₂CN | Q-15 | CH₂CN |
| CH₂(2-(CH₃)C₆H₄) | CH₂CN | CH₂(2-BrC₆H₄) | CH₂CN |
| CH₂(3-(CH₃)C₆H₄) | CH₂CN | CH₂(2,6-Br₂C₆H₃) | CH₂CN |
| CH₂(4-(CH₃)C₆H₄) | CH₂CN | CH₂(2-Cl,6-FC₆H₃) | CH₂CN |
| CH₂(2,4,6-(CH₃)₃C₆H₂) | CH₂CN | | |
| CH₂(2-(OCH₃)C₆H₄) | CH₂CN | CH₂(C₆H₅) | CH₂S(O)CH₃ |
| CH₂(2-(CN)C₆H₄) | CH₂CN | CH₂(2-FC₆H₄) | CH₂S(O)CH₃ |
| CH₂(2-(CF₃)C₆H₄) | CH₂CN | CH₂(2,6-F₂C₆H₃) | CH₂S(O)CH₃ |
| CH₂(2-(OCF₃)C₆H₄) | CH₂CN | CH₂(2-ClC₆H₄) | CH₂S(O)CH₃ |
| CH₂(2-(SCH₃)C₆H₄) | CH₂CN | CH₂(2,6-Cl₂C₆H₃) | CH₂S(O)CH₃ |
| CH₂(2-(CH=CH₂)C₆H₄) | CH₂CN | CH₂(2-(CH₃)C₆H₄) | CH₂S(O)CH₃ |
| CH₂(2-(C≡CH)C₆H₄) | CH₂CN | CH₂(2-(CN)C₆H₄) | CH₂S(O)CH₃ |
| CH₂(C₆H₅) | CH₂CH=CH₂ | CH₂(2-BrC₆H₄) | CH₂S(O)CH₃ |
| CH₂(2-FC₆H₄) | CH₂CH=CH₂ | CH₂(2,6-Br₂C₆H₃) | CH₂S(O)CH₃ |
| CH₂(2,6-F₂C₆H₃) | CH₂CH=CH₂ | Q-1 | CH₂S(O)CH₃ |
| CH₂(2-ClC₆H₄) | CH₂CH=CH₂ | CH₂(2-Cl,6-FC₆H₃) | CH₂S(O)CH₃ |
| CH₂(2,6-Cl₂C₆H₃) | CH₂CH=CH₂ | CH₂(2-pyridyl) | CH₂S(O)CH₃ |
| CH₂(2-(CH₃)C₆H₄) | CH₂CH=CH₂ | CH₂(C₆H₅) | CH₂CO₂CH₃ |

TABLE 2-continued

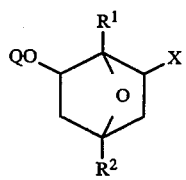

I

| Q | X | Q | X |
|---|---|---|---|
| CH$_2$(2-(CN)C$_6$H$_4$) | CH$_2$CH=CH$_2$ | CH$_2$(2-FC$_6$H$_4$) | CH$_2$CO$_2$CH$_3$ |
| CH$_2$(2-BrC$_6$H$_4$) | CH$_2$CH=CH$_2$ | CH$_2$(2,6-F$_2$C$_6$H$_3$) | CH$_2$CO$_2$CH$_3$ |
| CH$_2$(2,6-Br$_2$C$_6$H$_3$) | CH$_2$CH=CH$_2$ | CH$_2$(2-ClC$_6$H$_4$) | CH$_2$CO$_2$CH$_3$ |
| Q-1 | CH$_2$CH=CH$_2$ | CH$_2$(2,6-Cl$_2$C$_6$H$_3$) | CH$_2$CO$_2$CH$_3$ |
| CH$_2$(2-Cl,6-FC$_6$H$_3$) | CH$_2$CH=CH$_2$ | CH$_2$(2-(CH$_3$)C$_6$H$_4$) | CH$_2$CO$_2$CH$_3$ |
| CH$_2$(2-pyridyl) | CH$_2$CH=CH$_2$ | CH$_2$(2-(CN)C$_6$H$_4$) | CH$_2$CO$_2$CH$_3$ |
| CH$_2$(C$_6$H$_5$) | CH$_2$SCH$_3$ | CH$_2$(2-BrC$_6$H$_4$) | CH$_2$CO$_2$CH$_3$ |
| CH$_2$(2-FC$_6$H$_4$) | CH$_2$SCH$_3$ | CH$_2$(2,6-Br$_2$C$_6$H$_3$) | CH$_2$CO$_2$CH$_3$ |
| CH$_2$(2,6-F$_2$C$_6$H$_3$) | CH$_2$SCH$_3$ | Q-1 | CH$_2$CO$_2$CH$_3$ |
| CH$_2$(2-ClC$_6$H$_4$) | CH$_2$SCH$_3$ | CH$_2$(2-Cl,6-FC$_6$H$_3$) | CH$_2$CO$_2$CH$_3$ |
| CH$_2$(2,6-Cl$_2$C$_6$H$_3$) | CH$_2$SCH$_3$ | CH$_2$(2-pyridyl) | CH$_2$CO$_2$CH$_3$ |
| CH$_2$(2-(CH$_3$)C$_6$H$_4$) | CH$_2$SCH$_3$ | CH$_2$(C$_6$H$_5$) | CH$_2$C≡CH |
| CH$_2$(2-(CN)C$_6$H$_4$) | CH$_2$SCH$_3$ | CH$_2$(2-FC$_6$H$_4$) | CH$_2$C≡CH |
| CH$_2$(2-BrC$_6$H$_4$) | CH$_2$SCH$_3$ | CH$_2$(2,6-F$_2$C$_6$H$_3$) | CH$_2$C≡CH |
| CH$_2$(2,6-Br$_2$C$_6$H$_3$) | CH$_2$SCH$_3$ | CH$_2$(2-ClC$_6$H$_4$) | CH$_2$C≡CH |
| Q-1 | CH$_2$SCH$_3$ | CH$_2$(2,6-Cl$_2$C$_6$H$_3$) | CH$_2$C≡CH |
| CH$_2$(2-Cl,6-FC$_6$H$_3$) | CH$_2$SCH$_3$ | CH$_2$(2-(CH$_3$)C$_6$H$_4$) | CH$_2$C≡CH |
| CH$_2$(2-pyridyl) | CH$_2$SCH$_3$ | CH$_2$(2-(CN)C$_6$H$_4$) | CH$_2$C≡CH |
| CH$_2$(2-BrC$_6$H$_4$) | CH$_2$C≡CH | CH$_2$(C$_6$H$_5$) | CH$_2$CH$_2$CN |
| CH$_2$(2,6-Br$_2$C$_6$H$_3$) | CH$_2$C≡CH | CH$_2$(2-FC$_6$H$_4$) | CH$_2$CH$_2$CN |
| Q-1 | CH$_2$C≡CH | CH$_2$(2,6-F$_2$C$_6$H$_3$) | CH$_2$CH$_2$CN |
| CH$_2$(2-Cl,6-FC$_6$H$_3$) | CH$_2$C≡CH | CH$_2$(2-ClC$_6$H$_4$) | CH$_2$CH$_2$CN |
| CH$_2$(2-pyridyl) | CH$_2$C≡CH | CH$_2$(2,6-Cl$_2$C$_6$H$_3$) | CH$_2$CH$_2$CN |
| CH$_2$(C$_6$H$_5$) | CH$_2$N$_3$ | CH$_2$(2-(CH$_3$)C$_6$H$_4$) | CH$_2$CH$_2$CN |
| CH$_2$(2-FC$_6$H$_4$) | CH$_2$N$_3$ | CH$_2$(2-(CN)C$_6$H$_4$) | CH$_2$CH$_2$CN |
| CH$_2$(2,6-F$_2$C$_6$H$_3$) | CH$_2$N$_3$ | CH$_2$(2-BrC$_6$H$_4$) | CH$_2$CH$_2$CN |
| CH$_2$(2-ClC$_6$H$_4$) | CH$_2$N$_3$ | CH$_2$(2,6-Br$_2$C$_6$H$_3$) | CH$_2$CH$_2$CN |
| CH$_2$(2,6-Cl$_2$C$_6$H$_3$) | CH$_2$N$_3$ | Q-1 | CH$_2$CH$_2$CN |
| CH$_2$(2-(CH$_3$)C$_6$H$_4$) | CH$_2$N$_3$ | CH$_2$(2-Cl,6-FC$_6$H$_3$) | CH$_2$CH$_2$CN |
| CH$_2$(2-(CN)C$_6$H$_4$) | CH$_2$N$_3$ | CH$_2$(2-pyridyl) | CH$_2$CH$_2$CN |
| CH$_2$(2-BrC$_6$H$_4$) | CH$_2$N$_3$ | CH$_2$(C$_6$H$_5$) | CH$_2$CH$_2$CH$_2$CN |
| CH$_2$(2,6-Br$_2$C$_6$H$_3$) | CH$_2$N$_3$ | CH$_2$(2-FC$_6$H$_4$) | CH$_2$CH$_2$CH$_2$CN |
| Q-1 | CH$_2$N$_3$ | CH$_2$(2,6-F$_2$C$_6$H$_3$) | CH$_2$CH$_2$CH$_2$CN |
| CH$_2$(2-Cl,6-FC$_6$H$_3$) | CH$_2$N$_3$ | CH$_2$(2-ClC$_6$H$_4$) | CH$_2$CH$_2$CH$_2$CN |
| CH$_2$(2-pyridyl) | CH$_2$N$_3$ | CH$_2$(2,6-Cl$_2$C$_6$H$_3$) | CH$_2$CH$_2$CH$_2$CN |
| CH$_2$(C$_6$H$_5$) | CH$_2$S(O)$_2$CH$_3$ | CH$_2$(2-(CH$_3$)C$_6$H$_4$) | CH$_2$CH$_2$CH$_2$CN |
| CH$_2$(2-FC$_6$H$_4$) | CH$_2$S(O)$_2$CH$_3$ | CH$_2$(2-(CN)C$_6$H$_4$) | CH$_2$CH$_2$CH$_2$CN |
| CH$_2$(2,6-F$_2$C$_6$H$_3$) | CH$_2$S(O)$_2$CH$_3$ | CH$_2$(2-BrC$_6$H$_4$) | CH$_2$CH$_2$CH$_2$CN |
| CH$_2$(2-ClC$_6$H$_4$) | CH$_2$S(O)$_2$CH$_3$ | CH$_2$(2,6-Br$_2$C$_6$H$_3$) | CH$_2$CH$_2$CH$_2$CN |
| CH$_2$(2,6-Cl$_2$C$_6$H$_3$) | CH$_2$S(O)$_2$CH$_3$ | Q-1 | CH$_2$CH$_2$CH$_2$CN |
| CH$_2$(2-(CH$_3$)C$_6$H$_4$) | CH$_2$S(O)$_2$CH$_3$ | CH$_2$(2-Cl,6-FC$_6$H$_3$) | CH$_2$CH$_2$CH$_2$CN |
| CH$_2$(2-(CN)C$_6$H$_4$) | CH$_2$S(O)$_2$CH$_3$ | CH$_2$(2-pyridyl) | CH$_2$CH$_2$CH$_2$CN |
| CH$_2$(2-BrC$_6$H$_4$) | CH$_2$S(O)$_2$CH$_3$ | | |
| CH$_2$(2,6-Br$_2$C$_6$H$_3$) | CH$_2$S(O)$_2$CH$_3$ | | |
| Q-1 | CH$_2$S(O)$_2$CH$_3$ | | |
| CH$_2$(2-Cl,6-FC$_6$H$_3$) | CH$_2$S(O)$_2$CH$_3$ | | |
| CH$_2$(2-pyridyl) | CH$_2$S(O)$_2$CH$_3$ | | |
| | | R$^1$ is CH$_2$CH$_3$; R$^2$ is CH$_2$CH$_3$ | |
| CH$_2$(C$_6$H$_5$) | CH$_2$CN | | |
| CH$_2$(2-FC$_6$H$_4$) | CH$_2$CN | | |
| CH$_2$(2,6-F$_2$C$_6$H$_3$) | CH$_2$CN | | |
| CH$_2$(2-ClC$_6$H$_4$) | CH$_2$CN | | |
| CH$_2$(2,6-Cl$_2$C$_6$H$_3$) | CH$_2$CN | | |
| CH$_2$(2-(CH$_3$)C$_6$H$_4$) | CH$_2$CN | | |
| CH$_2$(2-(CN)C$_6$H$_4$) | CH$_2$CN | | |
| CH$_2$(2-BrC$_6$H$_4$) | CH$_2$CN | | |
| CH$_2$(2,6-Br$_2$C$_6$H$_3$) | CH$_2$CN | | |
| Q-1 | CH$_2$CN | | |
| CH$_2$(2-Cl,6-FC$_6$H$_3$) | CH$_2$CN | | |
| CH$_2$(2-pyridyl) | CH$_2$CN | | |

TABLE 3

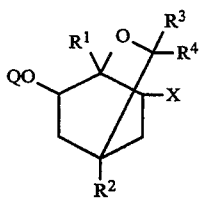

$R^1$ is $CH_3$; $R^2=R^3=R^4$ is H

| Q | X | Q | X |
|---|---|---|---|
| CH₂(C₆H₅) | CH₂CN | CH₂(2-pyridyl) | CH₂CN |
| CH₂(2-FC₆H₄) | CH₂CN | CH₂(2-thienyl) | CH₂CN |
| CH₂(3-FC₆H₄) | CH₂CN | CH₂(2-furanyl) | CH₂CN |
| CH₂(4-FC₆H₄) | CH₂CN | CH₂(2-tetrahydrofuranyl) | CH₂CN |
| CH₂(2,4-F₂C₆H₃) | CH₂CN | CH₂(2-tetrahydropyranyl) | CH₂CN |
| CH₂(2,6-F₂C₆H₃) | CH₂CN | Q-1 | CH₂CN |
| CH₂(2,4,6-F₃C₆H₂) | CH₂CN | Q-3 | CH₂CN |
| CH₂(2-ClC₆H₄) | CH₂CN | Q-4 | CH₂CN |
| CH₂(3-ClC₆H₄) | CH₂CN | Q-6 | CH₂CN |
| CH₂(4-ClC₆H₄) | CH₂CN | Q-7 | CH₂CN |
| CH₂(2,4-Cl₂C₆H₃) | CH₂CN | Q-8 | CH₂CN |
| CH₂(2,6-Cl₂C₆H₃) | CH₂CN | Q-15 | CH₂CN |
| CH₂(2-(CH₃)C₆H₄) | CH₂CN | CH₂(2-BrC₆H₄) | CH₂CN |
| CH₂(3-(CH₃)C₆H₄) | CH₂CN | CH₂(2,6-Br₂C₆H₃) | CH₂CN |
| CH₂(4-(CH₃)C₆H₄) | CH₂CN | CH₂(2-Cl,6-FC₆H₃) | CH₂CN |
| CH₂(2,4,6-(CH₃)₃C₆H₂) | CH₂CN | | |
| CH₂(2-(OCH₃)C₆H₄) | CH₂CN | CH₂(C₆H₅) | CH₂S(O)CH₃ |
| CH₂(2-(CN)C₆H₄) | CH₂CN | CH₂(2-FC₆H₄) | CH₂S(O)CH₃ |
| CH₂(2-(CF₃)C₆H₄) | CH₂CN | CH₂(2,6-F₂C₆H₃) | CH₂S(O)CH₃ |
| CH₂(2-(OCF₃)C₆H₄) | CH₂CN | CH₂(2-ClC₆H₄) | CH₂S(O)CH₃ |
| CH₂(2-(SCH₃)C₆H₄) | CH₂CN | CH₂(2,6-Cl₂C₆H₃) | CH₂S(O)CH₃ |
| CH₂(2-(CH=CH₂)C₆H₄ | CH₂CN | CH₂(2-(CH₃)C₆H₄) | CH₂S(O)CH₃ |
| CH₂(2-(C≡CH)C₆H₄) | CH₂CN | CH₂(2-(CN)C₆H₄) | CH₂S(O)CH₃ |
| CH₂(C₆H₅) | CH₂CH=CH₂ | CH₂(2-BrC₆H₄) | CH₂S(O)CH₃ |
| CH₂(2-FC₆H₄) | CH₂CH=CH₂ | CH₂(2,6-Br₂C₆H₃) | CH₂S(O)CH₃ |
| CH₂(2,6-F₂C₆H₃) | CH₂CH=CH₂ | Q-1 | CH₂S(O)CH₃ |
| CH₂(2-ClC₆H₄) | CH₂CH=CH₂ | CH₂(2-Cl,6-FC₆H₃) | CH₂S(O)CH₃ |
| CH₂(2,6-Cl₂C₆H₃) | CH₂CH=CH₂ | CH₂(2-pyridyl) | CH₂S(O)CH₃ |
| CH₂(2-(CH₃)C₆H₄) | CH₂CH=CH₂ | CH₂(C₆H₅) | CH₂CO₂CH₃ |
| CH₂(2-(CN)C₆H₄) | CH₂CH=CH₂ | CH₂(2-FC₆H₄) | CH₂CO₂CH₃ |
| CH₂(2-BrC₆H₄) | CH₂CH=CH₂ | CH₂(2,6-F₂C₆H₃) | CH₂CO₂CH₃ |
| CH₂(2,6-Br₂C₆H₃) | CH₂CH=CH₂ | CH₂(2-ClC₆H₄) | CH₂CO₂CH₃ |
| Q-1 | CH₂CH=CH₂ | CH₂(2,6-Cl₂C₆H₃) | CH₂CO₂CH₃ |
| CH₂(2-Cl,6-FC₆H₃) | CH₂CH=CH₂ | CH₂(2-(CH₃)C₆H₄) | CH₂CO₂CH₃ |
| CH₂(2-pyridyl) | CH₂CH=CH₂ | CH₂(2-(CN)C₆H₄) | CH₂CO₂CH₃ |
| CH₂(C₆H₅) | CH₂SCH₃ | CH₂(2-BrC₆H₄) | CH₂CO₂CH₃ |
| CH₂(2-FC₆H₄) | CH₂SCH₃ | CH₂(2,6-Br₂C₆H₃) | CH₂CO₂CH₃ |
| CH₂(2,6-F₂C₆H₃) | CH₂SCH₃ | Q-1 | CH₂CO₂CH₃ |
| CH₂(2-ClC₆H₄) | CH₂SCH₃ | CH₂(2-Cl,6-FC₆H₃) | CH₂CO₂CH₃ |
| CH₂(2,6-Cl₂C₆H₃) | CH₂SCH₃ | CH₂(2-pyridyl) | CH₂CO₂CH₃ |
| CH₂(2-(CH₃)C₆H₄) | CH₂SCH₃ | CH₂(C₆H₅) | CH₂C≡CH |
| CH₂(2-(CN)C₆H₄) | CH₂SCH₃ | CH₂(2-FC₆H₄) | CH₂C≡CH |
| CH₂(2-BrC₆H₄) | CH₂SCH₃ | CH₂(2,6-F₂C₆H₃) | CH₂C≡CH |
| CH₂(2,6-Br₂C₆H₃) | CH₂SCH₃ | CH₂(2-ClC₆H₄) | CH₂C≡CH |
| Q-1 | CH₂SCH₃ | CH₂(2,6-Cl₂C₆H₃) | CH₂C≡CH |
| CH₂(2-Cl,6-FC₆H₃) | CH₂SCH₃ | CH₂(2-(CH₃)C₆H₄) | CH₂C≡CH |
| CH₂(2-pyridyl) | CH₂SCH₃ | CH₂(2-(CN)C₆H₄) | CH₂C≡CH |
| CH₂(2-BrC₆H₄) | CH₂C≡CH | CH₂(C₆H₅) | CH₂CH₂CN |
| CH₂(2,6-Br₂C₆H₃) | CH₂C≡CH | CH₂(2-FC₆H₄) | CH₂CH₂CN |
| Q-1 | CH₂C≡CH | CH₂(2,6-F₂C₆H₃) | CH₂CH₂CN |
| CH₂(2-Cl,6-FC₆H₃) | CH₂C≡CH | CH₂(2-ClC₆H₄) | CH₂CH₂CN |
| CH₂(2-pyridyl) | CH₂C≡CH | CH₂(2,6-Cl₂C₆H₃) | CH₂CH₂CN |
| CH₂(C₆H₅) | CH₂N₃ | CH₂(2-(CH₃)C₆H₄) | CH₂CH₂CN |
| CH₂(2-FC₆H₄) | CH₂N₃ | CH₂(2-(CN)C₆H₄) | CH₂CH₂CN |
| CH₂(2,6-F₂C₆H₃) | CH₂N₃ | CH₂(2-BrC₆H₄) | CH₂CH₂CN |
| CH₂(2-ClC₆H₄) | CH₂N₃ | CH₂(2,6-Br₂C₆H₃) | CH₂CH₂CN |
| CH₂(2,6-Cl₂C₆H₃) | CH₂N₃ | Q-1 | CH₂CH₂CN |
| CH₂(2-(CH₃)C₆H₄) | CH₂N₃ | CH₂(2-Cl,6-FC₆H₃) | CH₂CH₂CN |
| CH₂(2-(CN)C₆H₄) | CH₂N₃ | CH₂(2-pyridyl) | CH₂CH₂CN |
| CH₂(2-BrC₆H₄) | CH₂N₃ | CH₂(C₆H₅) | CH₂CH₂CH₂CN |
| CH₂(2,6-Br₂C₆H₃) | CH₂N₃ | CH₂(2-FC₆H₄) | CH₂CH₂CH₂CN |
| Q-1 | CH₂N₃ | CH₂(2,6-F₂C₆H₃) | CH₂CH₂CH₂CN |
| CH₂(2-Cl,6-FC₆H₃) | CH₂N₃ | CH₂(2-ClC₆H₄) | CH₂CH₂CH₂CN |
| CH₂(2-pyridyl) | CH₂N₃ | CH₂(2,6-Cl₂C₆H₃) | CH₂CH₂CH₂CN |
| CH₂(C₆H₅) | CH₂S(O)₂CH₃ | CH₂(2-(CH₃)C₆H₄) | CH₂CH₂CH₂CN |
| CH₂(2-FC₆H₄) | CH₂S(O)₂CH₃ | CH₂(2-(CN)C₆H₄) | CH₂CH₂CH₂CN |
| CH₂(2,6-F₂C₆H₃) | CH₂S(O)₂CH₃ | CH₂(2-BrC₆H₄) | CH₂CH₂CH₂CN |
| CH₂(2-ClC₆H₄) | CH₂S(O)₂CH₃ | CH₂(2,6-Br₂C₆H₃) | CH₂CH₂CH₂CN |
| CH₂(2,6-Cl₂C₆H₃) | CH₂S(O)₂CH₃ | Q-1 | CH₂CH₂CH₂CN |

TABLE 3-continued

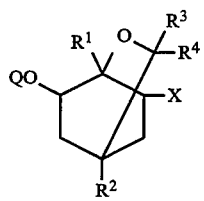

| Q | X | Q | X |
|---|---|---|---|
| CH$_2$(2-(CH$_3$)C$_6$H$_4$) | CH$_2$S(O)$_2$CH$_3$ | CH$_2$(2-Cl,6-FC$_6$H$_3$) | CH$_2$CH$_2$CH$_2$CN |
| CH$_2$(2-(CN)C$_6$H$_4$) | CH$_2$S(O)$_2$CH$_3$ | CH$_2$(2-pyridyl) | CH$_2$CH$_2$CH$_2$CN |
| CH$_2$(2-BrC$_6$H$_4$) | CH$_2$S(O)$_2$CH$_3$ | | |
| CH$_2$(2,6-Br$_2$C$_6$H$_3$) | CH$_2$S(O)$_2$CH$_3$ | | |
| Q-1 | CH$_2$S(O)$_2$CH$_3$ | | |
| CH$_2$(2-Cl,6-FC$_6$H$_3$) | CH$_2$S(O)$_2$CH$_3$ | | |
| CH$_2$(2-pyridyl) | CH$_2$S(O)$_2$CH$_3$ | | |
| | R$^1$ is CH$_3$; R$^2$ is H; R$^3$=R$^4$ is CH$_3$ | | |
| CH$_2$(C$_6$H$_5$) | CH$_2$CN | | |
| CH$_2$(2-FC$_6$H$_4$) | CH$_2$CN | | |
| CH$_2$(2,6-F$_2$C$_6$H$_3$) | CH$_2$CN | | |
| CH$_2$(2-ClC$_6$H$_4$) | CH$_2$CN | | |
| CH$_2$(2,6-Cl$_2$C$_6$H$_3$) | CH$_2$CN | | |
| CH$_2$(2-(CH$_3$)C$_6$H$_4$) | CH$_2$CN | | |
| CH$_2$(2-(CN)C$_6$H$_4$) | CH$_2$CN | | |
| CH$_2$(2-BrC$_6$H$_4$) | CH$_2$CN | | |
| CH$_2$(2,6-Br$_2$C$_6$H$_3$) | CH$_2$CN | | |
| Q-1 | CH$_2$CN | | |
| CH$_2$(2-Cl,6-FC$_6$H$_3$) | CH$_2$CN | | |
| CH$_2$(2-pyridyl) | CH$_2$CN | | |

TABLE 4

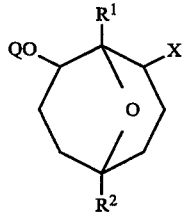

IV

| Q | X | Q | X |
|---|---|---|---|
| | R$^1$ is CH$_3$; R$^2$ is H | | |
| CH$_2$(C$_6$H$_5$) | CH$_2$CN | CH$_2$(2-pyridyl) | CH$_2$CN |
| CH$_2$(2-FC$_6$H$_4$) | CH$_2$CN | CH$_2$(2-thienyl) | CH$_2$CN |
| CH$_2$(3-FC$_6$H$_4$) | CH$_2$CN | CH$_2$(2-furanyl) | CH$_2$CN |
| CH$_2$(4-FC$_6$H$_4$) | CH$_2$CN | CH$_2$(2-tetrahydrofuranyl) | CH$_2$CN |
| CH$_2$(2,4-F$_2$C$_6$H$_3$) | CH$_2$CN | CH$_2$(2-tetrahydropyranyl) | CH$_2$CN |
| CH$_2$(2,6-F$_2$C$_6$H$_3$) | CH$_2$CN | Q-1 | CH$_2$CN |
| CH$_2$(2,4,6-F$_3$C$_6$H$_2$) | CH$_2$CN | Q-3 | CH$_2$CN |
| CH$_2$(2-ClC$_6$H$_4$) | CH$_2$CN | Q-4 | CH$_2$CN |
| CH$_2$(3-ClC$_6$H$_4$) | CH$_2$CN | Q-6 | CH$_2$CN |
| CH$_2$(4-ClC$_6$H$_4$) | CH$_2$CN | Q-7 | CH$_2$CN |
| CH$_2$(2,4-Cl$_2$C$_6$H$_3$) | CH$_2$CN | Q-8 | CH$_2$CN |
| CH$_2$(2,6-Cl$_2$C$_6$H$_3$) | CH$_2$CN | Q-15 | CH$_2$CN |
| CH$_2$(2-(CH$_3$)C$_6$H$_4$) | CH$_2$CN | CH$_2$(2-BrC$_6$H$_4$) | CH$_2$CN |
| CH$_2$(3-(CH$_3$)C$_6$H$_4$) | CH$_2$CN | CH$_2$(2,6-Br$_2$C$_6$H$_3$) | CH$_2$CN |
| CH$_2$(4-(CH$_3$)C$_6$H$_4$) | CH$_2$CN | CH$_2$(2-Cl,6-FC$_6$H$_3$) | CH$_2$CN |
| CH$_2$(2,4,6-(CH$_3$)$_3$C$_6$H$_2$) | CH$_2$CN | | |
| CH$_2$(2-(OCH$_3$)C$_6$H$_4$) | CH$_2$CN | | |
| CH$_2$(2-(CN)C$_6$H$_4$) | CH$_2$CN | CH$_2$(C$_6$H$_5$) | CH$_2$I |
| CH$_2$(2-(CF$_3$)C$_6$H$_4$) | CH$_2$CN | CH$_2$(2-FC$_6$H$_4$) | CH$_2$I |
| CH$_2$(2-(OCF$_3$)C$_6$H$_4$) | CH$_2$CN | CH$_2$(2,6-F$_2$C$_6$H$_3$) | CH$_2$I |
| CH$_2$(2-(SCH$_3$)C$_6$H$_4$) | CH$_2$CN | CH$_2$(2-ClC$_6$H$_4$) | CH$_2$I |
| CH$_2$(2-(CH=CH$_2$)C$_6$H$_4$ | CH$_2$CN | CH$_2$(2,6-Cl$_2$C$_6$H$_3$) | CH$_2$I |
| CH$_2$(2-(C≡CH)C$_6$H$_4$) | CH$_2$CN | CH$_2$(2-(CH$_3$)C$_6$H$_4$) | CH$_2$I |
| CH$_2$(C$_6$H$_5$) | CH$_2$Cl | CH$_2$(2-(CN)C$_6$H$_4$) | CH$_2$I |
| CH$_2$(2-FC$_6$H$_4$) | CH$_2$Cl | CH$_2$(2-BrC$_6$H$_4$) | CH$_2$I |
| CH$_2$(2,6-F$_2$C$_6$H$_3$) | CH$_2$Cl | CH$_2$(2,6-Br$_2$C$_6$H$_3$) | CH$_2$I |
| CH$_2$(2-ClC$_6$H$_4$) | CH$_2$Cl | Q-1 | CH$_2$I |
| CH$_2$(2,6-Cl$_2$C$_6$H$_3$) | CH$_2$Cl | CH$_2$(2-Cl,6-FC$_6$H$_3$) | CH$_2$I |
| CH$_2$(2-(CH$_3$)C$_6$H$_4$) | CH$_2$Cl | CH$_2$(2-pyridyl) | CH$_2$I |
| CH$_2$(2-(CN)C$_6$H$_4$) | CH$_2$Cl | CH$_2$(C$_6$H$_5$) | CH$_2$CH=CH$_2$ |
| CH$_2$(2-(BrC$_6$H$_4$) | CH$_2$Cl | CH$_2$(2-FC$_6$H$_4$) | CH$_2$CH=CH$_2$ |
| CH$_2$(2,6-Br$_2$C$_6$H$_4$) | CH$_2$Cl | CH$_2$(2,6-F$_2$C$_6$H$_3$) | CH$_2$CH=CH$_2$ |

TABLE 4-continued

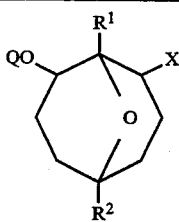

| Q | X | Q | X |
|---|---|---|---|
| Q-1 | CH$_2$Cl | CH$_2$(2-ClC$_6$H$_4$) | CH$_2$CH=CH$_2$ |
| CH$_2$(2-Cl,6-FC$_6$H$_3$) | CH$_2$Cl | CH$_2$(2,6-Cl$_2$C$_6$H$_3$) | CH$_2$CH=CH$_2$ |
| CH$_2$(2-pyridyl) | CH$_2$Cl | CH$_2$(2-(CH$_3$)C$_6$H$_4$) | CH$_2$CH=CH$_2$ |
| CH$_2$(C$_6$H$_5$) | CH$_2$Br | CH$_2$(2-(CN)C$_6$H$_4$) | CH$_2$CH=CH$_2$ |
| CH$_2$(2-FC$_6$H$_4$) | CH$_2$Br | CH$_2$(2-BrC$_6$H$_4$) | CH$_2$CH=CH$_2$ |
| CH$_2$(2,6-F$_2$C$_6$H$_3$) | CH$_2$Br | CH$_2$(2,6-Br$_2$C$_6$H$_3$) | CH$_2$CH=CH$_2$ |
| CH$_2$(2-ClC$_6$H$_4$) | CH$_2$Br | Q-1 | CH$_2$CH=CH$_2$ |
| CH$_2$(2,6-Cl$_2$C$_6$H$_3$) | CH$_2$Br | CH$_2$(2-Cl,6-FC$_6$H$_3$) | CH$_2$CH=CH$_2$ |
| CH$_2$(2-(CH$_3$)C$_6$H$_4$) | CH$_2$Br | CH$_2$(2-pyridyl) | CH$_2$CH=CH$_2$ |
| CH$_2$(2-(CN)C$_6$H$_4$) | CH$_2$Br | | |
| CH$_2$(2-BrC$_6$H$_4$) | CH$_2$Br | | |
| CH$_2$(2,6-Br$_2$C$_6$H$_3$) | CH$_2$Br | | |
| Q-1 | CH$_2$Br | | |
| CH$_2$(2-Cl,6-FC$_6$H$_3$) | CH$_2$Br | | |
| CH$_2$(2-pyridyl) | CH$_2$Br | | |
| CH$_2$(C$_6$H$_5$) | CH$_2$SCH$_3$ | CH$_2$(C$_6$H$_5$) | CH$_2$CO$_2$CH$_3$ |
| CH$_2$(2-FC$_6$H$_4$) | CH$_2$SCH$_3$ | CH$_2$(2-FC$_6$H$_4$) | CH$_2$CO$_2$CH$_3$ |
| CH$_2$(2,6-F$_2$C$_6$H$_3$) | CH$_2$SCH$_3$ | CH$_2$(2,6-F$_2$C$_6$H$_3$) | CH$_2$CO$_2$CH$_3$ |
| CH$_2$(2-ClC$_6$H$_4$) | CH$_2$SCH$_3$ | CH$_2$(2-ClC$_6$H$_4$) | CH$_2$CO$_2$CH$_3$ |
| CH$_2$(2,6-Cl$_2$C$_6$H$_3$) | CH$_2$SCH$_3$ | CH$_2$(2,6-Cl$_2$C$_6$H$_3$) | CH$_2$CO$_2$CH$_3$ |
| CH$_2$(2-(CH$_3$)C$_6$H$_4$) | CH$_2$SCH$_3$ | CH$_2$(2-(CH$_3$)C$_6$H$_4$) | CH$_2$CO$_2$CH$_3$ |
| CH$_2$(2-(CN)C$_6$H$_4$) | CH$_2$SCH$_3$ | CH$_2$(2-(CN)C$_6$H$_4$) | CH$_2$CO$_2$CH$_3$ |
| CH$_2$(2-BrC$_6$H$_4$) | CH$_2$SCH$_3$ | CH$_2$(2-BrC$_6$H$_4$) | CH$_2$CO$_2$CH$_3$ |
| CH$_2$(2,6-Br$_2$C$_6$H$_3$) | CH$_2$SCH$_3$ | CH$_2$(2,6-Br$_2$C$_6$H$_3$) | CH$_2$CO$_2$CH$_3$ |
| Q-1 | CH$_2$SCH$_3$ | Q-1 | CH$_2$CO$_2$CH$_3$ |
| CH$_2$(2-Cl,6-FC$_6$H$_3$) | CH$_2$SCH$_3$ | CH$_2$(2-Cl,6-FC$_6$H$_3$) | CH$_2$CO$_2$CH$_3$ |
| CH$_2$(2-pyridyl) | CH$_2$SCH$_3$ | CH$_2$(2-pyridyl) | CH$_2$CO$_2$CH$_3$ |
| CH$_2$(C$_6$H$_5$) | CH$_2$S(O)CH$_3$ | CH$_2$(C$_6$H$_5$) | CH$_2$C≡CH |
| CH$_2$(2-FC$_6$H$_4$) | CH$_2$S(O)CH$_3$ | CH$_2$(2-FC$_6$H$_4$) | CH$_2$C≡CH |
| CH$_2$(2,6-F$_2$C$_6$H$_3$) | CH$_2$S(O)CH$_3$ | CH$_2$(2,6-F$_2$C$_6$H$_3$) | CH$_2$C≡CH |
| CH$_2$(2-ClC$_6$H$_4$) | CH$_2$S(O)CH$_3$ | CH$_2$(2-ClC$_6$H$_4$) | CH$_2$C≡CH |
| CH$_2$(2,6-Cl$_2$C$_6$H$_3$) | CH$_2$S(O)CH$_3$ | CH$_2$(2,6-Cl$_2$C$_6$H$_3$) | CH$_2$C≡CH |
| CH$_2$(2-(CH$_3$)C$_6$H$_4$) | CH$_2$S(O)CH$_3$ | CH$_2$(2-(CH$_3$)C$_6$H$_4$) | CH$_2$C≡CH |
| CH$_2$(2-(CN)C$_6$H$_4$) | CH$_2$S(O)CH$_3$ | CH$_2$(2-(CN)C$_6$H$_4$) | CH$_2$C≡CH |
| CH$_2$(2-BrC$_6$H$_4$) | CH$_2$S(O)CH$_3$ | CH$_2$(2-BrC$_6$H$_4$) | CH$_2$C≡CH |
| CH$_2$(2,6-Br$_2$C$_6$H$_3$) | CH$_2$S(O)CH$_3$ | CH$_2$(2,6-Br$_2$C$_6$H$_3$) | CH$_2$C≡CH |
| Q-1 | CH$_2$S(O)CH$_3$ | Q-1 | CH$_2$C≡CH |
| CH$_2$(2-Cl,6-FC$_6$H$_3$) | CH$_2$S(O)CH$_3$ | CH$_2$(2-Cl,6-FC$_6$H$_3$) | CH$_2$C≡CH |
| CH$_2$(2-pyridyl) | CH$_2$S(O)CH$_3$ | CH$_2$(2-pyridyl) | CH$_2$C≡CH |
| CH$_2$(C$_6$H$_5$) | CH$_2$N$_3$ | CH$_2$(C$_6$H$_5$) | CH$_2$CH$_2$CN |
| CH$_2$(2-FC$_6$H$_4$) | CH$_2$N$_3$ | CH$_2$(2-FC$_6$H$_4$) | CH$_2$CH$_2$CN |
| CH$_2$(2,6-F$_2$C$_6$H$_3$) | CH$_2$N$_3$ | CH$_2$(2,6-F$_2$C$_6$H$_3$) | CH$_2$CH$_2$CN |
| CH$_2$(2-ClC$_6$H$_4$) | CH$_2$N$_3$ | CH$_2$(2-ClC$_6$H$_4$) | CH$_2$CH$_2$CN |
| CH$_2$(2,6-Cl$_2$C$_6$H$_3$) | CH$_2$N$_3$ | CH$_2$(2,6-Cl$_2$C$_6$H$_3$) | CH$_2$CH$_2$CN |
| CH$_2$(2-(CH$_3$)C$_6$H$_4$) | CH$_2$N$_3$ | CH$_2$(2-(CH$_3$)C$_6$H$_4$) | CH$_2$CH$_2$CN |
| CH$_2$(2-(CN)C$_6$H$_4$) | CH$_2$N$_3$ | CH$_2$(2-(CN)C$_6$H$_4$) | CH$_2$CH$_2$CN |
| CH$_2$(2-BrC$_6$H$_4$) | CH$_2$N$_3$ | CH$_2$(2-BrC$_6$H$_4$) | CH$_2$CH$_2$CN |
| CH$_2$(2,6-Br$_2$C$_6$H$_3$) | CH$_2$N$_3$ | CH$_2$(2,6-Br$_2$C$_6$H$_3$) | CH$_2$CH$_2$CN |
| Q-1 | CH$_2$N$_3$ | Q-1 | CH$_2$CH$_2$CN |
| CH$_2$(2-Cl,6-FC$_6$H$_3$) | CH$_2$N$_3$ | CH$_2$(2-Cl,6-FC$_6$H$_3$) | CH$_2$CH$_2$CN |
| CH$_2$(2-pyridyl) | CH$_2$N$_3$ | CH$_2$(2-pyridyl) | CH$_2$CH$_2$CN |
| CH$_2$(C$_6$H$_5$) | CH$_2$S(O)$_2$CH$_3$ | CH$_2$(C$_6$H$_5$) | CH$_2$CH$_2$CH$_2$CN |
| CH$_2$(2-FC$_6$H$_4$) | CH$_2$S(O)$_2$CH$_3$ | CH$_2$(2-FC$_6$H$_4$) | CH$_2$CH$_2$CH$_2$CN |
| CH$_2$(2,6-F$_2$C$_6$H$_3$) | CH$_2$S(O)$_2$CH$_3$ | CH$_2$(2,6-F$_2$C$_6$H$_3$) | CH$_2$CH$_2$CH$_2$CN |
| CH$_2$(2-ClC$_6$H$_4$) | CH$_2$S(O)$_2$CH$_3$ | CH$_2$(2-ClC$_6$H$_4$) | CH$_2$CH$_2$CH$_2$CN |
| CH$_2$(2,6-Cl$_2$C$_6$H$_3$) | CH$_2$S(O)$_2$CH$_3$ | CH$_2$(2,6-Cl$_2$C$_6$H$_3$) | CH$_2$CH$_2$CH$_2$CN |
| CH$_2$(2-(CH$_3$)C$_6$H$_4$) | CH$_2$S(O)$_2$CH$_3$ | CH$_2$(2-(CH$_3$)C$_6$H$_4$) | CH$_2$CH$_2$CH$_2$CN |
| CH$_2$(2-(CN)C$_6$H$_4$) | CH$_2$S(O)$_2$CH$_3$ | CH$_2$(2-(CN)C$_6$H$_4$) | CH$_2$CH$_2$CH$_2$CN |
| CH$_2$(2-BrC$_6$H$_4$) | CH$_2$S(O)$_2$CH$_3$ | CH$_2$(2-BrC$_6$H$_4$) | CH$_2$CH$_2$CH$_2$CN |
| CH$_2$(2,6-Br$_2$C$_6$H$_3$) | CH$_2$S(O)$_2$CH$_3$ | CH$_2$(2,6-Br$_2$C$_6$H$_3$) | CH$_2$CH$_2$CH$_2$CN |
| Q-1 | CH$_2$S(O)$_2$CH$_3$ | Q-1 | CH$_2$CH$_2$CH$_2$CN |
| CH$_2$(2-Cl,6-FC$_6$H$_3$) | CH$_2$S(O)$_2$CH$_3$ | CH$_2$(2-Cl,6-FC$_6$H$_3$) | CH$_2$CH$_2$CH$_2$CN |
| CH$_2$(2-pyridyl) | CH$_2$S(O)$_2$CH$_3$ | CH$_2$(2-pyridyl) | CH$_2$CH$_2$CH$_2$CN |
| | | $R^1$ is CH$_3$; $R^2$ is CH$_3$ | |
| CH$_2$(C$_6$H$_5$) | CH$_2$CN | CH$_2$(C$_6$H$_5$) | CH$_2$Br |
| CH$_2$(2-FC$_6$H$_4$) | CH$_2$CN | CH$_2$(2-FC$_6$H$_4$) | CH$_2$Br |
| CH$_2$(2,6-F$_2$C$_6$H$_3$) | CH$_2$CN | CH$_2$(2,6-F$_2$C$_6$H$_3$) | CH$_2$Br |
| CH$_2$(2-ClC$_6$H$_4$) | CH$_2$CN | CH$_2$(2-ClC$_6$H$_4$) | CH$_2$Br |
| CH$_2$(2,6-Cl$_2$C$_6$H$_3$) | CH$_2$CN | CH$_2$(2,6-Cl$_2$C$_6$H$_3$) | CH$_2$Br |

TABLE 4-continued

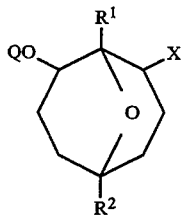

| Q | X | Q | X |
|---|---|---|---|
| $CH_2(2\text{-}(CH_3)C_6H_4)$ | $CH_2CN$ | $CH_2(2\text{-}(CH_3)C_6H_4)$ | $CH_2Br$ |
| $CH_2(2\text{-}(CN)C_6H_4)$ | $CH_2CN$ | $CH_2(2\text{-}(CN)C_6H_4)$ | $CH_2Br$ |
| $CH_2(2\text{-}BrC_6H_4)$ | $CH_2CN$ | $CH_2(2\text{-}BrC_6H_4)$ | $CH_2Br$ |
| $CH_2(2,6\text{-}Br_2C_6H_3)$ | $CH_2CN$ | $CH_2(2,6\text{-}Br_2C_6H_3)$ | $CH_2Br$ |
| Q-1 | $CH_2CN$ | Q-1 | $CH_2Br$ |
| $CH_2(2\text{-}Cl,6\text{-}FC_6H_3)$ | $CH_2CN$ | $CH_2(2\text{-}Cl,6\text{-}FC_6H_3)$ | $CH_2Br$ |
| $CH_2(2\text{-pyridyl})$ | $CH_2CN$ | $CH_2(2\text{-pyridyl})$ | $CH_2Br$ |
| $CH_2(C_6H_5)$ | $CH_2Cl$ | $CH_2(C_6H_5)$ | $CH_2I$ |
| $CH_2(2\text{-}FC_6H_4)$ | $CH_2Cl$ | $CH_2(2\text{-}FC_6H_4)$ | $CH_2I$ |
| $CH_2(2,6\text{-}F_2C_6H_3)$ | $CH_2Cl$ | $CH_2(2,6\text{-}F_2C_6H_3)$ | $CH_2I$ |
| $CH_2(2\text{-}ClC_6H_4)$ | $CH_2Cl$ | $CH_2(2\text{-}ClC_6H_4)$ | $CH_2I$ |
| $CH_2(2,6\text{-}Cl_2C_6H_3)$ | $CH_2Cl$ | $CH_2(2,6\text{-}Cl_2C_6H_3)$ | $CH_2I$ |
| $CH_2(2\text{-}(CH_3)C_6H_4)$ | $CH_2Cl$ | $CH_2(2\text{-}(CH_3)C_6H_4)$ | $CH_2I$ |
| $CH_2(2\text{-}(CN)C_6H_4)$ | $CH_2Cl$ | $CH_2(2\text{-}(CN)C_6H_4)$ | $CH_2I$ |
| $CH_2(2\text{-}BrC_6H_4)$ | $CH_2Cl$ | $CH_2(2\text{-}BrC_6H_4)$ | $CH_2I$ |
| $CH_2(2,6\text{-}Br_2C_6H_3)$ | $CH_2Cl$ | $CH_2(2,6\text{-}Br_2C_6H_3)$ | $CH_2I$ |
| Q-1 | $CH_2Cl$ | Q-1 | $CH_2I$ |
| $CH_2(2\text{-}Cl,6\text{-}FC_6H_3)$ | $CH_2Cl$ | $CH_2(2\text{-}Cl,6\text{-}FC_6H_3)$ | $CH_2I$ |
| $CH_2(2\text{-pyridyl})$ | $CH_2Cl$ | $CH_2(2\text{-pyridyl})$ | $CH_2I$ |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE 5

| | Weight Percent* | | |
|---|---|---|---|
| | Active Ingredient | Diluent(s) | Surfactant(s) |
| Wettable Powders | 5–60 | 39–94 | 1–10 |
| Emulsifiable concentrates | 3–80 | 20–95 | 0–20 |
| Dusts | 1–25 | 70–99 | 0–5 |
| Granules and Pellets | 0.1–50 | 50–99.9 | 0–15 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed Dotland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineers Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, Jun. 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE A

Wettable Powder

| | |
|---|---|
| (2-endo,4-endo)-(+/−)-4-[(2,6-difluorophenyl)methoxy]-5-methyl-6-oxa-bicyclo[3.2.1]octane-2-acetonitrile | 60% |
| sodium alkylnaphthalenesulfonate | 2% |
| sodium ligninsulfonate | 2% |
| synthetic amorphous silica | 36% |

The active ingredient is first sprayed onto the amorphous silica, then the ingredients are blended, hammer-milled until all the solids are essentially under microns, reblended, and packaged.

EXAMPLE B

Wettable Powder

| | |
|---|---|
| (2-endo,4-endo)-(+/−)-4-[(2,6-difluorophenyl)-methoxy]-5-methyl-6-oxa-bicyclo[3.2.1]octane-2-acetonitrile | 50% |
| sodium alkylnaphthalenesulfonate | 2% |
| low viscosity methyl cellulose | 2% |
| diatomaceous earth | 46% |

The active ingredient is first sprayed onto the diatomaceous earth then the ingredients are blended, coarsely hammer-milled and then air-milled to produce particles essentially all below 10 microns in diameter. The product is reblended before packaging.

EXAMPLE C

Granule

Wettable Powder of Example B 5%
attapulgite granules 95% (U.S.S. 20–40 mesh; 0.84–0.42 mm)

A slurry of wettable powder containing 25% solids is sprayed on the surface of attapulgite granules in a double-cone blender. The granules are dried and packaged.

EXAMPLE D

Emulsifiable Concentrate

| | |
|---|---|
| (2-endo,4-endo)-(+/−)-4-[(2,6-difluorophenyl)-methoxy]-5-methyl-6-oxa-bicyclo[3.2.1]octane-2-acetonitrile | 40% |
| Atlox 3403F | 3% |
| Atlox 3404F | 3% |
| xylene | 54% |

The active ingredient and Atlox emulsifiers are dissolved in the solvent, filtered and packaged. Atlox 3403F and 3404F are blends of anionic and ionic emulsifiers from ICI Americas, Inc.

EXAMPLE E

Low Strength Granule

| | |
|---|---|
| (2-endo,4-endo)-(+/−)-4-[(2,6-difluorophenyl)-methoxy]-5-methyl-6-oxa-bicyclo[3.2.1]octane-2-acetonitrile | 5% |
| attapulgite granules (U.S.S. 20–40 mesh) | 95% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE F

Granule

| | |
|---|---|
| (2-endo,4-endo)-(+/−)-4-[(2,6-difluorophenyl)-methoxy]-5-methyl-6-oxa-bicyclo[3.2.1]octane-2-acetonitrile | 50% |
| wetting agent | 1% |
| crude ligninsulfonate salt (containing 5–20% of the natural sugars) | 10% |
| attapulgite clay | 39% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE G

Concentrated Emulsion

| | |
|---|---|
| (2-endo,4-endo)-(+/−)-4-[(2,6-difluorophenyl)-methoxy]-5-methyl-6-oxa-bicyclo[3.2.1]octane-2-acetonitrile | 25% |
| xylene | 25% |
| Atlox 3404F | 5% |
| G1284 | 5% |
| ethylene glycol | 8% |
| water | 32% |

The active ingredient, solvent and emulsifiers are blended together. This solution is added to a mixture of the ethylene glycol and water with stirring.

EXAMPLE H

Solution (2-endo, 4-endo)-(±)-4-[(2,6-difluorophenyl)-methoxy]-5-methyl-6-oxa-bicyclo[3.2.1]octane-2-acetonitrile 5%
water 95%

The compound is added directly to the water with stirring to produce the solution, which may then be packaged for use.

EXAMPLE I

Dust

| | |
|---|---|
| (2-endo,4-endo)-(+/−)-4-[(2,6-difluorophenyl)-methoxy]-5-methyl-6-oxa-bicyclo[3.2.1]octane-2-acetonitrile | 10% |

| | |
|---|---|
| attapulgite | 10% |
| Pyrophyllite | 80% |

The active ingredient is sprayed onto the attapulgite and then passed through a hammer-mill to produce particles substantially all below 200 microns. The ground concentrate is then blended with powdered pyrophyllite until homogeneous.

UTILITY

Test results indicate compounds of this invention are active postemergence and, in particular, preemergence herbicides. Many compounds in this invention are useful for the control of selected grass and broadleaf weeds with tolerance to important agronomic crops (both normal and gene altered for crop tolerance) such as barley (*Hordeum vulgara*), corn (*Zea maya*), cotton (*Gossypium hirsutum*), rape (*Brassica napus*), rice (*Oryza sativa*), sorghum (*Sorghum bicolor*), soybean (*Glycine max*), sugar beet (*Beta vulgaris*), and wheat (*Triticum aestivum*), and to vegetable crops.

Examples of compounds of this invention are particularly useful with outstanding crop tolerance include but not limited to: Compounds 16, 17 and 62 for corn and soybean compounds 9 and 61 for soybean, cotton, wheat, barley and rape; compounds 18 and 34 for rice, wheat, barley and rape compound 27 for corn, sorgh, rice, wheat and barley and compound 28 for corn, soybean, cotton, rice, wheat, barley and sugarbeet. Grass and broadleaf weed species controlled include, but are not limited to, barnyardgrass (*Echinochloa crus-galli*), blackgrass (*Alopecurus myosuroides*), crabgrass (Digitaria spp.), foxtail (Setaria spp.), velvetleaf (*Afutilon theophrasti*), lambsquarters (Chenopodium spp.), umbrella sedge (*Cyperus difformis*), pigweed (*Amaranthus retroflexus*), chickweed (*Stellaria media*) and wild buckwheat (*Polygon convolvulus*).

These compounds also have utility for weed control of selected vegetation in specified areas such as around storage tanks, parking lots, highways, and railways; in fallow crop areas; and in citrus and plantation crops such as banana, coffee, oil palm, and rubber. Alternatively, these compounds are useful to modify plant growth.

An effective amount of the compounds of the invention is determined by a number of factors. These factors include: formulation selected, method of application, amount and type of vegetation present, growing conditions, etc. In general terms, an effective amount of the compounds of the invention should be applied at rates from 0.01 to 20 kg/ha with a preferred rate range of 0.03 to I kg/ha. Although a small number of compounds show no herbicidal activity at the rates tested, it is anticipated these compounds are herbicidally active at higher application rates. One skilled in the art can easily determine application rates necessary for desired level of weed control.

Compounds of this invention may be used alone or in combination with other commercial herbicides, insecticides, or fungicides. The following list exemplifies some of the herbicides suitable for use in mixtures. A combination of a compound from this invention with one or more of the following herbicides may be particularly useful for weed control.

| Common Name | Chemical Name |
|---|---|
| acetochlor | 2-chloro-N-(ethoxymethyl)-N-(2-ethyl-6-methylphenyl)acetamide |
| acifluorfen | 5-[2-chloro-4-(trifluoromethyl)-phenoxy]-2-nitrobenzoic acid |
| aclonifen | 2-chloro-6-nitro-3-phenoxybenzenamine |
| acrolein | 2-propenal |
| alachlor | 2-chloro-N-(2,6-diethylphenyl)-N-(methoxymethyl)acetamide |
| alloxydim | methyl 2,2-dimethyl-4,6-dioxo-5-[1-[(2-propenyloxy)amino]butylidene]cyclohexanecarboxylate |
| ametryn | N-ethyl-N'-(1-methylethyl)-6-(methylthio)-1,3,5-triazine-2,4-diamine |
| amitrole | 1H-1,2,4-triazol-3-amine |
| AMS | ammonium sulfamate |
| anilofos | S-[2-[(4-chlorophenyl)(1-methylethyl)amino]-2-oxoethyl] O,O-dimethyl phosphorodithioate |
| asulam | methyl [(4-aminophenyl)sulfonyl]carbamate |
| atrazine | 6-chloro-N-ethyl-N'-(1-methylethyl)-1,3,5-triazine-2,4-diamine |
| aziprotryne | 4-azido-N-(1-methylethyl)-6-methylthio-1,3,5-triazin-2-amine |
| azoluron | N-(1-ethyl-1H-pyrazol-5-yl)-N'-phenylurea |
| barban | 4-chloro-2-butynyl 3-chlorocarbamate |
| benazolin | 4-chloro-2-oxo-3(2H)-benzothiazoleacetic acid |
| benfluralin | N-butyl-N-ethyl-2,6-dinitro-4-(trifluoromethyl)benzenamine |
| bensulfuron | 2-[[[[(4,6-dimethoxy-2-pyrimidinyl)amino]methylcarbonyl]amino]sulfonyl]methyl]benzoic acid, methyl ester |
| bensulide | O,O-bis(1-methylethyl) S-[2-[(phenylsulfonyl)amino]ethyl]-phosphorodithioate |
| bentazon | 3-(1-methylethyl)-(1H)-2,1,3-benzothiadiazin-4(3H)-one, 2,2-dioxide |
| benzofluor | N-[4-(ethylthio)-2-(trifluoromethyl)phenyl]methanesulfonamide |
| benzoylprop | N-benzoyl-N-(3,4-dichlorophenyl)-DL-alanine |
| benzthiazuron | N-2-benzothiazolyl-N'-methylurea |
| bialaphos | 4-(hydroxymethylphosphinyl)-L-2-aminobutanoyl-L-alanyl-L-alanine |
| bifenox | methyl 5-(2,4-dichlorophenoxy)-2-nitrobenzoate |
| bromacil | 5-bromo-6-methyl-3-(1-methylpropyl)-2,4(1H,3H)pyrimidinedione |
| *bromobutide | (+)2-bromo-3,3-dimethyl-N-(1-methyl-1-phenylethyl)butanamide |
| bromofenoxim | 3,5-dibromo-4-hydroxybenzaldehyde O-(2,4-dinitrophenyl)oxime |
| bromoxynil | 3,5-dibromo-4-hydroxybenzonitrile |
| bromuron | N'-(4-bromophenyl)-N,N-dimethylurea |
| buminafos | dibutyl [1-(butylamino)cyclohexyl]-phosphonate |
| butachlor | N-(butoxymethyl)-2-chloro-N-(2,6-diethylphenyl)acetamide |
| butamifos | O-ethyl O-(5-methyl-2-nitrophenyl)-(1methylpropyl)phosphoramidothioate |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N-(1-methylpropyl)-2,6-dinitrobenzenamine |
| butylate | S-ethyl bis(2-methylpropyl)-carbamothioate |
| cacodylic acid | dimethyl arsinic oxide |
| carbetamide | (R)-N-ethyl-2-[[(phenylamino)-carbonyl]oxy]propanamide |
| CDAA | 2-chloro-N,N-di-2-propenylacetamide |
| CDEC | 2-chloroallyl diethyldithiocarbamate |
| chlomethoxyfen | 4-(2,4-dichlorophenoxy)-2-methoxy-1-nitrobenzene |

-continued

| Common Name | Chemical Name |
| --- | --- |
| chloramben | 3-amino-2,5-dichlorobenzoic acid |
| chlorbromuron | 3-(4-bromo-3-chlorophenyl)-1-methoxy-1-methylurea |
| chlorbufam | 1-methyl-2-propynl(3-chlorophenyl)-carbamate |
| chlorfenac | 2,3,6-trichlorobenzeneacetic acid |
| chlorflurecol methyl | methyl 2-chloro-9-hydroxy-9H-fluorene-9-carboxylate |
| chloridazon | 5-amino-4-chloro-2-phenyl-3(2H)-pyridazinone |
| chlorimuron | 2-[[[[(4-chloro-6-methoxy-2-pyrimidinyl)ethylamino]carbonyl]amino]sulfonyl]benzoic acid, ethyl ester |
| chlornitrofen | 1,3,5-trichloro-2-(4-nitrophenoxy)-benzene |
| chloropicrin | trichloronitromethane |
| chloroxuron | N'-[4-(4-chlorophenoxy)phenyl]-N,N-dimethylurea |
| chlorpropham | 1-methylethyl 3-chlorophenyl-carbamate |
| chlorsulfuron | 2-chloro-N-[[(4-methoxy-6-methyl-1,3,5-triazin-2-yl)amino]-carbonyl]benzenesulfonamide |
| chlorthal-dimethyl | dimethyl 2,3,5,6-tetrachloro-1,4-benzenedicarboxylate |
| chlorthiamid | 2,6-dichlorobenzene carbodithioamide |
| chlortoluron | N'-(3-chloro-4-methyl-phenyl)-N,N-dimethylurea |
| cinmethylin | exo-1-methyl-4-(1-methylethyl)-2-[(2-methylphenyl)methoxy]-7-oxabicyclo-[2.2.1]heptane |
| clethodim | (E,E)-(+)-2-[1-[[(3-chloro-2-propenyl)oxy]imino]propyl]-5-[2-(ethylthio)propyl]-3-hydroxy-2-cyclohexen-1-one |
| clomazone | 2-[(2-chlorophenyl)methyl]-4,4-dimethyl-3-isoxazolidinone |
| cloproxydim | (E,E)-2-[1-[[(3-chloro-2-propenyl)-oxy)imino]butyl]-5-[2-(ethylthio)-propyl]-3-hydroxy-2-cyclohexen-1-one |
| clopyralid | 3,6-dichloro-2-pyridinecarboxylic acid |
| CMA | calcium salt of MAA |
| cyanazine | 2-[[4-chloro-6-(ethylamino)-1,3,5-triazin-2-yl]amino]-2-methyl-propanenitrile |
| cycloate | S-ethyl cyclohexylethylcarbamothioate |
| cycloxydim | 2-[1-ethoxyimino)butyl]-3-hydroxy-5-(tetrahydro-2H-thiopyran-3-yl)-2-cyclohexene-1-one |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N-[5-(2-chloro-1,1-dimethylethyl)-1,3,4-thiadiazol-2-yl]cyclo-propanecarboxamide |
| cypromid | 3',4'-dichlorocyclopropanecarbox-anilide |
| dalapon | 2,2-dichloropropanoic acid |
| dazomet | tetrahydro-3,5-dimethyl-2H-1,3,5-thiadiazine-2-thione |
| DCPA | dimethyl 2,3,5,6-tetrachloro-1,4-benzenedicarboxylate |
| desmedipham | ethyl 3-[[[(phenylamino)carbonyl]-oxy]phenyl]carbamate |
| desmetryn | 2-(isopropylamino)-4-(methylamino)-6-(methylthio)-s-triazine |
| diallate | S-(2,3-dichloro-2-propenyl)bis(1-methylethyl)carbamothioate |
| dicamba | 3,6-dichloro-2-methoxybenzoic acid |
| dichlobenil | 2,6-dichlorobenzonitrile |
| dichlorprop | (+)-2-(2,4-dichlorophenoxy)propanoic acid |
| *diclofopmethyl | (+)-2-[4-(2,4-dichlorophenoxy)-phenoxy]propanoic acid, methyl ester |
| diethatyl | N-(chloroacetyl)-N-(2,6-diethyl-phenyl)glycine |
| difenoxuron | N'-[4-(4-methoxyphenoxy)phenyl]-N,N-dimethylurea |
| difenzoquat | 1,2-dimethyl-3,5-diphenyl-1H-pyrazolium ion |
| diflufenican | N-(2,4-difluorophenyl)-2-(3-tri-fluoromethylphenoxy)pyridine-3-carboxamide |
| dimefuron | N'-[3-chloro-4-[5-(1,1-dimethyl-ethyl)-2-oxo-1,3,4-oxadiazol-3(2H)-yl]phenyl]-N,N-dimethylurea |
| dimethachlor | 2-chloro-N-(2,6-dimethylphenyl)-N-(2-methoxyethyl)acetamide |
| dimethametryn | N-(1,2-dimethylpropyl)-N'-ethyl-6-(methylthio)-1,3,5-triazine-2,4-diamine |
| dimethipin | 2,3-dihydro-5,6-dimethyl-1,4-dithiin 1,1,4,4-tetraoxide |
| dimethylarsinic | dimethylarsinic acid |
| dinitramine | $N^3,N^3$-diethyl-2,4-dinitro-6-(tri-fluoromethyl)-1,3-benzenediamine |
| dinoseb | 2-(1-methylpropyl)-4,6-dinitrophenol |
| dinoterb | 2-(1,1-dimethylethyl)-4,6-dinitro-phenol |
| diphenamid | N,N-dimethyl-α-phenylbenzene-acetamide |
| dipropetryn | 6-(ethylthio)-N,N'-bis(1-methyl-ethyl)-1,3,5-triazine-2,4-diamine |
| diquat | 6,7-dihydrodipyrido[1,2-a:2',1'-c]-pyrazinediium ion |
| diuron | N'-(3,4-dichlorophenyl)-N,N-dimethylurea |
| DNOC | 2-methyl-4,6-dinitrophenol |
| DPX-V9360 | 2-[[(4,6-dimethoxypyrimidin-2-yl)-aminocarbonyl]aminosulfonyl]-N,N-dimethyl 3-pyridinecarboxamide |
| DSMA | disodium salt of MAA |
| dymron | N-(4-methylphenyl)-N'-(1-methyl-1-phenylethyl)urea |
| eglinazine-ethyl | N-[4-chloro-6-(ethylamino)-1,3,5-triazin-2-yl]glycine ethyl ester |
| endothall | 7-oxabicyclo[2.2.1]heptane-2,3-dicarboxylic acid |
| EPTC | S-ethyl dipropylcarbamothioate |
| ethalfluralin | N-ethyl-N-(2-methyl-2-propenyl)-2,6-dinitro-4-(trifluoromethyl)-benzenamine |
| ethidimuron | N-[5-(ethylsulfonyl)-1,3,4-thia-diazol-2-yl]-N,N'-dimethylurea |
| *ethofumesate | (+)-2-ethoxy-2,3-dihydro-3,3-dimethyl-5-benzofuranyl methanesulfonate |
| fenac | 2,3,6-trichlorobenzeneacetic acid |
| *fenoprop | (+)-2-(2,4,5-trichlorophenoxy)-propanoic acid |
| *fenoxaprop | (+)-2-[4-[(6-chloro-2-benzoxazolyl)-oxy]phenoxy]propanoic acid |
| fenuron | N,N-dimethyl-N'-phenylurea |
| fenuron TCA | Salt of fenuron and TCA |
| flamprop-M-isopropyl | 1-methylethyl N-benzoyl-N-(3-chloro-4-fluorophenyl)-D-alanine |
| flamprop-methyl | methyl N-benzoyl-N-(3-chloro-4-fluorophenyl)-DL-alaninate |
| *fluazifop | (+)-2-[4-[[5-(trifluoromethyl)-2-pyridinyl]oxy]phenoxy]propanoic acid |
| fluazifop-P | (R)-2-[4-[[5-(trifluoromethyl)-2-pyridinyl]oxy]phenoxy]propanoic acid |
| fluchloralin | N-(2-chloroethyl)-2,6-dinitro-N-propyl-4-(trifluoromethyl)benzen-amine |
| fluometuron | N,N-dimethyl-N'-[3-(trifluoro-methyl)phenyl]urea |
| fluralin | N-butyl-N-ethyl-2,6-dinitro-4-(trifluoromethyl)benzenamine |
| fluorodifen | p-nitrophenyl α,α,α-trifluoro-2-nitro-p-tolyl ether |
| fluoroglycofen | carboxymethyl 5-[2-chloro-4-(tri-fluoromethyl)phenoxy]-2-nitro-benzoate |

| Common Name | Chemical Name |
|---|---|
| flurecol-butyl | butyl 9-hydroxy-9H-fluorene-9-carboxylate |
| fluridone | 1-methyl-3-phenyl-5-[3-(trifluoromethyl)phenyl]-4(1H)-pyridinone |
| flurochloridone | 3-chloro-4-(chloromethyl)-1-[3-(trifluoromethyl)phenyl]-2-pyrrolidinone |
| fluroxypyr | [(4-amino-3,5-dichloro-6-fluoro-2-pyridinyl)oxy]acetic acid |
| fomesafen | 5-[2-chloro-4-(trifluoromethyl)phenoxy]-N-(methylsulfonyl)-2-nitrobenzamide |
| fosamineammonium | ethyl hydrogen (aminocarbonyl)phosphonate ammonium ethyl |
| glufosinate-ammonium | ammonium 2-amino-4-(hydroxymethylphosphinyl)butanoate |
| glyphosate | N-(phosphonomethyl)glycine |
| haloxyfop | 2-[4-[[3-chloro-5-(trifluoromethyl)-2-pyridinyl]oxy]phenoxy]propanoic acid |
| hexaflurate | potassium hexafluoroarsenate |
| hexazinone | 3-cyclohexyl-6-(dimethylamino)-1-methyl-1,3,5-triazine-2,4(1H,3H)-dione |
| imazamethabenz | 6-(4-isopropyl-4-methyl-5-oxo-2-imidazolin-2-yl)-m-toluic acid, methyl ester and 6-(4-isopropyl-4-methyl-5-oxo-2-imidazolin-2-yl)-p-toluic acid, methyl ester |
| imazapyr | (+)-2-[4,5-dihydro-4-methyl-4-(1-methylethyl)-5-oxo-1H-imidazol-2-yl]-3-pyridinecarboxylic acid |
| imazaquin | 2-[4,5-dihydro-4-methyl-4-(1-methylethyl)-5-oxo-1H-imidazol-2-yl]-3-quinolinecarboxylic acid |
| imazethapyr | (+)-2-[4,5-dihydro-4-methyl-4-(1-methylethyl)-5-oxo-1H-imidazol-2-yl]-5-ethyl-3-pyridinecarboxylic acid |
| ioxynil | 4-hydroxy-3,5-diiodobenzonitrile |
| isocarbamid | N-(2-methylpropyl)-2-oxo-1-imidazolidinecarboxamide |
| isopropalin | 4-(1-methylethyl)-2,6-dinitro-N,N-dipropylbenzenamine |
| isoproturon | N-(4-isopropylphenyl)-N',N'-dimethyl urea |
| isouron | N'-[5-(1,1-dimethylethyl)-3-isoxazolyl]-N,N-dimethylurea |
| isoxaben | N-[3-(1-ethyl-1-methylpropyl)-5-isoxazolyl]-2,6-dimethoxybenzamide |
| karbutilate | 3-[[(dimethylamino)carbonyl]amino]phenyl-(1,1-dimethylethyl)carbamate |
| lactofen | (+)-2-ethoxy-1-methyl-2-oxoethyl 5-[2-chloro-4-(trifluoromethyl)phenoxy]-2-nitrobenzoate |
| lenacil | 3-cyclohexyl-6,7-dihydro-1H-cyclopentapyrimidine-2,4(3H,5H)-dione |
| linuron | N'-(3,4-dichlorophenyl)-N-methoxy-N-methylurea |
| MAA | methylarsonic acid |
| MAMA | monoammonium salt of MAA |
| MCPA | (4-chloro-2-methylphenoxy)acetic acid |
| MCPA-thioethyl | S-ethyl (4-chloro-2-methylphenoxy)ethanethioate |
| MCPB | 4-(4-chloro-2-methylphenoxy)butanoic acid |
| mecoprop | (+)-2-(4-chloro-2-methylphenoxy)propanoic acid |
| mefenacet | 2-(2-benzothiazolyloxy)-N-methyl-N-phenyl acetamide |
| mefluidide | N-[2,4-dimethyl-5-[[(trifluoromethyl)sulfonyl]amino]phenyl]-acetamide |
| metamitron | 4-amino-3-methyl-6-phenyl-1,2,4-triazin-5(4H)-one |
| metazachlor | 2-chloro-N-(2,6-dimethylphenyl)-N-(1(H)-pyrazol-1-ylmethyl)acetamide |
| methabenz-thiazuron | 1,3-dimethyl-3-(2-benzothiazolyl)urea |

| Common Name | Chemical Name |
|---|---|
| methalpropalin | N-(2-methyl-2-propenyl)-2,6-dinitro-N-propyl-4-(trifluoromethyl)benzenamide |
| metham | methylcarbamodithioic acid |
| methazole | 2-(3,4-dichlorophenyl)-4-methyl-1,2,4-oxadiazolidine-3,5-dione |
| methoxuron | N'-(3-chloro-4-methoxyphenyl)-N,N-dimethylurea |
| methoxyphenone | (4-methoxy-3-methylphenyl)(3-methylphenyl)methanone |
| methyldymron | N-methyl-N'-(1-methyl-1-phenylethyl)-N-phenylurea |
| metobromuron | N'-(4-bromophenyl)-N-methoxy-N-methylurea |
| metolachlor | 2-chloro-N-(2-ethyl-6-methylphenyl)-N-(2-methoxy-1-methylethyl)-acetamide |
| metoxuron | N'-(3-chloro-4-methoxyphenyl)-N,N-dimethylurea |
| metribuzin | 4-amino-6-(1,1-dimethylethyl)-3-(methylthio)-1,2,4-triazin-5(4H)-one |
| metsulfuron methyl | 2-[[[[(4-methoxy-6-methyl-1,3,5-triazin-2-yl)amino]carbonyl]-amino]sulfonyl]benzoic acid, methyl ester |
| MH | 1,2-dihydro-3,6-pyridazinedione |
| molinate | S-ethyl hexahydro-1H-azepine-1-carbothioate |
| monalide | N-(4-chlorophenyl)-2,2-dimethylpentanamide |
| monolinuron | 3-(p-chlorophenyl)-1-methoxy-1-methylurea |
| monuron | N'-(4-chlorophenyl)-N,N-dimethylurea |
| MSMA | monosodium salt of MAA |
| naproanilide | 2-(2-naphthalenyloxy)-N-phenylpropanamide |
| napropamide | N,N-diethyl-2-(1-naphthalenyloxy)-propanamide |
| naptalam | 2-[(1-naphthalenylamino)carbonyl]-benzoic acid |
| neburon | 1-butyl-3-(3,4-dichlorophenyl)-1-methylurea |
| nitralin | 4-methylsulfonyl-2,6-dinitro-N,N-dipropylaniline |
| nitrofen | 2,4-dichloro-1-(4-nitrophenoxy)-benzene |
| nitrofluorfen | 2-chloro-1-(4-nitrophenoxy)-4-(trifluoromethyl)benzene |
| norea | N,N-dimethyl-N'-(octahydro-4,7-methano-1H-inden-5-yl)urea 3aα,4α,5α,7α,7aα-isomer |
| norflurazon | 4-chloro-5-(methylamino)-2-[3-(trifluoromethyl)phenyl]-3(2H)-pyridazinone |
| orbencarb | S-[2-(chlorophenyl)methyl] diethylcarbamothioate |
| oryzalin | 4-(dipropylamino)-3,5-dinitro-benzenesulfonamide |
| oxadiazon | 3-[2,4-dichloro-5-(1-methylethoxy)-phenyl]-5-(1,1-dimethylethyl)-1,3,4-oxadiazol-2(3H)-one |
| oxyfluorfen | 2-chloro-1-(3-ethoxy-4-nitrophenoxy)-4-(trifluoromethyl)-benzene |
| paraquat | 1,1'-dimethyl-4,4'-dipyridinium ion |
| pebulate | S-propyl butylethylcarbamothioate |
| pendimethalin | N-(1-ethylpropyl)-3,4-dimethyl-2,6-dinitrobenzenamine |
| perfluidone | 1,1,1-trifluoro-N-[2-methyl-4-(phenylsulfonyl)phenyl]methane-sulfonamide |
| phenisopham | 3-[[(1-methylethoxy)carbonyl]amino]-phenyl ethylphenylcarbamate |
| phenmedipham | 3-[(methoxycarbonyl)amino]phenyl (3-methylphenyl)carbamate |
| picloram | 4-amino-3,5,6-trichloro-2-pyridine-carboxylic acid |
| piperophos | S-[2-(2-methyl-1-piperidinyl)-2-oxoethyl]O,O-dipropyl phosphorodithioate |

-continued

| Common Name | Chemical Name |
|---|---|
| pretilachlor | 2-chloro-N-(2,6-diethylphenyl)-N-(2-propoxyethyl)acetamide |
| procyazine | 2-[[4-chloro-6-(cyclopropylamino)-1,3,5-triazine-2-yl]amino]-2-methylpropanenitrile |
| prodiamine | 2,4-dinitro-$N^3$,$N^3$-dipropyl-6-(trifluoromethyl)-1,3-benzenediamine |
| profluralin | N-(cyclopropylmethyl)-2,6-dinitro-N-propyl-4-(trifluoromethyl)benzenamine |
| proglinazine-ethyl | N-[4-chloro-6-[(1-methylethyl)-amino]-1,3,5-triazin-2-yl]glycine ethyl ester |
| prometon | 6-methoxy-N,N'-bis(1-methylethyl)-1,3,5-triazine-2,4-diamine |
| prometryn | N,N'-bis(1-methylethyl)-6-(methylthio)-1,3,5-triazine-2,4-diamine |
| pronamide | 3,5-dichloro-N-(1,1-dimethyl-2-propynyl)benzamide |
| propachlor | 2-chloro-N-(1-methylethyl)-N-phenyl-acetamide |
| propanil | N-(3,4-dichlorophenyl)propanamide |
| propaquizafop | 2-[[(1-methylethylidene)amino]oxy]-ethyl 2-[4-[(6-chloro-2-quinoxalinyl)oxy]phenoxy]propanoate |
| propazine | 6-chloro-N,N'-bis(1-methylethyl)-1,3,5-triazine-2,4-diamine |
| propham | 1-methylethyl phenylcarbamate |
| propyzamide | 3,5-dichloro-N-(1,1-dimethyl-2-propynyl)benzamide |
| prosulfalin | N-[[4-(dipropylamino)-3,5-dinitrophenyl]sulfonyl]-S,S-dimethyl-sulfilimine |
| prosulfocarb | S-benzyldipropylthiocarbamate |
| prynachlor | 2-chloro-N-(1-methyl-2-propynyl)-acetanilide |
| pyrazon | 5-amino-4-chloro-2-phenyl-3(2H)-pyridazinone |
| pyrazosulfuron-ethyl | ethyl 5-[[[[(4,6-dimethoxy-2-pyrimidinyl)amino]carbonyl]amino]-sulfonyl]-1-methyl-1H-pyrazole-4-carboxylate |
| pyrazoxyfen | 2-[[4-(2,4-dichlorobenzoyl)-1,3-dimethyl-1H-pyrazol-5-yl]oxy]-1-phenylethanone |
| pyridate | O-(6-chloro-3-phenyl-4-pyridazinyl) S-octyl carbonothioate |
| quizalofop ethyl | (+)-2-[4-[(6-chloro-2-quinoxalinyl)-oxy]phenoxy]propanoic acid, ethyl ester |
| secbumeton | N-ethyl-6-methoxy-N'-(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexen-1-one |
| siduron | N-(2-methylcyclohexyl)-N'-phenylurea |
| simazine | 6-chloro-N,N'-diethyl-1,3,5-triazine-2,4-diamine |
| simetryn | N,N'-diethyl-6-(methylthio)-1,3,5-triazine-2,4-diamine |
| sodium chlorate | sodium chlorate |
| sodium monochloroacetate | chloroacetic acid, sodium salt |
| sulfometuron methyl | 2-[[[[(4,6-dimethyl-2-pyrimidinyl)-amino]carbonyl]amino]sulfonyl]-benzoic acid, methyl ester |
| 2,4,5-T | (2,4,5-trichlorophenoxy)acetic acid |
| 2,3,6-TBA | 2,3,6-trichlorobenzoic acid |
| TCA | trichloroacetic acid |
| tebutam | 2,2-dimethyl-N-(1-methylethyl)-N-(phenylmethyl)propanamide |
| tebuthiuron | N-[5-(1,1-dimethylethyl)-1,3,4-thiadiazol-2-yl]-N,N'-dimethylurea |
| terbacil | 5-chloro-3-(1,1-dimethylethyl)-6-methyl-2,4(1H,3H)-pyrimidinedione |
| terbuchlor | N-(butoxymethyl)-2-chloro-N-[2-(1,1-dimethylethyl)-6-methylphenyl]-acetamide |
| terbumeton | N-(1,1-dimethylethyl)-N'-ethyl-6-methoxy-1,3,5-triazine-2,4-diamine |
| terbuthylazine | 2-(tert-butylamino)-4-chloro-6-(ethylamino)-s-triazine |
| terbutol | 2,6-di-tert-butyl-p-tolyl methylcarbamate |
| terbutryn | N-(1,1-dimethylethyl)-N'-ethyl-6-(methylthio)-1,3,5-triazine-2,4-diamine |
| thifensulfuron | 3-[[[[(4-methoxy-6-methyl-1,3,5,-triazin-2-yl)amino]carbonyl]-amino]sulfonyl]-2-thiophene-carboxylic acid, methyl ester |
| thiameturon-methyl | methyl 3-[[[[(4-methoxy-6-methyl-1,3,5-triazin-2-yl)amino]-carbonyl]amino]sulfonyl]2-thiophenecarboxylate |
| thiazafluron | N,N'-dimethyl-N-[5-(trifluoromethyl)-1,3,4-thiadiazol-2-yl]urea |
| thiobencarb | S-[(4-chlorophenyl)methyl] diethyl-carbamothioate |
| tiocarbazil | S-(phenylmethyl) bis(1-methylpropyl)carbamothioate |
| tralkoxydim | 2-[1-(ethoxyimino)propyl]-3-hydroxy-5-(2,4,6-trimethylphenyl)-2-cyclohexen-1-one |
| triallate | S-(2,3,3-trichloro-2-propenyl) bis(1-methylethyl)carbamothioate |
| triasulfuron | 2-(2-chloroethoxy)-N-[[(4-methoxy-6-methyl-1,3,5-triazin-2-yl)amino]-carbonyl]benzenesulfonamide |
| tribenuron methyl | 2-[[[[N-(4-methoxy-6-methyl-1,3,5-triazine-2-yl)-N-methylamino]-carbonyl]amino]sulfonyl]benzoic acid, methyl ester |
| triclopyr | [(3,5,6-trichloro-2-pyridinyl)oxy]-acetic acid |
| *tridiphane | (+)2-(3,5-dichlorophenyl)-2-(2,2,2-trichloroethyl)oxirane |
| trietazine | 6-chloro-N,N,N'-triethyl-1,3,5-triazine-2,4-diamine |
| trifluralin | 2,6-dinitro-N,N-dipropyl-4-(trifluoromethyl)benzenamine |
| trimeturon | 1-(p-chlorophenyl)-2,3,3-trimethyl-pseudourea |
| 2,4-D | (2,4-dichlorophenoxy)acetic acid |
| 2,4-DB | 4-(2,4-dichlorophenoxy)butanoic acid |
| vernolate | S-propyl dipropylcarbamothioate |
| xylachlor | 2-chloro-N-(2,3-dimethylphenyl)-N-(1-methylethyl)acetamide |

TABLE OF CHEMICAL STRUCTURES

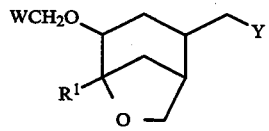

III

| Cmpd | $R^1$ | Y | W | Physicochemical/Spectra data ($\delta$ in CDCl$_3$) |
|---|---|---|---|---|

-continued

| # | | | | |
|---|---|---|---|---|
| 1 | Et | SMe | Ph | wax, NMR: 7.3m(5H), 4.65d(1H), 4.40d(1H), 3.87d(1H), 3.80dd(2H), 3.36dd(1H), 2.45m(3H), 2.26dt(1H), 2.10s(3H), 1.97dq(1H), 1.83dd(1H), 1.80m(1H), 1.61m(1H), 1.42d(1H), 1.30dt(1H), 0.82t(3H) |
| 2 | Et | SMe | (2-F)Ph | oil, NMR: 7.42t(1H), 7.24m(1H), 7.10t(1H), 7.00t(1H), 4.70d(1H), 4.46d(1H), 3.80(2H), 3.39dd(1H), 2.45d(2H), 2.42–2.2m(2H), 2.11s(3H), 2.0–1.2m, 0.82t(3H) |
| 3 | Et | SMe | (2,6-F$_2$)Ph | m.p. 62–64° C. |
| 4 | Et | SMe | (2-Cl)Ph | oil, NMR: 7.52dd(1H), 7.26m(3H), 4.78d(1H), 4.45d(1H), 3.88d(1H), 3.81dd(1H), 3.42dd(1H), 2.46d(2H), 2.4m(1H), 2.31dt(1H), 2.11s(3H), 2.1–1.2m, 0.85t(3H) |
| 5 | Et | SMe | (2-Cl, 6-F)Ph | m.p. 52–54° C. |
| 6 | Et | SMe | 2,6-Cl$_2$)Ph | m.p. 72–74° |
| 7 | Et | S(O)Me | Ph | oil, NMR: 7.31br(5H), 4.61dd(1H), 4.40dd(1H), 3.86m(2H), 3.38m(1H), 2.8–1.2m, 2.60 and 2.59s(3H), 0.82t(3H) |
| 8 | Me | CN | Ph | m.p. 70–72° C. |
| 9 | Me | CN | (2-F)Ph | m.p. 86–88° C. |
| 10 | Et | S(O)Me | (2-F)Ph | wax, NMR: 7.4t(1H), 7.23m(1H), 7.10d(1H), 7.01t(1H), 4.69dd(1H), 4.47dd(1H), 3.86m(2H), 3.40m(1H), 2.8–1.3m, 2.60 and 2.61s(3H), 0.82t(3H) |
| 11 | Me | SMe | Ph | oil, NMR: 7.32m(5H), 4.65d(1H), 4.45d(1H), 3.82d(2H), 3.22dd(1H), 2.41d(2H), 2.20dt(1H), 2.09s(3H), 1.8dd(1H), 1.8m(2H), 1.49d(1H), 1.37s(3H), 1.3m(1H) |
| 12 | Me | S(O)Me | (2-F)Ph | oil, NMR: 7.4t(1H), 7.27m(1H), 7.10t(1H), 7.01t(1H), 4.70dd(1H), 4.50dd(1H), 3.89m(2H), 3.25m(1H), 2.8–1.3m, 2.60 and 2.59s(3H), 1.36s(3H) |
| 13 | Me | S(O)Me | (2,6-F$_2$)Ph | wax, NMR: 7.25m(1H), 6.85m(2H), 4.7dd(1H), 4.5dd(1H), 3.85m(2H), 3.25m(1H), 2.8–1.2m, 2.60 and 2.59s(3H), 1.30s(3H) |
| 14 | Me | S(O)Me | (2-Cl)Ph | oil, NMR: 7.5m(1H), 7.24m(3H), 4.7dd(1H), 4.55dd(1H), 3.88m(2H), 3.31m(1H), 1.8–1.3m, 2.60 and 2.59s(3H), 1.40s(3H) |
| 15 | Me | S(O)Me | (2-Cl,6-F)Ph | m.p. 137–140° C. |
| 16 | Me | Br | Ph | m.p. 99–100° C. |
| 17 | Me | CN | (2,6-F$_2$)Ph | m.p. 96–98° C. |
| 18 | Me | CN | (2-Cl,6-F)Ph | m.p. 95–97° C. |
| 19 | Me | CN | (2-Cl)Ph | m.p. 81–83° C. |
| 20 | Me | CN | (2,6-Cl$_2$)Ph | m.p. 110–112° C. |
| 21 | Me | CN | (2-Me)Ph | m.p. 75–77° C. |
| 22 | Me | SCN | Ph | oil, NMR: 7.35m(5H), 4.65d(1H), 4.50dd(1H), 3.8m(2H), 3.25m(1H), 2.87m(2H), 2.49m(1H), 2.2m(1H), 2.1–1.8m, 1.49d(1H), 1.38s(3H), 1.26m |
| 23 | Me | −N(triazole) | Ph | oil, NMR: 8.01 s(1H), 7.96s(1H), 7.31m(5H), 4.60d(1H), 4.41d(1H), 4.08m(2H), 3.90m(2H), 3.22dd(1H), 2.25m(1H), 2.10m(1H), 2.0–1.75m(3H), 1.49m(1H), 1.37s(3H) |
| 24 | Me | I | Ph | m.p. 61.62° C. |
| 25 | Et | CN | Ph | m.p. 70–72° C. |
| 26 | Et | CN | (2,6-F$_2$)Ph | m.p. 108–110° C. |
| 27 | Et | CN | (2-F)Ph | m.p. 85–87° C. |
| 28 | Et | I | (2-F)Ph | m.p. 59–61° C. |
| 29 | Me | SH | Ph | oil, NMR: 7.32m(5H), 4.62d(1H), 4.42d(1H), 3.8m(2H), 3.2m(1H), 2.8m(1H), 2.6m(1H), 2.4m(2H), 2.2–1.1m, 1.37s(3H) |
| 30 | Me | CH=CH$_2$ | Ph | oil, NMR: 7.34m(5H), 5.75m(1H), |

-continued

| | | | | |
|---|---|---|---|---|
| | | | | 5.00d(2H), 4.64m(1H), 4.45d(1H), 3.85m(2H), 3.2dd(1H), 2.2m(1H), 2.0m(4H), 1.8m(1H), 1.6m(1H), 1.5m(1H), 1.36s(3H), 1.25m(1H), |
| 31 | Et | I | (2,6-F$_2$)Ph | m.p. 88–90° C. |
| 32 | Et | I | (2-Cl,6-F)Ph | m.p. 92–94° C. |
| 33 | Et | I | (2-Me)Ph | m.p. 91–93° C. |
| 34 | Et | I | (2-F)Ph | m.p. 43–45° C. |
| 35 | Et | I | (2,6-F$_2$)Ph | m.p. 99–101 C. |
| 36 | Et | I | (2-Cl,6-F)Ph | m.p. 95–97° C. |
| 37 | Et | I | Ph | m.p. 75–77° C. |
| 38 | Me | CN | (2,4-F$_2$)Ph | m.p. 60–62° C. |
| 39 | Me | Br | (2,6-F2)Ph | m.p. 107–109° C. |
| 40 | Me | Br | (2-F)Ph | m.p. 72–74° C. |
| 41 | Me | Br | (2-Cl,6-F)Ph | m.p. 68–70° C. |
| 42 | Me | Br | (2-Me)Ph | m.p. 74–76° C. |
| 43 | Me | CN | (2-Br)Ph | m.p. 88–90° C. |
| 44 | Me | I | (2-Br)Ph | m.p. 88–90° C. |
| 45 | Me | Br | (2-Cl)Ph | m.p. 78–80° C. |
| 46 | Et | CN | (2-Cl,6-F)Ph | m.p. 102–104° C. |
| 47 | Et | CN | (2-Cl)Ph | m.p. 59–61° C. |
| 48 | Me | I | (2,4-F$_2$)Ph | m.p. 42–45° C. |
| 49 | Me | CN | (2,4,6-Me$_3$)Ph | m.p. 120–122° C. |
| 50 | Me | I | (2,4,6-Me$_3$)Ph | m.p. 101–103° C. |
| 51 | Me | I | (2-Cl)Ph | m.p. 55–57° C. |
| 52 | Et | CN | (2-Me)Ph | m.p. 58–60° C. |
| 53 | Me | H | Ph | oil, NMR: 7.33m(5H), 4.62d(1H), 4.45d(1H), 3.87d(1H), 3.80dd(1H), 3.20dd(1H), 2.1–1.95m(2H), 1.79dd(1H), 1.65m(1H), 1.50d(1H), 1.36s(3H), 1.25dd(1H), 0.91d(3H) |
| 54 | Me | CN | (2-CN)Ph | m.p. 125–127° C. |
| 55 | Et | Me | Ph | oil, NMR: 7.31m(5H), 4.63dd(1H), 4.40d(1H), 3.85dd(1H), 3.78dd(1H), 3.34dd(1H), 2.2–1.2m, 0.89t(3H), 0.82t(3H) |
| 56 | Me | Me | Ph | oil, NMR: 7.33m(5H), 4.63d(1H), 4.45d(1H), 3.84m(2H), 3.20dd(1H), 2.20m(1H), 2.10m(1H), 1.80dd(1H), 1.45d(1H), 1.36s(3H), 1.20m(4H), 0.89t(3H) |
| 57 | Et | H | Ph | oil, NMR: 7.33m(5H), 4.62d(1H), 4.40d(1H), 3.89d(1H), 3.78dd(1H), 3.35dd(1H), 2.1–1.2m, 0.93d(3H), 0.82t(3H) |
| 58 | Et | CH=CH$_2$ | Ph | oil, NMR: 7.33m(5H), 5.78m(1H), 5.01m(2H), 4.63d(1H), 4.40d(1H), 3.90d(1H), 3.80d(1H), 3.35dd(1H), 2.2–1.2m, 0.82t(3H) |
| 59 | Me | CN | 2-(pyridyl) | m.p. 113–117° C. |
| 60 | Me | H | (2-F)Ph | oil, NMR: 7.45t(1H), 7.26m(1H), 7.11t(1H), 7.01t(1H), 4.66d(1H), 4.52d(1H), 3.88d(1H), 3.81dd(1H), 3.23dd(1H), 2.06m(2H), 1.80dd(1H), 1.72m(1H), 1.53d(1H), 1.34s(3H), 1.22m(1H), 0.93d(3H) |
| 61 | Me | H | (2,6-F$_2$)Ph | oil, NMR: 7.25m(1H), 6.90m(2H), 4.70d(1H), 4.52d(1H), 3.85d(1H), 3.80dd(1H), 3.2dd(1H), 2.06m(2H), 1.8m(2H), 1.52d(1H), 1.27s(3H), 1.27m(1H), 0.92d(3H) |
| 62 | Me | H | (2-Cl, 6-F)Ph | oil, NMR: 7.20m(2H), 6.98m(1H), 4.78d(1H), 4.60dd(1H), 3.85d(1H), 3.80dd(1H), 3.20dd(1H), 2.1m(2H), 1.8dd(1H), 1.72m(1H), 1.51d(1H), 1.29s(3H), 1.25m(1H), 0.93d(3H) |
| 63 | Me | N3 | Ph | oil, NMR: 7.32m(5H), 4.62d(1H), 4.48d(1H), 3.84m(2H), 3.20m(3H), 2.39m(1H), 2.10dt(1H), 1.82m(2H), 1.52d(1H), 1.37s(3H), 1.30dd(1H), |
| 64 | Et | H | (2-F)Ph | oil, NMR: 7.42t(1H), 7.23m(1H), 7.11t(1H), 6.99t(1H), 4.70d(1H), 4.45d(1H), 3.89d(1H), 3.79dd(1H), 3.39dd(1H), 2.1m(2H), 2.0–1.2m, 0.8t(3H), |

-continued

| Cmpd | R¹ | Z | W | Physicochemical/Spectra data ($\delta$ in CDCl$_3$) |
|---|---|---|---|---|
| 65 | Et | H | (2-Cl,6-F)Ph | 0.93d(3H)<br>oil, NMR: 7.20m(2H), 6.99m(1H), 4.75dd(1H), 4.55dd(1H), 3.87d(1H), 3.78dd(1H), 3.32dd(1H), 2.10dt(1H), 2.08m(1H), 2.10–1.2m, 0.94d(3H) |

| Cmpd | R¹ | Z | W | Physicochemical/Spectra data ($\delta$ in CDCl$_3$) |
|---|---|---|---|---|
| 66 | Et | H | (2,6-F$_2$)Ph | oil, NMR: 7.26m(1H), 6.88m(2H), 4.70d(1H), 4.48d(1H), 3.87d(1H), 3.78dd(1H), 3.35dd(1H), 2.18dt(1H), 2.09m(1H), 2.0–1.2m, 0.75t(3H), 0.94d(3H) |
| 70 | Et | N3 | Ph | oil, NMR: 7.33m(5H), 4.62d(1H), 4.40d(1H), 3.84m(2H), 3.39dd(1H), 3.20m(2H), 2.39m(1H), 2.11dt(1H), 2.0–1.1m, 0.87t(3H) |
| 71 | Me | N3 | (2,6-F$_2$)Ph | oil, NMR: 7.26m(1H), 6.85m(2H), 4.69d(1H), 4.52d(1H), 3.82m(2H), 3.20m(3H), 2.39m(1H), 2.12dt(1H), 1.88m(2H), 1.54d(1H), 1.29s(3H), 1.28m(1H) |

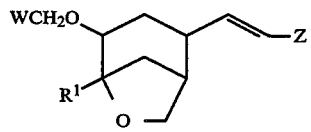

III

| Cmpd | R¹ | Z | W | Physicochemical/Spectra data ($\delta$ in CDCl$_3$) |
|---|---|---|---|---|
| 67 | Et | CO$_2$CH$_2$CH$_3$ | Ph | oil, NMR: 7.32m(5H), 6.89d(1H), 5.80dd(1H), 4.63d(1H), 4.44d(1H), 4.20q(2H), 3.80m(2H), 3.40dd(1H), 2.42m(1H), 2.39m(1H), 2.19dt(1H), 2.0–1.2m, 1.29t(3H), 0.84t(3H) |
| 68 | Me | H(exo) | Ph | oil, NMR: 7.34m(5H), 5.80m(1H), 5.01m(2H), 4.62d(1H), 4.48d(1H), 4.02dd(1H), 3.82d(1H), 3.26dd(1H), 2.55m(1H), 2.32m(1H), 2.09dd(1H), 1.8m(1H), 1.35s(3H) |
| 69 | Me | H(endo) | Ph | oil, NMR: 7.34m(5H), 5.79m(1H), 5.02m(2H), 4.65d(1H), 4.45d(1H), 3.82m(2H), 3.25dd(1H), 2.45m, 2.09dt(1H), 1.8dd(1H), 1.5m, 1.37s(3H) |
| 72 | Et | H | Ph | oil, NMR: 7.34m(5H), 6.80m(1H), 5.02m(2H), 4.65d(1H), 4.01d(1H), 3.89d(1H), 3.80dd(1H), 3.39dd(1H), 2.3–1.2m |
| 83 | Me | C(O)CH$_3$ | Ph | m.p. 58–60° C. |
| 84 | Me | CO$_2$CH$_3$ | Ph | oil, NMR: 7.3m(5H), 6.90dd(1H), 5.80d(1H), 4.65d(1H), 4.51d(1H), 3.84m(2H), 3.74s(3H), 3.29dd(1H), 2.45m(1H), 2.35m(1H), 2.1dt(1H), 1.85dd(1H), 1.6m, 1.38s(3H) |
| 85 | Et | CO$_2$CH$_3$ | Ph | oil, NMR: 7.3m(5H), 6.90dd(1H), 5.81d(1H), 4.83d(1H), 4.41d(1H), 3.8m(2H), 3.74s(3H), 3.30dd(1H), 2.42–1.2m |
| 86 | Me | CO$_2$CH$_2$CH$_3$ | Ph | oil, NMR: 7.33m(5H), 6.88dd(1H), 5.80dd(1H), 4.63d(1H), 4.50d(1H), 4.20q(2H), 3.84m(2H), 3.26dd(1H), 2.42m(1H), 2.19m(1H), 2.10dt(1H), 1.85dd(1H), 1.6m, 2.38s(3H), 1.26t(3H) |

Mixtures of

-continued

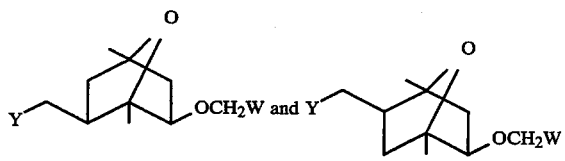

I

| Cmpd | Y | W | Physicochemical/Spectra data (δ in CDCl₃) |
|---|---|---|---|
| 73 | CN | Ph | oil, 1:1 mix, NMR: 7.32m(5H), 4.55d and d(1H), 4.40d and d(1H), 3.51m(1H), 2.42ddd(1H), 2.10m(2H), 1.89dd(1H), 1.65m(1H), 1.22m, 1.50s and 1.49s(3H), 1.42s and 1.43s(3H) |
| 74 | CN | (2-F)Ph | oil, 1:1 mix, NMR: 7.41m(1H), 7.28m(1H), 7.11t(1H), 7.01t(1H), 4.56dd and dd(1H), 4.45dd and dd(1H), 3.56m(1H), 2.43ddd(1H), 2.2m(1H), 2.01m(2H), 1.19dd(1H), 1.61m(1H), 1.50s and 1.49s(3H), 1.42s and 1.41s(3H), 1.29dd(1H) |
| 75 | CN | (2,6-F₂)Ph | oil, 1.5 mix, NMR: 7.29m(1H), 6.88m(2H), 4.59d(1H), 4.49d(1H), 3.55m(1H), 2.41dd(1H), 2.2dd(1H), 2.05m(1H), 1.90dd(1H), 1.62dd(1H), 1.28dd(1H), 1.42s(3H), 1.40s(3H) |
| 79 | SO₂CH₃ | Ph | oil, 1:1 mix, NMR: 7.31m(5H), 4.52d(1H), 4.40d and d(1H), 3.59m(1H), 3.20m(1H), 2.92m(1H), 2.88s and 2.89s(3H), 2.25m(1H), 2.10m(2H), 1.90dd(1H), 1.6m, 1.49s and 1.50s(3H), 1.40s(3H) |
| 80 | SCH₃ | (2,6-F₂)Ph | oil, 1:1 mix, NMR: 7.22m(1H), 6.86t(2H), 4.59d(1H), 4.49d(1H), 3.51m(1H), 2.77m(1H), 2.23m(1H), 2.07s(3H), 1.85-1.2m, 1.47s and 1.40s(3H), 1.39s and 1.35s(3H) |
| 81 | SO₂CH₃ | (2-F)Ph | m.p. 101–103° C., 1:1 mix |
| 82 | SO₂CH₃ | (2,6-F₂)Ph | oil, 1:1 mix, NMR: 7.31m(1H), 6.88m(2H), 4.59d(1H), 4.48d and d(1H), 3.59m(1H), 3.2m(1H), 2.95m(1H), 2.92s and 2.91s(3H), 2.29m(1H), 2.15m(1H), 2.06 and 1.95dd(1H), 1.7m, 1.48s and 1.42s(3H), 1.40s and 1.33s(3H) |

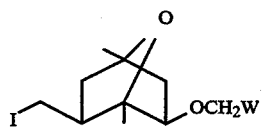

I

| Cmpd | W | Physicochemical/Spectra data (δ in CDCl₃) |
|---|---|---|
| 76 | Ph | oil, NMR: 7.31m(5H), 4.52d(1H), 4.39d(1H), 3.50dd(1H), 3.41dd(1H), 2.91dd(1H), 2.1-1.8m(3H), 1.6m(1H), 1.18m(1H), 1.49s(3H), 1.42s(3H) |
| 77 | (2-F)Ph | oil, NMR: 7.36t(1H), 7.19m(1H), 7.04t(1H), 6.85t(1H), 4.48d(1H), 4.40d(1H), 3.41dd(1H), 3.38dd(1H), 2.86dd(1H), 2.05-1.8m(3H), 1.5m(1H), 1.1m(1H), 1.41s(3H), 1.33s(3H) |
| 78 | (2,6-F₂)Ph | oil, NMR: 7.02m(1H), 6.80m(2H), 4.50d(1H), 4.40d(1H), 3.41dd(1H), 3.38dd(1H), 2.58dd(1H), 205-1.8m(3H), 1.5dd(1H), 1.08m(1H), 1.41s(3H), 1.26s(3H) |

TEST A

Seeds of barley (*Hordeum vulgara*), barnyardgrass (*Echinochloa crus-galli*), bedstraw (*Galium aparine*), blackgrass (*Aloperurus myosuroides*), cheatgrass (*Bromus secalinus*), chickweed (*Stellaria media*), cocklebur (*Xanthium pensylvanicum*), corn (*Zea mays*), cotton (*Gossypium hirsutum*), crabgrass (Digitaria spp.), giant foxtail (*Setaria faberii*), lambsquarters (*Chenopodium album*), morningglory (*Ipomoea hederacea*), rape (*Brassica napus*), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), wild buckwheat (*Polygonum convolvulus*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table A, are based on a scale of 0 to 10 where 0 is no effect and 10 is complete control. A dash (-) response means no test result.

TABLE A

| Rate (200 g/ha) | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
|---|---|---|---|---|---|---|---|---|---|---|---|---|---|---|---|---|---|---|---|---|---|---|---|---|---|---|---|
| | | | | | | | | | | | | | | POSTEMERGENCE | | | | | | | | | | | | | |
| Barley | 0 | 0 | 0 | 0 | 0 | 0 | 0 | 2 | 9 | 0 | 0 | 0 | 5 | 0 | 3 | 0 | 8 | 4 | 0 | 0 | 0 | 0 | 0 | 0 | 5 | 8 | 8 |
| Barnyardgrass | 7 | 9 | 4 | 0 | 3 | 0 | 6 | 3 | 9 | 6 | 7 | 9 | 9 | 5 | 9 | 9 | 10 | 9 | 9 | 7 | 9 | 3 | 9 | 9 | 10 | 10 | 9 |
| Bedstraw | 0 | 0 | 0 | 0 | 0 | 0 | 0 | 3 | 4 | 0 | 3 | 2 | 2 | 3 | 5 | 2 | 3 | 2 | 1 | 0 | 3 | 0 | 5 | 0 | 4 | 2 | 6 |
| Blackgrass | 0 | 1 | 2 | 0 | 0 | 0 | 1 | 4 | 6 | 0 | 0 | 0 | 6 | 2 | 4 | 3 | 8 | 8 | 7 | 0 | 3 | 0 | 2 | 3 | 8 | 9 | 9 |
| Cheatgrass | 0 | 2 | 0 | 0 | 0 | 0 | 2 | 5 | 3 | 2 | 0 | 2 | 2 | 1 | 3 | 0 | 6 | 4 | 2 | 0 | 0 | 0 | 0 | 0 | 7 | 8 | 8 |
| Chickweed | 0 | 2 | 0 | 0 | 3 | 0 | 3 | 5 | 3 | 1 | 9 | 3 | 7 | 8 | 7 | 0 | 5 | 0 | 0 | 0 | 0 | 0 | 0 | 0 | 5 | 5 | 6 |
| Cocklebur | — | — | — | — | — | — | — | — | — | — | — | — | — | — | — | — | — | — | — | — | — | 5 | 2 | 2 | — | — | — |
| Corn | 5 | 7 | 4 | 3 | 2 | 0 | 3 | 3 | 9 | 4 | 2 | 5 | 7 | 3 | 5 | 1 | 7 | 0 | 6 | 1 | 1 | 0 | 2 | 0 | 5 | 9 | 2 |
| Cotton | 1 | 10 | 0 | 3 | 2 | 2 | 4 | 0 | 2 | 2 | 8 | 3 | 4 | 0 | — | 0 | 2 | 1 | 0 | 1 | 0 | 2 | 2 | 0 | 8 | 1 | 0 |
| Crabgrass | 2 | 3 | 6 | 0 | 0 | 0 | 0 | 0 | 8 | 5 | 0 | 1 | 0 | 0 | 0 | 4 | 8 | 5 | 1 | 1 | 1 | 0 | 2 | 7 | 9 | 9 | 9 |
| Giant foxtail | 5 | 7 | 7 | 3 | 0 | 0 | 0 | 5 | 9 | 0 | 3 | 3 | 4 | 0 | 2 | 8 | 9 | 8 | 7 | 6 | 5 | 0 | 6 | 1 | 9 | 9 | 9 |
| Lambsquarters | 4 | 4 | 2 | 2 | 4 | 0 | 0 | 2 | 4 | 0 | 5 | 1 | 4 | 3 | 7 | 6 | 2 | 4 | 5 | 0 | 2 | 4 | 7 | 7 | 8 | 7 | 7 |
| Morningglory | 0 | 0 | 1 | 1 | 0 | 0 | 1 | 0 | 1 | 0 | 1 | 5 | 0 | 0 | 1 | 0 | 1 | 0 | 1 | 0 | 0 | 1 | 7 | 0 | 3 | 4 | 0 |
| Nutsedge | 0 | 0 | 0 | 0 | 0 | 0 | 0 | 0 | 9 | 0 | 0 | 0 | — | 0 | — | 0 | — | — | — | 0 | 0 | 7 | 0 | 0 | 9 | — | 0 |
| Rape | 0 | 0 | 1 | 0 | 0 | 0 | 0 | 2 | 5 | 0 | 0 | 0 | 0 | 0 | 0 | 5 | 0 | 0 | 1 | 0 | 0 | 2 | 0 | 1 | 1 | 1 | 1 |
| Rice | 3 | 3 | 9 | 0 | 2 | 2 | 0 | 4 | 9 | 0 | 0 | 2 | — | — | — | 0 | 9 | 2 | 0 | 2 | 0 | 1 | 2 | 0 | 9 | 9 | 7 |
| Sorghum | 0 | 0 | 0 | 0 | 0 | 0 | 0 | 2 | 1 | 0 | — | 0 | 3 | 0 | 2 | 0 | 3 | 1 | 0 | 0 | 0 | 0 | 0 | 0 | 4 | 2 | 2 |
| Soybean | 6 | 6 | 6 | 3 | 2 | 1 | 5 | 5 | 6 | 6 | 5 | 8 | 7 | 5 | 3 | 0 | 7 | 7 | 8 | 8 | 2 | 5 | 6 | 1 | 9 | 8 | 8 |
| Sugar beet | 3 | 0 | 2 | 1 | 1 | 0 | 0 | 4 | 6 | 2 | 2 | 5 | 5 | 2 | 3 | 1 | 5 | 1 | 4 | 2 | 2 | 2 | 4 | 2 | 5 | 7 | 7 |
| Velvetleaf | 6 | 8 | 8 | 3 | 2 | 2 | 2 | 0 | 5 | 3 | 3 | 2 | 2 | 0 | 3 | 0 | 5 | 5 | 1 | 5 | 2 | 1 | 5 | 3 | 3 | 6 | 5 |
| Wheat | 1 | 0 | 0 | 0 | 0 | 0 | 0 | 2 | 9 | 1 | 0 | 0 | 2 | 0 | 2 | 0 | 7 | 3 | 2 | 0 | 0 | 0 | 0 | 0 | 6 | 0 | 0 |
| Wild buckwheat | 1 | — | 0 | 0 | 0 | 0 | 3 | 7 | 3 | 2 | 8 | 3 | 2 | 2 | 2 | 6 | 5 | 3 | 3 | 0 | 0 | 8 | 2 | 9 | 6 | 7 | 7 |
| Wild oat | 0 | 0 | 0 | 0 | 0 | 0 | 0 | 4 | 6 | 2 | 0 | 0 | 0 | 0 | 0 | 0 | 5 | 0 | 0 | 0 | 0 | 0 | 0 | 0 | 7 | 7 | 7 |

| Rate (200 g/ha) | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 |
|---|---|---|---|---|---|---|---|---|---|---|---|---|---|---|---|---|---|---|---|---|---|---|---|---|---|---|---|
| | | | | | | | | | | | | | | POSTEMERGENCE | | | | | | | | | | | | | |
| Barley | 0 | 0 | 2 | 2 | 0 | 0 | 2 | 2 | 0 | 1 | 7 | 0 | 0 | 0 | 0 | 3 | 0 | 0 | 1 | 4 | 0 | 0 | 0 | 0 | 2 | 0 |
| Barnyardgrass | 9 | 0 | 9 | 9 | 9 | 9 | 9 | 9 | 8 | 8 | 6 | 9 | 9 | 5 | 9 | 9 | 0 | 3 | 8 | 8 | 0 | 0 | 3 | 9 | 9 | 0 |
| Bedstraw | 0 | 0 | 2 | 0 | 0 | 0 | 2 | 0 | 0 | 1 | 0 | 2 | 0 | 0 | 2 | 0 | 0 | 0 | 3 | 2 | 0 | 0 | 0 | 2 | 2 | 0 |
| Blackgrass | 3 | 0 | 9 | 6 | 2 | 4 | 5 | 5 | 2 | — | 8 | 9 | 9 | 5 | 3 | 5 | 2 | 3 | 8 | 8 | 2 | 0 | 3 | 3 | 9 | 0 |
| Cheatgrass | 0 | 0 | 2 | 1 | 0 | 0 | 0 | 1 | 0 | 0 | 5 | 3 | 3 | 2 | 1 | 3 | 2 | 0 | 7 | 1 | 0 | 0 | 1 | 3 | 2 | 0 |
| Chickweed | 0 | 0 | 0 | 0 | 0 | 2 | 0 | 0 | 0 | 0 | 5 | 0 | 0 | 0 | 0 | 5 | 0 | 0 | 3 | 2 | 0 | 0 | 0 | 4 | 2 | 0 |
| Cocklebur | — | — | — | — | — | — | — | — | — | — | 1 | 1 | 1 | 1 | 1 | 3 | 3 | 2 | 3 | 1 | 1 | 0 | 0 | 1 | 2 | 1 | 0 |
| Corn | 1 | 0 | 5 | 1 | 1 | 1 | 0 | 1 | 1 | 1 | 1 | 2 | 5 | 0 | 1 | 2 | 0 | 0 | 3 | 0 | 0 | 0 | 0 | 7 | 7 | 0 |
| Cotton | 0 | 3 | 0 | 0 | 3 | 0 | 7 | 4 | 3 | 6 | 0 | 0 | 0 | 0 | 0 | 0 | 0 | 0 | 1 | 5 | 0 | 0 | 2 | 0 | 0 | 2 |
| Crabgrass | 3 | 2 | 8 | 9 | — | 0 | 3 | 1 | 2 | 2 | 6 | 9 | 5 | 0 | 3 | 4 | 0 | 0 | 8 | 7 | 3 | 0 | 0 | 0 | 9 | 0 |
| Giant foxtail | 0 | 0 | 2 | 3 | 0 | 0 | 1 | 3 | 0 | 0 | 2 | 3 | 5 | 0 | 2 | 3 | 0 | 0 | 6 | 3 | 0 | 0 | 0 | 9 | 5 | 0 |
| Lambsquarters | 9 | — | 8 | 5 | 5 | — | — | — | 8 | — | 7 | — | — | — | — | 9 | 7 | 5 | — | 2 | 3 | 0 | 0 | 8 | 5 | 7 | 0 |
| Morningglory | 0 | 2 | 0 | 2 | 0 | 0 | 0 | 0 | 1 | 0 | 0 | 0 | 0 | 0 | 0 | 0 | 0 | 0 | 0 | 0 | 0 | 0 | 0 | 0 | 1 | 0 |
| Nutsedge | 0 | 0 | — | 0 | 0 | 0 | 0 | 0 | 0 | — | 0 | 0 | 0 | 0 | 0 | 0 | — | 0 | 0 | 0 | 0 | — | 0 | 0 | — | — | 0 |
| Rape | 0 | 0 | 1 | 3 | 3 | 1 | 5 | 1 | 3 | 1 | 0 | 2 | 2 | 2 | 0 | 0 | 0 | 3 | 2 | 1 | 0 | 0 | 3 | 0 | 0 | 0 |
| Rice | 0 | 0 | 3 | 0 | 1 | 2 | 0 | 0 | 2 | 0 | 9 | 4 | 1 | 3 | 3 | 2 | 0 | 2 | 2 | 7 | 0 | 0 | 0 | 6 | 0 | 0 |
| Sorghum | 0 | 0 | 0 | 2 | 0 | 1 | 1 | 0 | 0 | 0 | 0 | 0 | 0 | 0 | 0 | 0 | 0 | 1 | 1 | 0 | 0 | 0 | 0 | 0 | 0 | 0 |
| Soybean | 2 | 2 | 6 | 2 | 2 | 3 | 2 | 3 | 4 | 2 | 4 | 4 | 3 | 1 | 3 | 4 | 3 | 2 | 6 | 8 | 0 | 0 | 0 | 2 | 3 | 1 | 3 |
| Sugar beet | 0 | 0 | 4 | 5 | 1 | 0 | 4 | 6 | 4 | 1 | 2 | 0 | 2 | 2 | 0 | 0 | 0 | 0 | 7 | 6 | 6 | 0 | 0 | 2 | 0 | 5 | 0 |
| Velvetleaf | 4 | 1 | 3 | 4 | 0 | 0 | 3 | 5 | 7 | 2 | 0 | 0 | 0 | 0 | 0 | 5 | 0 | 1 | 7 | 1 | 5 | 0 | 0 | 3 | 3 | 2 | 1 |
| Wheat | 0 | 0 | 0 | 2 | 0 | 0 | 0 | 0 | 0 | 0 | 2 | 0 | 0 | 0 | 0 | 0 | 0 | 0 | 3 | 2 | 0 | 0 | 0 | 7 | 0 | 3 | 0 |
| Wild buckwheat | 5 | — | 10 | 2 | 5 | — | — | 5 | 0 | 9 | 7 | 0 | 5 | 0 | 0 | 3 | 2 | 0 | 2 | 1 | 2 | 0 | 0 | 7 | 0 | 2 | 0 |
| Wild oat | 0 | 0 | 0 | 0 | 0 | 0 | 0 | 0 | 0 | 0 | 5 | 0 | 0 | 0 | 0 | 2 | 0 | 0 | 1 | 0 | 0 | 0 | 0 | 0 | 0 | 0 |

| Rate (200 g/ha) | 55 | 56 | 57 | 58 | 59 | 60 | 61 | 62 | 63 | 64 | 65 | 66 | 67 | 73 | 74 | 75 | 76 | 77 | 78 | 79 | 80 | 81 | 82 | 84 | 85 | 86 |
|---|---|---|---|---|---|---|---|---|---|---|---|---|---|---|---|---|---|---|---|---|---|---|---|---|---|---|
| | | | | | | | | | | POSTEMERGENCE | | | | | | | | | | | | | | | | |
| Barley | 0 | 0 | 0 | 0 | 0 | 3 | 3 | 0 | 0 | 0 | 0 | 2 | 8 | 0 | 0 | 3 | 0 | 0 | 0 | 0 | 0 | 0 | 0 | 7 | 0 | 6 |
| Barnyardgrass | 5 | 7 | 9 | 7 | 0 | 9 | 9 | 9 | 9 | 9 | 9 | 2 | 5 | 9 | 0 | 0 | 0 | 0 | 0 | 0 | 0 | 0 | 5 | 5 | 7 |
| Bedstraw | 4 | 2 | 2 | 2 | 0 | 0 | 2 | 0 | 2 | 0 | 0 | 0 | 0 | 0 | 0 | 2 | 0 | 0 | 0 | 0 | 0 | 0 | 0 | 0 | 0 | 0 |
| Blackgrass | 7 | 9 | 9 | 0 | 0 | 6 | 7 | 2 | 9 | 4 | 2 | 6 | 0 | 1 | 0 | 3 | 0 | 0 | 1 | 0 | 0 | 0 | 0 | 2 | 0 | 2 |
| Cheatgrass | 2 | 3 | 3 | 0 | 0 | 2 | 2 | 0 | 3 | 3 | 0 | 0 | 2 | 0 | 0 | 3 | 0 | 0 | 0 | 0 | 0 | 0 | 0 | 0 | 0 | 0 |
| Chickweed | 2 | 6 | 0 | 0 | 0 | 0 | 2 | 0 | 7 | 0 | 0 | 0 | 0 | 2 | 0 | 5 | 0 | 0 | 0 | — | 0 | — | 0 | 0 | 8 |

TABLE A-continued

| | | | | | | | | | | | | | | | | | | | | | | | | | | | |
|---|---|---|---|---|---|---|---|---|---|---|---|---|---|---|---|---|---|---|---|---|---|---|---|---|---|---|---|
| Cocklebur | 1 | 1 | 4 | 1 | 2 | 1 | 1 | 0 | 1 | 1 | 0 | 0 | 3 | 1 | 1 | 4 | 0 | 0 | 0 | 0 | 1 | 1 | 1 | 1 | 2 | 0 | |
| Corn | 0 | 0 | 0 | 0 | 0 | 4 | 9 | 5 | 2 | 5 | 0 | 4 | 0 | 0 | 4 | 3 | 0 | 0 | 0 | 0 | 0 | 0 | 0 | 0 | 0 | 0 | |
| Cotton | 0 | 0 | 0 | 10 | 3 | 3 | 0 | 0 | 3 | 0 | 0 | 0 | 2 | 2 | 4 | 4 | 0 | 0 | 0 | 6 | 0 | 0 | 0 | 0 | 3 | 0 | |
| Crabgrass | 0 | 0 | 5 | 2 | 0 | 8 | 9 | 7 | 3 | 3 | 2 | — | 0 | 0 | 1 | 2 | 0 | 0 | 0 | 0 | 0 | 0 | 0 | 3 | 2 | 0 | |
| Giant foxtail | 2 | 3 | 0 | 0 | 0 | 6 | 7 | 5 | 5 | 2 | 0 | 1 | 0 | 0 | 2 | 3 | 0 | 0 | 0 | 0 | 0 | 0 | 0 | 0 | 0 | 0 | |
| Lambsquarters | 7 | 7 | 5 | 5 | 5 | 4 | 4 | 3 | 9 | 0 | 0 | 2 | — | 0 | 0 | 0 | 0 | 0 | 0 | 2 | 0 | 0 | 0 | 0 | 5 | 5 | |
| Morningglory | 0 | 0 | 0 | 0 | 0 | 0 | 0 | 0 | 1 | 0 | 0 | 0 | 0 | 3 | 4 | 6 | 0 | 0 | 0 | 0 | 0 | 0 | 0 | 0 | 0 | 0 | |
| Nutsedge | 0 | 0 | 0 | 0 | 0 | 8 | 9 | 0 | — | 4 | 0 | 0 | 2 | — | 0 | 0 | 0 | 0 | 0 | 0 | 0 | 0 | 0 | 0 | 0 | — | |
| Rape | 0 | 1 | 0 | 0 | 0 | 2 | 2 | 3 | 1 | 0 | 0 | 0 | 1 | 0 | 0 | 0 | 0 | 0 | 0 | 0 | 0 | 0 | 0 | 0 | 0 | 0 | |
| Rice | 0 | 0 | 0 | 0 | 0 | 2 | 8 | 2 | 8 | 0 | 2 | 7 | 2 | 0 | 0 | 2 | 0 | 0 | 0 | 0 | 0 | 0 | 0 | 5 | 0 | 0 | |
| Sorghum | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 0 | |
| Soybean | 4 | 2 | 3 | 7 | 5 | 2 | 0 | 2 | 6 | 1 | 0 | 0 | 1 | 2 | 3 | 5 | 0 | 0 | 0 | 0 | 0 | 0 | 0 | 0 | 0 | 0 | |
| Sugar beet | 2 | 4 | 4 | 2 | 0 | 7 | 4 | 2 | 5 | 0 | 0 | 0 | 0 | 2 | 0 | 2 | 0 | 0 | 0 | 0 | 0 | 0 | 0 | 0 | 0 | 0 | |
| Velvetleaf | 1 | 2 | 4 | 7 | 0 | 2 | 6 | 6 | 2 | 8 | 5 | 6 | 4 | 4 | 4 | 7 | 0 | 1 | 0 | 0 | 1 | 0 | 0 | 3 | 0 | 0 | |
| Wheat | 0 | 0 | 2 | 0 | 0 | 4 | 4 | 0 | 2 | 0 | 0 | 0 | 5 | 0 | 0 | 0 | 0 | 0 | 0 | 4 | 0 | 0 | 0 | 0 | 0 | 0 | |
| Wild buckwheat | 3 | 5 | — | — | — | — | — | — | — | — | — | — | 1 | 0 | — | — | — | — | — | — | 0 | 0 | 0 | 4 | 0 | 0 | |
| Wild oat | 0 | 0 | 3 | 3 | 2 | 2 | 0 | 3 | 0 | 0 | 0 | 0 | 3 | 0 | 0 | 0 | 0 | 0 | 0 | 0 | 0 | 0 | 0 | 0 | 0 | 0 | |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate (50 g/ha) | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | |
| | POSTEMERGENCE | | | | | | | | | | | | | | | | | | | | | | | | | | | |
| Barley | 0 | 0 | 0 | 0 | 0 | 0 | 0 | 0 | 2 | 0 | 0 | 0 | 2 | 0 | 0 | 0 | 6 | 0 | 0 | 0 | 0 | 0 | 0 | 0 | 0 | 0 | 0 | |
| Barnyardgrass | 2 | 0 | 0 | 0 | 0 | 0 | 0 | 0 | 3 | 2 | 2 | 1 | 0 | 0 | 0 | 2 | 9 | 3 | 6 | 2 | 1 | 0 | 0 | 6 | 8 | 9 | 9 | |
| Bedstraw | 0 | 0 | 0 | 0 | 0 | 0 | 0 | 0 | 0 | 0 | 0 | 1 | 0 | 1 | 2 | 0 | 1 | 0 | 1 | 0 | 0 | 0 | 0 | 0 | 2 | 1 | 5 | |
| Blackgrass | 0 | 0 | 0 | 0 | 0 | 0 | 0 | 0 | 0 | 0 | 0 | 0 | 2 | 1 | 1 | 0 | 2 | 0 | 3 | 0 | 0 | 0 | 0 | 2 | 2 | 7 | 5 | |
| Cheatgrass | 0 | 0 | 0 | 0 | 0 | 0 | 0 | 2 | 2 | 0 | 0 | 0 | 2 | 0 | 0 | 2 | 2 | 0 | 0 | 0 | 0 | 0 | 0 | 0 | 0 | 2 | 3 | |
| Chickweed | 0 | 0 | 0 | 0 | 0 | 0 | 0 | 0 | 0 | 0 | 2 | 0 | 5 | 3 | 1 | 0 | 0 | 0 | 0 | 0 | 0 | 0 | — | 0 | 1 | 3 | 4 | |
| Cocklebur | — | — | — | — | — | — | — | — | — | — | — | — | — | — | — | — | — | — | — | — | — | 1 | 1 | — | — | — | — | |
| Corn | 0 | 1 | 1 | 0 | 0 | 0 | 2 | 3 | 3 | 0 | 0 | 0 | 2 | 0 | 0 | 0 | 7 | 3 | 1 | 0 | 0 | 0 | 0 | 0 | 3 | 0 | 0 | |
| Cotton | 0 | 2 | 0 | 0 | 0 | 0 | — | 0 | — | 0 | 1 | 0 | 6 | 0 | 1 | 0 | 0 | 0 | 0 | 0 | 0 | 0 | 0 | 0 | 7 | 0 | 0 | |
| Crabgrass | 0 | 0 | 2 | 0 | 0 | 0 | 0 | 0 | 1 | 0 | 0 | 0 | 0 | 0 | 0 | 0 | 5 | 1 | 0 | 0 | 0 | 0 | 0 | 0 | 4 | 8 | 6 | |
| Giant foxtail | 0 | 0 | 0 | 0 | 0 | 0 | 0 | 0 | 2 | 0 | 0 | 0 | 0 | 0 | 0 | 2 | 7 | 3 | 0 | 0 | 1 | 0 | 0 | 0 | 4 | 7 | 7 | |
| Lambsquarters | 0 | 0 | 0 | 0 | 0 | 0 | 0 | — | 2 | 0 | 3 | 0 | 0 | 0 | 2 | 4 | — | — | 0 | 0 | 0 | 3 | 0 | 3 | 5 | 5 | 3 | |
| Morningglory | 0 | 0 | 0 | 0 | 0 | 0 | 0 | 0 | 1 | 0 | 0 | 0 | 1 | 0 | 0 | 0 | 0 | 0 | 0 | 0 | 0 | 0 | 0 | 0 | 2 | 0 | 0 | |
| Nutsedge | — | — | 0 | 0 | 0 | 0 | 0 | 0 | 0 | 0 | 0 | — | 0 | 0 | 0 | 0 | 0 | 0 | 0 | 0 | — | 0 | — | — | 0 | 3 | 0 | |
| Rape | 0 | 0 | 0 | 0 | 0 | 0 | 0 | 0 | 0 | 0 | 0 | 0 | 0 | 0 | 0 | 4 | 0 | 0 | 0 | 0 | 0 | 0 | 0 | 0 | 0 | 0 | 0 | |
| Rice | 0 | 0 | 0 | 0 | 0 | 0 | 0 | 0 | 2 | 0 | — | 0 | — | — | — | 0 | 0 | 0 | 0 | 0 | 0 | 0 | 0 | 0 | 2 | 3 | 7 | |
| Sorghum | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | |
| Soybean | 2 | 1 | 2 | 0 | 2 | 0 | 4 | 3 | 6 | 0 | 2 | 4 | 2 | 0 | 2 | 0 | 7 | 3 | 4 | 1 | 0 | 2 | 5 | 1 | 8 | 5 | 6 | |
| Sugar beet | 0 | 0 | 0 | 0 | 0 | 0 | 0 | 4 | 2 | 0 | 0 | 1 | 0 | 0 | 0 | 2 | 2 | 0 | 1 | 0 | 0 | 0 | 2 | 2 | 3 | 3 | 4 | |
| Velvetleaf | 3 | 2 | 1 | 0 | 0 | 2 | 1 | 0 | 2 | 1 | 2 | 0 | 1 | 0 | 0 | 0 | 2 | 2 | 1 | 1 | 2 | 1 | 2 | 2 | 2 | 3 | 2 | |
| Wheat | 0 | 0 | 0 | 0 | 0 | 0 | 0 | 0 | 2 | 0 | 0 | 0 | 1 | 0 | 0 | 0 | 2 | 0 | 0 | 0 | 0 | 0 | 0 | 0 | 0 | 5 | 2 | |
| Wild buckwheat | 0 | 0 | 0 | 0 | 0 | 0 | 0 | 0 | 0 | 1 | 5 | 2 | 0 | 0 | 0 | 2 | 2 | 0 | 2 | 0 | 0 | 7 | 2 | 6 | 3 | 2 | 3 | |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate (50 g/ha) | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | |
| | POSTEMERGENCE | | | | | | | | | | | | | | | | | | | | | | | | | | | |
| Barley | 0 | 0 | 0 | 0 | 0 | 0 | 0 | 0 | 0 | 0 | 3 | 0 | 0 | 0 | 0 | 2 | 0 | 0 | 0 | 0 | 0 | 0 | 0 | 0 | 0 | 0 | 0 | |
| Barnyardgrass | 7 | 0 | 7 | 7 | 5 | 6 | 5 | 5 | 4 | 4 | 2 | 4 | 2 | 0 | 2 | 0 | 0 | 0 | 0 | 0 | 0 | 0 | 0 | 5 | 5 | 0 | | |
| Bedstraw | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 | | |
| Blackgrass | 0 | 0 | 3 | 1 | 0 | 2 | 0 | 2 | 2 | 2 | 5 | 2 | 0 | 0 | 3 | 0 | 2 | 0 | 0 | 0 | 0 | 0 | 0 | 3 | 3 | 0 | | |
| Cheatgrass | 0 | 0 | 0 | 0 | 0 | 0 | 0 | 0 | 0 | 0 | 2 | 0 | 0 | 0 | 2 | 0 | 0 | 0 | 0 | 0 | 0 | 0 | 0 | 0 | 0 | 0 | | |
| Chickweed | 0 | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | | |
| Cocklebur | — | — | — | — | — | — | — | — | — | — | 1 | 1 | 1 | 1 | 0 | 2 | 1 | 0 | 1 | 1 | 1 | 0 | 0 | 0 | 1 | 0 | | |
| Corn | 0 | 0 | 0 | 0 | 0 | 0 | 0 | 0 | 1 | 1 | 0 | 0 | 2 | 0 | 0 | 0 | 0 | 0 | 0 | 0 | 0 | 0 | 0 | 1 | 0 | 0 | | |
| Cotton | 0 | 2 | 0 | 0 | 0 | 0 | 6 | 2 | 0 | 0 | 0 | 0 | 0 | 0 | 0 | 0 | 0 | 0 | 0 | 0 | 0 | 0 | 0 | 0 | 0 | 0 | | |
| Crabgrass | 0 | 0 | 0 | 3 | 0 | 0 | 0 | 0 | 2 | 0 | 5 | 0 | 2 | 0 | 0 | 2 | 0 | 3 | 0 | 0 | 0 | 0 | 0 | 1 | 4 | 0 | | |
| Giant foxtail | 0 | 0 | 2 | 0 | 0 | 0 | 0 | 0 | 0 | 0 | 2 | 0 | 1 | 0 | 0 | 0 | 0 | 0 | 0 | 0 | 0 | 0 | 0 | 3 | 1 | 0 | | |
| Lambsquarters | — | 0 | 3 | 8 | 0 | — | — | 0 | 0 | — | — | 3 | 5 | 3 | 0 | — | — | — | 0 | 0 | 0 | 0 | 2 | 1 | 1 | 0 | | |
| Morningglory | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 0 | | |
| Nutsedge | 0 | 0 | 0 | — | — | 0 | 0 | 0 | 0 | 0 | 0 | 0 | — | — | 0 | 0 | 0 | 0 | 0 | 0 | 0 | 0 | — | 0 | — | 0 | | |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | | |
| Rice | 0 | 0 | 0 | 0 | 0 | 0 | 0 | 0 | 0 | 0 | 1 | 2 | 0 | 2 | 2 | 0 | 1 | 0 | 0 | 0 | 0 | 0 | 0 | 1 | 0 | 0 | | |
| Sorghum | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | | |
| Soybean | 2 | 1 | 2 | 2 | 2 | 2 | 2 | 2 | 3 | 2 | 1 | 1 | 1 | 1 | 0 | 3 | 0 | 1 | 1 | 2 | 0 | 0 | 0 | 2 | 0 | 3 | | |
| Sugar beet | 0 | 0 | 1 | 0 | 0 | 0 | 0 | 3 | 0 | 0 | 0 | 0 | 0 | 0 | 0 | 0 | 0 | 0 | 0 | 0 | 0 | 0 | 0 | 0 | 0 | 0 | | |
| Velvetleaf | 0 | 0 | 1 | 0 | 0 | 0 | 0 | 1 | 0 | 0 | 0 | 0 | 0 | 0 | 0 | 2 | 0 | 4 | 0 | 0 | 0 | 0 | 0 | 2 | 1 | 0 | | |
| Wheat | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | | |
| Wild buckwheat | 0 | 0 | 3 | 0 | 0 | 0 | — | 0 | 0 | 8 | 2 | 0 | 0 | 0 | 0 | 0 | 0 | 0 | 0 | 0 | 0 | 0 | 2 | 0 | 0 | 0 | | |
| Wild oat | 0 | 0 | 0 | 0 | 0 | 0 | 0 | 0 | 0 | 0 | 1 | 0 | 0 | 0 | 0 | 2 | 0 | 0 | 0 | 0 | 0 | 0 | 0 | 0 | 0 | 0 | | |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate (50 g/ha) | | 55 | 56 | 57 | 58 | 59 | 60 | 61 | 62 | 63 | 64 | 65 | 66 | 67 | 73 | 74 | 75 | 76 | 77 | 78 | 79 | 80 | 81 | 82 | 84 | 85 | 86 | |
| | POSTEMERGENCE | | | | | | | | | | | | | | | | | | | | | | | | | | | |
| Barley | | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | |
| Barnyardgrass | | 1 | 1 | 3 | 1 | 0 | 8 | 9 | 9 | 3 | 3 | 1 | 6 | 0 | 0 | 1 | 2 | 0 | 0 | 0 | 0 | 0 | 0 | 0 | 0 | 2 | 0 | |
| Bedstraw | | 0 | 0 | 0 | 0 | 0 | 0 | 0 | 0 | 0 | 0 | 0 | 0 | 0 | 0 | 1 | 0 | 0 | 0 | 0 | 0 | 0 | 0 | 0 | 0 | 0 | 1 | |
| Blackgrass | | 2 | 3 | 7 | 0 | 0 | 5 | 2 | 0 | 0 | 2 | 0 | 0 | 0 | 0 | 0 | 1 | 0 | 0 | 0 | 0 | 0 | 0 | 0 | 0 | 0 | — | |
| Cheatgrass | | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | |
| Chickweed | | 0 | 0 | 0 | 0 | 0 | 0 | 0 | 0 | 0 | 0 | 0 | 0 | 0 | 0 | 0 | 5 | 0 | 0 | 0 | 0 | — | 0 | 0 | 0 | 0 | — | |

TABLE A-continued

| | | | | | | | | | | | | | | | | | | | | | | | | | |
|---|---|---|---|---|---|---|---|---|---|---|---|---|---|---|---|---|---|---|---|---|---|---|---|---|---|
| Cocklebur | 1 | 1 | 2 | 0 | 0 | 0 | 0 | 0 | 0 | 0 | 0 | 0 | 0 | 1 | 1 | 1 | 0 | 0 | 0 | 1 | 0 | 0 | 1 | 0 | 1 | 0 |
| Corn | 0 | 0 | 0 | 0 | 0 | 0 | 2 | 0 | 2 | 3 | 0 | 3 | 0 | 0 | 0 | 0 | 0 | 0 | 0 | 0 | 0 | 0 | 0 | 0 | 0 | 0 |
| Cotton | 0 | 0 | 0 | 0 | 2 | 2 | 0 | 0 | 2 | 0 | 0 | 0 | 2 | 0 | 2 | 0 | 0 | 0 | 0 | 0 | 0 | 0 | 0 | 0 | 0 | 0 |
| Crabgrass | 0 | 0 | 0 | 0 | 0 | 7 | 0 | 0 | 0 | 0 | 2 | 2 | 0 | 0 | 1 | 1 | 0 | 0 | 0 | 0 | 0 | 0 | 0 | 0 | 0 | 0 |
| Giant foxtail | 0 | 0 | 0 | 0 | 0 | 1 | 0 | 0 | 0 | 0 | 0 | 0 | 0 | 0 | 1 | 1 | 0 | 0 | 0 | 0 | 0 | 0 | 0 | 0 | 0 | 0 |
| Lambsquarters | 2 | 2 | 0 | 0 | 2 | 2 | 0 | 2 | 5 | — | 0 | — | — | 0 | 0 | 0 | 0 | 0 | 0 | 0 | 0 | 0 | 0 | 0 | 4 | 0 |
| Morningglory | 0 | 0 | 0 | 0 | 0 | 0 | 0 | 0 | 0 | 0 | 0 | 0 | 0 | 0 | 1 | 0 | 0 | 0 | 0 | 0 | 0 | 0 | 0 | 0 | 0 | 0 |
| Nutsedge | 0 | 0 | — | 0 | 0 | 0 | — | 0 | 0 | 0 | 0 | 0 | 0 | 0 | — | 0 | 0 | 0 | 0 | 0 | 0 | 0 | 0 | 0 | 0 | 0 |
| Rape | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 2 | 0 | 0 | 4 | 0 | 0 | 0 | 0 | 0 | 0 | 0 | 0 | 0 | 0 | 0 | 0 | 0 | 0 |
| Sorghum | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Soybean | 2 | 1 | 0 | 0 | 3 | 1 | 0 | 0 | 3 | 0 | 0 | 0 | 0 | 0 | 1 | 1 | 2 | 0 | 0 | 0 | 0 | 0 | 0 | 0 | 0 | 0 |
| Sugar beet | 0 | 0 | 4 | 0 | 0 | 4 | 0 | 0 | 0 | 0 | 0 | 0 | 0 | 0 | 0 | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 | 3 | 0 | 0 | 2 | 4 | 0 | 0 | 0 | 0 | 0 | 0 | 0 | 0 | 0 | 0 |
| Wheat | 0 | 0 | 0 | 0 | 0 | 2 | 2 | 0 | 0 | 0 | 0 | 0 | 0 | 0 | 0 | 0 | 0 | 0 | 0 | 2 | 0 | 0 | 0 | 0 | 0 | 0 |
| Wild buckwheat | 0 | 2 | — | — | — | — | — | — | — | — | — | — | — | 0 | 0 | 0 | — | — | — | 0 | 0 | 0 | 0 | 0 | 0 | — |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | | | | | |
|---|---|---|---|---|---|---|---|---|---|---|---|---|---|---|---|---|---|---|---|---|---|---|---|---|---|---|---|
| Rate (200 g/ha) | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
| | PREEMERGENCE | | | | | | | | | | | | | | | | | | | | | | | | | | |
| Barley | 2 | 0 | 0 | 0 | 0 | 0 | 0 | 0 | 2 | 0 | 0 | 0 | 1 | 0 | 0 | 1 | 0 | 1 | 0 | 0 | 1 | 0 | 0 | 0 | 2 | 1 | 4 |
| Barnyardgrass | 10 | 10 | 10 | 9 | 9 | 2 | 9 | 10 | 10 | 10 | 10 | 10 | 10 | 9 | 9 | 10 | 10 | 10 | 10 | 10 | 10 | 9 | 10 | 10 | 10 | 10 | 10 |
| Bedstraw | 0 | 3 | 0 | 1 | 0 | 0 | 2 | 6 | 7 | 2 | 3 | 7 | 0 | 0 | 1 | — | 8 | 5 | 7 | 2 | 3 | 0 | 0 | 0 | 7 | 8 | 8 |
| Blackgrass | 5 | 6 | 8 | 0 | 3 | 2 | 2 | 7 | 9 | 5 | 9 | 6 | 9 | 0 | 6 | 6 | 10 | 9 | 8 | 5 | 9 | 1 | 8 | 10 | 10 | 9 | 9 |
| Cheatgrass | 8 | 8 | 8 | 5 | 6 | 2 | 6 | 6 | 9 | 5 | 6 | 5 | 5 | 2 | 5 | 7 | 8 | 8 | 7 | 5 | 5 | 2 | 6 | 6 | 10 | 8 | 8 |
| Chickweed | 6 | 7 | 7 | 7 | 6 | 7 | 7 | 9 | 9 | 6 | 7 | 8 | — | 7 | 8 | 5 | 6 | — | 7 | 5 | 5 | 9 | 1 | 2 | 7 | 8 | 7 |
| Cocklebur | — | — | — | — | — | — | — | — | — | — | — | — | — | — | — | 0 | 5 | 3 | 2 | 4 | 2 | 0 | — | 0 | — | — | — |
| Corn | 7 | 9 | 8 | 4 | 6 | 0 | 3 | 7 | 6 | 3 | 5 | 3 | 7 | 0 | 3 | 2 | 9 | 9 | 2 | 1 | 2 | 2 | 0 | 2 | 2 | 8 | 2 |
| Cotton | 2 | 0 | 0 | 3 | 3 | 0 | 0 | 0 | 2 | 1 | 0 | 1 | 5 | 0 | 0 | 2 | 6 | 6 | 3 | 8 | 3 | 0 | 0 | 0 | 0 | 7 | 6 |
| Crabgrass | 10 | 10 | 10 | 10 | 10 | 6 | 10 | 9 | 10 | 10 | 9 | 9 | 10 | 9 | 10 | 10 | 10 | 10 | 10 | 9 | 9 | 10 | 10 | 10 | 10 | 10 | 10 |
| Giant foxtail | 10 | 10 | 9 | 9 | 8 | 3 | 8 | 10 | 10 | 10 | 10 | 9 | 10 | 7 | 7 | 10 | 10 | 10 | 10 | 10 | 9 | 10 | 9 | 10 | 10 | 10 | 10 |
| Lambsquarters | 8 | 8 | 9 | 5 | 9 | 3 | 6 | 9 | 9 | 9 | 9 | 9 | 8 | 5 | 7 | 8 | 9 | 9 | — | 8 | 8 | 8 | 4 | 3 | — | 8 | 5 |
| Morningglory | 0 | 0 | 0 | 0 | 0 | 0 | 0 | 2 | 1 | 0 | 0 | 0 | 1 | 0 | 0 | 0 | 1 | 0 | 0 | 0 | 0 | 0 | 0 | 0 | 0 | 2 | 0 |
| Nutsedge | 0 | 4 | 0 | 0 | 0 | 0 | 7 | 0 | 2 | 0 | 0 | 4 | 5 | 0 | 7 | 3 | 10 | 10 | 6 | 10 | 0 | 6 | 0 | 10 | — | — | — |
| Rape | 0 | 1 | 3 | 0 | 0 | 0 | 0 | 2 | 2 | 0 | 0 | 1 | 0 | 0 | 0 | 3 | 6 | 3 | 5 | 5 | 3 | 1 | 0 | 1 | 5 | 7 | 4 |
| Rice | 1 | 0 | 0 | 0 | 0 | 0 | — | 5 | 6 | — | 0 | 1 | 3 | 0 | 0 | 0 | 2 | 0 | 1 | 0 | 0 | 0 | 0 | 1 | 0 | 2 | 8 | 5 |
| Sorghum | 1 | 6 | 0 | 1 | 0 | 0 | 4 | 0 | 4 | 5 | 1 | 3 | 5 | 0 | 2 | 9 | 9 | 5 | 6 | 1 | 7 | 0 | 2 | 9 | 3 | 9 | 4 |
| Soybean | 6 | 8 | 6 | 8 | 6 | 1 | 7 | 8 | 9 | 8 | 6 | 6 | 5 | 1 | 4 | 3 | 9 | 9 | 8 | 8 | 7 | 0 | 7 | 0 | 9 | 9 | 9 |
| Sugar beet | 7 | 3 | 2 | 2 | 1 | 0 | 2 | 7 | 0 | 2 | 6 | 5 | 7 | 1 | 2 | 6 | 5 | 6 | 5 | 2 | 2 | 2 | 0 | 3 | 7 | 7 | 7 |
| Velvetleaf | 4 | 8 | 7 | 8 | 6 | 2 | 1 | 2 | 7 | 3 | 2 | 2 | 6 | 1 | 6 | 2 | 7 | 5 | 6 | 5 | 5 | 2 | 6 | 5 | 7 | 7 | 8 |
| Wheat | 1 | 1 | 0 | 0 | 0 | 0 | 2 | 2 | 0 | 0 | 0 | 1 | 3 | 0 | 0 | 1 | 7 | 3 | 1 | 0 | 0 | 0 | 0 | 5 | 1 | 2 |
| Wild buckwheat | 5 | 5 | 2 | 1 | 2 | 2 | 5 | 7 | 8 | 6 | 6 | 6 | 7 | 3 | 5 | 7 | 7 | 5 | 7 | 5 | 0 | 3 | 3 | 2 | 5 | 10 | 8 |
| Wild oat | 1 | 1 | 0 | 0 | 0 | 0 | 0 | 2 | 3 | 0 | 0 | 0 | 5 | 0 | 5 | 2 | 8 | 4 | 4 | 0 | 2 | 0 | 2 | 2 | 9 | 7 | 9 |

| | COMPOUND | | | | | | | | | | | | | | | | | | | | | | | | | | |
|---|---|---|---|---|---|---|---|---|---|---|---|---|---|---|---|---|---|---|---|---|---|---|---|---|---|---|---|
| Rate (200 g/ha) | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 |
| | PREEMERGENCE | | | | | | | | | | | | | | | | | | | | | | | | | | |
| Barley | 0 | 0 | 1 | 0 | 0 | 0 | 1 | 0 | 0 | 0 | 0 | 2 | 0 | 2 | 0 | 0 | 0 | 0 | 0 | 0 | 0 | 0 | 0 | 0 | 0 | 0 | 0 |
| Barnyardgrass | 10 | 0 | 10 | 10 | 10 | 10 | 10 | 10 | 9 | 10 | 10 | 10 | 10 | 10 | 10 | 9 | 10 | 10 | 10 | 10 | 0 | 0 | 10 | 10 | 10 | 2 |
| Bedstraw | 0 | 0 | 3 | 6 | 0 | 0 | 1 | 1 | 0 | 2 | 2 | 0 | 0 | 0 | 0 | 2 | 0 | 5 | 3 | 2 | 0 | 0 | 1 | 0 | 1 | 0 |
| Blackgrass | 9 | 2 | 10 | 10 | 9 | 9 | 9 | 10 | 9 | 10 | 3 | 3 | 9 | 2 | 5 | 9 | 0 | 0 | 7 | 7 | 2 | 0 | 0 | 2 | 9 | 10 | 2 |
| Cheatgrass | 6 | 0 | 9 | 7 | 5 | 8 | 8 | 7 | 3 | 7 | 3 | 5 | 5 | 4 | 3 | 2 | 0 | 0 | 5 | 5 | — | 0 | 0 | 0 | 7 | 5 | 0 |
| Chickweed | 5 | 0 | 5 | 7 | 5 | 5 | 5 | 0 | 3 | 6 | 3 | 3 | 3 | 3 | 2 | 0 | 2 | 0 | 3 | 5 | 6 | 3 | 0 | 0 | 5 | 5 | 3 |
| Cocklebur | — | — | — | — | — | — | — | — | — | — | — | 0 | 0 | 0 | 0 | 0 | 0 | 0 | 0 | 0 | 0 | 0 | 0 | 0 | 0 | 1 | 0 |
| Corn | 0 | 0 | 9 | 1 | 0 | 0 | 4 | 3 | 2 | 3 | 2 | 2 | 0 | 8 | 3 | 0 | 0 | 2 | 5 | 5 | 2 | 0 | 0 | 3 | 4 | 9 | 2 |
| Cotton | 1 | — | 2 | 2 | 0 | 0 | 0 | 1 | 2 | 9 | 0 | 0 | 0 | 0 | 0 | 0 | 0 | 0 | 7 | 5 | 0 | 0 | 0 | 0 | 6 | 5 | 0 |
| Crabgrass | 10 | 3 | 10 | 10 | 9 | 9 | 10 | 10 | 6 | 10 | 10 | 10 | 10 | 9 | 10 | 10 | 7 | 9 | 9 | 9 | 7 | 0 | 0 | 9 | 10 | 10 | 7 |
| Giant foxtail | 10 | 0 | 10 | 10 | 9 | 9 | 10 | 10 | 10 | 10 | 10 | 10 | 10 | 10 | 10 | 10 | 8 | 10 | 9 | 9 | 8 | 0 | 0 | 9 | 10 | 10 | 9 |
| Lambsquarters | 9 | 3 | 9 | 9 | 8 | 9 | 8 | 7 | 5 | 9 | 3 | 5 | 5 | 5 | 5 | 5 | 5 | 5 | 6 | 8 | 7 | 0 | 0 | 5 | 7 | 8 | 3 |
| Morningglory | 0 | 0 | 0 | 0 | 0 | 0 | 0 | 0 | 3 | 0 | 0 | 0 | 0 | 0 | 0 | 0 | 0 | 0 | 1 | 0 | 0 | 0 | 0 | 0 | 0 | 2 | 0 |
| Nutsedge | 4 | 0 | 0 | — | — | — | 0 | — | 0 | — | 0 | 0 | 0 | 0 | 0 | 0 | 0 | 0 | 3 | 0 | 0 | 0 | 0 | 0 | 0 | 3 | 0 |
| Rape | 0 | 0 | 7 | 4 | 2 | 1 | 3 | 2 | 1 | 2 | 1 | 2 | 0 | 4 | 2 | 0 | 0 | 0 | 3 | 2 | 0 | 0 | 0 | 0 | 2 | 0 |
| Rice | 1 | 0 | 0 | 2 | 0 | 0 | 0 | 0 | 0 | 0 | 2 | 0 | 0 | 0 | 2 | 0 | 0 | 0 | 0 | 2 | 0 | 0 | 0 | 4 | 0 | 0 |
| Sorghum | 9 | 0 | 10 | 5 | 3 | 4 | 5 | 0 | 0 | 4 | 3 | 7 | 7 | 0 | 5 | 2 | 0 | 0 | 2 | 2 | 0 | 0 | 0 | 0 | 3 | 7 | 0 |
| Soybean | 0 | 0 | 9 | 1 | 0 | 0 | 0 | 1 | 0 | 1 | 4 | 6 | 0 | 0 | 0 | 8 | 0 | 0 | 9 | 9 | 0 | 0 | 0 | 0 | 8 | 6 | 7 |
| Sugar beet | 2 | 0 | 8 | 3 | 3 | 3 | 5 | 2 | 0 | 3 | 2 | 3 | 1 | 3 | 0 | 0 | 0 | 0 | 5 | 5 | 0 | 0 | 0 | 1 | 5 | 7 | 0 |
| Velvetleaf | 0 | 0 | 6 | 3 | 3 | 0 | 4 | 4 | 3 | 6 | 3 | 6 | 6 | 6 | 0 | 6 | 0 | 3 | 7 | 7 | 1 | 0 | 0 | 1 | 5 | 6 | 0 |
| Wheat | 0 | 0 | 2 | 0 | 0 | 0 | 0 | 3 | 0 | 0 | 0 | 0 | 2 | 0 | 2 | 2 | 0 | 0 | 0 | 0 | 0 | 0 | 0 | 1 | 0 | 0 |
| Wild buckwheat | — | — | — | — | 0 | — | 0 | — | 0 | — | 2 | 2 | 3 | 0 | 2 | 3 | 0 | 0 | 4 | 5 | 4 | 0 | — | 1 | 0 | 5 | — |
| Wild oat | 2 | 0 | 7 | 8 | 4 | 2 | 9 | 7 | 2 | 5 | 0 | 2 | 2 | 2 | 3 | 2 | 0 | 2 | 2 | 3 | 0 | 0 | 0 | 1 | 3 | 7 | 0 |

| | COMPOUND | | | | | | | | | | | | | | | | | | | | | | | | | | |
|---|---|---|---|---|---|---|---|---|---|---|---|---|---|---|---|---|---|---|---|---|---|---|---|---|---|---|---|
| Rate (200 g/ha) | 55 | 56 | 57 | 58 | 59 | 60 | 61 | 62 | 63 | 64 | 65 | 66 | 67 | 73 | 74 | 75 | 76 | 77 | 78 | 79 | 80 | 81 | 82 | 84 | 85 | 86 |
| | PREEMERGENCE | | | | | | | | | | | | | | | | | | | | | | | | | |
| Barley | 1 | 2 | 0 | 0 | 0 | 1 | 0 | 0 | 2 | 0 | 0 | 1 | 0 | 0 | 0 | 7 | 0 | 0 | 0 | 0 | 0 | 0 | 0 | 0 | 0 | 0 |
| Barnyardgrass | 10 | 10 | 10 | 10 | 0 | 10 | 10 | 10 | 10 | 10 | 10 | 10 | 2 | 10 | 10 | 20 | 5 | 9 | 8 | 0 | 5 | 1 | 7 | 8 | 3 | 8 |
| Bedstraw | 1 | 5 | 0 | 0 | 0 | 2 | 5 | 3 | 7 | 2 | 0 | 8 | 0 | 7 | 4 | 6 | 0 | — | 0 | 0 | 0 | 3 | 2 | 0 | 0 | 0 |
| Blackgrass | 10 | 10 | 10 | 7 | 3 | 10 | 10 | 10 | 7 | 9 | 7 | 10 | 0 | 9 | 10 | 10 | 2 | 2 | 0 | 0 | 0 | 0 | 0 | 3 | 7 | 2 |
| Cheatgrass | 7 | 8 | 9 | 7 | 0 | 8 | 9 | 7 | 6 | 8 | 6 | 9 | 0 | 2 | 3 | 5 | 0 | 0 | 0 | 0 | 0 | 0 | 0 | 0 | 0 | 0 |
| Chickweed | 5 | 2 | 5 | 3 | 3 | 3 | 2 | 3 | 3 | 5 | 6 | 0 | 7 | 0 | 4 | 3 | 5 | 0 | 0 | 0 | 2 | 2 | 0 | 2 | 3 | 0 | — |

TABLE A-continued

| | | | | | | | | | | | | | | | | | | | | | | | | | | | |
|---|---|---|---|---|---|---|---|---|---|---|---|---|---|---|---|---|---|---|---|---|---|---|---|---|---|---|---|
| Cocklebur | 0 | 0 | 0 | 1 | 0 | 1 | 0 | 0 | 0 | 0 | 0 | 0 | 0 | 1 | 2 | — | 0 | 0 | 0 | 0 | 0 | 0 | 0 | 0 | 0 | 0 | 0 |
| Corn | 9 | 9 | 7 | 0 | 0 | 8 | 8 | 4 | 1 | 9 | 2 | 10 | 0 | 0 | 0 | 3 | 5 | 0 | 0 | 0 | 2 | 0 | 0 | 0 | 0 | 0 | 0 |
| Cotton | 0 | 0 | — | 1 | 0 | 2 | 0 | 4 | 3 | 0 | 0 | 2 | 8 | 2 | 2 | 6 | 0 | 0 | 0 | 0 | 0 | 0 | 0 | 0 | 0 | 0 | 0 |
| Crabgrass | 10 | 10 | 10 | 9 | 8 | 10 | 10 | 10 | 10 | 10 | 9 | 10 | 0 | 10 | 10 | 9 | 10 | 5 | 6 | 7 | 0 | 7 | 5 | 8 | 7 | 2 | 2 |
| Giant foxtail | 10 | 10 | 10 | 10 | 0 | 10 | 10 | 10 | 10 | 10 | 10 | 10 | 0 | 10 | 10 | 10 | 6 | 4 | 7 | 0 | 1 | 0 | 1 | 1 | 0 | 2 |
| Lambsquarters | 8 | 8 | 7 | 5 | 1 | 5 | 8 | 5 | 10 | 8 | 7 | — | 0 | 3 | 3 | 4 | 4 | 0 | 0 | 0 | 0 | 2 | 0 | 0 | 2 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 10 | 5 | 0 | 10 | — | 10 | 0 | 10 | 0 | 0 | 0 | 0 | 0 | 0 | 0 | 0 | — | 0 |
| Rape | 2 | 4 | 0 | 0 | 0 | 0 | 2 | 0 | 1 | 2 | 3 | 1 | 0 | 0 | 0 | 0 | 0 | 0 | 0 | 0 | 0 | 0 | 0 | 0 | 0 | 0 |
| Rice | 0 | 2 | 0 | 0 | 0 | 0 | 0 | 0 | 1 | 0 | 0 | 0 | 0 | 0 | 0 | 1 | 0 | 0 | 0 | 0 | 0 | 0 | 0 | 2 | 0 | 0 |
| Sorghum | 8 | 9 | 3 | 4 | 0 | 0 | 0 | 0 | 8 | 2 | 2 | 2 | 0 | 4 | 0 | 8 | 0 | 0 | 2 | 0 | 0 | 0 | 0 | 0 | 0 | 0 |
| Soybean | 0 | 9 | 7 | 0 | 6 | 0 | 6 | 0 | 7 | 0 | 0 | 0 | 0 | 0 | 0 | 4 | 0 | 0 | 0 | 0 | 0 | 0 | 0 | 0 | 0 | 0 |
| Sugar beet | 7 | 7 | 3 | 4 | 0 | 2 | 2 | 3 | 7 | 3 | 3 | 3 | 0 | 0 | 6 | 3 | 0 | 0 | 0 | 0 | 0 | 0 | 0 | 0 | 0 | 0 |
| Velvetleaf | 8 | 8 | 8 | 7 | 0 | 6 | 8 | 8 | 4 | 8 | 7 | 0 | 2 | 3 | 4 | 4 | 2 | 1 | 0 | 0 | 0 | 0 | 2 | 0 | 0 | 0 |
| Wheat | 2 | 0 | 0 | 5 | 0 | — | 1 | 0 | 0 | 2 | 0 | 0 | 0 | 0 | 0 | 3 | 0 | 0 | 0 | 0 | 0 | 0 | 0 | 0 | 0 | 0 |
| Wild buckwheat | — | — | — | — | — | — | — | — | — | — | — | — | — | 0 | 0 | — | 0 | 0 | 0 | 0 | 3 | 2 | 3 | 2 | 0 | 0 | — |
| Wild oat | 9 | 2 | 7 | 3 | 0 | 5 | 8 | 5 | 2 | 5 | 7 | 8 | 0 | 2 | 4 | 5 | 0 | 0 | 0 | 0 | 0 | 0 | 0 | 0 | 0 | 0 | 0 |

| | COMPOUND |
|---|---|
| Rate (50 g/ha) | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
| | PREEMERGENCE |
| Barley | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 2 | 5 | 3 | 4 | 3 | 0 | 1 | 10 | 10 | 1 | 2 | 1 | 7 | 0 | 2 | 9 | 10 | 10 | 10 | 8 | 2 | 7 | 3 | 10 | 10 | 9 | 10 |
| Bedstraw | 0 | 0 | 0 | 0 | 0 | 0 | 0 | 0 | 0 | 0 | 0 | 0 | 0 | 0 | 0 | 5 | 5 | 2 | 4 | 0 | 0 | 0 | 0 | 3 | 2 | 2 | 2 |
| Blackgrass | 2 | 2 | 2 | 0 | 0 | 0 | 0 | 7 | 7 | 0 | 3 | 5 | 7 | 0 | 0 | 5 | 9 | 7 | 3 | 3 | 0 | 2 | 2 | 3 | 8 | 9 | 9 |
| Cheatgrass | 0 | 2 | 2 | 0 | 2 | 0 | 0 | 3 | 6 | 2 | 2 | 2 | 2 | 0 | 2 | 3 | 7 | 7 | 3 | 2 | 0 | 0 | 3 | 2 | 5 | 5 | 7 |
| Chickweed | 0 | 6 | 6 | 5 | 5 | 0 | 4 | 9 | 9 | 4 | 7 | 7 | — | 7 | 7 | 5 | 7 | 5 | 5 | 0 | 2 | 5 | 1 | 0 | 5 | 5 | 8 |
| Cocklebur | — | — | — | — | — | — | — | — | — | — | — | — | — | — | — | 0 | 0 | — | 0 | 0 | 0 | 0 | 0 | — | — | — | — |
| Corn | 0 | 1 | 2 | 0 | 0 | 0 | 0 | 0 | 4 | 0 | 0 | 0 | 2 | 0 | 0 | 0 | 3 | 1 | 0 | 0 | 0 | 0 | 0 | 0 | 0 | 0 | 0 |
| Cotton | 0 | 0 | 0 | 0 | 0 | 0 | 0 | 0 | 0 | 0 | 0 | 0 | 0 | 0 | 0 | 0 | 3 | 3 | 0 | 2 | 0 | 0 | 0 | 0 | 0 | 2 | 0 |
| Crabgrass | 6 | 9 | 9 | 6 | 7 | 2 | 5 | 3 | 9 | 0 | 6 | 3 | 8 | 0 | 8 | 9 | 10 | 9 | 9 | 8 | 3 | 6 | 9 | 9 | 10 | 10 | 10 |
| Giant foxtail | 3 | 6 | 7 | 6 | 4 | 2 | 0 | 7 | 9 | 0 | 1 | 3 | 1 | 0 | 2 | 10 | 10 | 10 | 10 | 8 | 5 | 5 | 8 | 10 | 10 | 10 | 10 |
| Lambsquarters | 5 | 0 | 5 | 0 | 2 | 0 | 0 | 4 | 8 | 7 | 7 | 5 | 9 | 2 | 5 | 7 | 8 | 3 | 6 | 2 | 2 | 0 | 3 | 2 | — | — | — |
| Morningglory | 0 | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 2 | 0 | 0 | 0 | 0 | 0 | 0 | 0 | 10 | 10 | 10 | 0 | — | 0 | 0 | 10 | — | — | 0 |
| Rape | 0 | 0 | 0 | 0 | 0 | 0 | 0 | 2 | 0 | 0 | 0 | 0 | 0 | 0 | 0 | 1 | 2 | 1 | 1 | 0 | 0 | 0 | 0 | 0 | 2 | 3 | 2 |
| Rice | 0 | 0 | 0 | 0 | 0 | 0 | — | 0 | 2 | — | 0 | 0 | 0 | 0 | 0 | 0 | 0 | 0 | 0 | 2 | 0 | 0 | 0 | 0 | 0 | 2 | 0 |
| Sorghum | 0 | 0 | 0 | 0 | 0 | 0 | 0 | 0 | 0 | 0 | 0 | 0 | 1 | 0 | 0 | 4 | 1 | 2 | 2 | 0 | 0 | 0 | 0 | — | 3 | 2 |
| Soybean | 0 | 1 | 0 | 0 | 0 | 0 | 0 | 2 | 4 | 0 | 0 | 0 | 2 | 0 | 0 | 9 | 5 | 0 | 5 | 0 | 0 | 0 | 0 | 8 | 8 | 8 |
| Sugar beet | 0 | 0 | 0 | 0 | 0 | 0 | 0 | 4 | 3 | 0 | 1 | 3 | 2 | 0 | 0 | 1 | 2 | 1 | 2 | 0 | 0 | 0 | 0 | 2 | 5 | 8 | 7 |
| Velvetleaf | 2 | 2 | 0 | 2 | 2 | 1 | 0 | 2 | 3 | 0 | 0 | 0 | 0 | 0 | 1 | 0 | 4 | 3 | 2 | 1 | 1 | 0 | 2 | 2 | 3 | 6 | 4 |
| Wheat | 0 | 0 | 0 | 0 | 0 | 0 | 0 | 0 | 0 | 0 | 0 | 0 | 0 | 0 | 0 | 2 | 2 | 0 | 0 | 0 | 0 | 0 | 0 | 0 | 0 | 1 | 0 |
| Wild buckwheat | 0 | 2 | 0 | 0 | 0 | 0 | 2 | 5 | 3 | 0 | 2 | 0 | 0 | 0 | 2 | 7 | 7 | 2 | 4 | 0 | 0 | 2 | 0 | 2 | 0 | 5 | 8 |
| Wild oat | 1 | 0 | 0 | 0 | 0 | 0 | 0 | 0 | 0 | 0 | 0 | 0 | 0 | 0 | 0 | 2 | 4 | 0 | 0 | 0 | 0 | 0 | 0 | 0 | 2 | 5 | 7 |

| | COMPOUND |
|---|---|
| Rate (50 g/ha) | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 |
| | PREEMERGENCE |
| Barley | 0 | 0 | 0 | 0 | 0 | 0 | 0 | 8 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 9 | 0 | 10 | 9 | 8 | 5 | 9 | 8 | 1 | 7 | 6 | 10 | 9 | 9 | 8 | 6 | 3 | 7 | 9 | 9 | 7 | 0 | 0 | 5 | 10 | 10 | 0 |
| Bedstraw | 0 | 0 | 2 | 6 | 0 | 0 | 0 | 0 | 0 | 0 | 0 | 0 | 0 | 0 | 0 | 0 | 2 | 0 | 0 | 0 | 0 | 0 | 0 | 0 | 0 | 1 | 0 |
| Blackgrass | 7 | 0 | 8 | 5 | 3 | 5 | 5 | 7 | 3 | 8 | 0 | 2 | 4 | 2 | 2 | 2 | 0 | 0 | 0 | 3 | 0 | 0 | 0 | 0 | 5 | 9 | 0 |
| Cheatgrass | 0 | 0 | 0 | 2 | 0 | 2 | 2 | 2 | 0 | 2 | 1 | 3 | 0 | 0 | 0 | 0 | 0 | 0 | 0 | 0 | — | 0 | 0 | 0 | 0 | 0 | 0 |
| Chickweed | 0 | 0 | 3 | 2 | 3 | 2 | 0 | 2 | 2 | 0 | 3 | 0 | 0 | 0 | 0 | 1 | 0 | 2 | 0 | 4 | 0 | 0 | 0 | 0 | 0 | 4 | 0 |
| Cocklebur | — | — | — | — | — | — | — | — | — | — | 4 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 2 | 0 | 0 | 0 | 0 | 2 | 0 | 0 | 0 | 0 | 0 | 6 | 0 |
| Cotton | 0 | 0 | 0 | 0 | 0 | 0 | 0 | 0 | 0 | 10 | 0 | 0 | 0 | 0 | 0 | 0 | 0 | 0 | 0 | 0 | 0 | 0 | 0 | 0 | 0 | 0 | 0 |
| Crabgrass | 6 | 0 | 9 | 9 | 3 | 3 | 3 | 5 | 2 | 3 | 9 | 10 | 10 | 9 | 7 | 9 | 6 | 6 | 9 | 9 | 1 | 0 | 0 | 1 | 9 | 10 | 0 |
| Giant foxtail | 8 | 0 | 10 | 10 | 7 | 6 | 9 | 8 | 2 | 7 | 8 | 10 | 9 | 9 | 10 | 10 | 7 | 8 | 8 | 7 | 5 | 0 | 0 | 5 | 9 | 10 | 0 |
| Lambsquarters | 3 | 0 | 8 | 8 | 5 | 7 | 5 | 3 | 2 | 5 | 4 | 2 | 3 | 4 | 2 | 2 | 0 | 3 | 2 | 2 | 1 | 0 | 0 | 0 | 5 | 7 | 0 |
| Morningglory | 0 | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | — | — | 0 | 0 | — | 0 | 0 | 0 | 0 | 0 | 0 | 0 | 0 | — | 0 | 0 | 0 | 0 | 0 | 0 | 0 | 0 | 0 | 0 |
| Rape | 0 | 0 | 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sorghum | 0 | 0 | 2 | 0 | 0 | 0 | 2 | 0 | 0 | 0 | 0 | 0 | 0 | 0 | 0 | 0 | 0 | 0 | 0 | 0 | 0 | 0 | 0 | 0 | 2 | 0 | 0 |
| Soybean | 0 | 0 | 0 | 0 | 0 | 0 | 0 | 0 | 0 | 0 | 1 | 0 | 0 | 0 | 0 | 5 | 0 | 0 | 0 | 0 | 0 | 0 | 0 | 0 | 0 | 0 | 0 |
| Sugar beet | 0 | 0 | 3 | 1 | 0 | 0 | 0 | 2 | 0 | 0 | 0 | 2 | 0 | 0 | 0 | 0 | 0 | 0 | 0 | 0 | 0 | 0 | 0 | 0 | 0 | 5 | 0 |
| Velvetleaf | 0 | 0 | 2 | 0 | 0 | 0 | 0 | 0 | 1 | 0 | 1 | 1 | 2 | 0 | 0 | 1 | 0 | 5 | 2 | 0 | 0 | 0 | 0 | 0 | 1 | 5 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | — | 0 | — | — | — | — | — | — | — | — | 0 | 0 | 2 | 0 | 0 | 2 | 0 | 0 | — | 0 | 0 | 0 | 0 | 0 | 0 | 0 | 0 |
| Wild oat | 0 | 0 | 2 | 0 | 0 | 0 | 0 | 2 | 0 | 0 | 0 | 0 | 0 | 0 | 0 | 0 | 0 | 0 | 0 | — | 0 | 0 | 0 | 0 | 0 | 3 | 0 |

| | COMPOUND |
|---|---|
| Rate (50 g/ha) | 55 | 56 | 57 | 58 | 59 | 60 | 61 | 62 | 63 | 64 | 65 | 66 | 67 | 73 | 74 | 75 | 76 | 77 | 78 | 79 | 80 | 81 | 82 | 84 | 85 | 86 |
| | PREEMERGENCE |
| Barley | 0 | 0 | 0 | 0 | 0 | 0 | 8 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 10 | 10 | 10 | 9 | 0 | 10 | 10 | 10 | 10 | 10 | 9 | 10 | 0 | 2 | 6 | 9 | 0 | 0 | 0 | 0 | 0 | 1 | 1 | 0 | 0 |
| Bedstraw | 0 | 0 | 0 | 0 | 0 | 2 | 3 | 0 | 0 | 0 | 0 | 0 | 0 | 2 | 1 | 5 | 0 | 0 | 0 | 0 | 0 | 0 | 0 | — | 0 |
| Blackgrass | 10 | 10 | 7 | 2 | 2 | 9 | 8 | 2 | 6 | 3 | 3 | 5 | 0 | 7 | 6 | 6 | 0 | 0 | 0 | 0 | 0 | 0 | 0 | 0 | 0 |
| Cheatgrass | 3 | 0 | 2 | 2 | 0 | 5 | 3 | 0 | 2 | 0 | 0 | 2 | 0 | 0 | 2 | 2 | 0 | 0 | 0 | 0 | 0 | 0 | 0 | 0 | 0 |
| Chickweed | 2 | 4 | 0 | 0 | 0 | 0 | 2 | 2 | 2 | 0 | 0 | 0 | 0 | 2 | 3 | 3 | 0 | 0 | 0 | 0 | 0 | 0 | 0 | 0 | 0 |

TABLE A-continued

| | | | | | | | | | | | | | | | | | | | | | | | | | |
|---|---|---|---|---|---|---|---|---|---|---|---|---|---|---|---|---|---|---|---|---|---|---|---|---|---|
| Cocklebur | 0 | 0 | 0 | 0 | 0 | 0 | 0 | 0 | 0 | 0 | 0 | 0 | 0 | — | 0 | 0 | 0 | 0 | — | 0 | 0 | 0 | 0 | 0 | 0 |
| Corn | 1 | 2 | 4 | 2 | 0 | 2 | 0 | 0 | 1 | 0 | 0 | 0 | 0 | 0 | 0 | 1 | 0 | 0 | 0 | 0 | 0 | 0 | 0 | 0 | 0 |
| Cotton | 0 | 0 | 0 | 0 | 0 | 0 | 0 | 0 | 0 | 0 | 0 | 0 | 0 | 0 | 0 | 0 | 5 | 0 | 0 | 0 | 0 | 0 | 0 | 0 | 0 |
| Crabgrass | 8 | 10 | 9 | 7 | 0 | 9 | 9 | 10 | 9 | 7 | 1 | 10 | 0 | 1 | 4 | 9 | 0 | 3 | 0 | 0 | 0 | 0 | 1 | 0 | 2 |
| Giant foxtail | 10 | 10 | 9 | 8 | 0 | 8 | 9 | 9 | 10 | 9 | 8 | 9 | 0 | 2 | 4 | 8 | 0 | 0 | 0 | 0 | 0 | 0 | 0 | 0 | 0 |
| Lambsquarters | 3 | 9 | 4 | 4 | 0 | — | 5 | 5 | 7 | — | 3 | — | 0 | 3 | 0 | 0 | 0 | 0 | 0 | 0 | 0 | 0 | 0 | 0 | 0 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 10 | 0 | — | 6 | 4 | 10 | 0 | 0 | 0 | — | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sorghum | 5 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugar beet | 2 | 3 | 2 | 0 | 0 | 0 | 0 | 0 | 4 | 0 | 0 | 0 | 0 | 0 | 0 | 0 | 0 | 0 | 0 | 0 | 0 | 0 | 0 | 0 | 0 |
| Velvetleaf | 2 | 2 | 1 | 0 | 0 | 3 | 8 | 2 | 0 | 0 | 0 | 4 | 0 | 3 | 3 | 3 | 0 | 0 | 0 | 0 | 0 | 0 | 0 | 0 | 0 |
| Wheat | 0 | 0 | 0 | 0 | 0 | — | — | 0 | 0 | 0 | 0 | 0 | 0 | 0 | 0 | 0 | 0 | 0 | 0 | 0 | 0 | 0 | 0 | 0 | 0 |
| Wild buckwheat | — | — | — | — | — | — | — | — | — | 0 | 0 | 0 | 0 | — | — | 0 | 0 | 0 | 0 | 0 | 0 | 0 | 0 | 0 | — |
| Wild oat | 0 | 0 | 3 | 2 | 0 | 5 | 5 | 3 | 0 | 2 | 2 | 4 | 0 | 0 | 2 | 0 | 0 | 0 | 0 | 0 | 0 | 0 | 0 | 0 | 0 |

TEST B

The compounds evaluated in this test were formulated in a non-phytoxic solvent and applied to the soil surface before plant seedlings emerged (preemergence application), to water that covered the soil surface (paddy application), and to plants that were in the one-to-four leaf stage (postemergence application). A sandy loam soil was used for the preemergence and postemergence tests, while a silt loam soil was used in the paddy test. Water depth was approximately 2.5 cm for the paddy test and was maintained at this level for the duration of the test.

Plant species in the preemergence and postemergence tests consisted of barley (*Hordeum vulgare*), bedstraw (*Galium aparine*), blackgrass (*Alopecurus myosuroides*), chickweed (*Stellaria media*), corn (*Zea mays*), cotton (*Gossypium hirsutum*), crabgrass (*Digitaria sanguinalis*), downy brome (*Bromus tectorum*), duck salad (*Heteranthera limosa*), giant foxtail (*Setaria faberii*), lambsquarters (*Chenopodium album*), morningglory (*Ipomoea hederacea*), pigweed (*Amaranthus retroflexus*), rape (*Brassica napus*), ryegrass (*Lolium multiflorum*), sorghum (*Sorghum bicolor*), soybean (*Glycine max*), speedwell (*Veronica persica*), sugar beet (*Beta vulgaris*), velvetleaf (*Abutilon theophrasti*), wheat (*Triticum aestivum*), wild buckwheat (*Polygonum convolvulus*), and wild oat (*Avena fatua*). All plant species were planted one day before application of the compound for the preemergence portion of this test. Plantings of these species were adjusted to produce plants of appropriate size for the postemergence portion of the test. Plant species in the paddy test consisted of barnyardgrass (*Echinochloa crus-galli*), rice (*Oryza sativa*), and umbrella sedge (*Cyperus difformis*).

All plant species were grown using normal greenhouse practices. Visual evaluations of injury expressed on treated plants, when compared to untreated controls, were recorded approximately fourteen to twenty-one days after application of the test compound. Plant response ratings, summarized in Table B, were recorded on a 0 to 10 scale where 0 is no injury and 10 is complete control. A dash (-) response means no test result.

TABLE B

| Rate (250 g/ha) | COMPOUND | | | | | | | | | | | | | | | | | | | | | | | | |
|---|---|---|---|---|---|---|---|---|---|---|---|---|---|---|---|---|---|---|---|---|---|---|---|---|---|
| | 8 | 9 | 16 | 17 | 18 | 19 | 24 | 25 | 26 | 27 | 31 | 34 | 39 | 40 | 41 | 43 | 46 | 47 | 53 | 56 | 57 | 60 | 61 | 62 | 63 | 75 |
| POSTEMERGENCE | | | | | | | | | | | | | | | | | | | | | | | | | | |
| Barley Igri | 3 | 4 | 2 | 3 | 3 | 2 | 2 | 8 | 9 | 6 | 0 | 0 | 4 | 0 | 0 | 0 | 0 | 0 | 2 | 0 | 0 | 4 | 4 | 0 | 4 | — |
| Bedstraw | 5 | 7 | 0 | 6 | 7 | 6 | 4 | 7 | 7 | 0 | 0 | 0 | 0 | 0 | 5 | 0 | 6 | 2 | 3 | 5 | 0 | 0 | 5 | 0 | 3 | — |
| Blackgrass | 10 | 10 | 8 | 9 | 9 | 8 | 7 | 9 | 10 | 10 | 8 | 7 | 7 | 7 | 3 | 7 | 9 | 9 | 9 | 9 | 10 | 10 | 10 | 10 | 10 | — |
| Chickweed | 10 | 10 | 0 | 9 | 7 | 7 | 6 | 9 | 9 | 9 | 0 | 3 | 2 | 0 | 2 | 6 | 0 | 4 | 6 | 6 | 0 | 5 | 6 | 0 | 10 | — |
| Corn | 6 | 9 | 0 | 7 | 3 | 0 | 5 | 7 | 8 | 9 | 2 | 2 | 0 | 0 | 2 | 3 | 2 | 5 | 5 | 6 | 0 | 3 | 5 | 2 | 7 | — |
| Cotton | 2 | 0 | 0 | 3 | 0 | 0 | 0 | 0 | 7 | 3 | 2 | 0 | 0 | 2 | 0 | 2 | 3 | 2 | 0 | 0 | 0 | 0 | 2 | 2 | 0 | — |
| Crabgrass | 8 | 8 | 3 | 8 | 8 | 6 | 3 | 9 | 8 | 8 | 7 | 3 | 5 | 3 | 5 | 7 | 6 | 3 | 3 | 3 | 0 | 8 | 7 | 4 | 6 | — |
| Downy brome | 4 | 7 | 4 | 8 | 0 | 0 | 2 | — | 7 | 9 | 0 | 3 | 3 | 2 | 0 | 0 | 0 | 2 | 0 | 3 | 6 | 2 | 0 | 4 | — |
| Duck salad | — | — | 9 | 9 | 8 | 7 | 9 | 10 | 10 | 10 | 5 | 8 | 8 | 8 | 8 | 8 | 9 | 9 | 9 | 10 | 9 | 9 | 9 | 9 | 9 | 9 |
| Giant foxtail | 8 | 7 | 8 | 8 | 7 | 8 | 7 | 9 | 9 | 9 | 7 | 7 | 7 | 8 | 3 | 9 | 9 | 8 | 7 | 4 | 6 | 8 | 9 | 8 | 9 | — |
| Lambsquarters | 10 | 10 | 8 | 9 | 9 | 10 | 9 | 9 | 8 | 9 | 9 | — | 10 | 5 | 8 | 9 | 5 | 6 | 9 | 9 | 9 | 9 | 10 | 6 | 10 | — |
| Morningglory | 0 | 0 | 0 | 4 | 3 | 4 | 0 | 0 | 0 | 5 | 0 | 0 | 0 | 0 | 0 | 0 | 0 | 0 | 0 | 0 | 0 | 0 | 0 | 3 | 3 | — |
| Pigweed | 5 | 5 | 4 | 6 | 4 | 0 | 4 | 2 | 4 | 8 | 0 | 3 | 0 | 3 | 2 | 0 | 4 | 3 | 4 | 4 | 4 | 7 | 6 | 7 | 0 | — |
| Rape | 0 | 3 | 2 | 2 | 0 | 0 | 3 | 0 | 5 | 5 | 0 | 0 | 0 | 1 | 0 | 0 | 2 | 3 | 0 | 0 | 0 | 0 | 0 | 0 | 0 | — |
| Ryegrass | 8 | 10 | 6 | 9 | 9 | 7 | 7 | 9 | 9 | 9 | 4 | 4 | 7 | 4 | 0 | 0 | 5 | 3 | 9 | 5 | 6 | 9 | 9 | 5 | 9 | — |
| Sorghum | 6 | 7 | 0 | 6 | 2 | 0 | 3 | 8 | 8 | 8 | 3 | 2 | 2 | 0 | 2 | 3 | 0 | 2 | 3 | 3 | 0 | 5 | 5 | 6 | 0 | — |
| Soybean | 2 | 5 | 0 | 6 | 5 | 5 | 3 | 8 | 8 | 9 | 0 | 0 | 3 | 2 | 4 | 5 | 3 | 5 | 3 | 3 | 3 | 3 | 4 | 4 | 3 | — |
| Speedwell | 9 | 8 | 0 | 10 | 9 | 9 | 3 | 9 | 9 | 7 | — | — | 2 | 0 | 0 | 6 | 8 | 4 | 8 | 7 | 0 | 5 | 7 | 0 | 8 | — |
| Sugar beet | 7 | 7 | 3 | 8 | 8 | 7 | 6 | 7 | 9 | 8 | 3 | 3 | 5 | 3 | 3 | 2 | 5 | 7 | 6 | 6 | 2 | 4 | 4 | 3 | 6 | — |
| Velvetleaf | 3 | 2 | 0 | 6 | 6 | 4 | 3 | 7 | 9 | 8 | 2 | 6 | 0 | 2 | 4 | 7 | 5 | 3 | 4 | 0 | 7 | 4 | 6 | 5 | 0 | — |
| Wheat | 3 | 4 | 2 | — | — | 1 | 2 | 0 | 6 | 6 | 2 | 0 | 2 | 2 | 0 | 0 | 0 | 5 | 0 | 0 | 6 | 5 | 0 | 8 | — |
| Wild buckwheat | 10 | 7 | 8 | 10 | 9 | 8 | 8 | 9 | 9 | 7 | 9 | 10 | 4 | 9 | 7 | 9 | 8 | 9 | 9 | 9 | 9 | — | — | 10 | — |
| Wild oat | 3 | 3 | 0 | 2 | 0 | 3 | 0 | 2 | 8 | 8 | 0 | 0 | 2 | 0 | 0 | 0 | 0 | 0 | 9 | 4 | 0 | 5 | 3 | 2 | 4 | — |
| Barnyardgrass | 9 | 10 | 10 | 9 | 9 | 10 | 10 | 10 | 10 | 10 | 10 | 10 | 10 | 10 | 9 | 10 | 10 | 10 | 10 | 10 | 10 | 10 | 10 | 10 | 10 | 10 |
| Rice Japonica | 9 | 9 | 8 | 10 | 9 | 9 | 9 | 10 | 10 | 10 | 9 | 5 | 9 | 9 | 7 | 9 | 8 | 9 | 7 | 8 | 9 | 9 | 10 | 9 | 10 | 9 |
| Umbrella sedge | 9 | 9 | 9 | 9 | 8 | 8 | 9 | 8 | 8 | 8 | 9 | 9 | 9 | 9 | 9 | 9 | 9 | 8 | 10 | 10 | 9 | 9 | 9 | 9 | 9 | 10 |
| Rate (125 g/ha) | COMPOUND | | | | | | | | | | | | | | | | | | | | | | | | |
| | 8 | 9 | 16 | 17 | 18 | 19 | 24 | 25 | 26 | 27 | 31 | 34 | 39 | 40 | 41 | 43 | 46 | 47 | 53 | 56 | 57 | 60 | 61 | 62 | 63 | 75 |
| POSTEMERGENCE | | | | | | | | | | | | | | | | | | | | | | | | | | |

TABLE B-continued

| | | | | | | | | | | | | | | | | | | | | | | | | | |
|---|---|---|---|---|---|---|---|---|---|---|---|---|---|---|---|---|---|---|---|---|---|---|---|---|---|
| Barley Igri | 0 | 0 | 0 | 3 | 1 | 0 | 0 | 8 | 9 | 5 | 0 | 0 | 2 | 0 | 0 | 0 | 0 | 0 | 0 | 0 | 0 | 3 | 0 | 0 | — |
| Bedstraw | 5 | 4 | 0 | 5 | 3 | 4 | 3 | 5 | 6 | 5 | 0 | 0 | 0 | 0 | 0 | 0 | 2 | 2 | 2 | 0 | 0 | 0 | 0 | 0 | 0 | — |
| Blackgrass | 6 | 7 | 4 | 9 | 8 | 7 | 5 | 9 | 9 | 9 | 7 | 7 | 5 | 4 | 0 | 4 | 6 | 7 | 9 | 9 | 3 | 10 | 9 | 7 | 10 | — |
| Chickweed | 8 | 8 | 0 | 9 | — | 7 | 4 | 9 | 6 | 9 | 0 | 0 | 0 | 0 | 0 | 4 | — | 0 | 0 | 0 | 0 | 0 | 3 | 0 | 10 | — |
| Corn | 4 | 4 | 0 | 4 | 2 | 0 | 3 | 5 | 5 | 8 | 0 | 0 | 0 | 0 | 2 | 2 | 0 | 5 | 5 | 4 | 0 | 2 | 2 | 0 | 3 | — |
| Cotton | 2 | 0 | 0 | 3 | 0 | 0 | 0 | 0 | 7 | 2 | 0 | 0 | 0 | 0 | 0 | 2 | 2 | 2 | 0 | 0 | 0 | 0 | 0 | 0 | 0 | — |
| Crabgrass | 7 | 8 | 2 | 7 | 7 | 5 | 0 | 7 | 8 | 6 | 4 | 2 | 5 | 1 | 5 | 2 | 4 | 2 | 2 | 2 | 0 | 7 | 5 | 4 | 2 | — |
| Downy brome | 3 | 4 | 2 | 6 | 0 | 0 | 0 | 6 | 6 | 6 | 0 | 0 | 0 | 0 | 0 | 0 | 0 | 2 | 0 | 0 | 0 | 0 | 0 | 0 | 2 | — |
| Duck salad | — | — | 8 | 6 | 7 | 7 | 9 | 10 | 10 | 10 | 3 | 4 | 5 | 7 | 7 | 7 | 8 | 9 | 9 | 9 | 9 | 9 | 9 | 8 | 9 | 6 |
| Giant foxtail | 7 | 7 | 5 | 7 | 7 | 6 | 3 | 9 | 9 | 9 | 4 | 7 | 7 | 6 | 2 | 5 | 9 | 5 | 7 | 4 | 5 | 4 | 9 | 8 | 6 | — |
| Lambsquarters | 10 | 10 | 7 | 9 | 8 | 6 | 8 | 9 | 7 | 6 | 5 | 7 | 9 | 5 | 5 | 5 | — | 6 | 9 | 9 | 9 | 9 | 9 | 4 | 9 | — |
| Morningglory | 0 | 0 | 0 | 3 | 0 | 3 | 0 | 0 | 0 | 2 | 0 | 0 | 0 | 0 | 0 | 0 | 0 | 0 | 0 | 0 | 0 | 0 | 0 | 0 | 2 | — |
| Pigweed | 3 | 2 | 0 | 4 | 3 | 0 | 2 | 2 | 2 | 4 | 0 | 0 | 0 | 2 | 0 | 0 | 0 | 2 | 0 | 0 | 0 | 5 | 6 | 5 | 0 | — |
| Rape | 0 | 2 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | — |
| Ryegrass | 5 | 7 | 5 | 8 | 5 | 3 | 4 | 8 | 7 | 7 | 2 | 0 | 2 | 2 | 0 | 0 | 4 | 0 | 6 | 4 | 0 | 8 | 8 | 5 | 8 | — |
| Sorghum | 4 | 5 | 0 | 5 | 0 | 0 | 2 | 7 | 7 | 5 | 3 | 0 | 2 | 0 | 0 | 2 | 0 | 0 | 0 | 3 | 0 | 2 | 5 | 4 | 0 | — |
| Soybean | 0 | 5 | 0 | 5 | 4 | 4 | 0 | 5 | 5 | 6 | 0 | 0 | 0 | 0 | 4 | 5 | 3 | 4 | 1 | 2 | 2 | 2 | 2 | 3 | 2 | — |
| Speedwell | 7 | 7 | 0 | 9 | 7 | 6 | 0 | 8 | 8 | 7 | — | — | 0 | 0 | 0 | 5 | 7 | 0 | 0 | 0 | 0 | 0 | 4 | 0 | 8 | — |
| Sugar beet | 6 | 6 | 2 | 7 | 5 | 6 | 6 | 7 | 7 | 7 | — | 3 | 1 | 1 | 0 | 2 | 4 | 6 | 2 | 0 | 0 | 0 | 4 | 0 | 5 | — |
| Velvetleaf | 1 | 2 | 0 | 5 | 4 | 0 | 0 | 5 | 5 | 6 | 0 | 4 | 0 | 0 | 2 | 7 | 5 | 2 | 0 | 0 | 5 | 2 | 3 | 5 | 0 | — |
| Wheat | 0 | 3 | 0 | — | — | 0 | 0 | 0 | 6 | 4 | 0 | 0 | 0 | 0 | 0 | 0 | 0 | 0 | 3 | 0 | 0 | 4 | 5 | 0 | 4 | — |
| Wild buckwheat | 8 | 5 | 4 | 8 | 6 | 6 | 8 | 9 | 8 | 7 | 9 | 8 | 0 | 7 | — | 6 | — | 8 | 5 | 7 | 8 | — | 9 | 0 | 9 | — |
| Wild oat | 2 | 2 | 0 | 0 | 0 | 0 | 2 | 3 | 5 | 4 | 0 | 0 | 0 | 0 | 0 | 0 | 0 | 0 | 7 | 0 | 0 | 0 | 3 | 0 | 2 | — |
| Barnyardgrass | 9 | 9 | 9 | 9 | 9 | 10 | 10 | 10 | 10 | 10 | 10 | 10 | 10 | 10 | 9 | 9 | 10 | 10 | 10 | 10 | 10 | 10 | 10 | 10 | 10 | 10 |
| Rice Japonica | 8 | 8 | 8 | 9 | 9 | 8 | 9 | 9 | 10 | 10 | 6 | 3 | 7 | 6 | 4 | 6 | 8 | 7 | 7 | 7 | 7 | 8 | 9 | 8 | 9 | 8 |
| Umbrella sedge | 9 | 9 | 9 | 8 | 8 | 8 | 9 | 8 | 8 | 8 | 9 | 9 | 9 | 9 | 9 | 9 | 9 | 8 | 10 | 10 | 9 | 9 | 9 | 9 | 9 | 9 |

COMPOUND

| Rate (62 g/ha) | 8 | 9 | 16 | 17 | 18 | 19 | 24 | 25 | 26 | 27 | 31 | 34 | 39 | 40 | 41 | 43 | 46 | 47 | 53 | 56 | 57 | 60 | 61 | 62 | 63 | 75 |
|---|---|---|---|---|---|---|---|---|---|---|---|---|---|---|---|---|---|---|---|---|---|---|---|---|---|---|

POSTEMERGENCE

| | | | | | | | | | | | | | | | | | | | | | | | | | | |
|---|---|---|---|---|---|---|---|---|---|---|---|---|---|---|---|---|---|---|---|---|---|---|---|---|---|---|
| Barley Igri | 0 | 0 | 0 | 0 | 0 | 0 | 0 | 0 | 4 | 3 | 0 | 0 | 0 | 0 | 0 | 0 | 0 | 0 | 0 | 0 | 0 | 0 | 0 | 0 | 0 | — |
| Bedstraw | 3 | 3 | 0 | 3 | 3 | 2 | 3 | 4 | 5 | 4 | 0 | 0 | 0 | 0 | 0 | 0 | 0 | 0 | 0 | 0 | 0 | 0 | 0 | 0 | 0 | — |
| Blackgrass | 5 | 6 | 0 | 7 | 3 | 2 | 2 | 9 | 7 | 6 | 5 | 5 | 2 | 2 | 0 | 0 | 2 | 3 | 9 | 6 | 0 | 9 | 9 | 5 | 9 | — |
| Chickweed | 7 | 8 | 0 | 7 | 6 | 3 | 3 | 6 | 3 | 3 | 0 | 0 | 0 | 0 | 0 | 0 | 0 | — | 0 | 0 | 0 | 0 | 0 | 0 | 4 | — |
| Corn | 2 | 2 | 0 | 3 | 0 | 0 | 0 | 5 | 5 | 5 | 0 | 0 | 0 | 0 | 0 | 0 | 0 | 2 | 4 | 0 | 0 | 0 | 0 | 0 | 3 | — |
| Cotton | 0 | 0 | 0 | 3 | 0 | 0 | 0 | 0 | 2 | 0 | 0 | 0 | 0 | 0 | 0 | 0 | 0 | 0 | 0 | 0 | 0 | 0 | 0 | 0 | 0 | — |
| Crabgrass | 4 | 4 | 0 | 7 | 5 | 5 | 0 | 4 | 7 | 5 | 2 | 0 | 1 | 0 | 3 | 2 | 3 | 0 | 0 | 0 | 0 | 2 | 3 | 2 | 0 | — |
| Downy brome | 3 | 3 | 0 | 0 | 0 | 0 | 0 | 0 | 0 | 6 | 0 | 0 | 0 | 0 | 0 | 0 | 0 | 0 | 0 | 0 | 0 | 0 | 0 | 0 | 0 | — |
| Duck salad | — | — | 0 | 1 | 5 | 0 | 9 | 10 | 10 | 9 | 0 | 3 | 1 | 2 | 0 | 0 | 3 | 4 | 8 | 9 | 8 | 7 | 9 | 7 | 7 | 3 |
| Giant foxtail | 5 | 4 | 0 | 7 | 6 | 6 | 2 | 7 | 8 | 9 | 4 | 3 | 2 | 4 | 0 | 2 | 8 | 4 | 5 | 3 | 3 | 4 | 4 | 7 | 3 | — |
| Lambsquarters | 6 | 7 | 5 | 6 | 6 | 6 | 7 | 4 | 4 | 3 | 5 | — | 9 | 5 | 5 | 4 | — | 3 | 9 | 8 | 8 | 9 | 8 | 4 | 9 | — |
| Morningglory | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | — |
| Pigweed | 1 | 0 | 0 | 3 | 0 | 0 | 0 | 0 | 0 | 3 | 0 | 0 | 0 | 0 | 0 | 0 | 0 | 0 | 0 | 0 | 0 | 2 | 4 | 2 | 0 | — |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — |
| Ryegrass | 4 | 4 | 2 | 3 | 0 | 0 | 1 | 3 | 3 | 7 | 0 | 0 | 0 | 0 | 0 | 0 | 0 | 0 | 4 | 0 | 0 | 0 | 5 | 0 | 6 | — |
| Sorghum | 2 | 3 | 0 | 4 | 0 | 0 | 0 | 5 | 3 | 3 | 0 | 0 | 0 | 0 | 0 | 0 | 0 | 0 | 0 | 0 | 0 | 2 | 4 | 3 | 0 | — |
| Soybean | 0 | 3 | 0 | 3 | 3 | 3 | 0 | 5 | 3 | 2 | 0 | 0 | 0 | 0 | 2 | 4 | 2 | 0 | 0 | 2 | 0 | 0 | 0 | 2 | 1 | — |
| Speedwell | 5 | 6 | 0 | 8 | 7 | 3 | 0 | 4 | 7 | 4 | — | — | 0 | 0 | 0 | 2 | 2 | 0 | 0 | 0 | 0 | 0 | 0 | 0 | 7 | — |
| Sugar beet | 0 | 5 | 0 | — | 4 | 1 | 4 | 6 | 3 | 6 | 2 | 0 | 0 | 0 | 0 | 0 | 3 | 2 | 0 | 0 | 0 | 0 | 0 | 0 | 5 | — |
| Velvetleaf | 0 | 2 | 0 | 4 | 2 | 0 | 0 | 2 | 2 | 2 | 0 | 2 | 0 | 0 | 0 | 2 | 2 | 0 | 0 | 0 | 0 | 0 | 3 | 2 | 0 | — |
| Wheat | 0 | 0 | 0 | — | — | 0 | 0 | 0 | 0 | 3 | 0 | 0 | 0 | 0 | 0 | 0 | 0 | 0 | 3 | 0 | 0 | 0 | 2 | 0 | 2 | — |
| Wild buckwheat | 6 | 3 | 4 | 4 | 5 | 3 | 5 | 7 | 4 | 4 | 2 | 8 | 0 | 2 | 6 | — | — | 5 | 5 | 7 | 6 | 0 | 2 | 0 | 9 | — |
| Wild oat | 2 | 0 | 0 | 0 | 0 | 0 | 0 | 0 | 0 | 3 | 0 | 0 | 0 | 0 | 0 | 0 | 0 | 0 | 0 | 0 | 0 | 0 | 2 | 0 | 0 | — |
| Barnyardgrass | 9 | 9 | 9 | 9 | 9 | 8 | 9 | 10 | 10 | 10 | 10 | 10 | 10 | 10 | 9 | 9 | 10 | 9 | 10 | 9 | 10 | 10 | 10 | 10 | 10 | 8 |
| Rice Japonica | 7 | 7 | 6 | 9 | 8 | 8 | 8 | 8 | 9 | 9 | 3 | 0 | 6 | 4 | 2 | 3 | 7 | 4 | 6 | 5 | 3 | 7 | 8 | 6 | 8 | 7 |
| Umbrella sedge | 9 | 9 | 8 | 8 | 8 | 8 | 9 | 8 | 8 | 8 | 9 | 8 | 8 | 8 | 8 | 9 | 8 | 7 | 10 | 9 | 9 | 8 | 9 | 9 | 9 | 9 |

COMPOUND

| Rate (31 g/ha) | 8 | 9 | 16 | 17 | 18 | 19 | 24 | 25 | 26 | 27 | 31 | 34 | 39 | 40 | 41 | 43 | 46 | 47 | 53 | 56 | 57 | 60 | 61 | 62 | 63 | 75 |
|---|---|---|---|---|---|---|---|---|---|---|---|---|---|---|---|---|---|---|---|---|---|---|---|---|---|---|

POSTEMERGENCE

| | | | | | | | | | | | | | | | | | | | | | | | | | | |
|---|---|---|---|---|---|---|---|---|---|---|---|---|---|---|---|---|---|---|---|---|---|---|---|---|---|---|
| Barley Igri | 0 | 0 | 0 | 0 | 0 | 0 | 0 | 8 | 2 | 2 | 0 | 0 | 0 | 0 | 0 | 0 | 0 | 0 | 0 | 0 | 0 | 0 | 0 | 0 | 0 | — |
| Bedstraw | 0 | 3 | 0 | 2 | 2 | 0 | 0 | 0 | 3 | 2 | 0 | 0 | 0 | 0 | 0 | 0 | 0 | 0 | 0 | 0 | 0 | 0 | 0 | 0 | 0 | — |
| Blackgrass | 4 | 3 | 0 | 6 | 2 | 0 | 0 | 0 | 6 | 3 | 3 | 2 | 0 | 0 | 0 | 0 | 0 | 0 | 8 | 6 | 0 | 7 | 9 | 0 | 4 | — |
| Chickweed | 5 | 6 | 0 | 6 | 3 | 0 | 0 | 0 | 3 | 3 | 0 | 0 | 0 | 0 | 0 | 0 | 0 | 0 | 0 | 0 | 0 | 0 | — | 0 | 0 | — |
| Corn | 0 | 0 | 0 | 2 | 0 | 0 | 0 | 4 | 3 | 2 | 0 | 0 | 0 | 0 | 0 | 0 | 0 | 0 | 0 | 0 | 0 | 0 | 0 | 0 | 0 | — |
| Cotton | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — |
| Crabgrass | 0 | 2 | 0 | 5 | 4 | 4 | 0 | 2 | 4 | 2 | 0 | 0 | 0 | 0 | 0 | 0 | 0 | 0 | 0 | 0 | 0 | 0 | 2 | 2 | 0 | — |
| Downy brome | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — |
| Duck salad | — | — | 0 | 0 | 0 | 0 | 3 | 5 | 9 | 6 | 0 | 0 | 0 | 0 | 0 | 0 | 0 | 0 | 1 | 2 | 2 | 3 | 6 | 1 | 4 | 2 |
| Giant foxtail | 1 | 2 | 0 | 7 | 0 | 4 | 0 | 3 | 8 | 9 | 2 | 1 | 0 | 2 | 0 | 0 | 3 | 0 | 3 | 0 | 2 | 2 | 3 | 4 | 2 | — |
| Lambsquarters | — | 6 | 4 | 6 | 5 | — | 5 | 4 | 0 | 3 | 5 | — | 0 | 0 | — | 2 | 0 | 0 | 6 | 2 | 7 | 6 | 5 | 0 | 9 | — |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — |
| Pigweed | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 2 | 0 | 0 | — |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — |
| Ryegrass | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 5 | 0 | 0 | — |
| Sorghum | 0 | 0 | 0 | 0 | 0 | 0 | 0 | 2 | 2 | 0 | 0 | 0 | 0 | 0 | 0 | 0 | 0 | 0 | 0 | 0 | 0 | 2 | 3 | 3 | 0 | — |
| Soybean | 0 | 2 | 0 | 0 | 2 | 0 | 0 | 2 | 2 | 0 | 0 | 0 | 0 | 0 | 0 | 3 | 0 | 0 | 0 | 0 | 0 | 0 | 0 | 0 | 0 | — |
| Speedwell | 3 | 3 | 0 | — | — | 0 | 0 | 2 | 3 | 4 | — | — | 0 | 0 | 0 | 0 | 0 | 0 | 0 | 0 | 0 | 0 | 0 | 0 | — | — |
| Sugar beet | 0 | 4 | 0 | 6 | 4 | 0 | 0 | 0 | 2 | 3 | 0 | 0 | 0 | 0 | 0 | 0 | 0 | 0 | 0 | 0 | 0 | 0 | 0 | 0 | 0 | — |
| Velvetleaf | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 2 | 0 | — |
| Wheat | 0 | 0 | 0 | — | — | 0 | 0 | 0 | 0 | 3 | 0 | 0 | 0 | 0 | 0 | 0 | 0 | 0 | 0 | 0 | 0 | 0 | 0 | 0 | 0 | — |

TABLE B-continued

| | | | | | | | | | | | | | | | | | | | | | | | | | |
|---|---|---|---|---|---|---|---|---|---|---|---|---|---|---|---|---|---|---|---|---|---|---|---|---|---|
| Wild buckwheat | 3 | 3 | 0 | 3 | 0 | 0 | 2 | 0 | 4 | 0 | 2 | 8 | 0 | 0 | 5 | — | — | — | 4 | 0 | 4 | 0 | — | 0 | 3 | — |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — |
| Barnyardgrass | 7 | 6 | 9 | 7 | 7 | 7 | 9 | 10 | 10 | 9 | 10 | 10 | 9 | 9 | 9 | 9 | 10 | 9 | 9 | 10 | 9 | 10 | 10 | 10 | 6 | 8 |
| Rice Japonica | 3 | 4 | 0 | 8 | 4 | 2 | 5 | 8 | 8 | 5 | 1 | 0 | 2 | 0 | 0 | 1 | 1 | 2 | 2 | 0 | 2 | 7 | 3 | 6 | 6 |
| Umbrella sedge | 8 | 9 | 7 | 6 | 7 | 7 | 9 | 8 | 8 | 8 | 8 | 7 | 3 | 2 | 0 | 0 | 3 | 1 | 8 | 8 | 9 | 8 | 9 | 9 | 9 | 8 |

| | COMPOUND |
|---|---|
| Rate (16 g/ha) | 8  9  16  17  18  19  24  25  26  27  31  34  39  40  41  43  46  47  53  56  57  60  61  62  63 |

POSTEMERGENCE

| | 8 | 9 | 16 | 17 | 18 | 19 | 24 | 25 | 26 | 27 | 31 | 34 | 39 | 40 | 41 | 43 | 46 | 47 | 53 | 56 | 57 | 60 | 61 | 62 | 63 |
|---|---|---|---|---|---|---|---|---|---|---|---|---|---|---|---|---|---|---|---|---|---|---|---|---|---|
| Barley Irgi | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Bedstraw | 0 | 0 | 0 | 0 | 2 | 0 | 0 | 0 | 3 | — | 0 | 0 | 0 | 0 | 0 | 0 | 0 | 0 | 0 | 0 | 0 | 0 | 0 | 0 | 0 |
| Blackgrass | 3 | 0 | 0 | 2 | 0 | 0 | 0 | 0 | 2 | 3 | 0 | 0 | 0 | 0 | 0 | 0 | 0 | 0 | 4 | 0 | 0 | 2 | 2 | 0 | 3 |
| Chickweed | 3 | 4 | 0 | 4 | 3 | — | 0 | 0 | 3 | — | 0 | — | 0 | 0 | 0 | 0 | 0 | 0 | 0 | 0 | 0 | 0 | 0 | 0 | 0 |
| Corn | 0 | 0 | 0 | 0 | 0 | 0 | 0 | 2 | 2 | 0 | 0 | 0 | 0 | 0 | 0 | 0 | 0 | 0 | 0 | 0 | 0 | 0 | 0 | 0 | 0 |
| Cotton | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 4 | 3 | 3 | 0 | 0 | 3 | 0 | 0 | 0 | 0 | 0 | 0 | 0 | 0 | 0 | 0 | 0 | 0 | 0 | 0 | 0 | 0 |
| Downy brome | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Duck salad | — | — | 0 | 0 | 0 | 0 | 2 | 4 | 7 | 3 | 0 | 0 | 0 | 0 | 0 | 0 | 0 | 0 | 0 | 0 | 0 | 0 | 0 | 0 | 0 |
| Giant foxtail | 0 | 0 | 0 | 4 | 0 | 0 | 0 | 0 | 4 | 5 | 0 | 0 | 0 | 0 | 0 | 0 | 0 | 0 | 2 | 0 | 0 | 0 | 3 | 2 | 0 |
| Lambsquarters | — | 6 | 4 | 5 | 4 | 4 | 2 | 0 | 0 | 0 | — | — | 0 | 0 | 0 | — | 0 | 0 | — | — | 5 | 0 | 5 | 0 | 0 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Pigweed | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ryegrass | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sorghum | 0 | 0 | 0 | 0 | 0 | 0 | 0 | 2 | 0 | 0 | 0 | 0 | 0 | 0 | 0 | 0 | 0 | 0 | 0 | 0 | 0 | 2 | 3 | 2 | 0 |
| Soybean | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 |
| Speedwell | 0 | 0 | 0 | 4 | 5 | 0 | 0 | 0 | 3 | 4 | — | — | 0 | 0 | 0 | 0 | 0 | 0 | 0 | 0 | 0 | 0 | 0 | 0 | 0 |
| Sugar beet | 0 | 0 | 0 | 6 | 2 | — | 0 | 0 | — | — | 0 | 0 | 0 | 0 | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat | 0 | 0 | 0 | — | — | — | 0 | 0 | 0 | 2 | 0 | 0 | 0 | 0 | 0 | 0 | 0 | 0 | 0 | 0 | 0 | 0 | 0 | 0 | 0 |
| Wild buckwheat | 0 | 0 | 0 | 0 | 0 | 0 | 0 | 0 | 2 | 0 | 0 | 6 | 0 | 0 | — | 5 | — | — | 0 | 0 | 3 | 0 | 0 | — | — |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 5 | 5 | 7 | 6 | 6 | 5 | 9 | 9 | 9 | 9 | 10 | 10 | 9 | 9 | 8 | 5 | 6 | 7 | 7 | 10 | 9 | 10 | 10 | 10 | 6 |
| Rice Japonica | 0 | 0 | 0 | 1 | 0 | 1 | 3 | 2 | 5 | 5 | 0 | 0 | 0 | 0 | 0 | 0 | 1 | 0 | 1 | 0 | 0 | 0 | 4 | 0 | 2 |
| Umbrella sedge | 0 | 7 | 5 | 1 | 0 | 0 | 9 | 8 | 7 | 7 | 0 | 0 | 1 | 0 | 0 | 0 | 1 | 0 | 3 | 0 | 9 | 8 | 9 | 9 | 6 |

| | COMPOUND |
|---|---|
| Rate (125 g/ha) | 8  9  16  17  18  19  24  25  26  27  31  34  39  40  41  43  46  47  53  56  57  60  61  62  63 |

POSTEMERGENCE

| | 8 | 9 | 16 | 17 | 18 | 19 | 24 | 25 | 26 | 27 | 31 | 34 | 39 | 40 | 41 | 43 | 46 | 47 | 53 | 56 | 57 | 60 | 61 | 62 | 63 |
|---|---|---|---|---|---|---|---|---|---|---|---|---|---|---|---|---|---|---|---|---|---|---|---|---|---|
| Barley Igri | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Bedstraw | 0 | 0 | 0 | 0 | 2 | 0 | 0 | 0 | 3 | — | 0 | 0 | 0 | 0 | 0 | 0 | 0 | 0 | 0 | 0 | 0 | 0 | 0 | 0 | 0 |
| Blackgrass | 3 | 0 | 0 | 2 | 0 | 0 | 0 | 0 | 2 | 3 | 0 | 0 | 0 | 0 | 0 | 0 | 0 | 0 | 4 | 0 | 0 | 2 | 2 | 0 | 3 |
| Chickweed | 3 | 4 | 0 | 4 | 3 | — | 0 | 0 | 3 | — | 0 | — | 0 | 0 | 0 | 0 | 0 | 0 | 0 | 0 | 0 | 0 | 0 | 0 | 0 |
| Corn | 0 | 0 | 0 | 0 | 0 | 0 | 0 | 2 | 2 | 0 | 0 | 0 | 0 | 0 | 0 | 0 | 0 | 0 | 0 | 0 | 0 | 0 | 0 | 0 | 0 |
| Cotton | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 4 | 3 | 3 | 0 | 0 | 3 | 0 | 0 | 0 | 0 | 0 | 0 | 0 | 0 | 0 | 0 | 0 | 0 | 0 | 0 | 0 | 0 |
| Downy brome | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Duck salad | — | — | 0 | 0 | 0 | 0 | 2 | 4 | 7 | 3 | 0 | 0 | 0 | 0 | 0 | 0 | 0 | 0 | 0 | 0 | 0 | 0 | 0 | 0 | 0 |
| Giant foxtail | 0 | 0 | 0 | 4 | 0 | 0 | 0 | 0 | 4 | 5 | 0 | 0 | 0 | 0 | 0 | 0 | 0 | 0 | 2 | 0 | 0 | 0 | 3 | 2 | 0 |
| Lambsquarters | — | 6 | 4 | 5 | 4 | 4 | 2 | 0 | 0 | 0 | — | — | 0 | 0 | 0 | — | 0 | 0 | — | — | 5 | 0 | 5 | 0 | 0 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Pigweed | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ryegrass | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sorghum | 0 | 0 | 0 | 0 | 0 | 0 | 0 | 2 | 0 | 0 | 0 | 0 | 0 | 0 | 0 | 0 | 0 | 0 | 0 | 0 | 0 | 2 | 3 | 2 | 0 |
| Soybean | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 | 0 |
| Speedwell | 0 | 0 | 0 | 4 | 5 | 0 | 0 | 0 | 3 | 4 | — | — | 0 | 0 | 0 | 0 | 0 | 0 | 0 | 0 | 0 | 0 | 0 | 0 | 0 |
| Sugar beet | 0 | 0 | 0 | 6 | 2 | — | 0 | 0 | — | — | 0 | 0 | 0 | 0 | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat | 0 | 0 | 0 | — | — | — | 0 | 0 | 0 | 2 | 0 | 0 | 0 | 0 | 0 | 0 | 0 | 0 | 0 | 0 | 0 | 0 | 0 | 0 | 0 |
| Wild buckwheat | 0 | 0 | 0 | 0 | 0 | 0 | 0 | 0 | 2 | 0 | 0 | 6 | 0 | 0 | — | 5 | — | — | 0 | 0 | 3 | 0 | 0 | — | — |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 5 | 5 | 7 | 6 | 6 | 5 | 9 | 9 | 9 | 9 | 10 | 10 | 9 | 9 | 8 | 5 | 6 | 7 | 7 | 10 | 9 | 10 | 10 | 10 | 6 |
| Rice Japonica | 0 | 0 | 0 | 1 | 0 | 1 | 3 | 2 | 5 | 5 | 0 | 0 | 0 | 0 | 0 | 0 | 1 | 0 | 1 | 0 | 0 | 0 | 4 | 0 | 2 |
| Umbrella sedge | 0 | 7 | 5 | 1 | 0 | 0 | 9 | 8 | 7 | 7 | 0 | 0 | 1 | 0 | 0 | 0 | 1 | 0 | 3 | 0 | 9 | 8 | 9 | 9 | 6 |

| | COMPOUND |
|---|---|
| Rate (250 g/ha) | 8  9  16  17  18  19  24  25  26  27  31  34  39  40  41  43  46  47  53  56  57  60  61  62  63  75 |

PREEMERGENCE

| | 8 | 9 | 16 | 17 | 18 | 19 | 24 | 25 | 26 | 27 | 31 | 34 | 39 | 40 | 41 | 43 | 46 | 47 | 53 | 56 | 57 | 60 | 61 | 62 | 63 | 75 |
|---|---|---|---|---|---|---|---|---|---|---|---|---|---|---|---|---|---|---|---|---|---|---|---|---|---|---|
| Barley Igri | 5 | 3 | 0 | 6 | 3 | 3 | 2 | 4 | 8 | 6 | 0 | 3 | 0 | 0 | 0 | 0 | 0 | 0 | 9 | 0 | 0 | 0 | 3 | 0 | 8 | — |
| Bedstraw | 10 | 10 | 10 | 10 | 8 | 7 | 0 | 10 | 10 | 10 | 5 | 4 | 5 | 10 | 0 | 7 | 10 | 6 | 10 | 10 | 0 | 10 | 10 | 9 | 9 | — |
| Blackgrass | 9 | 10 | 10 | 10 | 9 | 9 | 10 | 10 | 10 | 10 | 10 | 9 | 10 | 10 | 7 | 9 | 9 | 10 | 10 | 10 | 10 | 10 | 10 | 10 | 10 | — |
| Chickweed | 9 | 8 | 8 | 9 | 8 | 8 | 9 | 9 | 9 | 9 | 8 | 8 | 9 | 9 | 6 | 9 | 6 | 9 | 9 | 9 | 9 | 9 | 10 | 10 | 10 | — |
| Corn | 6 | 7 | 0 | 8 | 4 | 0 | 10 | 7 | 6 | 6 | 0 | 0 | 0 | 0 | 0 | 3 | 6 | 2 | 6 | 3 | 2 | 10 | 8 | 7 | 0 | — |
| Cotton | 6 | 6 | 2 | 7 | 3 | 0 | 0 | 7 | 0 | 1 | 2 | 0 | 0 | 0 | 0 | 0 | 5 | 0 | 0 | 2 | 0 | 0 | 2 | 0 | 0 | — |
| Crabgrass | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | — |
| Downy brome | 8 | 7 | 10 | 6 | 4 | 4 | 9 | 9 | 10 | 8 | 3 | 3 | 0 | 5 | 0 | 0 | 3 | 10 | 10 | 10 | 9 | 9 | 9 | 0 | 10 | — |
| Giant foxtail | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | — |
| Lambsquarters | 10 | 10 | 9 | 10 | 9 | 10 | 9 | 10 | 10 | 9 | 9 | 8 | 9 | 9 | 9 | 9 | 9 | 9 | 9 | 9 | 9 | 10 | 10 | 10 | 9 | — |
| Morningglory | 6 | 3 | 0 | 0 | 0 | 0 | 0 | 5 | 0 | 10 | 0 | 0 | 0 | 0 | 0 | 0 | 0 | 0 | 0 | 0 | 0 | 0 | 3 | 0 | 0 | — |
| Pigweed | 9 | 8 | 9 | 10 | 10 | 7 | 6 | 9 | 10 | 10 | 7 | 7 | 7 | 7 | 5 | 0 | 5 | 5 | 9 | 8 | 0 | 0 | 9 | 9 | 9 | — |

TABLE B-continued

| | | | | | | | | | | | | | | | | | | | | | | | | | |
|---|---|---|---|---|---|---|---|---|---|---|---|---|---|---|---|---|---|---|---|---|---|---|---|---|---|
| Rape | 3 | 4 | 0 | 6 | 6 | 4 | 6 | 4 | 6 | 2 | 3 | 0 | 6 | 3 | 6 | 3 | 3 | 5 | 4 | 3 | 2 | 5 | 6 | 4 | 0 | — |
| Ryegrass | 10 | 10 | 10 | 10 | 10 | 8 | 10 | 10 | 10 | 10 | 9 | 5 | — | 10 | 6 | 9 | 10 | 10 | 10 | 10 | 10 | 10 | 10 | 10 | 10 | — |
| Sorghum | 10 | 10 | 10 | 10 | 5 | 4 | 7 | 10 | 7 | 10 | 5 | 7 | 7 | 6 | 4 | 0 | 2 | 5 | 4 | 7 | 4 | 7 | 6 | 6 | 4 | — |
| Soybean | 9 | 8 | 0 | 8 | 8 | 0 | 0 | 9 | 9 | 9 | 1 | 0 | 0 | 0 | 0 | 0 | 6 | 0 | 2 | 0 | 0 | 0 | 5 | 0 | 6 | — |
| Speedwell | 9 | 9 | 8 | 9 | 9 | 9 | 10 | 9 | 9 | 10 | 8 | 8 | 9 | 7 | 7 | 9 | 9 | 9 | 10 | 10 | 9 | 9 | 10 | 9 | 9 | — |
| Sugar beet | 7 | 8 | 7 | 9 | 8 | 9 | 7 | 9 | 9 | 9 | 7 | 7 | 9 | 9 | 6 | 7 | 8 | 7 | 9 | 9 | 8 | 8 | 9 | 8 | 9 | — |
| Velvetleaf | 8 | 9 | 7 | 8 | 8 | 7 | 6 | 8 | 9 | 9 | 8 | 8 | 7 | 8 | 6 | 7 | 9 | 9 | 8 | 7 | 8 | 9 | 9 | 9 | 8 | — |
| Wheat | 4 | 6 | 0 | 6 | 2 | 2 | 3 | 0 | 3 | 9 | 0 | 2 | 0 | 0 | 0 | 0 | 0 | 0 | 9 | 4 | 0 | 4 | 3 | 0 | 9 | — |
| Wild buckwheat | 10 | 10 | 9 | 9 | 8 | 8 | 9 | 9 | 9 | 10 | 9 | 9 | 9 | 10 | 8 | 9 | 9 | 9 | 9 | 9 | 9 | 10 | 10 | 10 | 10 | — |
| Wild oat | 4 | 4 | 0 | 4 | 4 | 2 | 4 | 5 | 9 | 9 | 4 | 0 | 0 | 2 | 3 | 0 | 2 | 0 | 10 | 3 | 10 | 10 | 10 | 9 | 6 | — |

| | COMPOUND | | | | | | | | | | | | | | | | | | | | | | | | |
|---|---|---|---|---|---|---|---|---|---|---|---|---|---|---|---|---|---|---|---|---|---|---|---|---|---|
| Rate (125 g/ha) | 8 | 9 | 16 | 17 | 18 | 19 | 24 | 25 | 26 | 27 | 31 | 34 | 39 | 40 | 41 | 43 | 46 | 47 | 53 | 56 | 57 | 60 | 61 | 62 | 63 | 75 |
| | PREEMERGENCE | | | | | | | | | | | | | | | | | | | | | | | | |
| Barley Igri | 4 | 0 | 0 | 6 | 3 | 2 | 0 | 4 | 4 | 4 | 0 | 2 | 0 | 0 | 0 | 0 | 0 | 0 | 0 | 0 | 0 | 0 | 0 | 0 | 0 | — |
| Bedstraw | 10 | 10 | 5 | 10 | 8 | 7 | 0 | 10 | 10 | 10 | 2 | 2 | 5 | 7 | 0 | 7 | 0 | 0 | 10 | 10 | 0 | 10 | 9 | 5 | 9 | — |
| Blackgrass | 9 | 10 | 5 | 10 | 9 | 7 | 10 | 10 | 9 | 10 | 9 | 9 | 10 | 5 | 6 | 7 | 5 | 9 | 10 | 10 | 10 | 10 | 10 | 10 | 10 | — |
| Chickweed | 9 | 8 | 7 | 9 | 8 | 8 | 8 | 9 | 9 | 9 | 7 | 7 | 9 | 6 | 5 | 9 | 6 | 6 | 9 | 9 | 8 | 9 | 10 | 9 | 10 | — |
| Corn | 5 | 5 | 0 | 7 | 2 | 0 | 5 | 4 | 5 | 5 | 0 | 0 | 0 | 0 | 0 | 0 | 2 | 0 | 5 | 3 | 0 | 7 | 8 | 2 | 0 | — |
| Cotton | 2 | 3 | 2 | 5 | 2 | 0 | 0 | 2 | 0 | 0 | 0 | 0 | 0 | 0 | 0 | 0 | 3 | 0 | 3 | 2 | 0 | 0 | 0 | 0 | 0 | — |
| Crabgrass | 10 | 10 | 10 | 10 | 10 | 10 | 10 | 10 | 10 | 10 | 10 | 9 | 10 | 10 | 10 | 10 | 10 | 10 | 10 | 10 | 10 | 10 | 10 | 10 | 10 | — |
| Downy brome | 7 | 6 | 5 | 6 | 3 | 0 | 4 | 3 | 9 | 2 | 2 | 2 | 0 | 0 | 0 | 0 | 2 | 0 | 9 | 6 | 0 | 2 | 3 | 0 | 8 | — |
| Giant foxtail | 10 | 10 | 10 | 10 | 10 | 10 | 10 | 10 | 10 | 10 | 10 | 9 | 10 | 10 | 10 | 10 | 10 | 10 | 10 | 10 | 10 | 10 | 10 | 10 | 10 | — |
| Lambsquarters | 10 | 10 | 8 | 10 | 9 | 9 | 9 | 9 | 9 | 9 | 6 | 6 | 9 | — | 9 | 9 | 9 | 9 | 9 | 9 | 9 | 10 | 10 | 10 | 9 | — |
| Morningglory | 2 | 2 | 0 | 0 | 0 | 0 | 0 | 1 | 0 | 4 | 0 | 0 | 0 | 0 | 0 | 0 | 0 | 0 | 0 | 0 | 0 | 0 | 0 | 0 | 0 | — |
| Pigweed | 8 | 7 | 8 | 8 | 7 | 6 | 2 | 8 | 10 | 8 | 7 | 7 | 7 | 7 | 3 | 0 | 5 | 3 | 8 | 7 | 7 | 8 | 8 | 7 | 9 | — |
| Rape | 2 | 3 | 0 | 3 | 5 | 3 | 4 | 2 | 3 | 0 | 2 | 0 | 4 | 1 | 5 | 0 | 1 | 0 | 2 | 2 | 0 | 4 | 0 | 3 | 0 | — |
| Ryegrass | 10 | 6 | 7 | 10 | 5 | 8 | 10 | 10 | 10 | 10 | 7 | 3 | 9 | 7 | 5 | 4 | 8 | 8 | 10 | 10 | 8 | 10 | 10 | 10 | 9 | — |
| Sorghum | 5 | 9 | 4 | 6 | 4 | 3 | 7 | 10 | 7 | 5 | 5 | 4 | 3 | 5 | 2 | 0 | 2 | 2 | 4 | 3 | 6 | 5 | 4 | 2 | — | |
| Soybean | 6 | 0 | 0 | 6 | 6 | 0 | 0 | 9 | 9 | 8 | 0 | 0 | 0 | 0 | 0 | 0 | 2 | 0 | 0 | 0 | 0 | 0 | 2 | 0 | 1 | — |
| Speedwell | 9 | 8 | 7 | 9 | 9 | 9 | 10 | 9 | 9 | 10 | 6 | 7 | 8 | 7 | 7 | 9 | 9 | 9 | 9 | 9 | 8 | 9 | 9 | 9 | 9 | — |
| Sugar beet | 7 | 8 | 6 | 8 | 5 | 8 | 7 | 9 | 9 | 9 | 4 | 5 | 6 | 7 | 6 | 6 | 4 | 7 | 8 | 8 | 8 | 5 | 6 | 3 | 8 | — |
| Velvetleaf | 7 | 8 | 3 | 8 | 7 | 4 | 3 | 8 | 8 | 8 | 5 | 7 | 7 | 3 | 5 | 7 | 8 | 2 | 5 | 5 | 6 | 8 | 9 | 8 | 7 | — |
| Wheat | 3 | 4 | 0 | 6 | 0 | 0 | 0 | 3 | 3 | 4 | 0 | 0 | 0 | 0 | 0 | 0 | 0 | 0 | 3 | 0 | 4 | 0 | 0 | 0 | 3 | — |
| Wild buckwheat | 10 | 10 | 9 | 9 | 8 | 8 | 9 | 9 | 9 | 9 | 7 | 7 | 9 | 9 | 8 | 9 | — | 9 | 9 | 9 | 3 | 10 | 10 | 9 | 10 | — |
| Wild oat | 3 | 3 | 0 | 4 | 3 | 0 | 0 | 3 | 3 | 3 | 0 | 0 | 0 | 0 | 3 | 0 | 2 | 0 | 4 | 0 | 5 | 10 | 10 | 4 | 0 | — |

| | COMPOUND | | | | | | | | | | | | | | | | | | | | | | | | |
|---|---|---|---|---|---|---|---|---|---|---|---|---|---|---|---|---|---|---|---|---|---|---|---|---|---|
| Rate (62 g/ha) | 8 | 9 | 16 | 17 | 18 | 19 | 24 | 25 | 26 | 27 | 31 | 34 | 39 | 40 | 41 | 43 | 46 | 47 | 53 | 56 | 57 | 60 | 61 | 62 | 63 | 75 |
| | PREEMERGENCE | | | | | | | | | | | | | | | | | | | | | | | | |
| Barley Igri | 3 | 0 | 0 | 5 | 2 | 0 | 0 | 3 | 2 | 3 | 0 | 0 | 0 | 0 | 0 | 0 | 0 | 0 | 0 | 0 | 0 | 0 | 0 | 0 | — | — |
| Bedstraw | 9 | 7 | 3 | 9 | 8 | 0 | 0 | 10 | 10 | 10 | 0 | 0 | 3 | 2 | 0 | 6 | 0 | 0 | 5 | 3 | 0 | 5 | 9 | 5 | 9 | — |
| Blackgrass | 8 | 8 | 4 | 9 | 6 | 4 | 10 | 9 | 8 | 10 | 8 | 9 | 10 | 5 | 4 | 6 | 5 | 5 | 10 | 10 | 7 | 10 | 10 | 9 | 10 | — |
| Chickweed | 8 | 7 | 6 | 9 | 7 | 7 | 8 | 9 | 9 | 9 | 4 | 4 | 9 | 3 | 0 | 9 | 3 | 4 | 8 | 8 | 8 | 9 | 9 | 9 | 10 | — |
| Corn | 4 | 4 | 0 | 3 | 0 | 0 | 2 | 3 | 5 | 4 | 0 | 0 | 0 | 0 | 0 | 0 | 0 | 0 | 1 | 2 | 0 | 3 | 6 | 0 | 0 | — |
| Cotton | 0 | 0 | 0 | 3 | 0 | 0 | 0 | 0 | 0 | 0 | 0 | 0 | 0 | 0 | 0 | 0 | 1 | 0 | 0 | 0 | 0 | 0 | 0 | 0 | 0 | — |
| Crabgrass | 10 | 10 | 10 | 10 | 10 | 10 | 8 | 10 | 10 | 10 | 9 | 6 | 9 | 9 | 5 | 10 | 10 | 10 | 9 | 10 | 8 | 10 | 10 | 10 | 9 | — |
| Downy brome | 4 | 5 | 3 | 3 | 1 | 0 | 3 | 0 | 3 | 2 | 2 | 0 | 0 | 0 | 0 | 0 | 0 | 0 | 6 | 0 | 0 | 0 | 0 | 0 | 0 | — |
| Giant foxtail | 9 | 9 | 9 | 10 | 10 | 10 | 10 | 10 | 10 | 10 | 10 | 9 | 9 | 10 | 10 | 9 | 10 | 10 | 8 | 9 | 10 | 10 | 10 | 10 | 10 | — |
| Lambsquarters | 9 | 10 | 7 | 9 | — | 6 | 8 | 8 | 8 | 8 | 5 | 6 | 9 | 9 | 9 | 9 | 8 | 7 | 9 | 9 | 9 | 9 | 10 | 10 | 9 | — |
| Morningglory | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | — |
| Pigweed | 8 | 7 | 7 | 7 | 5 | 5 | 0 | 8 | 7 | 8 | 5 | 3 | 2 | 6 | 0 | 0 | 3 | 3 | 7 | 7 | 4 | 7 | 8 | 7 | 8 | — |
| Rape | 0 | 2 | 0 | 1 | 4 | 2 | 2 | 0 | 1 | 0 | 2 | 0 | 0 | 0 | 0 | 0 | 0 | 0 | 0 | 2 | 0 | 0 | 0 | 0 | 0 | — |
| Ryegrass | 8 | 5 | 5 | 10 | 3 | 4 | 10 | 9 | 9 | 10 | 3 | 0 | 0 | 0 | 0 | 4 | 5 | 2 | 9 | 4 | 5 | 10 | 10 | 9 | 8 | — |
| Sorghum | 3 | 7 | 0 | 5 | 3 | 0 | 3 | 4 | 4 | 4 | 2 | 2 | 3 | 3 | 0 | 0 | 0 | 0 | 2 | 1 | 3 | 5 | 3 | 0 | — | — |
| Soybean | 2 | 2 | 0 | 4 | 3 | 0 | 0 | 5 | 2 | 6 | 0 | 0 | 0 | 0 | 0 | 0 | 0 | 0 | 0 | 0 | 0 | 0 | 1 | 0 | 0 | — |
| Speedwell | 8 | 7 | 6 | 9 | — | 5 | 8 | 8 | 9 | 9 | 5 | 3 | 8 | 5 | 6 | 8 | 9 | 8 | 9 | 8 | 8 | 8 | 9 | 6 | 9 | — |
| Sugar beet | 6 | 6 | 3 | 7 | 5 | 6 | 6 | 8 | 9 | 8 | 4 | 3 | 2 | 2 | 6 | 6 | 1 | 5 | 6 | 6 | 6 | 5 | 5 | 0 | 7 | — |
| Velvetleaf | 7 | 7 | 2 | 7 | 7 | 3 | 0 | 7 | 5 | 7 | 3 | 3 | 3 | 2 | 5 | 5 | 5 | 2 | 3 | 2 | 4 | 7 | 7 | 7 | 4 | — |
| Wheat | 0 | 3 | 0 | 4 | 0 | 0 | 0 | 2 | 2 | 3 | 0 | 0 | 0 | 0 | 0 | 0 | 0 | 0 | 0 | 0 | 0 | 4 | 0 | 0 | 0 | — |
| Wild buckwheat | 8 | 8 | 8 | 9 | 7 | 8 | 9 | 9 | 9 | 9 | 5 | 0 | 9 | 9 | 8 | 8 | — | 8 | 9 | 9 | — | 9 | 10 | — | 10 | — |
| Wild oat | 2 | 2 | 0 | 0 | 2 | 0 | 0 | 0 | 0 | 2 | 0 | 0 | 0 | 0 | 2 | 0 | 0 | 0 | 2 | 0 | 0 | 6 | 9 | 4 | — | — |

| | COMPOUND | | | | | | | | | | | | | | | | | | | | | | | | |
|---|---|---|---|---|---|---|---|---|---|---|---|---|---|---|---|---|---|---|---|---|---|---|---|---|---|
| Rate (31 g/ha) | 8 | 9 | 16 | 17 | 18 | 19 | 24 | 25 | 26 | 27 | 31 | 34 | 39 | 40 | 41 | 43 | 46 | 47 | 53 | 56 | 57 | 60 | 61 | 62 | 63 | 75 |
| | PREEMERGENCE | | | | | | | | | | | | | | | | | | | | | | | | |
| Barley Igri | 2 | 0 | 0 | 4 | 0 | 0 | 0 | 2 | 0 | 0 | 0 | 0 | 0 | 0 | 0 | 0 | 0 | 0 | 0 | 0 | 0 | 0 | 0 | 0 | 0 | — |
| Bedstraw | 8 | 6 | 0 | 9 | 3 | 0 | 0 | 9 | 10 | 9 | 0 | 0 | 0 | 0 | 0 | 5 | 0 | — | 3 | 0 | 5 | 7 | 5 | 5 | — | — |
| Blackgrass | 7 | 6 | 3 | 9 | 5 | 3 | 4 | 7 | 7 | 6 | 3 | 4 | 5 | 5 | 4 | 3 | 4 | 3 | 7 | 10 | 6 | 10 | 10 | 6 | 7 | — |
| Chickweed | 7 | 6 | 5 | 9 | 5 | 4 | 0 | 9 | 6 | 9 | 2 | 0 | — | 0 | 0 | 5 | 0 | 0 | 8 | 8 | 8 | 9 | 9 | 9 | 10 | — |
| Corn | 2 | 0 | 0 | 2 | 0 | 0 | 0 | 0 | 3 | 3 | 0 | 0 | 0 | 0 | 0 | 0 | 0 | 0 | 0 | 0 | 0 | 2 | 6 | 0 | 0 | — |
| Cotton | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — |
| Crabgrass | 9 | 9 | 9 | 10 | 10 | 9 | 4 | 10 | 10 | 10 | 7 | 5 | 6 | 6 | 3 | 5 | 9 | 9 | 8 | 7 | 3 | 10 | 10 | 10 | 8 | — |
| Downy brome | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | — |
| Giant foxtail | 9 | 9 | 9 | 10 | 9 | 8 | 8 | 10 | 10 | 10 | 6 | 9 | 8 | 8 | 8 | 6 | 7 | 8 | 8 | 7 | 8 | 10 | 10 | 10 | 8 | — |
| Lambsquarters | 8 | 10 | 6 | 7 | 6 | 5 | 7 | 7 | 6 | 8 | — | 0 | 8 | 9 | 8 | 9 | 4 | 7 | 9 | 9 | 9 | 9 | 10 | 9 | 9 | — |
| Morningglory | 0 | 0 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | — |
| Pigweed | 8 | 6 | 5 | 6 | 3 | 4 | 0 | 7 | 7 | 4 | 2 | 2 | 0 | 4 | 0 | 0 | 3 | 2 | 5 | 5 | 0 | 6 | 3 | 5 | 5 | — |
| Rape | 0 | 0 | 0 | 0 | 3 | 0 | 0 | 0 | 0 | 0 | 0 | 0 | 0 | 0 | — | 0 | 0 | 0 | 0 | 0 | 0 | 0 | 0 | 0 | 0 | — |
| Ryegrass | 4 | 3 | 0 | 6 | 3 | 3 | 9 | 7 | 7 | 8 | 0 | 0 | 3 | 0 | 3 | 0 | 0 | 6 | 4 | 0 | 7 | 9 | 6 | 5 | — | — |
| Sorghum | 2 | 5 | 0 | 3 | 0 | 0 | 2 | 2 | 2 | 3 | 0 | 0 | 3 | 2 | 0 | 0 | 0 | 0 | 0 | 0 | 0 | 3 | 2 | 0 | — | — |

TABLE B-continued

| | | | | | | | | | | | | | | | | | | | | | | | | | | |
|---|---|---|---|---|---|---|---|---|---|---|---|---|---|---|---|---|---|---|---|---|---|---|---|---|---|---|
| Soybean | 0 | 0 | 0 | 2 | 0 | 0 | 0 | 0 | 0 | 4 | 0 | 0 | 0 | 0 | 0 | 0 | 0 | 0 | 0 | 0 | 0 | 0 | 0 | 0 | 0 | — |
| Speedwell | 7 | 6 | 4 | 9 | 9 | 4 | 8 | 8 | 6 | 8 | 2 | 0 | 7 | 5 | 4 | 7 | 8 | 8 | 8 | 3 | 3 | 4 | 8 | 6 | 9 | — |
| Sugar beet | 5 | 6 | 0 | 4 | 2 | 0 | 4 | 4 | 3 | 6 | 3 | 2 | 2 | 0 | 3 | 3 | 0 | 0 | 5 | 3 | 5 | 4 | 5 | — | 4 | — |
| Velvetleaf | 6 | 5 | 0 | 7 | 3 | 0 | 0 | 5 | 5 | 3 | 0 | 0 | 0 | 0 | 3 | 0 | 3 | 0 | 3 | 0 | 3 | 3 | 3 | 5 | 4 | — |
| Wheat | 0 | 0 | 0 | 4 | 0 | 0 | 0 | 0 | 0 | 2 | 0 | 0 | 0 | 0 | 0 | 0 | 0 | 0 | 0 | 0 | 0 | 0 | 0 | 0 | 0 | — |
| Wild buckwheat | 8 | 7 | 4 | 9 | 4 | 4 | 8 | 9 | 6 | 9 | 2 | 0 | 8 | 8 | 8 | 8 | — | 8 | 9 | 9 | — | 4 | 10 | — | 8 | — |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 5 | 0 | 0 | — |

| | COMPOUND | | | | | | | | | | | | | | | | | | | | | | | | | |
|---|---|---|---|---|---|---|---|---|---|---|---|---|---|---|---|---|---|---|---|---|---|---|---|---|---|---|
| Rate (16 g/ha) | 8 | 9 | 16 | 17 | 18 | 19 | 24 | 25 | 26 | 27 | 31 | 34 | 39 | 40 | 41 | 43 | 46 | 47 | 53 | 56 | 57 | 60 | 61 | 62 | 63 | |
| PREEMERGENCE | | | | | | | | | | | | | | | | | | | | | | | | | | |
| Barley Igri | 0 | 0 | 0 | 0 | 0 | 0 | 0 | 8 | 0 | 0 | 0 | 0 | 0 | 0 | 0 | 0 | 0 | 0 | 0 | 0 | 0 | 0 | 0 | 0 | 0 | |
| Bedstraw | 5 | 6 | 0 | 4 | 0 | 0 | 0 | 5 | 3 | 2 | 0 | 0 | 0 | 0 | 0 | 5 | 0 | 0 | 5 | 0 | 0 | 3 | 6 | 0 | 4 | |
| Blackgrass | 3 | 5 | 2 | 7 | 3 | 2 | 2 | 3 | 2 | 4 | 0 | 2 | 3 | 5 | 2 | 3 | 0 | 0 | 5 | 5 | 0 | 9 | 9 | 0 | 4 | |
| Chickweed | 7 | 6 | 4 | 7 | 3 | 3 | 0 | 8 | 6 | 5 | 0 | 0 | 4 | 0 | 0 | 5 | 0 | 0 | 8 | 7 | 0 | 9 | 9 | 0 | 4 | |
| Corn | 2 | 0 | 0 | 0 | 0 | 0 | 0 | 0 | 0 | 0 | 0 | 0 | 0 | 0 | 0 | 0 | 0 | 0 | 0 | 0 | 0 | 2 | 2 | 0 | 0 | |
| Cotton | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | |
| Crabgrass | 9 | 9 | 6 | 10 | 10 | 7 | 2 | 8 | 10 | 10 | 3 | 3 | 4 | 5 | 0 | 0 | 8 | 8 | 5 | 3 | 0 | 8 | 10 | 9 | 2 | |
| Downy brome | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 | |
| Giant foxtail | 6 | 9 | 8 | 10 | 8 | 7 | 4 | 8 | 8 | 10 | 2 | 7 | 4 | 7 | 3 | 0 | 7 | 6 | 6 | 6 | 2 | 10 | 10 | 9 | 5 | |
| Lambsquarters | 4 | 9 | 3 | 5 | 6 | 5 | 6 | 2 | 0 | 6 | 0 | 0 | 8 | 8 | 6 | 9 | 4 | 5 | 9 | 8 | 3 | 9 | 10 | 9 | 8 | |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | |
| Pigweed | 7 | 6 | 5 | 5 | 3 | 3 | 0 | 7 | 5 | 4 | 0 | 0 | 0 | 0 | 0 | 0 | 2 | 0 | 0 | 4 | 0 | 6 | 0 | 5 | 2 | |
| Rape | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | |
| Ryegrass | 4 | 0 | 0 | 4 | 0 | 0 | 4 | 5 | 2 | 2 | 0 | 0 | 0 | 0 | 0 | 2 | 0 | 0 | 3 | 0 | 0 | 5 | 6 | 0 | 0 | |
| Sorghum | 0 | 3 | 0 | 0 | 0 | 0 | 0 | 0 | 0 | 2 | 0 | 0 | 2 | 0 | 0 | 0 | 0 | 0 | 0 | 0 | 0 | 0 | 0 | 0 | 0 | |
| Soybean | 0 | 0 | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | |
| Speedwell | 6 | 5 | 0 | 9 | 8 | 4 | 3 | 7 | 6 | 4 | 0 | 0 | 4 | 5 | 4 | 7 | 7 | 3 | 8 | 2 | 0 | — | 4 | 5 | — | |
| Sugar beet | 4 | 5 | 0 | 3 | 0 | 0 | 0 | 3 | 3 | 4 | 0 | 0 | 2 | 0 | 2 | — | 0 | 0 | 4 | 0 | 4 | 0 | 0 | 0 | 4 | |
| Velvetleaf | 6 | 3 | 0 | 0 | 0 | 0 | 0 | 2 | 3 | 2 | 0 | 0 | 0 | 0 | 0 | 0 | 0 | 0 | 0 | 0 | 2 | 0 | 0 | 0 | 4 | |
| Wheat | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | |
| Wild buckwheat | 7 | 6 | 3 | 6 | 4 | 3 | 5 | 5 | 5 | 6 | 0 | 0 | 6 | 6 | 5 | 8 | — | — | 8 | 8 | 0 | 0 | 0 | 0 | 6 | |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 4 | 0 | 0 | |

TEST C

Seeds of barnyardgrass (*Echinochloa crus-galli*), corn (*Zea mays*), cotton (*Gossypium hirsutam*), crabgrass (*Digitaria* spp.), fall panicum (*Panicum dicholomiflorum*), giant foxtail (*Setaria faberii*), green foxtail (*Setaria vividis*), johnson grass (*Sorghum halepense*), signalgrass (*Brachiaria platyphylla*), soybean (*Glycine max*) and wild proso (*Pancium miliaceum*) were planted into a silt loam soil. Test chemicals, dissolved in a non-phytotoxic solvent, were then applied to the soil surface within one day after the seeds were planted. Pots receiving these preemergence treatments were placed in the greenhouse and maintained according to routine greenhouse procedures.

Treated plants and untreated controls were maintained in the greenhouse approximately 21 days after application of the test compound. Visual evaluations of plant injury responses were then recorded. Plant response ratings, summarized in Table C, are reported on a 0 to 10 scale where 0 is no effect and 10 is complete control.

TABLE C

| | COMPOUND | | | | | | | | | | | | | | | | | | | | | | | |
|---|---|---|---|---|---|---|---|---|---|---|---|---|---|---|---|---|---|---|---|---|---|---|---|---|
| | Rate (500 g/ha) | | | | Rate (250 g/ha) | | | | | | | | | | | | | Rate (125 g/ha) | | | | | | |
| | 39 | 40 | 43 | 46 | 8 | 9 | 16 | 18 | 25 | 26 | 27 | 39 | 40 | 43 | 46 | 60 | 61 | 62 | 8 | 9 | 16 | 17 | 18 | 25 | 26 |
| PREEMERGENCE | | | | | | | | | | | | | | | | | | | | | | | | | |
| Barnyardgrass | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 |
| Corn G4689A | 7 | 7 | 8 | 9 | 8 | 10 | 4 | 8 | 8 | 10 | 10 | 5 | 6 | 6 | 7 | 5 | 8 | 8 | 6 | 10 | 1 | 10 | 6 | 7 | 8 |
| Cotton | 0 | 0 | 1 | 1 | 3 | 1 | 7 | 6 | 3 | 8 | 7 | 0 | 0 | 0 | 0 | 0 | 4 | 3 | 2 | 2 | — | 7 | 5 | 0 | 4 |
| Crabgrass | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 |
| Fall Panicum | 10 | 10 | 10 | 10 | 10 | 10 | 10 | 10 | 10 | 10 | 10 | 10 | 10 | 7 | 10 | 10 | 10 | 10 | 10 | 10 | 10 | 10 | 10 | 10 | 10 |
| Giant Foxtail | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 |
| Green Foztail | 10 | 10 | 10 | 10 | 10 | 10 | 8 | 7 | 10 | 10 | 10 | 10 | 10 | 10 | 10 | 10 | 10 | 10 | 10 | 10 | 8 | 10 | 6 | 10 | 10 |
| Johnson Grass | 10 | 10 | 10 | 9 | 7 | 10 | 10 | 7 | 10 | 9 | 10 | 9 | 10 | 7 | 7 | 8 | 9 | 8 | 7 | 10 | 9 | 9 | 6 | 10 | 7 |
| Signalgrass | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 |
| Soybean | 1 | 1 | 7 | 1 | 4 | 5 | 2 | 9 | 8 | 8 | 9 | 1 | 0 | 5 | 0 | 0 | 4 | 0 | 1 | 3 | 1 | 8 | 6 | 0 | 8 |
| Wild Proso | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 |

| | COMPOUND | | | | | | | | | | | | | | | | | | | | | Rate (31 g/ha) | |
|---|---|---|---|---|---|---|---|---|---|---|---|---|---|---|---|---|---|---|---|---|---|---|---|
| | Rate (125 g/ha) | | | | | | | | Rate (62 g/ha) | | | | | | | | | | | | | | |
| | 27 | 39 | 40 | 43 | 46 | 60 | 61 | 62 | 8 | 8 | 16 | 17 | 18 | 26 | 26 | 27 | 39 | 40 | 43 | 46 | 60 | 61 | 62 | 8 | 9 |
| PREEMERGENCE | | | | | | | | | | | | | | | | | | | | | | | | | |
| Barnyardgrass | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 |
| Corn G4689A | 8 | 4 | 4 | 2 | 3 | 2 | 1 | 1 | 1 | 5 | 0 | 8 | 5 | 4 | 2 | 7 | 0 | 0 | 0 | 0 | 0 | 0 | 0 | 1 | 0 |
| Cotton | 3 | 0 | 0 | 0 | 0 | 0 | 0 | 0 | 0 | 0 | 0 | 6 | 3 | 0 | 0 | 2 | 0 | 0 | 0 | 0 | 0 | 0 | 0 | 0 | 0 |
| Crabgrass | 10 | 10 | 10 | 10 | 9 | 10 | 10 | 10 | 10 | 10 | 10 | 10 | 10 | 10 | 9 | 10 | 10 | 10 | 10 | 7 | 10 | 10 | 8 | 8 | 10 |
| Fall Panicum | 10 | 10 | 10 | 10 | 10 | 10 | 10 | 10 | 9 | 10 | 10 | 10 | 10 | 10 | 10 | 10 | 10 | 10 | 10 | 7 | 7 | 10 | 10 | 1 | 10 |
| Giant Foxtail | 10 | 10 | 10 | 10 | 9 | 10 | 10 | 10 | 9 | 10 | 10 | 10 | 10 | 10 | 10 | 10 | 10 | 10 | 10 | 7 | 7 | 10 | 10 | 8 | 10 |
| Green Foxtail | 10 | 10 | 10 | 10 | 9 | 10 | 10 | 10 | 10 | 10 | 9 | 10 | — | 7 | 7 | 7 | 7 | 7 | 6 | 6 | 10 | 10 | 9 | 10 | 10 |
| Johnson Grass | 10 | 8 | 9 | 6 | 6 | 7 | 8 | 8 | 6 | 9 | 8 | 7 | 5 | 7 | 6 | 4 | 5 | 6 | 2 | 4 | 5 | 7 | 5 | 5 | 8 |

TABLE C-continued

| | 16 | 17 | 18 | 25 | 26 | 27 | 39 | 40 | 43 | 46 | 60 | 61 | 62 | 8 | 9 | 16 | 17 | 18 | 25 | 26 | 27 | 60 | 61 | 62 | 17 |
|---|---|---|---|---|---|---|---|---|---|---|---|---|---|---|---|---|---|---|---|---|---|---|---|---|---|
| Signalgrass | 10 | 10 | 10 | 7 | 10 | 10 | 10 | 10 | 10 | 10 | 10 | 10 | 10 | 10 | 10 | 10 | 10 | 10 | 1 | 4 | 10 | 10 | 10 | 4 | 10 |
| Soybean | 8 | 1 | 0 | 2 | 0 | 0 | 0 | 0 | 0 | 1 | 1 | 7 | 0 | 0 | 4 | 5 | 0 | 0 | 0 | 0 | 0 | 0 | 0 | 0 | 0 |
| Wild Proso | 10 | 10 | 10 | 10 | 10 | 10 | 10 | 10 | 8 | 10 | 10 | 10 | 10 | 10 | 10 | 10 | 10 | 10 | 10 | 10 | 10 | 10 | 10 | 8 | 10 |

| | COMPOUND | | | | | | | | | | | | | | | | | | | | | | | | |
|---|---|---|---|---|---|---|---|---|---|---|---|---|---|---|---|---|---|---|---|---|---|---|---|---|---|
| | Rate (31 g/ha) | | | | | | | | | | | | Rate (16 g/ha) | | | | | | | | | | | | Rate (8 g/ha) |
| | 16 | 17 | 18 | 25 | 26 | 27 | 39 | 40 | 43 | 46 | 60 | 61 | 62 | 8 | 9 | 16 | 17 | 18 | 25 | 26 | 27 | 60 | 61 | 62 | 17 |
| PRE-EMERGENCE | | | | | | | | | | | | | | | | | | | | | | | | | |
| Barnyardgrass | 10 | 10 | 8 | 10 | 10 | 10 | 4 | 10 | 6 | 5 | 9 | 10 | 9 | 0 | 10 | 4 | 10 | 2 | 10 | 10 | 6 | 4 | 8 | 8 | 6 |
| Corn G4689A | 0 | 6 | 0 | 0 | 1 | 1 | 0 | 0 | 0 | 0 | 0 | 0 | 0 | 1 | 0 | 0 | 4 | 0 | 0 | 0 | 0 | 0 | 0 | 0 | 0 |
| Cotton | 0 | 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 8 | 10 | 10 | 10 | 8 | 5 | 6 | 9 | 8 | 4 | 7 | 9 | 6 | 2 | 9 | 4 | 5 | 7 | 7 | 8 | 4 | 4 | 6 | 4 | 3 |
| Fall Panicum | 10 | 10 | 10 | 10 | 10 | 10 | 6 | 9 | 6 | 1 | 9 | 9 | 7 | 0 | 8 | 9 | 10 | 9 | 10 | 9 | 9 | 7 | 7 | 6 | 9 |
| Giant Foxtail | 9 | 10 | 10 | 10 | 10 | 10 | 8 | 10 | 10 | 6 | 10 | 10 | 10 | 0 | 10 | 6 | 9 | 7 | 6 | 7 | 6 | 6 | 9 | 6 | 0 |
| Green Foxtail | 1 | 6 | 5 | 4 | 6 | 1 | 3 | 6 | 4 | 3 | 10 | 10 | 8 | 0 | 1 | 1 | 1 | 0 | 0 | 0 | 0 | 4 | 7 | 6 | 0 |
| Johnson Grass | 7 | 6 | 0 | 4 | 4 | 2 | 1 | 5 | 1 | 2 | 5 | 6 | 4 | 2 | 5 | 3 | 6 | 0 | 0 | 0 | 0 | 0 | 3 | 4 | 0 |
| Signalgrass | 10 | 8 | 7 | 9 | 10 | 10 | 0 | 3 | 0 | 0 | 10 | 9 | 10 | 0 | 6 | 0 | 8 | 0 | 0 | 0 | 0 | 7 | 7 | 7 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild Proso | 10 | 9 | 10 | 10 | 10 | 10 | 7 | 10 | 7 | 3 | 10 | 10 | 10 | 4 | 9 | 9 | 9 | 7 | 10 | 9 | 10 | 6 | 10 | 10 | 7 |

TEST D

Plastic pots were partially filled with silt loam soil. The soil was then aturated with water. Japonica rice (*Oryza sativa*) seedlings at the 2.0 to 2.5 leaf stage, seeds selected from barnyardgrass (*Echinochloa crus-galli*), duck salad (*Heteranthera limosa*), umbrella sedge (*Cyperus difformis*), and tubers selected from arrowhead (*Sagittaria spp.*), waterchestnut (*Eleocharis spp.*), were planted into this soil. After planting, water levels were raised to 3 cm above the soil surface and maintained at this level throughout the test. Chemical treatments were formulated in a non-phytotoxic solvent and applied directly to the paddy water. Treated plants and controls were maintained in a greenhouse for approximately 21 days, after which all species were compared to controls and visually evaluated. Plant response ratings, summarized in Table D, are reported on a 0 to 10 scale where 0 is no effect and 10 is complete control. A dash (-) response means no test result.

tion) and to plants that were in the one-to-four leaf stage (postemergence application). A sandy loam soil was used for the preemergence test while a mixture of sandy loam soil and greenhouse potting mix in a 60:40 ratio was used for the postemergence test. Test compounds were applied within approximately one day after planting seeds for the preemergence test. Plantings of these crops and weed species were adjusted to produce plants of appropriate size for the postemergence test. All plant species were grown using normal greenhouse practices. Crop and weed species include winter barley (*Hordeum vulgare* cv. 'Igri'), bedstraw (*Galium aparine*), blackgrass (*Alopecurus myosuroides*), chickweed (*Stellaria media*), downy brome (*Bromus tectorum*, field violet (*Viola arvensis*), green foxtail (*Setaria viridis*), kochia (*Kochia scoparia*), lambsquarters (*Chenopodium album*), Persian speedwell (*Veronica persica*), rape (*Brassica napus* cv. 'Jet Neuf'), ryegrass (*Lolium multiflorum*), sugar beet (*Beta vulgaris* cv. 'US1'), sunflower (*Helianthus annus* cv. 'Russian Giant'), spring wheat (*Triticum aestivum* cv. 'ERA'), winter wheat (*Triticum aestivum* cv. 'Talent'), wild buckwheat (*Polygonum convolvulus*), wild mustard (*Sinapis arvensis*), wild oat (*Avenafatua*), and wild radish (*Raphanus raphanistrum*). Blackgrass and wild oat were treated postemergence at two

TABLE D

| | COMPOUND | | | | | | | | | | | | | | | | | | | | | | | |
|---|---|---|---|---|---|---|---|---|---|---|---|---|---|---|---|---|---|---|---|---|---|---|---|---|
| | Rate (1000 g/ha) | | | Rate (500 g/ha) | | | | Rate (250 g/ha) | | | | Rate (125 g/ha) | | | | | | | | | Rate (80 g/ha) | | | |
| | 25 | 26 | 27 | 25 | 26 | 27 | 30 | 25 | 26 | 27 | 30 | 9 | 25 | 26 | 27 | 30 | 42 | 60 | 61 | 62 | | 9 | 9 | 25 | 26 |
| PADDY | | | | | | | | | | | | | | | | | | | | | | | | | |
| Arrowhead | 9 | 9 | 9 | 9 | 9 | 9 | 9 | 8 | 8 | 9 | 8 | 0 | 7 | 8 | 8 | 7 | — | — | — | — | | 0 | 2 | 7 | 8 |
| Barnyardgrass | 10 | 10 | 10 | 10 | 10 | 10 | 10 | 10 | 10 | 10 | 10 | 10 | 10 | 10 | 10 | 10 | 9 | 10 | 10 | 9 | | 3 | 10 | 10 | 10 |
| Duck salad | | | | | | | | | | | 10 | — | 10 | 10 | — | 8 | 10 | 10 | 10 | | | 0 | 10 | — | 10 |
| Japonica rice | 9 | 9 | 9 | 7 | 9 | 7 | 8 | 6 | 7 | 5 | 4 | 4 | 4 | 5 | 4 | 4 | 1 | 0 | 2 | 1 | | 0 | 9 | 9 | 9 |
| Umbrella sedge | 10 | 10 | 9 | 9 | 10 | 9 | 9 | 9 | 9 | 9 | 9 | 9 | 9 | 9 | 9 | 9 | 9 | 9 | 9 | 9 | | 0 | 9 | 9 | 9 |
| Waterchestnut | 9 | 9 | 9 | 7 | — | — | 8 | 8 | — | — | 7 | — | 7 | — | 7 | — | — | — | — | | | — | 8 | — | 4 |

| | COMPOUND | | | | | | | | | | | | | | | | | | | | | | | | |
|---|---|---|---|---|---|---|---|---|---|---|---|---|---|---|---|---|---|---|---|---|---|---|---|---|---|
| | Rate (64 g/ha) | | | | | | Rate (32 g/ha) | | | | | | | Rate (16 g/ha) | | | | | | Rate (8 g/ha) | | | | | |
| | 27 | 30 | 46 | 60 | 61 | 62 | 9 | 26 | 27 | 30 | 46 | 60 | 61 | 62 | 9 | 26 | 27 | 46 | 60 | 61 | 62 | 26 | 27 | 46 | 60 | 61 | 62 |
| PADDY | | | | | | | | | | | | | | | | | | | | | | | | | |
| Arrowhead | 8 | 4 | — | — | — | — | 0 | — | 4 | 0 | — | — | — | — | 0 | — | 0 | — | — | — | — | 0 | — | — | — | — | — |
| Barnyardgrass | 10 | 10 | 7 | 10 | 10 | 8 | 9 | 7 | 10 | 10 | 8 | 10 | 10 | 7 | 6 | 6 | 7 | 4 | 8 | 7 | 7 | 3 | 6 | 4 | 7 | 7 | 4 |
| Duck salad | 10 | — | 9 | 10 | 10 | 9 | 5 | 6 | 10 | — | 4 | 7 | 7 | 8 | 4 | 0 | 9 | 0 | 9 | 5 | 1 | 0 | 3 | 0 | 0 | 3 | 0 |
| Japonica rice | 3 | 1 | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 |
| Umbrella sedge | 9 | 9 | 9 | 9 | 9 | 9 | 8 | 9 | 9 | 9 | 6 | 8 | 9 | 9 | 7 | 4 | 7 | 0 | 9 | 9 | 6 | 1 | 0 | 0 | 6 | 6 | 2 |
| Waterchestnut | 4 | 7 | — | — | — | — | — | — | — | 4 | — | — | — | — | | | | | | | | | | | | | |

TEST E

Compounds evaluated in this test were formulated in a non-phytotoxic solvent ad applied to the soil surface before plant seedlings emerged (preemergence applicagrowth stages. The first stage (1) was when the plants had two to three leaves. The second stage (2) was when the plants had approximately four leaves or in the initial stages of tillering. Treated plants and untreated controls were maintained in a greenhouse for approximately 21 to 28 days, after which all treated plants were compared to untreated controls and visually evaluated. Plant response ratings, summarized in Table E, are based upon a 0 to 10 scale where 0 is no effect and 10 is complete control. A dash response (-) means no test result.

TABLE E

| Rate (500 g/ha) | COMPOUND | | | | | | | | |
|---|---|---|---|---|---|---|---|---|---|
| | 11 | 15 | 18 | 25 | 39 | 53 | 60 | 61 | 63 |
| POST-EMERGENCE | | | | | | | | | |
| Blackgrass (1) | 0 | 0 | 3 | 3 | 3 | 8 | 7 | 0 | 0 |
| Blackgrass (2) | 0 | 0 | 4 | 3 | 2 | 6 | 8 | 0 | 0 |
| Chickweed | 0 | 3 | 4 | 4 | 0 | 0 | 0 | 0 | 0 |
| Downy brome | 0 | 0 | 2 | 3 | 0 | 0 | 0 | 0 | 0 |
| Field violet | 0 | 3 | 4 | 3 | 2 | 0 | 0 | 0 | 0 |
| Galium (1) | 0 | 3 | 2 | 3 | 0 | 0 | 0 | 0 | 0 |
| Galium (2) | — | — | — | 2 | 0 | 0 | 0 | 0 | 0 |
| Green foxtail | 0 | 0 | 5 | 8 | 2 | 0 | 2 | 0 | 0 |
| Kochia | 0 | 2 | 3 | 0 | 0 | 0 | 0 | 0 | 0 |
| Lambsquarters | 0 | 2 | 3 | 3 | 4 | 4 | 0 | 0 | 0 |
| Persn Speedwell | 0 | 3 | 5 | 4 | 3 | 0 | 0 | 0 | 0 |
| Rape | 0 | 2 | 2 | 4 | 0 | 0 | 0 | 0 | 0 |
| Ryegrass | 0 | 0 | 4 | 6 | 5 | 4 | 4 | 0 | 0 |
| Sugar beet | 0 | 4 | 4 | 0 | 2 | 2 | 0 | 0 | 0 |
| Sunflower | 0 | 3 | 4 | 9 | 0 | 0 | 0 | 0 | 0 |
| Wheat (Spring) | 0 | 0 | 3 | 6 | 2 | 0 | 0 | 0 | 0 |
| Wheat (Winter) | 0 | 0 | 4 | 5 | 3 | 0 | 0 | 0 | 0 |
| Wild buckwheat | 0 | 0 | 6 | 4 | 2 | 0 | 0 | 0 | 0 |
| Wild mustard | 0 | 0 | 0 | 0 | 0 | 0 | 0 | 0 | 0 |
| Wild oat (1) | 0 | 0 | 3 | 6 | 2 | 2 | 4 | 0 | 0 |
| Wild oat (2) | 0 | 0 | 3 | 8 | 2 | 2 | 5 | 0 | 0 |
| Wild radish | 0 | 0 | 4 | 0 | 0 | 0 | 0 | 0 | 0 |
| Winter Barley | 0 | 0 | 2 | 10 | 2 | 0 | 0 | 0 | 0 |

| Rate (500 g/ha) | COMPOUND | | | | | | | | |
|---|---|---|---|---|---|---|---|---|---|
| | 11 | 15 | 18 | 25 | 39 | 53 | 60 | 61 | 63 |
| PRE-EMERGENCE | | | | | | | | | |
| Blackgrass (1) | 8 | 8 | 10 | 10 | 10 | 10 | 10 | 10 | 6 |
| Blackgrass (2) | 8 | 7 | 10 | 9 | 10 | 10 | 10 | 10 | 7 |
| Chickweed | 10 | 10 | 10 | 10 | 10 | 10 | 9 | 10 | 10 |
| Downy brome | 10 | 7 | 8 | 10 | 3 | 9 | 4 | 10 | 4 |
| Field violet | 9 | 9 | 10 | 10 | 10 | 10 | — | — | — |
| Galium (1) | 10 | 9 | 10 | 10 | 6 | 10 | 10 | 9 | 7 |
| Galium (2) | — | — | — | 10 | 5 | 10 | 10 | 8 | 7 |
| Green foxtail | 10 | 10 | 10 | 10 | 10 | 10 | 10 | 10 | 10 |
| Kochia | 4 | 4 | 6 | 8 | 3 | 8 | 9 | 5 | 7 |
| Lambsquarters | 10 | 10 | 10 | 10 | 10 | — | — | — | — |
| Persn Speedwell | 8 | 7 | 10 | 10 | 9 | 10 | 5 | 8 | 10 |
| Rape | 2 | 3 | 6 | 4 | 2 | 7 | 3 | 2 | 2 |
| Ryegrass | 8 | 9 | 10 | 10 | 10 | 10 | 10 | 10 | 10 |
| Sugar beet | 8 | 4 | 10 | 10 | 8 | 10 | 6 | 5 | 5 |
| Sunflower | 5 | 4 | 9 | 8 | 2 | 4 | 0 | 0 | 2 |
| Wheat (Spring) | 5 | 9 | 7 | 10 | 2 | 8 | 4 | 6 | 0 |
| Wheat (Winter) | 5 | 9 | 8 | 10 | 2 | 8 | 4 | 6 | 0 |
| Wild buckwheat | 10 | 8 | 9 | 10 | 9 | 10 | 9 | 10 | 10 |
| Wild mustard | 2 | 2 | 7 | 7 | 4 | 8 | 6 | 6 | 7 |
| Wild oat (1) | 5 | 7 | 6 | 9 | 6 | 10 | 3 | 7 | 0 |
| Wild oat (2) | 6 | 7 | 7 | 9 | 7 | 9 | 4 | 7 | 0 |
| Wild radish | 2 | 2 | 6 | 8 | 3 | 9 | 0 | 2 | 3 |
| Winter Barley | 7 | 9 | 8 | 10 | 2 | 8 | 4 | 6 | 0 |

| Rate (250 g/ha) | COMPOUND | | | | | | | | | |
|---|---|---|---|---|---|---|---|---|---|---|
| | 11 | 15 | 18 | 25 | 39 | 53 | 57 | 60 | 61 | 62 | 63 |
| POST-EMERGENCE | | | | | | | | | | |
| Blackgrass (1) | 0 | 0 | 2 | 0 | 0 | 7 | 6 | 3 | 0 | 4 | 0 |
| Blackgrass (2) | 0 | 0 | 2 | 0 | 0 | 5 | 4 | 3 | 0 | 0 | 0 |
| Chickweed | 0 | 2 | 2 | 0 | 0 | 0 | 0 | 0 | 0 | 0 | 0 |
| Downy brome | 0 | 0 | 0 | 0 | 0 | 0 | 0 | 0 | 0 | 0 | 0 |
| Field violet | 0 | 2 | 2 | 0 | 0 | 0 | 2 | 0 | 0 | — | 0 |
| Galium (1) | 0 | 0 | 0 | 0 | 0 | 0 | 0 | 0 | 0 | 0 | 0 |
| Galium (2) | — | — | — | 0 | 0 | 0 | 0 | 0 | 0 | 0 | 0 |
| Green foxtail | 0 | 0 | 2 | 3 | 0 | 0 | 3 | 0 | 0 | 0 | 0 |
| Kochia | 0 | 0 | 0 | 0 | 0 | 0 | 0 | 0 | 0 | 0 | 0 |
| Lambsquarters | 0 | 0 | 0 | 0 | 2 | 2 | 7 | 0 | 0 | 0 | 0 |
| Persn Speedwell | 0 | 0 | 2 | 2 | 0 | 0 | 0 | 0 | 0 | 0 | 0 |
| Rape | 0 | 0 | 0 | 0 | 0 | 0 | 0 | 0 | 0 | 0 | 0 |
| Ryegrass | 0 | 0 | 2 | 3 | 2 | 2 | 2 | 2 | 0 | 2 | 0 |
| Sugar beet | 0 | 2 | 2 | 0 | 0 | 0 | 0 | 0 | 0 | 0 | 0 |
| Sunflower | 0 | 2 | 2 | 4 | 0 | 0 | 0 | 0 | 0 | 0 | 0 |
| Wheat (Spring) | 0 | 0 | 2 | 3 | 0 | 0 | 0 | 0 | 0 | 0 | 0 |
| Wheat (Winter) | 0 | 0 | 2 | 2 | 0 | 0 | 0 | 0 | 0 | 0 | 0 |
| Wild buckwheat | 0 | 0 | 3 | 2 | 0 | 0 | 4 | 0 | 0 | 0 | 0 |
| Wild mustard | 0 | 0 | 0 | 0 | 0 | 0 | 0 | 0 | 0 | 0 | 0 |
| Wild oat (1) | 0 | 0 | 0 | 4 | 0 | 0 | 0 | 2 | 0 | 0 | 0 |
| Wild oat (2) | 0 | 0 | 0 | 7 | 0 | 0 | 0 | 2 | 0 | 0 | 0 |
| Wild radish | 0 | 0 | 0 | 0 | 0 | 0 | 0 | 0 | 0 | 0 | 0 |
| Winter Barley | 0 | 0 | 0 | 4 | 0 | 0 | 0 | 0 | 0 | 0 | 0 |

| Rate (250 g/ha) | COMPOUND | | | | | | | | | |
|---|---|---|---|---|---|---|---|---|---|---|
| | 11 | 15 | 18 | 25 | 39 | 53 | 57 | 60 | 61 | 62 | 63 |
| PRE-EMERGENCE | | | | | | | | | | |
| Blackgrass (1) | 4 | 6 | 10 | 9 | 7 | 10 | 8 | 10 | 10 | 4 | 2 |
| Blackgrass (2) | 6 | 5 | 9 | 8 | 6 | 10 | 8 | 9 | 10 | 3 | 3 |
| Chickweed | 10 | 9 | 10 | 10 | 10 | 10 | 5 | 8 | 9 | — | 9 |
| Downy brome | 7 | 5 | 5 | 8 | 0 | 7 | 4 | 3 | 7 | 0 | 2 |
| Field violet | 7 | 8 | 10 | 9 | 10 | 10 | — | — | — | 10 | — |
| Galium (1) | 9 | 8 | 8 | 8 | 4 | 9 | 4 | 9 | 8 | 0 | 5 |
| Galium (2) | — | — | — | 9 | 3 | 8 | 5 | 8 | 7 | 0 | 5 |
| Green foxtail | 10 | 10 | 10 | 10 | 10 | 10 | 10 | 10 | 10 | 10 | 10 |
| Kochia | 0 | 2 | 4 | 7 | 0 | 7 | 0 | 7 | 3 | — | 5 |
| Lambsquarters | 10 | 10 | 10 | 10 | 10 | — | 8 | — | — | 10 | — |
| Persn Speedwell | 6 | 5 | 10 | 10 | 7 | 10 | 5 | 3 | 7 | 2 | 8 |
| Rape | 0 | 0 | 3 | 2 | 0 | 4 | 0 | 2 | 0 | 2 | 0 |
| Ryegrass | 4 | 7 | 10 | 10 | 10 | 10 | 10 | 9 | 9 | 9 | 8 |
| Sugar beet | 4 | 2 | 10 | 9 | 5 | 9 | 6 | 4 | 3 | 4 | 3 |
| Sunflower | 3 | 2 | 7 | 6 | 0 | 2 | 3 | 0 | 0 | 0 | 0 |
| Wheat (Spring) | 3 | 6 | 5 | 8 | 0 | 7 | 0 | 2 | 3 | 0 | 0 |
| Wheat (Winter) | 3 | 6 | 6 | 8 | 0 | 7 | 0 | 2 | 3 | 0 | 0 |
| Wild buckwheat | 10 | 6 | 7 | 10 | 6 | 9 | 3 | 7 | 8 | 3 | 10 |
| Wild mustard | 0 | 0 | 5 | 3 | 0 | 6 | 0 | 4 | 4 | 0 | 5 |
| Wild oat (1) | 3 | 4 | 4 | 6 | 3 | 8 | 6 | 2 | 5 | 3 | 0 |
| Wild oat (2) | 4 | 5 | 5 | 6 | 3 | 7 | 5 | 2 | 5 | 3 | 0 |
| Wild radish | 0 | 0 | 4 | 6 | 0 | 8 | 4 | 0 | 0 | 4 | 2 |
| Winter Barley | 4 | 6 | 5 | 8 | 0 | 6 | 0 | 2 | 4 | 0 | 0 |

| Rate (125 g/ha) | COMPOUND | | | | | | | | | |
|---|---|---|---|---|---|---|---|---|---|---|
| | 11 | 15 | 18 | 25 | 39 | 53 | 57 | 60 | 61 | 62 | 63 |
| POST-EMERGENCE | | | | | | | | | | |
| Blackgrass (1) | 0 | 0 | 0 | 0 | 0 | 3 | 3 | 0 | 0 | 0 | 0 |
| Blackgrass (2) | 0 | 0 | 0 | 0 | 0 | 2 | 2 | 0 | 0 | 0 | 0 |
| Chickweed | 0 | 0 | 0 | 0 | 0 | 0 | 0 | 0 | 0 | 0 | 0 |
| Downy brome | 0 | 0 | 0 | 0 | 0 | 0 | 0 | 0 | 0 | 0 | 0 |
| Field violet | 0 | 0 | 0 | 0 | 0 | 0 | 0 | 0 | 0 | — | 0 |
| Galium (1) | 0 | 0 | 0 | 0 | 0 | 0 | 0 | 0 | 0 | 0 | 0 |
| Galium (2) | — | — | — | 0 | 0 | 0 | 0 | 0 | 0 | 0 | 0 |
| Green foxtail | 0 | 0 | 0 | 0 | 0 | 0 | 0 | 0 | 0 | 0 | 0 |
| Kochia | 0 | 0 | 0 | 0 | 0 | 0 | 0 | 0 | 0 | 0 | 0 |
| Lambsquarter3 | 0 | 0 | 0 | 0 | 0 | 0 | 3 | 0 | 0 | 0 | 0 |
| Persn Speedwell | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 |
| Ryegrass | 0 | 0 | 0 | 2 | 0 | 0 | 0 | 0 | 0 | 0 | 0 |
| Sugar beet | 0 | 0 | 0 | 0 | 0 | 0 | 0 | 0 | 0 | 0 | 0 |
| Sunflower | 0 | 0 | 0 | 0 | 0 | 0 | 0 | 0 | 0 | 0 | 0 |
| Wheat (Spring) | 0 | 0 | 0 | 0 | 0 | 0 | 0 | 0 | 0 | 0 | 0 |
| Wheat (Winter) | 0 | 0 | 0 | 0 | 0 | 0 | 0 | 0 | 0 | 0 | 0 |
| Wild buckwheat | 0 | 0 | 0 | 0 | 0 | 0 | 0 | 0 | 0 | 0 | 0 |
| Wild mustard | 0 | 0 | 0 | 0 | 0 | 0 | 0 | 0 | 0 | 0 | 0 |
| Wild oat (1) | 0 | 0 | 0 | 2 | 0 | 0 | 0 | 0 | 0 | 0 | 0 |
| Wild oat (2) | 0 | 0 | 0 | 3 | 0 | 0 | 0 | 0 | 0 | 0 | 0 |
| Wild radish | 0 | 0 | 0 | 0 | 0 | 0 | 0 | 0 | 0 | 0 | 0 |
| Winter Barley | 0 | 0 | 0 | 0 | 0 | 0 | 0 | 0 | 0 | 0 | 0 |

| Rate (125 g/ha) | COMPOUND | | | | | | | | | |
|---|---|---|---|---|---|---|---|---|---|---|
| | 11 | 15 | 18 | 25 | 39 | 53 | 57 | 60 | 61 | 62 | 63 |
| PRE-EMERGENCE | | | | | | | | | | |
| Blackgrass (1) | 2 | 3 | 8 | 7 | 3 | 10 | 6 | 8 | 8 | 2 | 0 |
| Blackgrass (2) | 3 | 3 | 8 | 6 | 2 | 10 | 7 | 7 | 8 | 0 | 0 |
| Chickweed | 10 | 7 | 8 | 8 | 8 | 8 | 2 | 7 | 7 | — | 6 |
| Downy brome | 4 | 3 | 2 | 7 | 0 | 5 | 2 | 0 | 4 | 0 | 0 |
| Field violet | 6 | 6 | 8 | 8 | 8 | 9 | — | — | — | 8 | — |

TABLE E-continued

| | COMPOUND | | | | | | | | | | |
|---|---|---|---|---|---|---|---|---|---|---|---|
| Rate (64 g/ha) | | 11 | 15 | 18 | 25 | 39 | 53 | 57 | 60 | 61 | 62 | 63 |
| Galium (1) | | 8 | 7 | 5 | 6 | 2 | 6 | 3 | 6 | 5 | 0 | 3 |
| Galium (2) | | — | — | — | 7 | 2 | 7 | 2 | 7 | 5 | 0 | 2 |
| Green foxtail | | 10 | 7 | 10 | 10 | 10 | 10 | 10 | 10 | 10 | 10 | 7 |
| Kochia | | 0 | 0 | 2 | 5 | 0 | 6 | 0 | 5 | 2 | — | 3 |
| Lambsquarters | | 9 | 8 | 8 | 10 | 9 | — | 5 | — | — | 10 | — |
| Persn Speedwell | | 5 | 3 | 9 | 10 | 5 | 9 | 2 | 2 | 4 | 0 | 5 |
| Rape | | 0 | 0 | 0 | 0 | 0 | 2 | 0 | 0 | 0 | 0 | 0 |
| Ryegrass | | 3 | 4 | 8 | 10 | 9 | 8 | 7 | 7 | 8 | 6 | 5 |
| Sugar beet | | 2 | 0 | 8 | 9 | 3 | 7 | 2 | 3 | 2 | 3 | 0 |
| Sunflower | | 2 | 0 | 5 | 4 | 0 | 0 | 0 | 0 | 0 | 0 | 0 |
| Wheat (Spring) | | 2 | 3 | 3 | 5 | 0 | 3 | 0 | 0 | 2 | 0 | 0 |
| Wheat (Winter) | | 2 | 4 | 3 | 6 | 0 | 4 | 0 | 0 | 2 | 0 | 0 |
| Wild buckwheat | | 8 | 5 | 4 | 10 | 3 | 7 | 0 | 5 | 6 | 0 | 8 |
| Wild mustard | | 0 | 0 | 3 | 0 | 0 | 3 | 0 | 2 | 2 | 0 | 2 |
| Wild oat (1) | | 2 | 2 | 2 | 4 | 0 | 6 | 3 | 0 | 2 | 0 | 0 |
| Wild oat (2) | | 2 | 3 | 3 | 5 | 0 | 5 | 3 | 0 | 2 | 0 | 0 |
| Wild radish | | 0 | 0 | 2 | 4 | 0 | 5 | 2 | 0 | 0 | 2 | 0 |
| Winter Barley | | 2 | 3 | 4 | 5 | 0 | 3 | 0 | 0 | 2 | 0 | 0 |

| | COMPOUND | | | | | | | | | | |
|---|---|---|---|---|---|---|---|---|---|---|---|
| Rate (64 g/ha) | | 11 | 15 | 18 | 25 | 39 | 53 | 57 | 60 | 61 | 62 | 63 |
| POST-EMERGENCE | | | | | | | | | | | | |
| Blackgrass (1) | | 0 | 0 | 0 | 0 | 0 | 0 | 0 | 0 | 0 | 0 | 0 |
| Blackgrass (2) | | 0 | 0 | 0 | 0 | 0 | 0 | 0 | 0 | 0 | 0 | 0 |
| Chickweed | | 0 | 0 | 0 | 0 | 0 | 0 | 0 | 0 | 0 | 0 | 0 |
| Downy brome | | 0 | 0 | 0 | 0 | 0 | 0 | 0 | 0 | 0 | 0 | 0 |
| Field violet | | 0 | 0 | 0 | 0 | 0 | 0 | 0 | 0 | — | 0 | 0 |
| Galium (1) | | 0 | 0 | 0 | 0 | 0 | 0 | 0 | 0 | 0 | 0 | 0 |
| Galium (2) | | — | — | — | 0 | 0 | 0 | 0 | 0 | 0 | 0 | 0 |
| Green foxtail | | 0 | 0 | 0 | 0 | 0 | 0 | 0 | 0 | 0 | 0 | 0 |
| Kochia | | 0 | 0 | 0 | 0 | 0 | 0 | 0 | 0 | 0 | 0 | 0 |
| Lambsquarters | | 0 | 0 | 0 | 0 | 0 | 0 | 0 | 0 | 0 | 0 | 0 |
| Persn Speedwell | | 0 | 0 | 0 | 0 | 0 | 0 | 0 | 0 | 0 | 0 | 0 |
| Rape | | 0 | 0 | 0 | 0 | 0 | 0 | 0 | 0 | 0 | 0 | 0 |
| Ryegrass | | 0 | 0 | 0 | 0 | 0 | 0 | 0 | 0 | 0 | 0 | 0 |
| Sugar beet | | 0 | 0 | 0 | 0 | 0 | 0 | 0 | 0 | 0 | 0 | 0 |
| Sunflower | | 0 | 0 | 0 | 0 | 0 | 0 | 0 | 0 | 0 | 0 | 0 |
| Wheat (Spring) | | 0 | 0 | 0 | 0 | 0 | 0 | 0 | 0 | 0 | 0 | 0 |
| Wheat (Winter) | | 0 | 0 | 0 | 0 | 0 | 0 | 0 | 0 | 0 | 0 | 0 |
| Wild buckwheat | | 0 | 0 | 0 | 0 | 0 | 0 | 0 | 0 | 0 | 0 | 0 |
| Wild mustard | | 0 | 0 | 0 | 0 | 0 | 0 | 0 | 0 | 0 | 0 | 0 |
| Wild oat (1) | | 0 | 0 | 0 | 0 | 0 | 0 | 0 | 0 | 0 | 0 | 0 |
| Wild oat (2) | | 0 | 0 | 0 | 0 | 0 | 0 | 0 | 0 | 0 | 0 | 0 |
| Wild radish | | 0 | 0 | 0 | 0 | 0 | 0 | 0 | 0 | 0 | 0 | 0 |
| Winter Barley | | 0 | 0 | 0 | 0 | 0 | 0 | 0 | 0 | 0 | 0 | 0 |

| | COMPOUND | | | | | | | | | | |
|---|---|---|---|---|---|---|---|---|---|---|---|
| Rate (64 g/ha) | | 11 | 15 | 18 | 25 | 39 | 53 | 57 | 60 | 61 | 62 | 63 |
| PRE-EMERGENCE | | | | | | | | | | | | |
| Blackgrass (1) | | 0 | 0 | 5 | 5 | 0 | 8 | 4 | 5 | 6 | 0 | 0 |
| Blackgrass (2) | | 0 | 0 | 6 | 5 | 0 | 8 | 4 | 4 | 6 | 0 | 0 |
| Chickweed | | 8 | 5 | 5 | 7 | 7 | 7 | 0 | 6 | 5 | — | 3 |
| Downy brome | | 2 | 0 | 0 | 5 | 0 | 2 | 0 | 0 | 2 | 0 | 0 |
| Field violet | | 4 | 4 | 7 | 5 | 6 | 8 | — | — | — | 5 | — |
| Galium (1) | | 4 | 4 | 3 | 4 | 0 | 5 | 0 | 4 | 3 | 0 | 0 |
| Galium (2) | | — | — | — | 5 | 0 | 5 | 0 | 5 | 2 | 0 | 0 |
| Green foxtail | | 7 | 5 | 10 | 8 | 10 | 10 | 9 | 8 | 8 | 10 | 3 |
| Kochia | | 0 | 0 | 0 | 3 | 0 | 4 | 0 | 3 | 0 | — | 0 |
| Lambsquarters | | 7 | 5 | 6 | 8 | 7 | — | 2 | — | — | 9 | — |
| Persn Speedwell | | 3 | 0 | 7 | 8 | 3 | 7 | 0 | 0 | 2 | 0 | 2 |
| Rape | | 0 | 0 | 0 | 0 | 0 | 0 | 0 | 0 | 0 | 0 | 0 |
| Ryegrass | | 2 | 2 | 5 | 9 | 7 | 6 | 3 | 3 | 6 | 3 | 2 |
| Sugar beet | | 0 | 0 | 7 | 8 | 2 | 6 | 0 | 2 | 0 | 2 | 0 |
| Sunflower | | 0 | 0 | 3 | 2 | 0 | 0 | 0 | 0 | 0 | 0 | 0 |
| Wheat (Spring) | | 0 | 0 | 2 | 2 | 0 | 0 | 0 | 0 | 0 | 0 | 0 |
| Wheat (Winter) | | 0 | 2 | 2 | 3 | 0 | 2 | 0 | 0 | 0 | 0 | 0 |
| Wild buckwheat | | 6 | 3 | 2 | 7 | 2 | 3 | 0 | 3 | 4 | 0 | 4 |
| Wild mustard | | 0 | 0 | 2 | 0 | 0 | 0 | 0 | 0 | 0 | 0 | 0 |
| Wild oat (1) | | 0 | 0 | 0 | 2 | 0 | 3 | 0 | 0 | 0 | 0 | 0 |
| Wild oat (2) | | 0 | 0 | 0 | 3 | 0 | 2 | 0 | 0 | 0 | 0 | 0 |
| Wild radish | | 0 | 0 | 0 | 2 | 0 | 3 | 0 | 0 | 0 | 0 | 0 |
| Winter Barley | | 0 | 0 | 2 | 2 | 0 | 0 | 0 | 0 | 0 | 0 | 0 |

| | COMPOUND | | |
|---|---|---|---|
| Rate (32 g/ha) | 11 | 15 | 25 |
| POST-EMERGENCE | | | |
| Blackgrass (1) | 0 | 0 | 0 |
| Blackgrass (2) | 0 | 0 | 0 |
| Chickweed | 0 | 0 | 0 |
| Downy brome | 0 | 0 | 0 |
| Field violet | 0 | 0 | 0 |
| Galium (1) | 0 | 0 | 0 |
| Galium (2) | — | — | 0 |
| Green foxtail | 0 | 0 | 0 |
| Kochia | 0 | 0 | 0 |
| Lambsquarters | 0 | 0 | 0 |
| Persn Speedwell | 0 | 0 | 0 |
| Rape | 0 | 0 | 0 |
| Ryegrass | 0 | 0 | 0 |
| Sugar beet | 0 | 0 | 0 |
| Sunflower | 0 | 0 | 0 |
| Wheat (Spring) | 0 | 0 | 0 |
| Wheat (Winter) | 0 | 0 | 0 |
| Wild buckwheat | 0 | 0 | 0 |
| Wild mustard | 0 | 0 | 0 |
| Wild oat (1) | 0 | 0 | 0 |
| Wild oat (2) | 0 | 0 | 0 |
| Wild radish | 0 | 0 | 0 |
| Winter Barley | 0 | 0 | 0 |

| | COMPOUND | | | | | | | | | |
|---|---|---|---|---|---|---|---|---|---|---|
| Rate (32 g/ha) | 11 | 15 | 18 | 25 | 39 | 53 | 57 | 60 | 61 | 62 | 63 |
| PRE-EMERGENCE | | | | | | | | | | | |
| Blackgrass (1) | 0 | 0 | 3 | 2 | 0 | 6 | 2 | 3 | 4 | 0 | 0 |
| Blackgrass (2) | 0 | 0 | 4 | 2 | 0 | 7 | 2 | 2 | 3 | 0 | 0 |
| Chickweed | 5 | 3 | 2 | 6 | 3 | 6 | 0 | 2 | 3 | — | 0 |
| Downy brome | 0 | 0 | 0 | 2 | 0 | 0 | 0 | 0 | 0 | 0 | 0 |
| Field violet | 2 | 2 | 4 | 2 | 4 | 5 | — | — | — | 2 | — |
| Galium (1) | 0 | 2 | 0 | 2 | 0 | 3 | 0 | 2 | 0 | 0 | 0 |
| Galium (2) | — | — | — | 3 | 0 | 3 | 0 | 2 | 0 | 0 | 0 |
| Green foxtail | 3 | 3 | 8 | 7 | 6 | 9 | 7 | 7 | 6 | 9 | 0 |
| Kochia | 0 | 0 | 0 | 2 | 0 | 2 | 0 | 2 | 0 | — | 0 |
| Lambsquarters | 4 | 3 | 4 | 5 | 4 | — | 0 | — | — | 8 | — |
| Persn Speedwell | 0 | 0 | 6 | 6 | 2 | 5 | 0 | 0 | 0 | 0 | 0 |
| Rape | 0 | 0 | 0 | 0 | 0 | 0 | 0 | 0 | 0 | 0 | 0 |
| Ryegrass | 0 | 0 | 4 | 6 | 3 | 4 | 2 | 0 | 3 | 0 | 0 |
| Sugar beet | 0 | 0 | 6 | 7 | 0 | 4 | 0 | 0 | 0 | 0 | 0 |
| Sunflower | 0 | 0 | 0 | 0 | 0 | 0 | 0 | 0 | 0 | 0 | 0 |
| Wheat (Spring) | 0 | 0 | 0 | 0 | 0 | 0 | 0 | 0 | 0 | 0 | 0 |
| Wheat (Winter) | 0 | 0 | 0 | 0 | 0 | 0 | 0 | 0 | 0 | 0 | 0 |
| Wild buckwheat | 4 | 2 | 0 | 5 | 0 | 0 | 0 | 0 | 2 | 0 | 2 |
| Wild mustard | 0 | 0 | 0 | 0 | 0 | 0 | 0 | 0 | 0 | 0 | 0 |
| Wild oat (1) | 0 | 0 | 0 | 0 | 0 | 0 | 0 | 0 | 0 | 0 | 0 |
| Wild oat (2) | 0 | 0 | 0 | 0 | 0 | 0 | 0 | 0 | 0 | 0 | 0 |
| Wild radish | 0 | 0 | 0 | 0 | 0 | 0 | 0 | 0 | 0 | 0 | 0 |
| Winter Barley | 0 | 0 | 0 | 0 | 0 | 0 | 0 | 0 | 0 | 0 | 0 |

| | COMPOUND |
|---|---|
| Rate (16 g/ha) | 25 |
| POST-EMERGENCE | |
| Blackgrass (1) | 0 |
| Blackgrass (2) | 0 |
| Chickweed | 0 |
| Downy brome | 0 |
| Field violet | 0 |
| Galium (1) | 0 |
| Galium (2) | 0 |
| Green foxtail | 0 |
| Kochia | 0 |
| Lambsquarters | 0 |
| Persn Speedwell | 0 |
| Rape | 0 |
| Ryegrass | 0 |
| Sugar beet | 0 |
| Sunflower | 0 |
| Wheat (Spring) | 0 |
| Wheat (Winter) | 0 |
| Wild buckwheat | 0 |
| Wild mustard | 0 |
| Wild oat (1) | 0 |
| Wild oat (2) | 0 |
| Wild radish | 0 |
| Winter Barley | 0 |

| | COMPOUND | | | | | | | |
|---|---|---|---|---|---|---|---|---|
| Rate (16 g/ha) | 18 | 25 | 39 | 53 | 57 | 60 | 61 | 62 |

TABLE E-continued

| PRE-EMERGENCE | | | | | | | | |
|---|---|---|---|---|---|---|---|---|
| Blackgrass (1) | 2 | 0 | 0 | 4 | 0 | 0 | 2 | 0 |
| Blackgrass (2) | 2 | 0 | 0 | 4 | 0 | 0 | 2 | 0 |
| Chickweed | 0 | 4 | 2 | 4 | 0 | 0 | 0 | — |
| Downy brome | 0 | 0 | 0 | 0 | 0 | 0 | 0 | 0 |
| Field violet | 2 | 0 | 2 | 3 | — | — | — | 0 |
| Galium (1) | 0 | 0 | 0 | 2 | 0 | 0 | 0 | 0 |
| Galium (2) | — | 0 | 0 | 2 | 0 | 0 | 0 | 0 |
| Green foxtail | 6 | 5 | 3 | 7 | 3 | 3 | 4 | 7 |
| Kochia | 0 | 0 | 0 | 0 | 0 | 0 | 0 | — |
| Lambsquarters | 2 | 2 | 2 | — | 0 | — | — | 6 |
| Persn Speedwell | 3 | 4 | 0 | 3 | 0 | 0 | 0 | 0 |
| Rape | 0 | 0 | 0 | 0 | 0 | 0 | 0 | 0 |
| Ryegrass | 3 | 3 | 0 | 2 | 0 | 0 | 0 | 0 |
| Sugar beet | 3 | 5 | 0 | 2 | 0 | 0 | 0 | 0 |
| Sunflower | 0 | 0 | 0 | 0 | 0 | 0 | 0 | 0 |
| Wheat (Spring) | 0 | 0 | 0 | 0 | 0 | 0 | 0 | 0 |
| Wheat (Winter) | 0 | 0 | 0 | 0 | 0 | 0 | 0 | 0 |
| Wild buckwheat | 0 | 2 | 0 | 0 | 0 | 0 | 0 | 0 |
| Wild mustard | 0 | 0 | 0 | 0 | 0 | 0 | 0 | 0 |
| Wild oat (1) | 0 | 0 | 0 | 0 | 0 | 0 | 0 | 0 |
| Wild oat (2) | 0 | 0 | 0 | 0 | 0 | 0 | 0 | 0 |
| Wild radish | 0 | 0 | 0 | 0 | 0 | 0 | 0 | 0 |
| Winter Barley | 0 | 0 | 0 | 0 | 0 | 0 | 0 | 0 |

TEST F

Plastic pots were partially filled with silt loam soil. The soil was then flooded with water, Japonica rice (*Oryza sativa*) sprouted seeds and 1.5 leaf transplants were planted in the soil. Seeds of barnyardgrass (*Echinochloa crus-galli*) were planted in saturated soil and plants grown to the 1 leaf, 2 leaf and 3 leaf stages for testing. At testing, the water level for all plantings was raised to 2 cm above the soil surface. Chemical treatments were formulated in a non-phytotoxic solvent and applied directly to the paddy water. Treated plants and controls were maintained in a greenhouse for approximately 21 days, after which all species were compared to controls and visually evaluated. Plant response ratings, summarized in Table F are reported on a 0 to 10 scale where 0 is no effect and 10 is complete control. A dash (-) response means no test result.

TABLE F

| | COMPOUND | | | | | | | | | |
|---|---|---|---|---|---|---|---|---|---|---|
| Rate (1000 g/ha) | 24 | | | | | | | | | |
| Flood | | | | | | | | | | |
| 1-LF B.Y.Grass | 10 | | | | | | | | | |
| 2-LF B.Y.Grass | 9 | | | | | | | | | |
| 3-lf B.Y.Grass | 9 | | | | | | | | | |
| Jap Direct Seed | 10 | | | | | | | | | |
| Jap Rice Eff | 5 | | | | | | | | | |
| | COMPOUND | | | | | | | | | |
| Rate (500 g/ha) | 24 | 30 | 34 | | | | | | | |
| Flood | | | | | | | | | | |
| 1-LF B.Y.Grass | 10 | 10 | 10 | | | | | | | |
| 2-LF B.Y.Grass | 9 | 10 | 9 | | | | | | | |
| 3-lf B.Y.Grass | 8 | 10 | 8 | | | | | | | |
| Jap Direct Seed | 10 | 10 | 8 | | | | | | | |
| Jap Rice Eff | 0 | 2 | 0 | | | | | | | |
| | COMPOUND | | | | | | | | | |
| Rate (250 g/ha) | 24 | 25 | 26 | 27 | 30 | 34 | 40 | 57 | 61 | 62 |
| Flood | | | | | | | | | | |
| 1-LF B.Y.Grass | 10 | 10 | 10 | 10 | 10 | 10 | 10 | — | — | — |
| 2-LF B.Y.Grass | 8 | 9 | 10 | 9 | 10 | 10 | 8 | 10 | 10 | 10 |
| 3-lf B.Y.Grass | 8 | 10 | 9 | 10 | 10 | 8 | 8 | 10 | 10 | 9 |
| Jap Direct Seed | 9 | 10 | 10 | 10 | 10 | 7 | 9 | 10 | 10 | 9 |
| Jap Rice Eff | 0 | 6 | 4 | 7 | 1 | 0 | 5 | 4 | 9 | 5 |

TABLE F-continued

| | COMPOUND | | | | | | | | | |
|---|---|---|---|---|---|---|---|---|---|---|
| Rate (125 g/ha) | 24 | 25 | 26 | 27 | 30 | 34 | 39 | 40 | 57 | 61 | 62 |
| Flood | | | | | | | | | | | |
| 1-LF B.Y.Grass | 9 | 10 | 10 | 10 | 10 | 10 | 10 | 10 | — | — | — |
| 2-LF B.Y.Grass | 8 | 9 | 9 | 9 | 10 | 9 | 7 | 8 | 9 | 10 | 9 |
| 3-lf B.Y.Grass | 7 | 9 | 9 | 9 | 9 | 7 | 6 | 6 | 9 | 10 | 8 |
| Jap Direct Seed | 9 | 10 | 10 | 10 | 9 | 5 | 8 | 8 | 9 | 10 | 9 |
| Jap Rice Eff | 0 | 2 | 1 | 2 | 2 | 0 | 1 | 1 | 1 | 8 | 4 |
| | COMPOUND | | | | | | | | | |
| Rate (64 g/ha) | 24 | 25 | 26 | 27 | 30 | 34 | 39 | 40 | 57 | 61 | 62 |
| Flood | | | | | | | | | | | |
| 1-LF B.Y.Grass | 9 | 8 | 9 | 8 | 10 | 10 | 10 | 9 | — | — | — |
| 2-LF B.Y.Grass | 6 | 9 | 9 | 9 | 9 | 9 | 6 | 7 | 9 | 10 | 8 |
| 3-lf B.Y.Grass | 5 | 6 | 7 | 8 | 8 | 4 | 5 | 5 | 7 | 10 | 7 |
| Jap Direct Seed | 5 | 8 | 9 | 10 | 9 | 3 | 7 | 6 | 8 | 9 | 8 |
| Jap Rice Eff | 0 | 0 | 0 | 1 | 0 | 0 | 0 | 2 | 1 | 5 | 0 |
| | COMPOUND | | | | | | | | | |
| Rate (32 g/ha) | | 25 | 26 | 27 | 30 | 34 | 39 | 40 | 57 | 61 | 62 |
| Flood | | | | | | | | | | | |
| 1-LF B.Y.Grass | | 8 | 5 | 7 | 10 | 8 | 6 | 8 | — | — | — |
| 2-LF B.Y.Grass | | 5 | 5 | 5 | 8 | 7 | 5 | 4 | 8 | 9 | 8 |
| 3-lf B.Y.Grass | | 4 | 6 | 7 | 7 | 3 | 1 | 2 | 6 | 7 | 6 |
| Jap Direct Seed | | 5 | 8 | 8 | 6 | 2 | 4 | 3 | 7 | 9 | 8 |
| Jap Rice Eff | | 0 | 0 | 0 | 0 | 0 | 1 | 0 | 4 | 0 | |
| | COMPOUND | | | | | | | |
| Rate (16 g/ha) | | 25 | 26 | 27 | 39 | 40 | 57 | 61 | 62 |
| Flood | | | | | | | | | |
| 1-LF B.Y.Grass | | 5 | 5 | 6 | 5 | 3 | — | — | — |
| 2-LF B.Y.Grass | | 4 | 4 | 3 | 0 | 0 | 7 | 6 | 6 |
| 3-lf B.Y.Grass | | 0 | 2 | 4 | 0 | 0 | 5 | 6 | 5 |
| Jap Direct Seed | | 2 | 4 | 7 | 0 | 1 | 1 | 8 | 2 |
| Jap Rice Eff | | 0 | 0 | 0 | 0 | 0 | 0 | 0 | 0 |
| | COMPOUND | |
| Rate (0 g/ha) | 39 | 40 |
| Flood | | |
| 1-LF B.Y.Grass | 0 | 3 |
| 2-LF B.Y.Grass | 0 | 0 |
| 3-lf B.Y.Grass | 0 | 0 |
| Jap Direct Seed | 0 | 1 |
| Jap Rice Eff | 0 | 1 |

What is claimed is:

1. Compounds of Formula III:

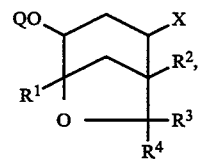

III wherein
R$^1$ is straight chain C$_1$-C$_3$alkyl;
R$^2$ is H, C$_1$-C$_4$alkyl, C$_2$-C$_4$alkenyl or C$_2$-C$_4$alkynyl;
R$^3$ and R$^4$ are independently H, C$_1$-C$_4$alkyl, C$_2$-C$_4$alkenyl, C$_2$-C$_4$alkynyl or C$_1$-C$_3$alkyl substituted with OCH$_3$ or OCH$_2$CH$_3$;
X is CR$^5$R$^6$Y$^1$, CR$^5$=CR$^6$Y$^3$ or

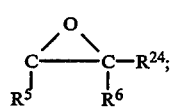

R$^5$ and R$^6$ are independently H or C$_1$-C$_3$alkyl;
Y$^1$ is H; C$_1$-C$_4$alkyl optionally substituted with Y$^2$; C$_3$-C$_6$cycloalkyl; CN; C(O)NR$^7$R$^8$; C(O)NHOR$^9$;

CO$_2$R$^{10}$; C(O)R$^{11}$; C(OR$^{22}$)(OR$^{23}$)R$^{11}$; CHO; CH(OR$^{22}$)(OR$^{23}$); CH=NOR$^{16}$; CR$^{11}$=NOR$^{17}$; SR$^{15}$; halogen; C$_2$-C$_4$alkenyl optionally substituted with 1-3 halogens, CO$_2$(C$_1$-C$_3$alkyl), CN or CHO; C$_2$-C$_4$alkynyl optionally substituted with halogen; S(O)$_n$R$^{12}$; SO$_2$NR$^{13}$R$^{14}$; NO$_2$; N$_3$; SCN; phenyl optionally substituted with 1-3 substituents selected from CH$_3$, OCH$_3$, SCH$_3$, CF$_3$ and halogen; imidazole; triazole; tetrazole; or

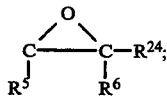

Y$^2$ is CN; C(O)NR$^7$R$^8$; C(O)NHOR$^9$; CO$_2$R$^{10}$; C(O)R$^{11}$; CHO; CH=NOR$^{16}$; CR$^{11}$=NOR$^{17}$; SR$^{15}$; 1-3 halogens; C$_2$-C$_4$alkenyl optionally substituted with 1-3 halogens; C$_2$-C$_4$alkynyl optionally substituted with halogen; S(O)$_n$R$^{12}$; SO$_2$NR$^{13}$R$^{14}$; NO$_2$; N$_3$; SCN; phenyl optionally substituted with 1-3 substituents selected from CH$_3$, OCH$_3$, SCH$_3$, CF$_3$ and halogen; imidazole; triazole; tetrazole; or

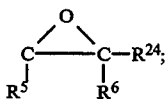

Y$^3$ is H, C$_1$-C$_3$alkyl, CN, CO$_2$R$^{10}$, C(O)R$^{11}$, CHO or halogen;
R$^7$, R$^8$, R$^{13}$ and R$^{14}$ are independently H or C$_1$-C$_3$alkyl; R$^7$ and R$^8$ may be taken together to form a 5- or 6-membered ring and R$^{13}$ and R$^{14}$ may be token together to form a 5- or 6-membered ring;
R$^9$, R$^{12}$, R$^6$ and R$^7$ are independently C$_1$-C$_3$alkyl;
R$^{10}$ is H; C$_1$-C$_6$alkyl optionally substituted with 1-3 halogens, OR$^{18}$, CN or phenyl optionally substituted with 1-3 substituents selected from halogen, CH$_3$ and OCH$_3$; C$_3$-C$_4$alkenyl or C$_3$-C$_4$akynyl;
R$^{11}$ is C$_1$-C$_6$alkyl optionally substituted with 1-3 halogens, OR$^{18}$, CN or phenyl optionally substituted with 1-3 substituents selected from halogen, CH$_3$ and OCH$_3$; C$_2$-C$_4$akenyl C$_2$-C$_4$alkynyl; or phenyl optionally substituted with 1-3 substituents selected from halogen, CH$_3$ and OCH$_3$;
R$^{15}$ is H, C$_1$-C$_3$alkyl or benzyl
n is 1 or 2;
Q is CH$_2$W or

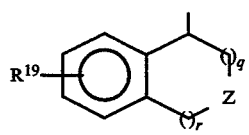

q and r are independently 0-2;
R$^{18}$ is H or C$_1$-C$_3$alkyl;
R$^{19}$ is H, halogen, C$_1$-C$_3$alkyl, OR$^{20}$, SR$^{20}$ or CN;
R$^{20}$ is C$_1$-C$_3$alkyl or C$_1$-C$_3$haloalkyl;
Z is CH$_2$, NR$^{21}$, O, S or may be CH and taken to form a double bond with an adjacent carbon;
R$^{21}$ is H or C$_1$-C$_3$alkyl;
R$^{22}$ and R$^{23}$ are independently C$_1$-C$_3$alkyl or may be taken together to from a 5- or 6-membered ring;
R$^{24}$, is H or C$_1$-C$_2$alkyl;

W is phenyl optionally substituted with 1-3 substituents selected from halogen, C$_1$-C$_3$alkyl, C$_1$-C$_3$alkoxy, OH, CN, C$_1$-C$_3$haloalkyl, C$_1$-C$_3$haloalkoxy, C$_1$-C$_3$alkylthio, C$_2$-C$_4$alkenyl and C$_2$-C$_4$alkynyl; or W is a 5-, 6- or 7-membered heterocyclic ring containing 1 to 3 heteroatoms selected from the group 0-2 nitrogens, 0-2 oxygens and 0-2 sulfurs, each ring optionally substituted with 1-2 substituents selected from halogen, CH$_3$ and OCH$_3$;
provided that
1 the sum of q and r is 0-2; and
2 if the sum of q and r is 0 then Z is CH$_2$.

2. The compounds of claim 1 wherein:
W is phenyl optionally substituted by 1-2 substituenzs selected from F, Cl, Br, CH$_3$ and OCH$_3$; or W is tetrahydropyran, tetrahydrofuran, thiophene, isoxazole, pyridine or pyrazine; each ring optionally substituted with 1-2 substituents selected from F Cl, Br, CH$_3$ and OCH$_3$;
Q is CH$_2$W or

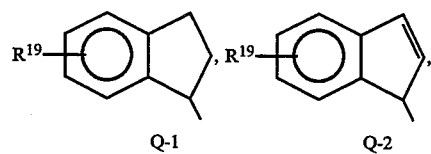

Q-1　　　　Q-2

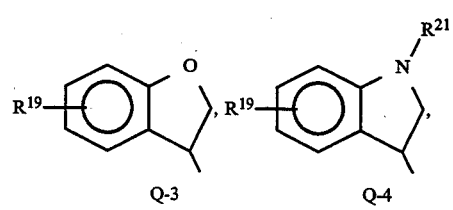

Q-3　　　　Q-4

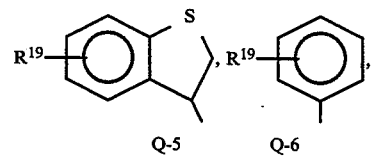

Q-5　　　　Q-6

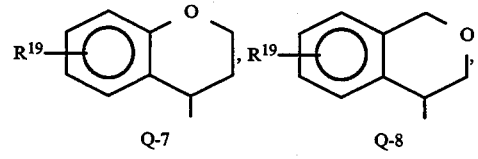

Q-7　　　　Q-8

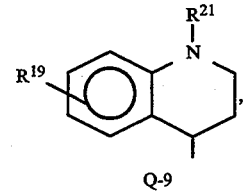

Q-9

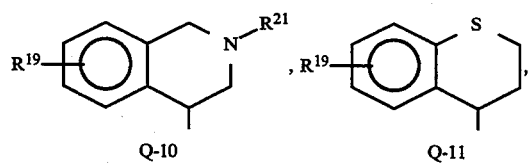

Q-10　　　　Q-11

-continued

Q-12, Q-13, Q-14, Q-15

3. The compounds of claim 2 wherein:
$R^2$ is H, $C_1$–$C_3$alkyl, $C_2$–$C_3$alkenyl or $C_2$–$C_3$alkynyl.

4. The compounds of claim 3 wherein:
$Y^1$ is H; $C_1$–$C_2$alkyl $C_3$–$C_6$ cycloalkyl; CN; $C(O)NR^7R^8$; $C(O)NHOR^9$; $CO_2R^{10}$; $C(O)R^{11}$; $C(O)R^{11}$; $C(OR^{22})(OR^{23})R^{11}$; CHO; $CH(OR^{22})(OR^{23})$; $CH=NOR^{16}$; $CR^{11}=NOR^{17}$; halogen; $C_2$–$C_4$alkenyl optionally substituted with 1–2 halogens, $CO_2(C_1$–$C_3$ alkyl), CN, or CHO; $C_2$–$C_4$alkynyl optionally substituted with halogen; $SO_2NR^{13}R^{14}$; $NO_2$; $N_3$; phenyl optionally substituted with 1–3 substituents selected from $CH_3$, $OCH_3$, $SCH_3$, $CF_3$ and halogen; imidazole; triazole; tetrazole; or

[epoxide structure with $R^5$, $R^6$, $R^{24}$]

5. The compounds of claim 4 wherein:
Q is $CH_2W$ or Q-1, Q-3, Q-4, Q-6, Q-7, Q-8 or Q-15;
$R^5$ and $R^6$ are H;
W is phenyl optionally substituted with 1–2 substituents selected from F, Cl, Br and $CH_3$; tetrahydrofuran; thiophene optionally substituted with Cl or Br; or pyridine.

6. The compounds of claim 5 wherein:
$R^1$ is $CH_3$ or $CH_2CH_3$;
$R^2$ is H, $CH_3$, $CH_2CH_3$ or allyl
$R^3$ and $R^4$ are H;
$Y^1$ is CN, $C(O)N(CH_3)_2$, $CO_2(C_1$–$C2$alkyl), halogen, $C_2$–$C_4$alkenyl or $C_2$–$C_4$alkynyl;
$Y^3$ is H, $C_1$–$C_3$alkyl, CN, $CO_2$ ($C_1$–$C_2$alkyl) or halogen.

7. The compound of claim 5 which is:
(2-endo, 4-endo)-(±)-5-ethyl-4-[(2-fluorophenyl)methoxy]-6-oxabicyclo[3.2.1]-octane-2-acetonitrile.

8. An agriculturally suitable composition for controlling the growth of undesired vegetation comprising an effective amount of a compound of claim 1 and at least one of the following: surfactant, solid diluent or liquid diluent.

9. A method of controlling the growth of undesired vegetation which comprises applying to the locus to be protected an effective amount of a compound of claim 1.

* * * * *